US008546074B2

(12) United States Patent
Guarente et al.

(10) Patent No.: US 8,546,074 B2
(45) Date of Patent: *Oct. 1, 2013

(54) SIR2 ACTIVITY

(75) Inventors: Leonard P. Guarente, Newton, MA (US); Homayoun Vaziri, Montreal (CA); Shin-Ichiro Imai, St. Louis, MO (US)

(73) Assignees: Massachusetts Institute of Technology, Cambridge, MA (US); Whitehead Institute for Biomedical Research, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/523,412

(22) Filed: Jun. 14, 2012

(65) Prior Publication Data
US 2013/0071378 A1 Mar. 21, 2013

Related U.S. Application Data

(60) Continuation of application No. 12/408,575, filed on Mar. 20, 2009, now abandoned, which is a division of application No. 11/404,146, filed on Apr. 13, 2006, now Pat. No. 7,572,575, which is a continuation-in-part of application No. 09/735,786, filed on Dec. 13, 2000, and a continuation-in-part of application No. 11/155,025, filed on Jun. 15, 2005, now abandoned, which is a continuation-in-part of application No. 10/191,121, filed on Jul. 8, 2002, now abandoned, which is a continuation-in-part of application No. 10/190,159, filed on Jul. 5, 2002, now abandoned.

(60) Provisional application No. 60/303,370, filed on Jul. 6, 2001, provisional application No. 60/303,456, filed on Jul. 6, 2001.

(51) Int. Cl.
*C12Q 1/00* (2006.01)
*G01N 33/53* (2006.01)
*G01N 33/567* (2006.01)

(52) U.S. Cl.
USPC ............... 435/4; 435/7.1; 435/7.2; 435/7.21

(58) Field of Classification Search
None
See application file for complete search history.

(56) References Cited

U.S. PATENT DOCUMENTS

| | | |
|---|---|---|
| 4,873,191 A | 10/1989 | Wagner et al. |
| 5,010,175 A | 4/1991 | Rutter et al. |
| 5,093,246 A | 3/1992 | Chech et al. |
| 5,223,409 A | 6/1993 | Ladner et al. |
| 5,270,163 A | 12/1993 | Gold et al. |
| 5,270,170 A | 12/1993 | Schatz et al. |
| 5,283,173 A | 2/1994 | Fields et al. |
| 5,288,514 A | 2/1994 | Ellman |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,565,323 A | 10/1996 | Parker et al. |
| 5,569,588 A | 10/1996 | Ashby et al. |
| 5,593,853 A | 1/1997 | Chen et al. |
| 5,705,350 A | 1/1998 | Mudryj et al. |
| 5,744,300 A | 4/1998 | Linskens et al. |
| 5,817,782 A | 10/1998 | Jazwinski et al. |
| 5,840,493 A | 11/1998 | Davis et al. |
| 5,874,210 A | 2/1999 | Guarente et al. |
| 5,919,618 A | 7/1999 | Guarente et al. |
| 5,965,543 A | 10/1999 | Campisi et al. |
| 5,998,131 A | 12/1999 | Barr et al. |
| 6,027,883 A | 2/2000 | Herrnstadt et al. |
| 6,146,831 A | 11/2000 | Davis et al. |
| 6,218,512 B1 | 4/2001 | Guarente et al. |
| 6,228,583 B1 | 5/2001 | Guarente et al. |
| 6,291,172 B1 | 9/2001 | Davis et al. |
| 6,787,300 B2 | 9/2004 | Guarente et al. |
| 6,835,563 B1 | 12/2004 | Lawn et al. |
| 6,884,597 B1 | 4/2005 | Taya et al. |
| 7,452,664 B2 | 11/2008 | Guarente et al. |
| 7,572,575 B2 | 8/2009 | Guarente et al. |
| 2003/0082668 A1 | 5/2003 | Tamai et al. |
| 2003/0124101 A1 | 7/2003 | Gu et al. |
| 2003/0207325 A1 | 11/2003 | Guarente et al. |
| 2003/0228607 A1 | 12/2003 | Wagner et al. |
| 2004/0091951 A1 | 5/2004 | Schultz |
| 2005/0136429 A1 | 6/2005 | Guarente et al. |
| 2005/0164969 A1 | 7/2005 | Guarente et al. |
| 2006/0252076 A1 | 11/2006 | Guarente et al. |

(Continued)

FOREIGN PATENT DOCUMENTS

| | | |
|---|---|---|
| WO | WO 91/19735 | 12/1991 |
| WO | WO 92/00091 | 1/1992 |

(Continued)

OTHER PUBLICATIONS

Abraham et al., "Posttranslational modification of p53 protein in response to ionizing radiation analyzed y mass spectrometry," J. Mol. Biol., 2000, vol. 295, pp. 853-864.

Alfred, "Counting the calories to immortality," Nat. Rev. Genet., 2000, vol. 1(2), p. 88.

Allsopp, R.C., et al., "Telomere Length Predicts Replicative Capacity of Human Fibroblasts", *Proc. Natl. Acad. Sci. USA* 89:10114-10118 (Nov. 1992).

Angello, J.C., et al., "Cell Enlargement: One Possible Mechanism Underlying Cellular Senescence", *J. Cell. Physiol.* 140:288-294 (Feb. 1989).

Angello, J.C., et al., "Proliferative Potential of Human Fibroblasts: An Inversive Dependence on Cell Size", *J. Cell. Physiol.* 132:125-130 (1987).

Aparicio, O.M., et al., "Modifiers of Position Effect are Share Between Telomeric and Silent Mating-Type Loci in *S. cerevisiae*," *Cell*, 66:1279-1287 (Sep. 1991).

(Continued)

*Primary Examiner* — Albert Navarro
(74) *Attorney, Agent, or Firm* — Hamilton, Brook, Smith & Reynolds, P.C.

(57) ABSTRACT

Methods for screening a compound, by providing a test mixture comprising a transcription factor, Sir2, and a Sir2 cofactor with the compound, and evaluating an activity of a component of the test mixture in the presence of the compound are described.

21 Claims, 33 Drawing Sheets

(56) References Cited

U.S. PATENT DOCUMENTS

| | | | |
|---|---|---|---|
| 2007/0099830 | A1 | 5/2007 | Guarente et al. |
| 2009/0155834 | A1 | 6/2009 | Guarente et al. |
| 2010/0105036 | A1 | 4/2010 | Guarente et al. |
| 2010/0240029 | A1 | 9/2010 | Guarente et al. |
| 2011/0098190 | A1 | 4/2011 | Guarente et al. |

FOREIGN PATENT DOCUMENTS

| | | |
|---|---|---|
| WO | WO 93/20242 | 10/1993 |
| WO | WO 95/05459 | 2/1995 |
| WO | WO 96/05850 | 2/1996 |
| WO | WO 98/17823 | 4/1998 |
| WO | WO 99/10482 | 3/1999 |
| WO | WO 01/12851 | 2/2001 |
| WO | WO 01/12851 A2 | 2/2001 |
| WO | WO 01/79842 | 10/2001 |
| WO | WO 02/31111 A2 | 4/2002 |
| WO | WO 02/102981 A2 | 12/2002 |
| WO | WO 03/004621 A2 | 1/2003 |
| WO | WO 03/046207 A2 | 6/2003 |
| WO | WO 2005/002527 A2 | 1/2005 |
| WO | WO 2007/146023 A1 | 12/2007 |

OTHER PUBLICATIONS

Appella et al., "Signaling to p53: breaking the posttranslational modification code," Pathol. Biol., 2000, vol. 48, pp. 227-245.

Ashcroft, "Stress signals utilize multiple pathways to stabilize p53", Mol. Cell Biol., 2000, vol., 20(9), pp. 3224-3233.

Avalos, Jose L., et al., "Structure of a Sir2 Enzyme Bound to an Acetylated p53 Peptide", Molecular Cell, 2002, vol. 20, No. 3, pp. 523-535.

Avantaggiati et al., "Recruitment of p300/CB0 in p53-dependent signal pathways", Cell, 1997, vol. 89, pp. 1175-1184.

Bairoch, A., "Go Hunting in Sequence Databases but Watch Out for the Traps," Trends in Genetics, 12(10): 425-427 (Oct. 1996).

Barak et al., "mdm2 expression is induced by6 wild type p53 activity", EMBO J., 1993, vol. 12, pp. 461-468.

Bedalov et al., "Identification of a small molecule inhibitor of Sir2p", Proc. Natl. Acad. Sci., Dec. 2001, vol. 98, pp. 15113-15118.

Bernstein et al., "Genomewide studies of histone deacetylase function in yeast", Proc. Natl. Acad. Sci. USA, 2000. vol. 97, pp. 13708-13713.

Bertrand, H., et al., "An Extrachromosomal Plasmid Is the Etiological Precursor of kalDNA Insertion Sequences in the Mitochondrial Chromosome of Senescent Neurospora", Cell, 47:829-837 (Dec. 1986).

Bork, P., "Powers and Pitfalls in Sequence Analysis: the 70% Hurdle," Genome Research, 10:398-400 (2000).

Bowie, J.U., et al., "Deciphering the Message in Protein Sequences: Tolerance to Amino Acid Substitutions," Science, 247:1306-1310 (Mar. 1990).

Brachmann et al., "The SIR2 gene family, conserved from bacteria to humans, functions in silencing, cell cycle progression, and chromosome stability", Genes Dev., 1995, vol. 9, pp. 2888-2902.

Braunstein, M., et al., "Efficient Transcriptional Silencing in *Saccharomyces cerevisiae* Requires a Heterochromatin Histone Acetylation Pattern," Molecular and Cellular Biology, 16(8):4349-4356 (Aug. 1996).

Braunstein, M., et al., "Transcriptional Silencing in Yeast Associated with Reduced Acetylation," Genes & Development, 7(4):592-604 (Feb. 1993).

Brenner, S.E., "Errors in Genome Annotation," Trends in Genetics, 15(4):132-133 (Apr. 1999).

Brower et al., "Growth of cell lines and clinical specimens of human non-small cel;l lung cancer in a serum-free defined medium", Cancer Research, 1986, vol. 46(2), pp. 798-806.

Bryk, M., et al., "Transcriptional Silencing of Ty1 Elements in the *RDN1* Locus of Yeast," Genes & Development, 11:255-269 (1997).

Buckley et al., "Alteration in pim-1 and c-myc expression associated with sodium butyrate-induced growth factor dependency in autonomous rat Nb2 lymphoma cells", Cell Growth Differ., 1996, vol. 7, pp. 1713-1721.

Burnett, C., et al., "Absence of Effects of Sir2 Overexpression on Lifespan in *C. elegans* and *Drosphila*," Nature, 477:482 (2011).

Butler et al., "Suberoylanilide hydroxamic acid, an inhibitor of histone deacetylas suppresses the growth of prostate cancer cell in vitro and in vivo", Cancer Res., 2000, vol. 60, pp. 5165-5170.

Cabib, E., et al., "A Molecular Model for Morphogenesis: The Primary Septum of Yeast", Curr. Top. Cell. Regul.,8:1-32 (1974).

Campbell et al., J. Org. Chem., 1994, vol. 59, p. 658.

Campisi, J., "Aging, chromatin, and food restriction-connecting the dots", Science, 2000, vol. 289, pp. 2062-2063.

Canman et al., "Activation of the ATM kinase by ionizing radiation and phosphorylation of p53", Science, 1998, vol. 281, pp. 1677-1679.

Carroll et al., "Photoaffinity labeling of active site residues in ADP-ribosylating toxins", Methods Enzymo9l., 1994, vol. 235, pp. 631-639.

Chao et al., "p53 transcriptional activity is essential for p53-dependent apoptosis following DNA damage", EMBO J., 2000, vol. 19, pp. 4967-4975.

Chehab et al., "Phosphorylation of Ser-20 mediates stabilization of human p53 in response to DNA damage", Proc. Natl. Acad. Sci. USA, 1999, vol. 96, pp. 13777-13782.

Chen et al., "Apoptosis or senescence-like growth arrest: influence of cell-cycle position, p53, p21 and bax in H2O2 response of normal human fibroblasts", Biochem. J., 2000, vol. 347, pp. 543-551.

Chen et al., "sir2 mutants of *Kluyveromyces lactis* are hypersensitive to KNA-targeting drugs", Mol. Cell. Biol., 1994, vol. 14, 4501-4508.

Cheung et al., "Signaling to chromatin through histone modifications", Cell, 2000, vol. 103, pp. 263-271.

Chien et al., "The two-hybrid system: a method to identify and clone genes for proteins that interact with a protein of interest", Proc. Natl. Acad. Sci. USA, 1991, vol. 88, pp. 9578-9582.

Cho et al., "An unnatural biopolymer", Science, 1993, vol. 261, p. 1303.

Chresta et al., "Oddball p53 in testicular tumors", Nat. Med., 1996, vol. 2, pp. 745-746.

Cristofalo, V.J. and D.Kritchevsky, "Cell Size and Nucleic Acid Content in the Diploid Human Cell Line WI-38 During Aging", Med. Exp. 19:313-320 (1969).

Cristofalo, V.J., et al., "Growth factors as Probes of Cell Aging", Exp. Gerontol. 24:367-374 (1989).

Cull et al., "Screening for receptor ligands using large libraries of peptides linked to the C terminus of the lac repressor", Proc. Natl. Acad. Sci. USA, 1992, vol. 89, pp. 1865-1869.

Cummings, D.J., et al., "Excision—Amplification of Mitochrondial DNA During Senescence in *Podospora anserina*", J. Mol. Biol., 185:659-680 (Mar. 1985).

Cwirla et al., "Peptides on phage: a vast library of peptides for identifying ligands", Proc. Natl. Acad. Sci. USA, 1990, vol. 87, pp. 6378-6382.

Cziepluch, C., et al., "Sequencing Analysis of a 40.2 kb Fragment of Yeast Chromosome X Reveals 19 Open Reading Frames Including URA2 (5' end), TRK1, PBS2, SPT10, GCD14, RPE1, PHO86, NCA3, ASF1, CCT7, GZF3, Two tRNA Genes, Three Remnant Delta Elements and a Ty4 Rransposon", Yeast, 12:1471-1474 (Jun. 1996).

De Witt et al., "Diversomes': An approach to nonpeptide, nonoligomeric chemical diversity", Proc. Natl. Acad. Sci. USA, 1993, vol. 90, p. 6909.

deBeus, E., et al., "Yeast NOP2 Encodes an Essential Nuleolar Protein with Homology to a Human Proliferation Marker," Journal of Biological Chemisty, 127(6):1799-1813 (Dec. 1994).

Devlin et al., "Random peptide libraries: a source of specific protein binding moledules", Science, 1990, vol. 249, pp. 404-406.

Dhar et al., "Inactivation of 14-3 3sigma influences telomere behavior and ionizing radiation-induced chromosomal instability", Mol. Cell. Biol. 2000, vol. 20, pp. 7764-7772.

Di Cristofano et al., "Impaired Fas respopnse and autoimmunity in pten+/− mice", Science, 1999, vol. 285, pp. 2122-2125.

Dimri, G.P., et al., "A Biomarker that Identifies Senescent Human Cells in Culture and in Aging Skin in vivo," Proc. Natl. Acad. Sci. USA, 92:9363-9367 (Sep. 1995).

D'Mello, N.P. et al., "Molecular Analysis of a Young-Specific Gene in the Yeast *Saccharomyces cerevisiae*," *Abstracts of the 92nd General Meeting of the American Society for Microbiology*, H-284, p. 230 (May 26-30, 1992).
Doerks, T., "Protein Annotation: Detective Work for Function Prediction," *Genetwork*, 14(6): 248-250 (Jun. 1998).
Dumaz and Meek, "Serine 15 phosphorylation stimulates p53 transactivation but does not directly influence interaction with HDM2", EMBO J., 1999, vol. 18(24), pp. 7002-7010.
Edington, BIO/Technology, 1993, vol. 11, p. 285.
Egilmez, N.K. and S.M. Jazwinski, "Evidence for the Involvement of a Cytoplasmic Factor in the Aging of the Yeast *Saccharomyces cerevisiae*," *Journal of Bacteriology*, 171(1):37-42 (Jun. 1989).
Egilmez, N.K., et al., "Preparation and Partial Characterization of Old Yeast Cells", *J. Gerontol. Biol. Sci.* 45:B9-B17 (1990).
Egilmez, N.K., et al., "Specific Alterations in Transcript Prevalence During the Yeast Life Span," *The Journal of Biological Chemistry*, 264(24):14312-14317 (Apr. 1989).
El-Deriry et al., "WAF1, a potential mediator of p53 tumor suppression", Cell, 1993, vol. 75, pp. 817-825.
Erb et al., "Recursive deconvolution of combinatorial chemical libraries", Proc. Natl. Acad. Sci. USA, 1994, vol. 91, p. 11422.
Felici, "Selection of antibody ligands from a large library of oligopeptides expressed on a multivalent exposition vector", J. Mol. Biol., 1991, vol. 222, pp. 301-310.
Ferbeyre et al., "MIL is induced by oncogenic ras and promotes premature senescence", Genes Dev., 2000, vol. 14, pp. 2015-2027.
Finkel and Holbrook, "Oxidants, oxidative stress and the giology of ageing", Nature, 2000, vol. 208, pp. 239-247.
Finnin, M.S., et al., "Structure of the Histone Deacetylase SIRT2", *Nat. Struct. Biol.*, 8:621-625 (Jul. 2001).
Finnin, M.S., et al., "Structures of a Histone Deacetylase Homologue Bound to the TSA and SAHA Inhibitors", *Nature*, 401: 188-193 (Sep. 1999).
Fleming, J.E., et al., "Role of Oxidative Stress in *Drosophila* Aging," *Mutation Research*, 275:267-279 (May 1992).
Fodor, S.P.A., et al., "Multiplexed Biochemical Assays with Biological Chips",*Nature*, 364:555-556 (Aug. 1993).
Franco, S., et al., Clonal Variation in Phenotype and Life Span of Huamn Embryonic Fibroblasts (MRC-5) Transduced with the Catalytic Component of Telemerase (hTERT), Experimental Cell Research, 2001, 268:14-25 (2001), doi:10.1006/excr.2001.5264, available online at http://www.ideallibrary.com.
Freedman, D.A., et al., "Functions of the MDM2 Oncoprotein", *Cell. Mol. Life Sci.*, 55(1):96-107 (1999).
Friedman, D.B. and T.E. Johnson, "A Mutation in the *age-1* Gene in *Caenorhabditis elegans* Lengthens Life and Reduces Hermaphrodite Fertility", *Genetics*, 118:75-86 (Jan. 1988).
Frye, R.A., "Characterization of Five Human cDNAs with Homology to the Yeast SIR2 Gene: Sir2-Like Proteins (Sirtuins) Metabolize NAD and May Have Protein ADP-Ribosyltransferase Activity," *Biochemical and Biophysical Res. Comm.*, 260:273-279 (May 1999).
Frye, R.A., "Human Sir2-Like Proteins (sirtuins) are NAD-Metabolizing Protein (ADP-Ribosyl) Tranferases,"*Proc. of American Assoc. for Cancer Res.*, 40:436 (Mar. 1999).
Frye, R.A., "Phylogenetic classification of prokaryotic and eukaryotic Sir2-like proteins", Biochem. Biophys. Res. Commun., 2000,vol. 273, pp. 793-798.
Furka, A., et al. "General method for rapid synthesis of multicomponent peptide mixtures", Int. J. Pept. Prot. Res., 37:487-493 (1991).
Gallop, M.A., et al., "Applications of Combinatorial Technologies to Drug Discovery. I. Background and Peptide Combinatorial Libraries", J. Med. Chem., 37:1233 (Apr. 1994).
Garrus, J.E., et al., "Tsg101 and the Vacuolar Protein Sorting Pathway are Essential for HIV-1 Budding", *Cell*, 107(1):55-65 (Oct. 2001).
Gartenberg, M.R. "The Sir proteins of *Saccharomyces cerevisiae*: mediators of transcriptional silencing and much more", *Curr. Opin. Microbiol.*, vol. 3, pp. 132-137 (2000).
Gayther et al., "Mutations truncating the EP300 acetylase in human cancers", *Nat. Genet.*, vol. 24(3), pp. 300-303 (2000).
GenBank Accession No. AI466061 (1999).
GenBank Accession No. NP_036372; GI No. 6912662, first seen at NCBI on Feb. 7, 2000.
GenBank Accession No. AA105536 (1996).
GenBank Accession No. AA199012 (1997).
GenBank Accession No. AA260334 (1997).
GenBank Accession No. AI465098 (1999).
GenBank Accession No. AI65820 (1999).
Giaccia, A.J. and M.B. Kastan, "The complexity of p53 modulation: emerging patterns from divergent signals", *Genes Dev.*, 12:2973-2983 (Oct. 1998).
Giles, R.H., et al., "Conjunction dysfunction: CBP/p300 in human disease", *Elsevier Science Ltd.* vol. 14(5), pp. 178-183 (1998).
Goodman, R.H. and S. Smolik, "CBP/p300 in cell growth, transformation, and development", *Genes Dev.*, 14(13):1553-1577 (2000).
Gordon, J.W., "Transgenic Animals," *Intl. Rev. Cytol.*, 115:171-229 (1989).
Gotta, M., et al., "The Clustering of Telomeres and Colocalization with Rap1, Sir3 and Sir4 Proteins in Wild-Type *Saccharomyces cerevisae*," *Journal of Cell Biology*, 134(6):1349-1363 (Sep. 1996).
Gottlieb, S., et al., "A New Role for Yeast Transcriptional Silencer Gene, SIR2, in Regulation of Recombination in Ribosoman DNA," *Cell*, 56:771-776 (Mar. 1989).
Gottschling, D.E., "Gene silencing: two faces of SIR2", *Curr. Biol.*, 10: R708-R711 (2000).
Gray and Ekstrom, "The human histone deacetylase family", Exp. Cell Res., 2001, vol. 262, pp. 75-83.
Grozinger, C.M., et al., "Identification of a Class of Small Molecule Inhibitors of the Sirtuin Family of NAD-Dependent Deacetylases by Phenotypic Screening," *Jour. of Biol. Chem.*, 276(42):38837-38843 (Oct. 2001).
Grunstein, M., "Yeast Heterochromatin: Regulation of Its Assembly and Inheritence by Histones," *Cell*, 93:325-328 (May 1998).
Gu W., et al., "A Novel Human SRB/MED-Containing Cofactor Complex, SMCC, Involved in Transcription Regulation", *Mol. Cell*, 3:97-108 (Jan. 1999).
Gu W., et al., "Activation of p53 Sequence-Specific DNA Binding by Acetylation of the p53 C-Terminal Domain", *Cell*, 90:595-606 (Aug. 1997).
Gu, W., et al., "Synergistic Activation of Transcription by CBP and p53", *Nature*, 387:819-823 (Jun. 1997).
Guarente, L. "UASs and Enhancers: Common Mechanism of Transcriptional Activation in Yeast and Mammals", *Cell*, 52:303-305 (Feb. 1988).
Guarente, L., "Diverse and dynamic functions of the Sir silencing complex", Nat. Genet., vol. 23, pp. 281-285 (1999).
Guarente, L., "SIR2 and Aging—the Exception that Proves the Rule," *Trends in Genetics*, 17(7):391-392 (Jul. 2001).
Guarente, L., "Sir2 links chromatin silencing, metabolism, and aging", Genes Dev., 2000, vol. 14, pp. 1021-1026.
Guarente, L., et al., "Genetic Pathways That Regulate Ageing in Model Organisms", *Nature*, 408:255-262 (Nov. 2000).
Guo, A., et al., "The function of PML in p53-dependent apoptosis", *Nat. Cell Biol.*, vol. 2, pp. 730-736 (2000).
Guo, J.C., et al., "Dual Analyte Flow Injection Fluorescence Immunoassays Using Thiophilic Gel Reactors and Synchronous Scanning Detection", *Analyst*, 125 (10): 1707-1708 (Sep. 2000).
Hagihara, M., et al., "Vinylogous Polypeptides: An Alternataive Peptide Backbone," J. Amer. Chem. Soc., 114: 6568 (1992).
Hamlyn, N., et al. EMBL/GenBank/DDBJ databases Accession No. Z46833 (Nov. 1994).
Hardy, C.F.J., et al., "A RAP1-Interacting Protein Involved in Transcriptional Silencing and Telemere Length Regulation," *Genes & Development*, 6:801-814 (Mar. 1992).
Harley, C.B., et al., "Telomeres Shorten During Ageing of Human Fibroblasts", *Nature*, 345:458-460 (May 1990).
Hass et al., "Effects of caloric restriction in animals on cellular function, oncogene expression, and DNA methylation in vitro", *Mutat. Res.*, 295(4-6): 281-289 (Oct. 1993).
Hayflick, I. and P.S. Moorhead, "The Serial Cultivation of Human Diploid Cell Trains", *Exp. Cell Res.*, 25:585-621 (May 1961).
Hayflick, I., "The Limited in vitro Lifetime of Human Diploid Cell Strains", *Exp. Cell Res.*, 37:614-636 (1965).

Herrero-Yraola, A., et al., "Regulation of Glutamate Dehydrogenase by Reversible ADP-Ribosylation in Mitochondria," *The EMBO Journal*, 20(10):2404-2412 (Mar. 2001).
Hill, A.A., et al., "Genomic Analysis of Gene Expression in *C. elegans*", *Science*, 290: 809-812 (Oct. 2000).
Hirao, A., et al., "DNA damage-induced activation of p53 by the checkpoint kinase Chk2", *Science*, 287(5459):1824-1827 (Mar. 2000).
Hirsch, H.R., "Accumulation of a Senescence Factor in Yeast Cells," *Experimental Gerontology*, 28(2):195-204 (1993).
Hirschmann et al., "Nonpeptidal Peptidomimetics with a B-D-Glucose Scaffolding. A Partial Somatostatin Agonist Bearing a Close Structural Relationship to a Potent, Selective Substance P Antagonist", *J. Amer. Chem. Soc.*, vol. 114, pp. 9217-9218 (1992).
Hollstein et al., "New approaches to understanding p53 gene tumor mutation spectra", *Mutat. Res.*, vol. 431(2), pp. 199-209 (1999).
Hollstein, M., et al., "Database of p53 Gene Somatic Mutations in Human Tumors and Cell Lines", *Nucleic Acids Res.*, 22:3551-3555 (1994).
Holtzman, et al., "synthetic-lethal interactions identify two novel genes, SLA1 and SLA2, that control membrane cytoskeleton assembly in *Saccharomyces cerevisiae*", J. Cell Bio., 122:635-644 (1993).
Honda, R. and H. Yasuda, "Association of p19(ARF) With Mdm2 Inhibits Ubiquitin Ligase Activity of Mdm2 for Tumor Suppressor p53", *EMBO J.*, 18(I):22-27 (1999).
Houghten, R.A., et al. "The Use of Synthetic Peptide Combinatorial Libraries for the Identification of Bioactive Peptides," *Biotechniques*, 13:412-421 (1992).
Houghten, R.A., et al., "Generation and Use of Synthetic Peptide Combinatorial Libraries for Basic Research and Drug Discovery", *Nature*, 354:84-88 (Nov. 1991).
Imai, S., et al., "Sir2: an NAD-Dependent Histone Deacetylase that Connects Chromatin Silencing, Metabolism, and Aging," *Cold Spring Harbor Symp. Quant. Biol.*, 65:297-302 (2000).
Imai, S., et al., "Transcriptional silencing and longevity protein Sir2 is an NAD-dependent histone deacetylase", *Nature*, 403:795-800 (Feb. 2000).
International Search Report for PCT/US04/21630 Dated Mar. 27, 2006.
International Search Report for PCT/US94/09351 Dated Jan. 23, 1995.
International Search Report PCT/US02/21461 dated Jan. 25, 2005.
International Search Report PCT/US07/13384 dated Nov. 14, 2007.
Ito, A., et al., "p300/CBP[mediated p53 Acetylation is Commonly Induced by p532-Activating Agents and Inhibited by MDM2", *EMBO J.*, 20:1331-1340 (2001).
Ito, M., et al., "Identity between TRAP and SMCC Complexes Indicates Novel Pathways for the Function of Nuclear Receptors and Diverse Mammalian Activators", *Mol. Cell.*, 3:361-370 (Mar. 1999).
Ivy, J.M., et al., "Cloning and Characterization of Four SIR Genes of *Saccharomyces cerevisiae*," Molecular and Cellular Biology, 6(2):688-702 (Feb. 1986).
Ivy, J.M., et al., "Map Positions of Yeast Genes SIR1, SIR3 and SIR4," *Genetics III*, 735-744 (Dec. 1985).
Jamet-Vierny, C., et al., "Senesence in *Podospora anserina*: Amplification of a Mitochondrial DNA Sequence," *Cell*, 21:189-194 (Aug. 1980).
Jazwinski, M., "Longevity, Genes, and Aging", *Science*, 273:54-59 (Jul. 1996).
Jazwinski, S.M., "Aging and Senescence of the Budding Yeast *Saccharomyces cerevisiae*," Molecular Microbiology, 4(3):337-343 (Oct. 1990).
Jazwinski, S.M., "Genes of Youth: Genetics of Aging in Baker's Yeast," *ASM News*, 59(4):172-178 (1993).
Jazwinski, S.M., et al., "Replication Control and Differential Gene Expression in Aging Yeast," *Molecular Biology of Aging*, 189-203 (Mar. 1989).
Jimenez et al., "A transactivation-deficient mouse model provides insights into Trp53 regulation and function", *Nat. Genet.*, vol. 26, pp. 37-43 (2000).
Juan, L., et al., "Histone Deacetylases Specifically Down-Regulate p53-Dependent Gene Activation", *J. Biol. Chem.*, 275(27):20436-20443 (Jul. 2000).

Kadowaki, T., et al., "Nuclear mRNA Accumulation Causes Nucleolar Fragmentation in Yeast mtr2 Mutant," *Molecular Biology of the Cell*, 5:1253-1263 (Nov. 1994).
Kaeberlein, M., et al., "The SIR2/3/4 Complex and SIR2 Alone Promote Longevity in *Saccharomyces cerevisiae* by Two Different Mechanisms," *Genes & Development*, 13:2570-2580 (Aug. 1999).
Kari, F.W., et al., "Roles for Insulin-Like Growth Factor-1 in Mediating the Anti-Carcinogenic Effects of Caloric Restriction", J. Nutr. Health Aging, 3(2):92-101 (1999).
Karpen, G.H., and R.C. Allshire, "The Case for Epigenetic Effects on Centromere Identity and Function," *TIG*, 13(12):489-496 (Dec. 1997).
Kastan et al., "A mammalian cell cycle checkpoint pathway utilizing p 53 and TGADD45 is defective in ataxia-telangiectasis", Cell, 1992, vol. 71, pp. 587-597.
Kennedy, B.K., et al., "Redistribution of Silencing Proteins from Telomeres to the Nucleolus is Associated with Extension of Life Span in *S. cerevisiae*," *Cell*, 89:381-391 (May 1997).
Kenyon, C., et al., "A *C. elegans* Mutant That Lives Twice as Long as Wild Type", *Nature*,366:461-464 (Dec. 1993).
Khanna et al., "ATM associates with and phosphorylates p53: mapping the region of interaction", *Nat. Genet.*, vol. 20(4), pp. 398-400 (1998).
Kobet et al., "MDM2 inhibits p300-mediated p53 acetylation and activation by forming a ternary complex with the two proteins", *Proc. Natl. Acad. Sci. USA*, 2000, vol. 97, pp. 12547-12552.
Kofler, B., et al., "Purification and Characterization of NAD+: ADP-Ribosyltransferase (Polymerizing) from *Dictyostelium discoideum*," *Biochem. J.*, 293:275-281 (1993).
Kohl, N.E., et al., "Selective Inhibition of ras-Dependent Transformation by a Farnesyltransferase Inhibitor", *Science*, 260:1934 (Jun. 1993).
Koll, F., et al., "A 1100-bp Sequence of Mitochondiral DNA Is Involved in Senescence Process in *Podospora*: Study of Senescent and Mutant Cultures", *Plasmid*, 14:106-117 (Jun. 1985).
Kouzarides, T., "Acetylation: a Regulatory Modification to Rival Phosphorylation?" *EMBO J.*, 19:1176-1179 (2000).
Kung, A.L., et al., "Gene Dose-Dependent Control of Hematopoiesis and Hematologic Tumor Suppression by CBP", *Genes Dev.*, 14(3):272-277 (2000).
Kuo, M.H., et al., "Roles of histone acetyltransferases and deacetylases in gene regulation", BioEssays, vol. 20, pp. 615-626 (1998).
Lam, K.S., et al."A New Type of Synthetic Peptide Library for Identifying Ligand-Binding Activity", *Nature*, 354:82-84 (Nov. 1991).
Lambert et al., "Use of primary cultures of rat hepatocytes for the study of ageing and caloric restriction", Exp. Gerontol., vol. 35(5), pp. 583-594 (2000).
Lambert, P.F., et al., "Phosphorylation of p53 Serine 15 Increases Interaction with CBP", *J. Biol Chem.*, 273:33048-33053 (Dec. 1998).
Landry, J., et al., "Role of NAD(+) in the Deacetylase Activity of the SIR2-like Proteins", *Biochem. Biophys. Res. Commun.*, 278:685-690 (Oct. 2000).
Landry, J., et al., "The Silencing Protein SIR2 and its Homolog are NAD-Dependent Protein Deacetylases," PNAS, 97(11):5807-5811 (May 2000).
Lavitrano, M., et al., "Sperm Cells as Vectors for Introducing Foreign DNA into Eggs: Genetic Transformation of Mice", *Cell*, 57:717-723 (Jun. 1989).
Lazarus, C.M., et al., "Amplification of a Mitochondrial DNA Sequence in the Cytoplasmically Inherited 'Ragged' Mutant of *Aspergillus amstelodami*", *Eur. J. Biochem*, 106:663-641 (1980).
Ledford, H., "Longevity Genes Challenged," [on-line], Sep. 21, 2011, retrieved from the internet URL: http://www.nature.com/news/2011/110921/full/news.2011.549.html;doi:10.1038/news.2011.549.
Lee, S. and D.S. Gross, "Conditional Silencing: The HMRE Mating-Type Silencer Exerts a Rapidly Reversible Position Effect on the Yeast HSP82 Heat Shock Gene," *Molecular and Cellular Biology*, 13(2):727-738 (1993).
Lee, S.E., et al., "Role of Yeast Sir Genes and Mating Type in Directing DNA Double-Strand Breaks to Homologous and Non-Homologous Repair Paths", *Curr. Biol.*, 9:767-770 (Jul. 1999).

Levine, AJ, "p53, the Cellular Gatekeeper for Growth and Division", *Cell*, 88:323-331 (Feb. 1997).

Li, X. et al., Interventions in Aging and Age-Related Diseases: The Present and the Future, *AGE*, 28(1):1-75 (Mar. 2006).

Li, Y., et al., "Long-Term Caloric Restriction Delays Age-Related Decline in Proliferation Capacity of Murine Lens Epithelial Cells in vitro and in vivo", *Invest. Ophthalmol.*, 38(1):100-107 (Jan. 1997).

Liang, R., et al., "Parallel Synthesis and Screening of a Solid Phase Carbohydrate Library", *Science*, 274:1520-1522 (Nov. 1996).

Lill, N.L., et al., "Binding and Modulation of p53 by p300/CBP Coactivators", *Nature*, 387:823-827 (Jun. 1997).

Lin, S., et al., "Requirement of NAD and SIR2 for Life-Span Extension by Calorie Restriction in *Saccharomyces cerevisiae*" Science, 289:2126-2128 (Sep. 2000).

Liu, L., et al., "p53 Sites Acetylated in vitro by PCAF and p300 are Acetylated in vivo in Response to DNA Damage", *Mol. Cell. Biol.*, 19:1202-1209 (Feb. 1999).

Lo, C.W., "Transformation by Iontophoretic Microinjection of DNA: Multiple Integrations Without Tandem Insertions", *Mol. Cell Biol.*, 3:1803-1814 (Oct. 1983).

Lohrum, M. and K.H. Vousden, "Regulation and Activation of p53 and its Family Members", *Cell Death Differ.*, 6(12):1162-1168 (Oct. 1999).

Lombard, D.B., et al., "Longevity Hits a Roadblock," Nature 477: 410-411 (2011).

Longtine, M.S., et al., "Telomere-Mediated Plasmid Segregation in *Saccharomyces cerevisiae* Involves Gene Products Required for Transcriptional Repression at Silencers and Telomeres," *Genetics*, 133:171-182 (Feb. 1993).

Lumpkin, C.K., et al., "Existence of High Abundance Antiproliferative mRNA's in Senescent Human Diploid Fibroblasts", *Science*, 232:393-395 (Apr. 1986).

Lundblad, V., et al., "A Mutant With a Defect in Telomere Elongation Leads to Senescence in Yeast," *Cell*, 57:633-643 (May 1989).

Luo, J., et al., "Deacetylation of p53 Modulates its Effect on Cell Growth and Apoptosis," *Nature*, 408:377-381 (Nov. 2000).

Luo, J., et al., "Negative Control of p53 by Sir2α Promotes Cell Survival Under Stress," *Cell*, 107:137-148 (Oct. 2001).

Lutzker et al., "A functionally inactive p53 protein in teratocarcinoma cells is activated by either DNA damage or cellular differentiation", *Nat. Med.*, vol. 2, pp. 804-810 (1996).

Marasco, W.A., et al., "Design, Intracellular Expression, and Activity of a Human Anti-Human Immunodeficiency Virus Type 1 gp120 Single-Chain Antibody", *Proc. Natl. Acad. Sci. USA*, 90:7889-7893 (Aug. 1993).

Marbois, B., et al., "The COQ7 Gene Encodes a Protein in *Saccharomyces cerevisiae* Necessary for Ubiquinone Biosynthesis", *J. Biol. Chem.*, 271(6), pp. 2995-3004 (Feb. 1996).

Marks, P.A., et al., "Histone Deacetylase Inhibitors: Inducers of Differentiation or Apoptosis of Transformed Cells", J. Nat'l Cancer Inst., 92(15):1210-1216 (Aug. 2000).

Marks, P.A., et al., "Inhibitors of Histone Deacetylase are Potentially Effective Anticancer Agents", *Clin. Cancer Res.*, 7: 759-760 (Apr. 2001).

Marshall, M., et al., "Functional Domains of SIR4, a Gene Required for Position Effect Regulation in *Saccharomyces cerevisiae*," *Molecular and Cellular Biology*, 7(12):4441-4452 (Dec. 1987).

Martin, S.G., et al., "Relocalization of Telomeric Ku and SIR Proteins in Response to DNA Strand Breaks in Yeast," *Cell*, 97:621-63 (May 1999).

Maya, R., et al., "ATM-Dependent Phosphorylation of Mdm2 on Serine 395: Role in p53 Activation by DNA Damage" *Genes Dev.*, 15:1067-1077 (Feb. 2001).

McAinsh, A.D., et al., "DNA Damage Triggers Disruption of Telomeric Silencing and Mec1p-Dependent Relocation of Sir3p", *Curr. Biol.*, 9:963-966 (Aug. 1999).

McConnell, S.J., et al., "Temperate-sensitive Yeast Mutants Defective in Mitochondrial Inheritance", *J. Cell Biol.* 111:967-976 (Sep. 1990).

Migliaccio, E., et al., "The p66$^{shc}$ Adaptor Protein Controls Oxidative Stress Response and Life Span in Mammals", *Nature*, 402:309-313 (Nov. 1999).

Mills, K.D., et al., "MEC1-Dependent Redistribution of the Sir3 Silencing Protein from Telomeres to DNA Double-Strand Breaks," *Cell*, 97:609-620 (May 1999).

Min, J., et al., "Crystal Structure of a SIR2 Homolog-NAD Complex", *Cell*, 105:269-279 (Apr. 2001).

Mitsudomi, T., et al., "p53 gene mutations in non-small-cell lung cancer cell lines and their correlation with the presence of ras mutations and clinical features", Oncogene, 7:171-180 (1992).

Miura, T. and R. Sato, "Cellular Senescence in Yeast Caused by Carbon-Source Starvation," *J. Biochem.*, 76(3):593-601 (1974).

Miura, T. and T. Yanagita, "Cellular Senescence in Yeast Caused by Carbon-Source Starvation," *J. Biochem.*, 72(1):141-148 (1972).

Moazed, D., "Common Themes in Mechanisms of Gene Silencing," *Molecular Cell*, 8:489-498 (Sep. 2001).

Moazed, D., "Enzymatic Activities of Sir2 and Chromatin Silencing", Curr. Opin. Cell Biol, 13: 232-238 (Apr. 2001).

Moretti, P., et al., "Evidence That a Complex of SIR Proteins Interacts with the Silencer and Telomere-Binding Protein RAP1," *Genes & Development*, 8:2257-2269 (Aug. 1994).

Morgenstern, J.P., et al., "Advanced Mammalian Gene Transfer: High Titre Retroviral Vectors with Multiple Drug Selection Markers and a Complementary Helper-Free Packaging Cell Line", *Nucl. Acids Res.*, 18:3587-3596 (May 1990).

Mortimer, R.K. and J.R. Johnston, "Life Span of Individual Yeast Cells", *Nature*, 183:1751-1752 (1959).

Muller, I. and F. Wolf, "A Correlation Between Shortened Life Span and UV-Sensitivity in Some Strain of *Saccharomyces cerevisiae*", *Mol. Gen. Genet.*, 160:231-234 (1978).

Muller, I., "Experiments on Ageing in Single Cells of *Saccharomyces cerevisiae*", *Arch. Mikrobiol.*, 77:20-25 (Dec. 1971).

Muller, I., "Parental Age and the Life-Span of Zygotes of *Saccharomyces cerevisiae*", Antonie van Leeuwenhoek, 51:1-10 (1985).

Muller, I., et al., "Calendar Life Span Versus Budding Life Span of *Saccharomyces cerevisiae*," Mechanisms of Aging and Development, 12(1):47-52 (1980).

Muth. V., et al., "Acetylation of TAF(1)68, a subunit of TIF=IB/SL1, activates RNA polymerase I transcription", *EMBO J.*, 20(6):1353-1362 (2001) (month not available).

Nakamura, S., et al., "Multiple lysine mutations in the C-terminal domain of p53 interfere with MDM2-dependent protein degradation and ubiquitination", *Mol. Cell. Biol.*, 20:9391-9398 (Dec. 2000).

Nakano, K., et al., "PUMA, a Novel Proapoptotic Gene, is Induced by p53", *Mol. Cell*, 7:683-694 (Mar. 2001).

Nehlin et al., "The Werner syndrome. A model for the study of human aging", *Annals NY Acad. Sci.*, vol. 908, pp. 167-179 (2000).

Ngo, J.T., et al., "Computational Complexity, Protein Structure Prediction, and the Levinthal Paradox," The Protein Folding Problem and Tertiary Structure Prediction, 492-495 (1994).

Norwood, T.H., et al., "Dominance of the Senescent Phenotype in Heterokaryons Between Replicative and Post-Replicative Human Fibroblast-Like Cells", *Proc. Natl. Acad. Sci. USA*, 71:2231-2235 (Jun. 1974).

Oakes, M., et al., "Structural Alterations of the Nucleolus in Mutants of *Saccharomyces cerevisiae* Defective RNA Polymerase I," *Molecular and Cellular Biology*, 13(4):2441-2455 (Apr. 1993).

Oda, E., et al., "Noxa, a BH3-Only Member of the Bcl-2 Family and Candidate Mediator of p53-Induced Apoptosis", *Science*, 288(5468):1053-1058 (May 2000).

Oda, K., et al., "p53AIP1, a Potential Mediator of p53-Dependent Apoptosis, and its Regulation by Ser-46-Phosphorylated p53", *Cell*, 102(6), pp. 849-862 (Sep. 2000).

Okamoto, K. and D. Beach, "Cyclin G is a Transcriptional Target of the p53 Tumor Suppressor Protein", *EMBO J.*, 13:4816-4822 (1994).

Olovnikov, A.M., "A Theory of Marginotomy: The Incomplete Copying of Template Margin in Enzymic Synthesis of Polynucleotides and Biological Significance of the Phenomenon", *J. Theor. Biol.* 41:181-190 (1973).

Oren, M., "Regulation of the p53 Tumor Suppressor Protein", *J. Biol. Chem.*, 274:36031-36034 (Dec. 1999).

Orgel, L.E., "Ageing of Clones of Mammalian Cells", *Nature*, 243:441-445 (Jun. 1973).

Pabo, C.O."Transcription Factors: Structural Families and Principles of DNA Recognition," *Annu. Rev. Biochem.*, 61:1053-1075 (1992).

Palladino, F., et al., "SIR3 and SIR4 are Required for the Positioning and Integrity of Yeast Telomeres," *Cell*, 75:543-555 (Nov. 1993).

Park, P.U., et al., "Effects of Mutations in DNA Repair Genes on Formation of Ribosomal DNA Circles and Life Span in *Saccharomyces cerevisiae*," Molecular and Cellular Biology, 19:3848-3856 (May 1999).

Pearson et al., "PML regulates p53 acetylation and premature senescence induced by oncogenic Ras", Nature, 2000, vol. 406, pp. 207-210.

Pelissier, P., et al., "NCA3, a Nuclear Gene Involved in the Mitochondrial Eexpression of Subunits 6 and 8 of the Fo-Fl ATP Synthase of *S. cerevisiae*", *Curr. Genet.* 27:409-416 (1995).

Pereira-Smith, O.M. and J.R. Smith, "Genetic Analysis of Indefinite Division in Human cells: Identification of Four Complementation Groups", *Proc. Natl. Acad. Sci. USA* 85:604-60462 (Aug. 1988).

Pohley, H., "A formal Mortality Analysis for Populations of Unicellular Organisms (*Saccharomyces cerevisiae*)", *Mechanisms of Ageing and Development*, 38:231-243 (1987).

Pomerantz, J., et al., "The Ink4a Tumor Suppressor Gene Product, $p19^{Arf}$, Interacts with MDM2 and Neutralizes MDM2's Inhibition of p53", Cell, 92(6), pp. 713-723 (Mar. 1998).

Pringle, J.R., et al., "Fluorescence Microscopy Methods for Yeast", *Methods in Cell Biology*, 31:357-435 (1989).

Prives et al., "The p53 pathway", Pathol. J., vol. 187, pp. 112-126 (1999).

Proft, M., et al., "CAT5, a New Gene Necessary for Derepression of Gluconeogenic Enzymes in *Saccharomyces cerevisiae*", *EMBO J.*, 14(24):6116-6126 (1995).

Rine, J. and I. Hershkowitz, "Four Genes Responsible for a Position Effect on Expresson from *HML* and *HMR* in *Saccharomyces cerevisae*," Genetics, 116:9-22 (May 1987).

Rizki, G., et al., "The Evolutionary Conserved Longevity Determinants HCF-1 and SIR2.11 Collaborate to Regulate DAF-15/FOXO," PLoS Genetics, 7(9): e1002235, 1-16 (2011).

Rodriguez, M.S., et al., "Multiple C-Terminal Lysine Residues Target p53 for Ubiquitin-Proteasome-Mediated Degradation", *Mol. Cell. Biol.*, 20:8458-8467 (Nov. 2000).

Rogina et al., "Cu, Zn superoxide dismutase deficiency accelerates the time course of an age-related marker in *Drosophila melanogaster*", Biogerontology, vol. 1, pp. 163-169 (2000).

Rogina, B., et al., "*Drosophila* Drop-Dead Mutations Accelerate the Time Course of Age-Related Markers", *Proc. Natl. Acad. Sci. USA*, 94:6303-6306 (Jun. 1997).

Sainsard-Chanet, A. and O. Begel, "Transformation of Yeast and *Podospora*: Innocuity of Senescence-Specific DNAs," *Mol Gen Genet.*, 204:443-451 (1986).

Sakaguchi, K., et al., "DNA Damage Activates p53 Through a Phosphorylation-Acetylation Cascade", Genes Dev., 12:2831-2841 (Jul. 1998).

Sartorelli, V., et al., "The Link Between Chromatin Structure, Protein Acetylation and Cellular Diffierientiation," *Frontiers in Bioscience*, 6:1024-1047 (Sep. 2001).

Schnell, R., et al., "Genetic and Molecular Characterizations of Suppressors of SIR4 Mutations in *Saccharomyces cerevisiae*," Genetics,122:29-46 (May 1989).

Scott, J.K. and G.P. Smith, "Searching for Peptide Ligands with an Epitope Library", Science, 249:386-390 (Jun. 1990).

Seeler, J.S. and A. Dejean, "The PML Nuclear Bodies: Actors or Extras?," *Curr. Opin.* Genet. Dev., 9(3):362-367 (Jun. 1999).

Serrano, M., et al., "Oncogenic ras Provokes Premature Cell Senescence Associated with Accumulation of p53 and p16I8NK4a", *Cell*, 88(5):593-602 (Mar. 1997).

Sharpless, et al., "The INK4A/ARF locus and its two gene products", *Curr. Opin. Genet. Dev.*, vol. 9(1), pp. 22-30 (1999).

Sherman, J.M., and L. Pillus, "An Uncertain Silence," *TIG*, 13(8):308-313 (Aug. 1997).

Sherr, et al., "The ARF/p53 pathway", *Curr. Opin. Genet. Dev.*, vol. 10(1), pp. 94-99 (2000).

Shieh, S., et al., "DNA Damage-Induced Phosphorylation of p53 Alleviates Inhibition MDM2", *Cell*, 91:325-334 (Oct. 1997).

Shieh, S., et al., "The Human Homologs of Checkpoint Kinases Chk1 and Cds1 (Chk2) Phosphorylate p53 at Multiple DNA Damage-Inducible Sites", *Genes Dev.*, 14:289-300 (2000).

Shore D., "The Sir2 protein family: A novel deacetylase for gene silencing and more", Proc. Natl. Acad. Sci. USA, 2000, vol. 97, pp. 14030-14032.

Shou, W., et al., "Exit from Mitosis is Triggered by Tem1 -Dependent Release of the Protein Phosphatase Cdc14 from Nucleolar RENT Complex," *Cell*, 97:233-244 (Apr. 1999).

Siliciano, J.D., et al., "DNA Damage Induces Phosphorylation of the Amino Terminus of p53", *Genes Dev.*, 11:3471-3481 (Nov. 1997).

Simon, R.J., et al., "Peptoids: a Modular Approach to Drug Discovery" *Proc. Natl. Acad. Sci. USA*, 89:9367 (Oct. 1992).

Sinclair, D.A. and L. Guarente, "Extrachromosomal rDNA Circles—A Cause of Aging in Yeast," *Cell*, 97:1033-1042 (Dec. 1997).

Sinclair, D.A., et al. "Molecular Mechanisms of Yeast Aging," TIBS 23:131-134 (Apr. 1998).

Sinclair, D.A., et al., "Accelerated Aging and Nuclear Fragmentation in Yeast sgs1 Mutants," Science, 277:1313-1316 (Aug. 1997).

Skolnick, J., et al., "From Genes to Protein Structgure and Function: Novel Applications of Computational Approaches in the Genomoc Era," *Trends in Biology*, 18:34-39 (Jan. 2000).

Smith, J.S. and J.D. Boeke, "An Unusual Form of Transcriptional Silencing in Yeast Ribosomal DNA," *Genes & Development*, 11:241-254 (Dec. 1997).

Smith, J.S., et al., "A Phylogenetically Conserved NAD-Dependent Protein Deacetylase Activity in the Sir2 Protein Family", *Proc. Natl. Acad. Sci. USA*, 97:6658-6663 (Jun. 2000).

Smith, T.F. and X. Zhang, "The Challengers of Genome Sequence Annotation or 'The Devil in the Details'," Nature Biotechnology, 15:1222-1223 (Nov. 1997).

Sterner, D.E. and S.L. Berger, "Acetylation of histones and transcription-related factors", *Microbiol. Mol. Biol. Rev.*, 64(2), pp. 435-459 (Jun. 2000).

Supplementary Partial European Search Report EP 02 74 9837 dated Jun. 29, 2005.

Sussel, L. and D. Shore, "Separation of Transcriptional Activation and Silencing Functions of the RAP1-Encoded Repressor/Activator Protein 1: Isolation of Viable Mutants Affecting Both Silencing and Telomere Length," *Proc. Natl. Acad. Sci. USA*, 88:7749-7753 (Sep. 1991).

Sweeney, R. and V.A. Zakian, "Extrachromosomal Elements Cause a Reduced Division Potential in *nib1* Strains of *Saccharomyces cerevisiae*," Genetics, 122:749-757 (Aug. 1989).

Tani, T., et al., "Nucleolar Accumulation of Poly (A)+ RNA in Heat-Shocked Yeast Cells: Implicatin of Nucleolar Involvement in mRNA Transport," *Molecular Biology of the Cell*, 6:1515-1534 (Nov. 1995).

Tanner, K.G., et al., "Silent Information Regulator 2 Family of NAD-Dependent Histone/Protein Deacetylases Generates a Unique Product, 1-O-acetyl-ADP-Ribose", *Proc. Natl. Acad. Sci. USA*, 97:14178-14182 (Dec. 2000).

Tanny, J.C., et al., "An Enzymatic Activity in the Yeast Sir2 Protein that is Essential for Gene Silencing," *Cell*, 99:735-745 (Dec. 1999).

Tanny, J.C., et al., "Coupling of Histone Deacetylation of NAD Breakdown by the Yeast Silencing Protein Sir2: Evidence for Acetyl Transfer from Substrate to an NAD Breakdown Product", *Proc. Natl. Acad. Sci. USA*, 98:415-420 (Dec. 2001).

Tao, W., et al., "Nucleocytoplasmic shuttling of oncoprotein HDM1 is required for HDM2-Mediated Degradation of P53", *Proc. Natl. Acad. Sci. USA*, 96(6):3077-3080 (Mar. 1999).

Tao, W., et al., "$P19^{ARF}$ Stabilizes p53 by Blocking Nucleo-Cytoplasmic Shuttling of Mdm2", *Proc. Natl. Acad. Sci. USA*, 96(12):6937-6941 (Jun. 1999).

Taunton, J., et al., "A Mammalian Histone Deacetylase Related to the Yeast Transcriptional Regulator Rpd3p", *Science*, 272:408-411 (Apr. 1996).

Thompson et al., "Germ line transmission and expression of a corrected HPRT gene produced by gene targeting in embryonic stem cells", Cell, 1989, vol. 56, pp. 313-321.

Tibbetts, R.S., et al., "The DnaJ family of protein chaperones in *Trypanosoma cruzi*", *Mol. Biochem. Parasitol.*, 91(2):319-326 (1998).

Tissenbaum, H.A, M. et al., "Regulation of *Caenorhabditis elegans* Lifespan by Sir-2.1 Transgenes," Nature 477:E1-E2 (2011).

Tissenbaum, H.A., et al., "Increased Dosage of a sir-2 Gene Extends Lifespan in *Caenorhabditis elegans*", *Nature*, 410:227-230 (Mar. 2001).

Triolo, T., and R. Sternglanz, "Role of Interactions Between the Origin Recognition Complex and SIR1 in Transcriptional Silencing," *Nature*, 381:251-253 (May 1996).

Tsai, D.E., and J.D. Keene, "In Vitro Selection of RNA Epitopes Using Autoimmune Patient Serums[1]," *Immunology*, 150:1137 (Feb. 1993).

Tsai, D.E., et al., "In vitro Selection of an RNA Epitope Immunologically Cross-Reactive with a Peptide", Proc. Natl. Acad. Sci. USA, 89:8864-8868 (Oct. 1992).

Tsang, A.W., and J.C. Escalante-Semerena, "CobB, a New Member of the SIR2 Family of Eucaryotic Regulatory Proteins is Required to Compensate for the Lck of Nicotinate Mononucleotide:5,6-Dimethylbenzimidazole Phosphoribosyltransferase Activity in *cobT* Mutants During Cobalamin Biosynthesis in *Salmonella typhimurium* LT2*," *Journal of Biological Chemistry*, 273(48); 31788-31794 (Nov. 1998).

Tsang, N.M., et al., "Abrogation of p53 function by transfection of HPV16 E6 gene enhances the resistance of human diploid fibroblasts to ionizing radiation", Oncogene, 1995, vol. 10, pp. 2403-2408.

Tyner, S.D., et al., "p53 Mutant Mice that Display Early Ageing-Associated Phenotypes", *Nature*, 415:45-53 (Jan. 2002).

Unger, T., et al., "Critical Role for Ser20 of Human p53 in the Negative Regulation of p53 by Mdm2", *EMBO J.*, 18(7):1805-1814 (1999).

Urrestarazu, et al., Protein Sequence Database, Accession No. S38114 (May 3, 1994).

Van Der Putten, H., et al., "Efficient Insertion of Genes Into the Mouse Germ Line Via Retroviral Vectors", *Proc. Natl. Acad. Sci. USA*, 82:6148-6152 (Sep. 1985).

Vaughn, T.J., et al., "Human Antibodies with Sub-nanomolar Affinities Isolated from a Large Non-immunized Phage Display Library," *Nature Biotechnology*, 14(3):309-314 (Mar. 1996).

Vaziri, H., et al., "Analysis of Genomic Integrity and p53-Dependent G1 Checkpoint in Telomerase-Induced Extended-Life-Span Human Fibroblasts", *Mol. Cell. Biol.*, 19:2373-2379 (Mar. 1999).

Vaziri, H., et al., "ATM-Dependent Telomere Loss in Aging Human Diploid Fibroblasts and DNA Damage Lead to the Post-Translational Activation of p53 Protein Involving Poly (ADP-Ribose) Polymerase", *EMBO J.*, 16:6018-6033 (1997).

Vaziri, H., et al., "hSIR2sirt1 Functions as an NAD-Dependent p53 Deacetylase," *Cell*, 107:149-159 (Oct. 2001).

Viswanathan, M., et al., "A Role for SIR-2.1 Regulation of ER Stress Resonse Genes in Determining *C. elegans* Life Span," Development Cell, 9: 605-615 (2005).

Vogelstein, B., et al., "Surfing the p53 Network", *Nature*, 408:307-310 (Nov. 2000).

Vousden, K.H., "p53: Death Star", *Cell*, 103(5):691-694 (Nov. 2000).

Weber, et al., "Nucleolar Arf sequesters Mdm2 and activates p53", *Nat. Cell. Biol.*, vol. 1(1), pp. 20-26 (1999).

Weindruch, R., et al., "The Retardation of Aging in Mice by Dietary Restriction: Longevity, Cancer, Immunity and Lifetime Energy Intake", *Journal of Nutrition*, 116(4):641-654 (Nov. 1985).

Wells, J.A., "Additivity of Mutational Effects in Proteins," Perspectives in Biochemistry, 29(37):8509-8517 (Sep. 1990).

Wolf, et al., "The relationships of animal age and caloric intake to cellular replication in vivo and in vitro: a review", *J. Gerontol. A Bio. Sci. Med. Sci.*, vol. 54(11), pp. B502-B517 (1999).

Wolffe et al., "Review: Chromatin Structural Features and Targets That Regulate Transcription", *J. Struct. Biol.*, vol. 129(2-3), pp. 102-122 (2000).

Wu. W., et al., "The p53-mdm-2 Autoregulatory Feedback Loop", *Genes Dev.*, 7:1126-1132 (Apr. 1993).

Yin, Y., et al., "Involvement of p85 in p53-Dependent Apoptotic Response to Oxidative Stress", *Nature*, 391:707-710 (Feb. 1998).

Yoshida, M., et al., "Trichostatin A and trapoxin: novel chemical probes for the role of histone acetylation in chromatin structure and function", *Bioessays*, 5:423-430 (Feb. 1995).

Yu, A., et al., "Activation of p53 or loss of the Cockayne syndrome group B repair protein causes metaphase fragility of human U1, U2, and 58 genes", *Mol. Cell*, 5:801-810 (May 2000).

Yu, Y., et al., "PUMA Induces the Rapid Apoptosis of Colorectal Cancer Cell," *Molecular Cell*, 7:673-682 (Mar. 2001).

Zhang, Y., et al., "SAP30, a Novel Protein Conserved Between Human and Yeast, is a Component of a Histone Deacetylase Complex", *Mol. Cell*, 1:1021-1031 (Jun. 1998).

Ziegler, M., et al., "New Functions of a Long-Known Molecule—Emerging Roles of NAD in Cellular Signaling," *Eur. J. Biochem.*, 267:1550-1564 (Jan. 2000).

Zuckermann, R.N., et al., "Discovery of Nanomolar Ligands for 7-Transmembrane G-protein-coupled Receptors from a Diverse N-(Substituted)glycine Peptoid Library", *J. Med. Chem.*, 37:2678-2685 (1994).

U.S. Office Action dated Aug. 15, 2008 for U.S. Appl. No. 11/404,146.

U.S. Office Action dated Dec. 15, 2004 for U.S. Appl. No. 10/191,121.

U.S. Office Action dated Dec. 21, 2006 for U.S. Appl. No. 10/885,977.

U.S. Office Action dated Jan. 25, 2008 for U.S. Appl. No. 11/404,146.

U.S. Office Action dated Jul. 17, 2006 for U.S. Appl. No. 09/451,580.

U.S. Office Action dated Jul. 25, 2011 for U.S. Appl. No. 12/209,847.

U.S. Office Action dated Jul. 28, 2011 for U.S. Appl No. 12/209,847.

U.S. Office Action dated Jun. 27, 2007 for U.S. Appl. No. 11/404,146.

U.S. Office Action dated Mar. 19, 2008 for U.S. Appl. No. 10/885,977.

U.S. Office Action dated Mar. 26, 2004 for U.S. Appl. No. 09/461,580.

U.S. Office Action dated May 25, 2010 for U.S. Appl. No. 10/885,977.

Office Action dated Nov. 15, 2005 for U.S. Appl. No. 09/461,580.

U.S. Office Action dated Nov. 6, 2001 for U.S. Appl. No. 09/461,580.

U.S. Office Action dated Oct. 13, 2010 for U.S. Appl. No. 09/735,786.

U.S. Office Action dated Oct. 23, 2008 for U.S. Appl. No. 10/885,977.

U.S. Office Action dated Oct. 31, 2007 for U.S. Appl. No. 09/461,580.

U.S. Office Action dated Sep. 29, 2010 for U.S. Appl. No. 12/209,847.

Notice of Allowance dated Aug. 8, 2008 for U.S. Appl. No. 09/461,580.

U.S. Notice of Allowance dated Mar. 15, 2012 for U.S. Appl. No. 12/408,575.

U.S. Office Action dated Sep. 8, 2011 for U.S. Appl. No. 12/408,575.

U.S. Office Action dated Feb. 28, 2011 for U.S. Appl. No. 12/408,575.

Bitterman, K. J., et al., "Inhibition of Silencing and Accelerated Aging by Nicotinamide, a Putative Negative Regulator of Yeast Sir2 and Human SIRT1," *J. Biol. Chem.*, 277(47):45099-45107 (Nov. 2002).

Haigis, M. C., et al., "SIRT4 Inhibits Glutamate Dehydrogenase and Opposes the Effects of Calorie Restriction in Pancreatic β Cells," *Cell*, 126:941-954 (Sep. 2006).

Howitz, K. T., et al., "Small Molecule Activators of Sirtuins Extend *Saccharomyces cerevisiae* Lifespan," *Nature*, 425:191-196 (Sep. 2003).

Li, X., et al., "SIRT1 Deacetylates and Positively Regulates the Nuclear Receptor LXR," *Molecular Cell*, 28:91-106 (Oct. 2007).

Yang, Y. H., et al., "Cloning and Characterization of Two Mouse Genes with Homology to the Yeast *Sir2* Gene," *Genetics*, 69:355-369 (2000).

U.S. Office Action dated Jul. 1, 1996 for U.S. Appl. No. 08/396,001.

U.S. Notice of Allowance dated Apr. 11, 1997 for U.S. Appl. No. 08/396,001.

U.S. Office Action dated Jun. 1, 1998 for U.S. Appl. No. 08/861,464.

U.S. Notice of Allowance dated Jul. 20, 1998 for U.S. Appl. No. 08/861,464.

U.S. Office Action dated Apr. 7, 2000 for U.S. Appl. No. 09/323,433.

U.S. Notice of Allowance dated Oct. 4, 2000 for U.S. Appl. No. 09/323,433.

U.S. Office Action dated Apr. 18, 2003 for U.S. Appl. No. 09/826,752.

U.S. Office Action dated Dec. 10, 2003 for U.S. Appl. No. 09/826,752.
U.S. Notice of Allowance dated Mar. 31, 2004 for U.S. Appl. No. 09/826,752.
U.S. Office Action dated Sep. 5, 2003 for U.S. Appl. No. 09/461,580.
U.S. Office Action dated Nov. 3, 2008 for U.S. Appl. No. 11/409,170.
U.S. Office Action dated Jul. 15, 2009 for U.S. Appl. No. 11/409,170.
U.S. Office Action dated Apr. 9, 2012 for U.S. Appl. No. 12/851,225.
U.S. Office Action dated May 21, 2013 for U.S. Appl. No. 13/646,148.
U.S. Notice of Allowance dated May 21, 2013 for U.S. Appl. No. 13/646,148.
U.S. Office Action dated Mar. 23, 2006 for U.S. Appl. No. 10/993,903.
U.S. Office Action dated Oct. 23, 2006 for U.S. Appl. No. 10/993,903.
U.S. Office Action dated Apr. 23, 2007 for U.S. Appl. No. 10/993,903.
U.S. Office Action dated Nov. 15, 2007 for U.S. Appl. No. 10/993,903.
U.S. Office Action dated Jul. 21, 2009 for U.S. Appl. No. 10/993,903.
U.S. Office Action dated Jun. 9, 2010 for U.S. Appl. No. 10/993,903.
U.S. Office Action dated Jul. 8, 2011 for U.S. Appl. No. 10/993,903.
U.S. Office Action dated Mar. 28, 2012 for U.S. Appl. No. 10/993,903.
U.S. Office Action dated Mar. 18, 2011 for U.S. Appl. No. 12/303,721.
U.S. Office Action dated Oct. 31, 2011 for U.S. Appl. No. 12/303,721.
U.S. Notice of Allowance dated Dec. 30, 2008 for U.S. Appl. No. 11/404,146.

A

B

C p53 harlow -> Translate • 1-frame

DNA sequence    1546 bp    atggaggagccg ... actgttgaattc    linear

```
1/1                                          31/11
atg gag gag ccg cag tca gat cct agc gtc gag ccc cct ctg agt cag gaa aca ttt tca
 M   E   E   P   Q   S   D   P   S   V   E   P   P   L   S   Q   E   T   F   S
61/21                                        91/31
gac cta tgg aaa cta ctt cct gaa aac aac gtt ctg tcc ccc ttg ccg tcc caa gca atg
 D   L   W   K   L   L   P   E   N   N   V   L   S   P   L   P   S   Q   A   M
121/41                                       151/51
gat gat ttg atg ctg tcc ccg gac gat att gaa caa tgg ttc act gaa gac cca ggt cca
 D   D   L   M   L   S   P   D   D   I   E   Q   W   F   T   E   D   P   G   P
181/61                                       211/71
gat gaa gct ccc aga atg cca gag gct gct ccc ccc gtg gcc cct gca cca gca gct cct
 D   E   A   P   R   M   P   E   A   A   P   P   V   A   P   A   P   A   A   P
241/81                                       271/91
aca ccg gcg gcc cct gca cca gcc ccc tcc tgg ccc ctg tca tct tct gtc cct tcc cag
 T   P   A   A   P   A   P   A   P   S   W   P   L   S   S   S   V   P   S   Q
301/101                                      331/111
aaa acc tac cag ggc agc tac ggt ttc cgt ctg ggc ttc ttg cat tct ggg aca gcc aag
 K   T   Y   Q   G   S   Y   G   F   R   L   G   F   L   H   S   G   T   A   K
361/121                                      391/131
tct gtg act tgc acg tac tcc cct gcc ctc aac aag atg ttt tgc caa ctg gcc aag acc
 S   V   T   C   T   Y   S   P   A   L   N   K   M   F   C   Q   L   A   K   T
421/141                                      451/151
tgc cct gtg cag ctg tgg gtt gat tcc aca ccc ccg ccc ggc acc cgc gtc cgc gcc atg
 C   P   V   Q   L   W   V   D   S   T   P   P   P   G   T   R   V   R   A   M
481/161                                      511/171
gcc atc tac aag cag tca cag cac atg acg gag gtt gtg agg cgc tgc ccc cac cat gag
 A   I   Y   K   Q   S   Q   H   M   T   E   V   V   R   R   C   P   H   H   E
```

Figure 12A

```
541/181                                         571/191
cgc tgc tca gat agc gat ggt ctg gcc cct cct cag cat ctt atc cga gtg gaa gga aat
 R   C   S   D   S   D   G   L   A   P   P   Q   H   L   I   R   V   E   G   N
601/201                                         631/211
ttg cgt gtg gag tat ttg gat gac aga aac act ttt cga cat agt gtg gtg gtg ccc tat
 L   R   V   E   Y   L   D   D   R   N   T   F   R   H   S   V   V   V   P   Y
661/221                                         691/231
gag ccg cct gag gtt ggc tct gac tgt acc acc atc cac tac aac tac atg tgt aac agt
 E   P   P   E   V   G   S   D   C   T   T   I   H   Y   N   Y   M   C   N   S
721/241                                         751/251
tcc tgc acg ggc ggc atg aac cgg agg ccc atc ctc acc atc atc aca ctg gaa gac tcc
 S   C   M   G   G   M   N   R   R   P   I   L   T   I   I   T   L   E   D   S
781/261                                         811/271
agt ggt aat cta ctg gga cgg aac agc ttt gag gtg cat gtt tgt gcc tgt cct ggg aga
 S   G   N   L   L   G   R   N   S   F   E   V   H   V   C   A   C   P   G   R
841/281                                         871/291
gac cgg cgc aca gag gaa gag aat ctc cgc aag aaa ggg gag cct cac cac gag ctg ccc
 D   R   R   T   E   E   E   N   L   R   K   K   G   E   P   H   H   E   L   P
901/301                                         931/311
cca ggg agc act aag cga gca ctg ccc aac aac acc agc tcc tct ccc cag cca aag aag
 P   G   S   T   K   R   A   L   P   N   N   T   S   S   S   P   Q   P   K   K
961/321                                         991/331
aaa cca ctg gat gga gaa tat ttc acc ctt cag atc cgt ggg cgt gag cgc ttc gag atg
 K   P   L   D   G   E   Y   F   T   L   Q   I   R   G   R   E   R   F   E   M
```

Figure 12B p53 harlow -> Translate • 1-frame

```
1021/341                                          1051/351
ttc cga gag ctg aat gag gcc ttg gaa ctc aag gat gcc cag gct ggg aag gag cca ggg
 F   R   E   L   N   E   A   L   E   L   K   D   A   Q   A   G   K   E   P   G
1081/361                                          1111/371
ggg agc agg gct cac tcc agc cac ctg aag tcc aaa aag ggt cag tct acc tcc cgc cat
 G   S   R   A   H   S   S   H   L   K   S   K   K   G   Q   S   T   S   R   H
1141/381                                          1171/391
aaa aaa ctc atg ttc aag aca gaa ggg cct gac tca gac tga cat tct cca ctt ctt gtt
 K   K   L   M   F   K   T   E   G   P   D   S   D   *   H   S   P   L   L   V
1201/401                                          1231/411
ccc cac tga cag cct ccc acc ccc atc tct ccc tcc cct gcc att ttg ggt ttt ggg tct
 P   H   *   Q   P   P   T   P   I   S   P   S   P   A   I   L   G   F   G   S
1261/421                                          1291/431
ttg aac cct tgc ttg caa tag gtg tgc gtc aga gct acc cag gac ttc cat ttg ctt tgt
 L   N   P   C   L   Q   *   V   C   V   R   A   T   Q   D   F   H   L   L   C
1321/441                                          1351/451
ccc ggg gct cca ctg aac aag ttg gcc tgc act ggt gtt ttg ttg tgg gga gga gga tgg
 P   G   A   P   L   N   K   L   A   C   T   G   V   L   L   W   G   G   W
1381/461                                          1411/471
gga gta gga cat acc agc tta gat ttt aag gtt ttt act gtg agg gat gtt tgg gag atg
 G   V   G   H   T   S   L   D   F   K   V   F   T   V   R   D   V   W   E   M
1441/481                                          1471/491
taa gaa atg ttc ttg cag tta agg gtt agt tta caa tca gcc aca ttc tag gta ggg acc
 *   E   M   F   L   Q   L   R   V   S   L   Q   S   A   T   F   *   V   G   T
1501/501                                          1531/511
cac ttc acc gta cta acc agg gaa gct gcc ctc cac tgt gaa att c
 H   F   T   V   L   T   R   E   A   V   P   H   C   *   I
```

Figure 12C

BASE COUNT    401 a   513 c   460 g   386 t
ORIGIN    1 bp upstream of Sall site; Chromosome 17p13 [Unpublished (1985) C.
     1 gtgacccti tccaccctg gaagatggaa ataaacctgc gtgtgggtgg agtgttagga
    61 caaaaaaaaa aaaaaaaaag tctagagcca ccgtccaggg agcaggtagc tgctgggctc
   121 cggggacact ttgcgttcgg gctgggagcg tgctttccac gacggtgaca cgcttccctg
   181 gattggcagc cagactgcct tccggtcac tgccatggag gagccgcagt cagstcctag
   241 cgtcgagccc cctctgagtc aggaaacatt ttcagaccta tggaaactac ttcctgaaaa
   301 caacgttctg tcccccttgc cgtcccaagc aatggatgat ttgatgctgt ccccggacga
   361 tattgaacaa tggttcactg aagacccagg tcagatgaa gctccccagaa tgccagaggc
   421 tgctcccccc gtggccctg caccagcagc tcctacaccg gcggcccctg caccagcccc
   481 ctcctggccc ctgtcatctt cgtcccttc ccagaaaacc taccagggca gctacggttt
   541 ccgtctgggc ttcttgcatt ctgggacagc caagtctgtg acttgcacgt actcccctgc
   601 cctcaacaag atgttttgcc aactggccaa gacctgcct gtgcagctgt gggttgattc
   661 cacaccccg ccggcacc gcgtccgcgc catggccatc tacaagcagt cacagcacat
   721 gacggaggtt gtgaggcgct gcccccacca tgagcgctgc tcagatagcg atggtctggc
   781 ccctcctcag catctatcc gagtggaagg aaatttgcgt gtggagtatt tggatgacag
   841 aaacacttt cgacatagtg tggtggtgcc ctatgagccg cctgaggttg gctctgactg
   901 taccaccatc cactacaact acatgtgtaa cagttcctgc atgggcggca tgaaccggag
   961 gcccatcctc accatcatca cactggaaga cccagtggt aatctactgg gacggaacag
  1021 cttgagggtg catgttgtg cctgtcctgg gagagaccgg cgcacagagg aagagaatct
  1081 ccgcaagaaa gggagcctc accacgagct gccccaggg agcactaagc gagcactgcc
  1141 caacaacacc agctcctctc ccagccaaa gaagaaacca ctggatggag aatatttcac
  1201 ccttcagatc cgtgggcgtg agcgcttcga gatgttccga gagctgaatg aggccttgga
  1261 actcaaggat gcccaggctg ggaaggagcc aggggggagc agggctcact ccagccacct
  1321 gaagtccaaa aagggtcagt ctacctcccg ccataaaaaa ctcatgttca agacagaagg
  1381 gcctgactca gactgacatt ctccactct tgtccccac tgacagcctc ccaccccat
  1441 ctctccctcc cctgccattt tgggtttggg gtctttgaac cctgcttgc aataggtgtg
  1501 cgtcagaagc acccaggact tccattgct ttgtcccggg gctccactga acaagttggc
  1561 ctgcactggt gtttgttgt ggggaggagg atgggagta ggacatacca gcttagattt
  1621 taaggtttt actgtgaggg atgtttggga gatgtaagaa atgttcttgc agttaagggt
  1681 tagtttacaa tcagccacat tctaggtagg gacccacttc accgtactaa ccagggaagc
  1741 tgtccctcac tgttgaattc

Figure 13

```
          10         20         30         40         50         60
GCGGAGCAGAGGAGGCGAGGGCGGAGGGCCAGAGAGGCAGTTGGAAGATGGCGGACGAGG
                                                    M  A  D  E  V 70         80         90        100        110        120
TGGCGCTCGCCCTTCAGGCCGCCGGCTCCCCTTCCGCGGCGGCCGCCATGGAGGCCGCGT
 A  L  A  L  Q  A  A  G  S  P  S  A  A  A  A  M  E  A  A  S 130        140        150        160        170        180
CGCAGCCGGCGGACGAGCCGCTCCGCAAGAGGCCCCGCCGAGACGGGCCTGGCCTCGGGC
 Q  P  A  D  E  P  L  R  K  R  P  R  R  D  G  P  G  L  G  R 190        200        210        220        230        240
GCAGCCCGGCGAGCCGAGCGCAGCAGTGGCGCCGGCGGCCGCGGGGTGTGAGGCGGCGA
 S  P  G  E  P  S  A  A  V  A  P  A  A  A  G  C  E  A  A  S 250        260        270        280        290        300
GCGCCGCGGCCCCGGCGGCGCTGTGGCGGGAGGCGGCAGGGGCGGCGGCGAGCGCGGAGC
 A  A  A  P  A  A  L  W  R  E  A  A  G  A  A  A  S  A  E  R 310        320        330        340        350        360
GGGAGGCCCCGGCGACGGCCGTGGCCGGGGACGGAGACAATGGGTCCGGCCTGCGGCGGG
 E  A  P  A  T  A  V  A  G  D  G  D  N  G  S  G  L  R  R  E 370        380        390        400        410        420
AGCCGAGGGCGGCTGACGACTTCGACGACGACGAGGGCGAGGAGGAGGACGAGGCGGCGG
 P  R  A  A  D  D  F  D  D  D  E  G  E  E  E  D  E  A  A  A 430        440        450        460        470        480
CGGCAGCGGCGGCGGCAGCGATCGGCTACCGAGACAACCTCCTGTTGACCGATGGACTCC
 A  A  A  A  A  A  I  G  Y  R  D  N  L  L  L  T  D  G  L  L 490        500        510        520        530        540
TCACTAATGGCTTTCATTCCTGTGAAAGTGATGACGATGACAGAACGTCACACGCCAGCT
 T  N  G  F  H  S  C  E  S  D  D  D  D  R  T  S  H  A  S  S 550        560        570        580        590        600
CTAGTGACTGGACTCCGCGGCCGCGGATAGGTCCATATACTTTTGTTCAGCAACATCTCA
 S  D  W  T  P  R  P  R  I  G  P  Y  T  F  V  Q  Q  H  L  M 610        620        630        640        650        660
TGATTGGCACCGATCCTCGAACAATTCTTAAAGATTTATTACCAGAAACAATTCCTCCAC
 I  G  T  D  P  R  T  I  L  K  D  L  L  P  E  T  I  P  P  P 670        680        690        700        710        720
CTGAGCTGGATGATATGACGCTGTGGCAGATTGTTATTAATATCCTTTCAGAACCACCAA
 E  L  D  D  M  T  L  W  Q  I  V  I  N  I  L  S  E  P  P  K 730        740        750        760        770        780
AGCGGAAAAAAGAAAAGATATCAATACAATTGAAGATGCTGTGAAGTTACTGCAGGAGT
 R  K  K  R  K  D  I  N  T  I  E  D  A  V  K  L  L  Q  E  C 790        800        810        820        830        840
GTAAAAAGATAATAGTTCTGACTGGAGCTGGGGTTTCTGTCTCCTGTGGGATTCCTGACT
 K  K  I  I  V  L  T  G  A  G  V  S  V  S  C  G  I  P  D  F
```

Figure 14A

```
       850        860        870        880        890        900
TCAGATCAAGAGACGGTATCTATGCTCGCCTTGCGGTGGACTTCCCAGACCTCCCAGACC
  R  S  R  D  G  I  Y  A  R  L  A  V  D  F  P  D  L  P  D  P 910        920        930        940        950        960
CTCAAGCCATGTTTGATATTGAGTATTTTAGAAAAGACCCAAGACCATTCTTCAAGTTTG
  Q  A  M  F  D  I  E  Y  F  R  K  D  P  R  P  F  F  K  F  A 970        980        990       1000       1010       1020
CAAAGGAAATATATCCCGGACAGTTCCAGCCGTCTCTGTGTCACAAATTCATAGCTTTGT
  K  E  I  Y  P  G  Q  F  Q  P  S  L  C  H  K  F  I  A  L  S 1030       1040       1050       1060       1070       1080
CAGATAAGGAAGGAAAACTACTTCGAAATTATACTCAAAATATAGATACCTTGGAGCAGG
  D  K  E  G  K  L  L  R  N  Y  T  Q  N  I  D  T  L  E  Q  V 1090       1100       1110       1120       1130       1140
TTGCAGGAATCCAAAGGATCCTTCAGTGTCATGGTTCCTTTGCAACAGCATCTTGCCTGA
  A  G  I  Q  R  I  L  Q  C  H  G  S  F  A  T  A  S  C  L  I 1150       1160       1170       1180       1190       1200
TTTGTAAATACAAAGTTGATTGTGAAGCTGTTCGTGGAGACATTTTTAATCAGGTAGTTC
  C  K  Y  K  V  D  C  E  A  V  R  G  D  I  F  N  Q  V  V  P 1210       1220       1230       1240       1250       1260
CTCGGTGCCCTAGGTGCCCAGCTGATGAGCCACTTGCCATCATGAAGCCAGAGATTGTCT
  R  C  P  R  C  P  A  D  E  P  L  A  I  M  K  P  E  I  V  F 1270       1280       1290       1300       1310       1320
TCTTTGGTGAAAACTTACCAGAACAGTTTCATAGAGCCATGAAGTATGACAAAGATGAAG
  F  G  E  N  L  P  E  Q  F  H  R  A  M  K  Y  D  K  D  E  V 1330       1340       1350       1360       1370       1380
TTGACCTCCTCATTGTTATTGGATCTTCTCTGAAAGTGAGACCAGTAGCACTAATTCCAA
  D  L  L  I  V  I  G  S  S  L  K  V  R  P  V  A  L  I  P  S 1390       1400       1410       1420       1430       1440
GTTCTATACCCCATGAAGTGCCTCAAATATTAATAAATAGGGAACCTTTGCCTCATCTAC
  S  I  P  H  E  V  P  Q  I  L  I  N  R  E  P  L  P  H  L  H 1450       1460       1470       1480       1490       1500
ATTTTGATGTAGAGCTCCTTGGAGACTGCGATGTTATAATTAATGAGTTGTGTCATAGGC
  F  D  V  E  L  L  G  D  C  D  V  I  I  N  E  L  C  H  R  L 1510       1520       1530       1540       1550       1560
TAGGTGGTGAATATGCCAAACTTTGTTGTAACCCTGTAAAGCTTTCAGAAATTACTGAAA
  G  G  E  Y  A  K  L  C  C  N  P  V  K  L  S  E  I  T  E  K 1570       1580       1590       1600       1610       1620
AACCTCCACGCCCACAAAAGGAATTGGTTCATTTATCAGAGTTGCCACCAACACCTCTTC
  P  P  R  P  Q  K  E  L  V  H  L  S  E  L  P  P  T  P  L  H 1630       1640       1650       1660       1670       1680
ATATTTCGGAAGACTCAAGTTCACCTGAAAGAACTGTACCACAAGACTCTTCTGTGATTG
  I  S  E  D  S  S  P  E  R  T  V  P  Q  D  S  S  V  I  A 1690       1700       1710       1720       1730       1740
CTACACTTGTAGACCAAGCAACAAACAACAATGTTAATGATTTAGAAGTATCTGAATCAA
  T  L  V  D  Q  A  T  N  N  N  V  N  D  L  E  V  S  E  S  S
```

Figure 14B

```
        1750       1760       1770       1780       1790       1800
GTTGTGTGGAAGAAAAACCACAAGAAGTACAGACTAGTAGGAATGTTGAACATTAATG
   C  V  E  E  K  P  Q  E  V  Q  T  S  R  N  V  E  N  I  N  V
        1810       1820       1830       1840       1850       1860
TGGAAAATCCAGATTTTAAGGCTGTTGGTTCCAGTACTGCAGACAAAAATGAAAGAACTT
   E  N  P  D  F  K  A  V  G  S  S  T  A  D  K  N  E  R  T  S
        1870       1880       1890       1900       1910       1920
CAGTTGCAGAAACAGTGAGAAAATGCTGGCCTAATAGACTTGCAAAGGAGCAGATTAGTA
   V  A  E  T  V  R  K  C  W  P  N  R  L  A  K  E  Q  I  S  K
        1930       1940       1950       1960       1970       1980
AGCGGCTTGAGGGTAATCAATACCTGTTTGTACCACCAAATCGTTACATATTCCACGGTG
   R  L  E  G  N  Q  Y  L  F  V  P  P  N  R  Y  I  F  H  G  A
        1990       2000       2010       2020       2030       2040
CTGAGGTATACTCAGACTCTGAAGATGACGTCTTGTCCTCTAGTTCCTGTGGCAGTAACA
   E  V  Y  S  D  S  E  D  D  V  L  S  S  S  S  C  G  S  N  S
        2050       2060       2070       2080       2090       2100
GTGACAGTGGCACATGCCAGAGTCCAAGTTTAGAAGAACCCTTGGAAGATGAAAGTGAAA
   D  S  G  T  C  Q  S  P  S  L  E  E  P  L  E  D  E  S  E  I
        2110       2120       2130       2140       2150       2160
TTGAAGAATTCTACAATGGCTTGGAAGATGATACGGAGAGGCCCGAATGTGCTGGAGGAT
   E  E  F  Y  N  G  L  E  D  D  T  E  R  P  E  C  A  G  G  S
        2170       2180       2190       2200       2210       2220
CTGGATTTGGAGCTGATGGAGGGGATCAAGAGGTTGTTAATGAAGCTATAGCTACAAGAC
   G  F  G  A  D  G  G  D  Q  E  V  V  N  E  A  I  A  T  R  Q
        2230       2240       2250       2260       2270       2280
AGGAATTGACAGATGTAAACTATCCATCAGACAAATCATAACACTATTGAAGCTGTCCGG
   E  L  T  D  V  N  Y  P  S  D  K  S  *
        2290       2300       2310       2320       2330       2340
ATTCAGGAATTGCTCCACCAGCATTGGGAACTTTAGCATGTCAAAAAATGAATGTTTAC
        2350       2360       2370       2380       2390       2400
TTGTGAACTTGAACAAGGAAATCTGAAAGATGTATTATTTATAGACTGGAAAATAGATTG
        2410       2420       2430       2440       2450       2460
TCTTCTTGGATAATTTCTAAAGTTCCATCATTTCTGTTTGTACTTGTACATTCAACACTG
        2470       2480       2490       2500       2510       2520
TTGGTTGACTTCATCTTCCTTTCAAGGTTCATTTGTATGATACATTCGTATGTATGTATA
        2530       2540       2550       2560       2570       2580
ATTTTGTTTTTTGCCTAATGAGTTTCAACCTTTTAAAGTTTTCAAAAGCCATTGGAATGT
        2590       2600       2610       2620       2630       2640
TAATGTAAAGGGAACAGCTTATCTAGACCAAAGAATGGTATTTCACACTTTTTTGTTTGT
        2650       2660       2670       2680       2690       2700
AACATTGAATAGTTTAAAGCCCTCAATTTCTGTTCTGCTGAACTTTTATTTTTAGGACAG
        2710       2720       2730       2740       2750       2760
TTAACTTTTTAAACACTGGCATTTTCCAAAACTTGTGGCAGCTAACTTTTTAAAATCACA
```

Figure 14C

```
     2770      2780      2790      2800      2810      2820
GATGACTTGTAATGTGAGGAGTCAGCACCGTGTCTGGAGCACTCAAAACTTGGGCTCAGT 2830      2840      2850      2860      2870      2880
GTGTGAAGCGTACTTACTGCATCGTTTTGTACTTGCTGCAGACGTGGTAATGTCCAAAC 2890      2900      2910      2920      2930      2940
AGGCCCCTGAGACTAATCTGATAAATGATTTGGAAATGTGTTTCAGTTGTTCTAGAAACA 2950      2960      2970      2980      2990      3000
ATAGTGCCTGTCTATATAGGTCCCCTTAGTTTGAATATTTGCCATTGTTTAATTAAATAC 3010      3020      3030      3040      3050      3060
CTATCACTGTGGTAGAGCCTGCATAGATCTTCACCACAAATACTGCCAAGATGTGAATAT 3070      3080      3090      3100      3110      3120
GCAAAGCCTTTCTGAATCTAATAATGGTACTTCTACTGGGAGAGTGTAATATTTTGGAC 3130      3140      3150      3160      3170      3180
TGCTGTTTTCCATTAATGAGGAAAGCAATAGGCCTCTTAATTAAAGTCCCAAAGTCATA 3190      3200      3210      3220      3230      3240
AGATAAATTGTAGCTCAACCAGAAAGTACACTGTTGCCTGTTGAGGATTTGGTGTAATGT 3250      3260      3270      3280      3290      3300
ATCCCAAGGTGTTAGCCTTGTATTATGGAGATCAATACAGATCCAATAGTCAAATGAAAC 3310      3320      3330      3340      3350      3360
TAGTTCTTAGTTATTTAAAAGCTTAGCTTGCCTTAAAACTAGGGATCAATTTTCTCAACT 3370      3380      3390      3400      3410      3420
GCAGAAACTTTTAGCCTTTCAAACAGTTCACACCTCAGAAAGTCAGTATTTATTTTACAG 3430      3440      3450      3460      3470      3480
ACTTCTTTGGAACATTGCCCCCAAATTTAAATATTCATGTGGGTTTAGTATTTATTACAA 3490      3500      3510      3520      3530      3540
AAAAATGATTTGAAATATAGCTGTTCTTTATGCATAAAATACCCAGTTAGGACCATTACT 3550      3560      3570      3580      3590      3600
GCCAGAGGAGAAAAGTATTAAGTAGCTCATTTCCCTACCTAAAAGATAACTGAATTTATT 3610      3620      3630      3640      3650      3660
TGGCTACACTAAAGAATGCAGTATATTAGTTTTCCATTTGCATGATGTGTTTGTGCTAT 3670      3680      3690      3700      3710      3720
AGACAATATTTTAAATTGAAAAATTTGTTTTAAATTATTTTACAGTGAAGACTGTTTTC 3730      3740      3750      3760      3770      3780
AGCTCTTTTTATATTGTACATAGACTTTTATGTAATCTGGCATATGTTTGTAGACCGTT 3790      3800      3810      3820      3830      3840
TAATGACTGGATTATCTTCCTCCAACTTTTGAAATACAAAAACAGTGTTTATACTAAAA 3850      3860      3870
AAAAAAAAGTCGACGCGGCCGCGAATTC
```

Figure 14D

NCBI Sequence Viewer

☐ 1: AF214646 Mus musculus Sir2alpha   PubMed, Protein, Related Sequences, Taxonomy, OMIM, LinkOut
protein (Sir2alpha)
mRNA, complete cds

```
LOCUS       AF214646    3849 bp    mRNA             ROD       26-OCT-2000
DEFINITION  Mus musculus Sir2alpha protein (Sir2alpha) mRNA, complete cds.
ACCESSION   AF214646
VERSION     AF214646.1  GI:6693710
KEYWORDS
SOURCE      house mouse.
  ORGANISM  Mus musculus
            Eukaryota; Metazoa; Chordata; Craniata; Vertebrata; Euteleostomi;
            Mammalia; Eutheria; Rodentia; Sciurognathi; Muridae; Murinae; Mus.
REFERENCE   1  (bases 1 to 3849)
  AUTHORS   Imai,S., Armstrong,C.M., Kaeberlein,M. and Guarente,L.
  TITLE     Transcriptional silencing and longevity protein Sir2 is an
            NAD-dependent histone deacetylase
  JOURNAL   Nature 403 (6771), 795-800 (2000)
  MEDLINE   20155478
   PUBMED   10693811
REFERENCE   2  (bases 1 to 3849)
  AUTHORS   Imai,S., Armstrong,C.M. and Guarente,L.
  TITLE     Direct Submission
  JOURNAL   Submitted (10-DEC-1999) Dept. of Biology, Massachusetts Institute
            of Technology, 77 Massachusetts Avenue, Cambridge, MA 02139, USA
FEATURES             Location/Qualifiers
     source          1..3849
                     /organism="Mus musculus"
                     /strain="Swiss Webster/NIH"
                     /db_xref="taxon:10090"
                     /dev_stage="15-day embryo"
     gene            1..3849
                     /gene="Sir2alpha"
```

Figure 15A

NCBI Sequence Viewer

```
CDS             48..2261
                /gene="Sir2alpha"
                /function="have NAD-dependent histone deacetylase and
                putative mono-ADP-ribosyltransferase activities"
                /note="closest homolog to the yeast silencing and aging
                protein, Sir2p"
                /codon_start=1
                /product="Sir2alpha protein"
                /protein_id="AAF24983.1"
                /db_xref="GI:6693711"
                /translation="MADEVALALQAAGSPSAAAAMEAASQPADEPLRKRPRRDGPGLG
                RSPGEPSAAVAPAAAGCEAASAAAPAALWREAAGAAASAEREAPATAVAGDGDNGSGL
                RREPRAADDFDDDEGEEEDEAAAAAAAAAIGYRDNLLLTDGLLTNGFHSCESDDDDRT
                SHASSSDWTPRPRIGPYTFVQQHLMIGTDPRTILKDLLPETIPPPELDDMTLWQIVIN
                ILSEPPKRKKRKDINTIEDAVKLLQECKKIIVLTGAGVSVSCGIPDFRSRDGIYARLA
                YTQNIDTLEQVAGIQRILQCHGSFATASCLICKYKVDCEAVRGDIFNQVVPRCPRCPA
                DEPLAIMKPEIVFFGENLPEQFHRAMKYDKDEVDLLIVIGSSLKVRPVALIPSSIPHE
                VPQILINREPLPHLEPDVELLGDCDVIINELCHRLGGEYAKLCCNPVKLSEITEKPPR
                PQKELVELSELPPTPLHISEDSSSPERTVPQDSSVIATLVDQATNNNVNDLEVSESSC
                VEEKPQEVQTSRNVENINVENPDFKAVGSSTADKNERTSVAETVRKCWPNRLAKEQIS
                KRLEGNQYLFVPPNRYIFHGAEVYSDSEDDVLSSSSCGSNSDSGTCQSPSLEEPLEDE
                SEIEEFYNGLEDDTERPECAGGSGFGADGGDQEVVNEAIATRQELTDVNYPSDKS"
BASE COUNT      1118 a    761 c    889 g   1081 t
ORIGIN
        1 gcggagcaga ggaggcgagg gcggagggcc agagaggcag ttggaagatg gcggacgagg
       61 tggcgctcgc ccttcaggcc gccggctccc cttccgcggc ggccgc atg gaggccgcgt
      121 cgcagccggc ggacgagccg ctccgcaaga ggccccgccg agacgggcct ggcctcgggc
      181 gcagcccggg cgagccgagc gcagcagtgg cgccggcggc cgcggggtgt gaggcggcga
      241 gcgccgcggc cccggcggcg ctgtggcggg aggcggcagg ggcggcggcg agcgcggagc
      301 gggaggcccc ggcgacggcc gtggccgggg acggagacaa tgggtccggc ctgcggcggg
      361 agccgagggc ggctgacgac ttcgacgacg acgagggcga ggaggaggac gaggcggcgg
      421 cggcagcggc ggcggcagcg atcggctacc gagacaacct cctgttgacc gatggactcc
      481 tcactaatgg cttttcattcc tgtgaaagtg atgacgatga cagaacgtca cacgccagct
      541 ctagtgactg gactccgcgg ccgcggatag gtccatatac ttttgttcag caacatctca
      601 tgattggcac cgatcctcga acaattctta aagatttatt accagaaaca attcctccac
      661 ctgagctgga tgatatgacg ctgtggcaga ttgttattaa tatccttcta gaaccaccaa
      721 agcggaaaaa agaaaagat atcaatacaa ttgaagatgc tgtgaagtta ctgcaggagt
      781 gtaaaaagat aatagtttctg actggagctg gggtttctgt ctcctgtggg attcctgact
      841 tcagatcaag agacggtatc tatgctcgcc ttgcggtgga cttcccagac ctcccagacc
      901 ctcaagccat gtttgatatt gagtatttta gaaaagaccc aagaccattc ttcaagtttg
      961 caaaggaaat atatcccgga cagttccagc cgtctctgtg tcacaaattc atagctttgt
     1021 cagataagga aggaaaacta cttcgaaatt atactcaaaa tatagatacc ttggagcagg
     1081 ttgcaggaat ccaaaggatc cttcagtgtc atggttcctt tgcaacagca tcttgcctga
     1141 tttgtaaata caaagttgat tgtgaagctg ttcgtggaga catttttaat caggtagttc
     1201 ctcggtgccc taggtgccca gctgatgagc cacttgccat catgaagcca gagattgtct
     1261 tctttggtga aaacttacca gaacagtttc atagagccat gaagtatgac aaagatgaag
     1321 ttgaccttct cattgttatt ggatcttctc tgaaagtgag accagtagca ctaattccaa
     1381 gttctatacc ccatgaagtg cctcaaatat taataaatag ggaacctttg cctcatctac
     1441 attttgatgt agagctcctt ggagactgcg atgttataat taatgagttg tgtcataggc
     1501 taggtggtga atatgccaaa ctttgttgta acctgtaaa gcttcagaa attactgaaa
     1561 aacctccacg cccacaaaag gaattggttc atttatcaga gttgccacca acacctcttc
```

Figure 15B

NCBI Sequence Viewer

```
1621 atatttcgga agactcaagt tcacctgaaa gaactgtacc acaagactct tctgtgattg
1681 ctacacttgt agaccaagca acaaacaaca atgttaatga tttagaagta tctgaatcaa
1741 gttgtgtgga agaaaaacca caagaagtac agactagtag gaatgttgag aacattaatg
1801 tggaaaatcc agattttaag gctgttggtt ccagtactgc agacaaaaat gaaagaactt
1861 cagttgcaga aacagtgaga aaatgctggc ctaatagact tgcaaaggag cagattagta
1921 agcggcttga gggtaatcaa tacctgtttg taccaccaaa tcgttacata ttccacggtg
1981 ctgaggtata ctcagactct gaagatgacg tcttgtcctc tagttcctgt ggcagtaaca
2041 gtgacagtgg cacatgccag agtccaagtt tagaagaacc cttggaagat gaaagtgaaa
2101 ttgaagaatt ctacaatggc ttggaagatg atacggagag gcccgaatgt gctggaggat
2161 ctggatttgg agctgatgga ggggatcaag aggttgttaa tgaagctata gctacaagac
2221 aggaattgac agatgtaaac tatccatcag acaaatcata acactattga agctgtccgg
2281 attcaggaat tgctccacca gcattgggaa ctttagcatg tcaaaaaaat gaatgtttac
2341 ttgtgaactt gaacaaggaa atctgaaaga tgtattattt atagactgga aaatagattg
2401 tcttcttgga taatttctaa agttccatca tttctgtttg tacttgtaca ttcaacactg
2461 ttggttgact tcatcttcct ttcaaggttc atttgtatga tacattcgta tgtatgtata
2521 attttgtttt ttgcctaatg agtttcaacc ttttaaagtt ttcaaaagcc attggaatgt
2581 taatgtaaag ggaacagctt atctagacca aagaatggta tttcacactt tttttgttgt
2641 aacattgaat agtttaaagc cctcaatttc tgttctgctg aacttttatt tttaggacag
2701 ttaactttt aaacactggc attttccaaa acttgtggca gctaactttt taaaatcaca
2761 gatgacttgt aatgtgagga gtcagcaccg tgtctggagc actcaaaact tgggctcagt
2821 gtgtgaagcg tacttactgc atcgtttttg tacttgctgc agacgtggta atgtccaaac
2881 aggcccctga gactaatctg ataaatgatt tggaaatgtg tttcagttgt tctagaaaca
2941 atagtgcctg tctatatagg tcccccttagt ttgaatattt gccattgttt aattaaatac
3001 ctatcactgt ggtagagcct gcatagatct tcaccacaaa tactgccaag atgtgaatat
3061 gcaaagcctt tctgaatcta ataatggtac ttctactggg gagagtgtaa tatttggac
3121 tgctgttttt ccattaatga ggaaagcaat aggcctctta attaaagtcc caaagtcata
3181 agataaattg tagctcaacc agaaagtaca ctgttgcctg ttgaggattt ggtgtaatgt
3241 atcccaaggt gttagccttg tattatggag atgaatacag atccaatagt caaatgaaac
3301 tagttcttag ttatttaaaa gcttagcttg cctaaaaact agggatcaat tttctcaact
3361 gcagaaactt ttagcctttc aaacagttca cacctcagaa agtcagtatt tattttacag
3421 acttctttgg aacattgccc ccaaatttaa atattcatgt gggtttagta ttattacaa
3481 aaaaatgatt tgaaatatag ctgttcttta tgcataaaat acccagttag gaccattact
3541 gccagaggag aaaagtatta agtagctcat ttccctacct aaaagataac tgaatttatt
3601 tggctacact aaagaatgca gtatatttag ttttccattt gcatgatgtg tttgtgctat
3661 agacaatatt ttaaattgaa aaatttgttt taaattattt ttacagtgaa gactgttttc
3721 agctcttttt atattgtaca tagacttttta tgtaatctgg catatgtttt gtagaccgtt
3781 taatgactgg attatcttcc tccaacttt gaaatacaaa aacagtgttt tatactaaaa
3841 aaaaaaaaa
```

Figure 15C

NCBI Sequence Viewer

☐ 1: AF083107 Homo sapiens sirtuin type 2 (SIRT2) mRNA, complete cds   PubMed, Protein, Related Sequences, Taxonomy, OMIM, LinkOut

```
LOCUS       AF083107     1963 bp    mRNA              PRI       21-MAR-2001
DEFINITION  Homo sapiens sirtuin type 2 (SIRT2) mRNA, complete cds.
ACCESSION   AF083107
VERSION     AF083107.2  GI:13400019
KEYWORDS
SOURCE      human
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 1963)
  AUTHORS   Frye,R.A.
  TITLE     Characterization of five human cDNAs with homology to the yeast
            SIR2 gene: Sir2-like proteins (sirtuins) metabolize NAD and may
            have protein ADP-ribosyltransferase activity
  JOURNAL   Biochem. Biophys. Res. Commun. 260 (1), 273-279 (1999)
  MEDLINE   99310604
REFERENCE   2  (bases 1 to 1963)
  AUTHORS   Frye,R.A.
  TITLE     Direct Submission
  JOURNAL   Submitted (10-AUG-1998) Pathology, VA Med. Cent. (132L), Univ. of
            Pittsburgh, University Drive C, Pittsburgh, PA 15240, USA
COMMENT     On Mar 21, 2001 this sequence version replaced gi:5225319.
FEATURES             Location/Qualifiers
     source          1..1963
                     /organism="Homo sapiens"
                     /db_xref="taxon:9606"
                     /chromosome="19"
                     /map="19q13"
                     /tissue_type="testis"
     gene            1..1963
                     /gene="SIRT2"
     CDS             201..1370
                     /gene="SIRT2"
                     /note="yeast silent information regulator 2 (Sir2p)
                     homolog"
                     /codon_start=1
                     /product="sirtuin type 2"
                     /protein_id="AAD40850.2"
                     /db_xref="GI:13400020"
```

Figure 16A

NCBI Sequence Viewer

/translation="MAEPDPSHPLETQAGKVQEAQDSDSDSEGGAAGGEADMDFLRNL
FSQTLSLGSQKERLLDELTLBGVARYMQSERCRRVICLVGAGISTSAGIPDFRSPSTG
LYDNLEKYHLPYPEAIFEISYFKKHPEPFFALAKELYPGQFKPTICHYFMRLLKDKGL
LLRCYTQNIDTLERIAGLEQEDLVEARGIFYTSHCVSASCRHEYPLSWMKEKIFSEVT
PKCEDCQSLVKPDIVFFGESLPARFFSCMQSDFLKVDLLLVMGTSLQVQPFASLISKA
PLSTPRLLINKEKAGQSDPFLGMINGLGGGMDFDSKKAYRDVANLGECDQGCLALAEL
LGWKKELEDLVRREHASIDAQSGAGVPNPSTSASPKKSPPPAKDEARTTEREKPQ"

```
BASE COUNT     432 a    616 c     541 g     374 t
ORIGIN
        1 gtgttgtacg aaagcgcgtc tgcggccgca atgtctgctg agagttgtag ttctgtgccc
       61 tatcacggcc actcccattt ctggtgccgt cacgggacag agcagtcggt gacaggacag
      121 agcagtcggt gacgggacac agtggttggt gacgggacag agcgtcggt gacagcctca
      181 agggcttcag caccgcgccc atggcagagc cagacccctc tcaccctctg gagaccagg
      241 caggaaggt gcaggaggct caggactcag attcagactc tgagggagga gccgctggtg
      301 gagaagcaga catggacttc ctgcggaact tattctccca gacgctcagc ctgggcagcc
      361 agaaggagcg tctgctggac gagctgacct tggaaggggt ggccggtac atgcagagcg
      421 aacgctgtcg cagagtcatc tgtttggtgg gagctggaat ctccacatcc gcaggcatcc
      481 ccgactttcg ctctccatcc accggcctct atgacaacct agagaagtac catcttcct
      541 acccagaggc catctttgag atcagctatt tcaagaaaca tccggaaccc ttcttcgccc
      601 tcgccaagga actctatcct gggcagttca agcaaccat ctgtcactac ttcatgcgcc
      661 tgctgaagga caagggcta ctcctgcgct gctacacgca gaacatagat acctggagc
      721 gaatagcgg gctggaacag gaggacttgg tggaggcgca cggcaccttc tacacatcac
      781 actgcgtcag cgccagctgc cggcacgaat acccgctaag ctggatgaaa gagaagatct
      841 tctctgaggt gacgccaag tgtgaagact gtcagagcct ggtgaagcct gatatcgtct
      901 tttttggtga gagcctccca gcgcgttct tcctgtat gcagtcagac ttcctgaagg
      961 tggacctcct cctggtcatg ggtacctcct tgcaggtgca gcccttgcc tcctcatca
     1021 gcaaggcacc cctctccacc cctgcctgc tcatcaacaa ggagaaagct ggccagtcgg
     1081 atccttttct ggggatgatt atgggcctcg gaggagcat ggactttgac tccaagaagg
     1141 cctacaggga cgtggcctgg ctgggtgaat gcgaccaggg ctgctggcc cttgctgagc
     1201 tccttggatg gaagaaggag ctggaggacc ttgtccggag ggagcacgcc agcatagatg
     1261 cccagtcggg ggcggggtc cccaacccca gcacttcagc ttcccccaag aagtcccgc
     1321 cacctgccaa ggacgaggcc aggacaacag agagggagaa accccagtga cagctgcatc
     1381 tccaggcgg gatgccgagc tcctcaggga cagctgagcc ccaaccgggc ctggccct
     1441 cttaaccagc agttcttgtc tggggagctc agaacatccc ccaatctctt acagctcct
     1501 cccaaaact ggggtccag caacctggc cccaaccc agcaaatctc taacacctca
     1561 tagaggccaa ggcttaaaca ggcatctcta ccagccccac tgtctataac cactcctggg
     1621 ctaaggagta acctccctca tctctaactg ccccacggg gccagggcta cccagaact
     1681 tttaactctt ccaggacagg gagcttcggg ccccactct gtcttctgcc ccggggcc
     1741 tgtggctaag taaaccatac ctaacctacc ccagtgtggg tgtgggcctc tgaatataac
     1801 ccacacccag cgtagggga gtctgagtcg ggagggctcc cgagtctctg ccttcagctc
     1861 coaaagtggg tgtgggcc cctcacgtg ggacccactt cccatgctgg atgggcagaa
     1921 gacattgctt attggagaca aattaaaaac aaaaacaact aac
```

Figure 16B

NCBI Sequence Viewer

| PubMed | Nucleotide | Protein | Genome | Structure | PopSet | Taxonomy | OMIM |

Search Nucleotide for [        ]   Go  Clear
Limits   Index   History   Clipboard Display  Default View  as  HTML   Save   Add to Clipboard ☐ 1: AF083106 Homo sapiens sirtuin type  PubMed, Protein, Related Sequences, Taxonomy, OMIM, LinkOut
1 (SIRT1) mRNA,
complete cds

```
LOCUS       AF083106     4086 bp    mRNA           PRI       14-APR-2000
DEFINITION  Homo sapiens sirtuin type 1 (SIRT1) mRNA, complete cds.
ACCESSION   AF083106
VERSION     AF083106.2  GI:7555470
KEYWORDS    
SOURCE      human.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 4086)
  AUTHORS   Frye,R.A.
  TITLE     Characterization of five human cDNAs with homology to the yeast
            SIR2 gene: Sir2-like proteins (sirtuins) metabolize NAD and may
            have protein ADP-ribosyltransferase activity
  JOURNAL   Biochem. Biophys. Res. Commun. 260 (1), 273-279 (1999)
  MEDLINE   99310604
REFERENCE   2  (bases 1 to 4086)
  AUTHORS   Frye,R.A.
  TITLE     Direct Submission
  JOURNAL   Submitted (10-AUG-1998) Pathology, VA Med. Cent. (132L), Univ. of
            Pittsburgh, University Drive C, Pittsburgh, PA 15240, USA
REFERENCE   3  (bases 1 to 4086)
  AUTHORS   Frye,R.A.
  TITLE     Direct Submission
  JOURNAL   Submitted (14-APR-2000) Pathology, VA Med. Cent. (132L), Univ. of
            Pittsburgh, University Drive C, Pittsburgh, PA 15240, USA
  REMARK    Sequence update by submitter
COMMENT     On Apr 14, 2000 this sequence version replaced gi:5225317.
FEATURES             Location/Qualifiers
     source          1..4086
                     /organism="Homo sapiens"
                     /db_xref="taxon:9606"
                     /tissue_type="testis"
     gene            1..4086
                     /gene="SIRT1"
     CDS             54..2297
                     /gene="SIRT1"
                     /note="yeast silent information regulator 2 (Sir2p)
                     homolog"
                     /codon_start=1
                     /product="sirtuin type 1"
                     /protein_id="AAD40849.2"
                     /db_xref="GI:7555471"
                     /translation="MADEAALALQPGGSPSAAGADREAASSPAGEPLRKRPRRDGPGL
                     ERSPGEPGGAAPEREVPAAARGCPGAAAAALWREAEAEAAAGGEQEAQATAAAGEGD
```

Figure 17A

NCBI Sequence Viewer

```
                    NGPGLQGPSREPPLADNLYDEDDDDEGEEEEEAAAAAIGYFDNLLFGDEIITNGFHSC
                    ESDEEDRASHASSSDWTPRPRIGPYTFVQQHLMTGTDPRTILKDLLPETIPPPELDDM
                    TLWQIVINILSEPPKRKKRKDINTIEDAVKLLQECKKIIVLTGAGVSVSCGIPDFRSR
                    DGIYARLAVDFPDLPDPQAMFDIEYFRKDPRFFKFAKEIYPGQPQPSLCHKFIALSD
                    KEGKLLRNYTQNIDTLEQVAGIQRIIQCHGSFATASCLICKYKVDCEAVRGDIFNQVV
                    PRCPRCPADEPLAIMKFEIVFFGENLPEQFHRAMKYDKDEVDLLIVIGSSLKVRPVAL
                    IPSSIPHEVPQILINREPLPHLHFDVELLGDCDVIINELCHRLGGEYAKLCCNPVKLS
                    EITEKPPRTQKELAYLSELPPTPLHVSEDSSSPERTSPPDSSVIVTLLDQAAKSNDDL
                    DVSESKGCMEEKPQEVQTSRNVESIAEQMENPDLKNVGSSTGEKNERTSVAGTVRKCW
                    PNRVAKEQISPRLDGNQYLFLPPNRYIFHGAEVYSDSEDDVLSSSSCGSNSDSGTCQS
                    PSLEEPMEDESEIEEFYNGLEDEPDVPERAGGAGFGTDGDDQEAINEAISVKQEVTDM
                    NYPSNKS"
     misc_feature   750..767
                    /gene="SIRT1"
                    /note="encodes putative nuclear localization signal"
BASE COUNT    1225 a    732 c    925 g    1204 t
ORIGIN
        1 gtcgagcggg agcagaggag gcgagggagg agggccagag aggcagttgg aagatggcgg
       61 acgaggcggc cctcgccctt cagccggcg gctccccctc ggcggcgggg gccgacaggg
      121 aggccgcgtc gtcccccgcc ggggagccgc tccgcaagag gccgcggaga gatggtcccg
      181 gcctcgagcg gagcccgggc gagcccggtg gggcggcccc agagcgggag gtgccggcgg
      241 cggccagggg ctgccccggt gcggcggcgg cggcgctgtg gcggaggcg gaggcagagg
      301 cggcggcggc aggcgggag caagaggccc aggcgactgc ggcggctggg gaaggagaca
      361 atgggccggg cctgcagggc ccatctcggg agccaccgct ggccgacaac ttgtacgacg
      421 aagacgacga cgacgagggc gaggaggagg aagaggcggc ggcggcggcg attgggtacc
      481 gagataacct tctgttcggt gatgaaatta tcactaatgg ttttcattcc tgtgaaagtg
      541 atgaggagga tagagcctca catgcaagct ctagtgactg gactccaagg ccacggatag
      601 gtccatatac ttttgttcag caacatctta tgattggcac agatcctcga acaattctta
      661 aagatttatt gccggaaaca atacctccac ctgagttgga tgatatgaca ctgtggcaga
      721 ttgttattaa tatcctttca gaaccaccaa aaaggaaaaa gagaaagat attaatacaa
      781 ttgaagatgc tgtgaaatta ctgcaagagt gcaaaaaaat tatagttcta actggagctg
      841 gggtgtctgt ttcatgtgga atacctgact tcaggtcaag ggatggtatt tatgctcgcc
      901 ttgctgtaga ctttccagat cttcdagatc ctcaagcgat gtttgatatt gaatatttca
      951 gaaaagatcc aagaccattc ttcaagtttg caaaggaaat atatcctgga caattccagc
     1021 catctctctg tcacaaattc atagccttgt cagataagga aggaaaacta cttcgcaact
     1081 atacccagaa catagacacg ctggaacagg ttgcgggaat ccaaaggata attcagtgtc
     1141 atggttcctt tgcaacagca tcttgcctga tttgtaaata caaagttgac tgtgaagctg
     1201 tacgaggaga tatttttaat caggtagttc ctcgatgtcc taggtgccca gctgatgaac
     1261 cgcttgctat catgaaacca gagattgtgt ttttggtga aaatttacca gaacagtttc
     1321 atagagccat gaagtatgac aaagatgaag ttgacctcct cattgttatt gggtcttccc
     1381 tcaaagtaag accagtagca ctaattccaa gttccatacc ccatgaagtg cctcagatat
     1441 taattaatag agaaccttg cctcatctgc atttgatgt agagcttctt ggagactgtg
     1501 atgtcataat taatgaattg tgtcataggt taggtggtga atatgccaaa cttgctgta
     1561 accctgtaaa gctttcagaa attactgaaa aacctccacg aacacaaaaa gaattggctt
     1621 atttgtcaga gttgccaccc acacctcttc atgtttcaga ggactcaagt tcaccagaaa
     1681 gaacttcacc accagattct tcagtgattg tcacacttt agacactaagca gctaagagta
     1741 atgatgattt agatgtgtct gaatcaaaag gttgtatgga agaaaaacca caggaagtac
     1801 aaacttctag gaatgttgaa agtattgctg aacagatgga aaatccggat ttgaagaatg
     1861 ttggtcctag tactggggag aaaaatgaaa gaacttcagt ggctggaaca gtgagaaaat
     1921 gctggcctaa tagagtggca aggagcaga ttagtaggcg gcttgatggt aatcagtatc
     1981 tgtttttgcc accaaatcgt tacatttcc atggcgctga ggtatattca gactctgaag
     2041 atgacgtctt atcctctagt tcttgtggca gtaacagtga tagtgggaca tgccagagtc
     2101 caagtttaga agaacccatg gaggatgaaa gtgaaattga agaattctac aatggcttag
     2161 aagatgagcc tgatgttcca gagacagctg gaggagcggg atttgggact gatggagatg
     2221 atcaagaggc aattaatgaa gctatatctg tgaaacagga agtaacagac atgaactatc
     2281 catcaaacaa atcatagtgt aataattgtg caggtacagg aattgttcca ccagcattag
     2341 gaactttagc atgtcaaaat gaatgtttac ttgtgaactc gatagaycaa ggaaaccaga
     2401 aaggtgtaat attataggt tggtaaaata gattcttttt catggataat ttttaacttc
     2461 attatttctg tacttgtaca aactcaacac taaacttttt tttttaaaa aaaaaaggt
     2521 actaagtatc ttcaatcagc tgttgggtca agactaactt tctttaaag gttcatttgt
```

Figure 17B

```
2581 atgataaatt catatgtgta tatataatt tttttgtttt gtctagtgag tttcaacatt
2641 tttaaagttt tcaaaagcc atcggaatgt taaattaatg taaagggaca gctaatctag
2701 accaaagaat ggtattttca cttttctttg taacattgaa tggtttgaag tactcaaaat
2761 ctgttacgct aaactttga tctttaaca caattatttt taaacactgg cattttccaa
2821 aactgtggca gctaacttt taaaatctca aatgacatgc agtgtgagta gaaggaagtc
2881 aacaatatgt ggggagagca ctcggtgtc tttacttta aagtaatac ttggtgctaa
2941 gaatttcagg attattgtat ttacgttcaa atgaagatgg cttctgtact tcctgtggac
3001 atgtagtaat gtctatartg gctcataaaa ctaacctgaa aaacaaataa atgctttgga
3061 aatgtttcag ttgctttaga aacattagtg cctgcctgga tcccttagt tttgaaatat
3121 ttgccattgt tgtttaaata cctatcactg tggtagagct tgcattgatc ttttcacaa
3181 gtattaaact gccaaaatgt gaatatgcaa agcctttctg aatctataat aatggtactt
3241 ctactgggga gagtgtaata tttttggactg ctgttttcca ttaatgagga gagcaacagg
3301 cccctgatta tacagttcca aagtaataag atgttaattg taattcagcc agaaagtaca
3361 tgtctcccat tgggaggatt tggtgttaaa taccaaactg ctagccctag tattatggag
3421 atgaacatga tgatgtaact tgtaatagca gaatagttaa tgaatgaaac tagttcttat
3481 aattcatctt tatttaaaag cttagcctgc cttaaaacta gagatcaact ttctcagctg
3541 caaaagcttc tagtctttca agaagttcat actttatgaa attgcacagt aagcatttat
3601 tttttcagcc attttttgaac atcactccta aattaataaa gtattcctct gttgtttttag
3661 tatttattac aataaaaagg gtttgaaata tagctgttct ttatgcataa aacacccagc
3721 taggaccatt actgccagag aaaaaatcg tattgaatgg ccattccct acttataaga
3781 tgtctcaatc tgaatttatt tggctacact aaagaatgca gtatatttag ttttccatct
3841 gcatgatgtt tgctgctat agatgatatt ttaaattgaa aagtttgttt taaattattt
3901 ttacagtgaa gactgttttc agctcttttt atattgtaca tagtcttta tgtaatttac
3961 tggcatatgt tttgtagact gttaatgac tggatatctt ccttcaagtt ttgaaataca
4021 aaaccagtgt ttttactg tacactgttt taaagtctat taaaattgtc atttgacttt
4081 ttctg
```

Figure 17C

NCBI Sequence Viewer

/translation="MAFWGWRAAAALRLWGRVVERVEAGGGVGPFQACGCRLVLGGRD
DVSAGLRGSHGARGEPLDPARPLQRPPRPEVPRAFRRQPRAAAPSFFFSSIKGGRRSI
SFSVGASSVVGSGGSSDKGKLSLQDVAELIRARACQRVVVMVGAGISTPSGIPDFRSP
GSGLYSNLQQYDLPYPEAIFELPFPPHNPKPFFTLAKELYPGNYKPNVTHYFLRLLHD
KGLLLRLYTQNIDGLERVSGIPASKLVEAHGTFASATCTVCQRPFPGEDIRADVMADR
VPRCPVCTGVVKPDIVFFGEPLPQRFLLHVVDFPMADLLLILGTSLEVEPFASLTEAV
RSSVPRLLINRDLVGPLAWHPRSRDVAQLGDVVHGVESLVELLGWTEEMRDLVQRRTG
KLDGPDK"

```
BASE COUNT      361 a    507 c    593 g    408 t
ORIGIN
        1 ggcgccgggg gcggggtgg gaggcggagg cggggccggg gcgccgcggg cggggcgccg
       61 ggggcggggc gagtccggag gactcctcgg actgcgcgga acatggcgtt ctggggttgg
      121 cgcgccgcgg cagccctccg gctgtggggc cgggtagttg aacgggtcga ggccggggga
      181 ggcgtggggc cgtttcaggc ctgcggctgt cggctggtgc ttggcggcag ggacgatgtg
      241 agtgcggggc tgagaggcag ccatggggcc cgcggtgagc ccttggaccc ggcgcgcccc
      301 ttgcagaggc ctccagacc cgaggtgccc agggcattcc ggaggcagcc gagggcagca
      361 gctcccagtt tcttcttttc gagtattaaa ggtggaagaa ggtccatatc ttttctgtg
      421 ggtgcttcaa gtgttgttgg aagtggaggc agcagtgaca aggggaagct ttccctgcag
      481 gatgtagctg agctgattcg ggcagagcc tgccagacgg tggtcat ggtgggggcc
      541 ggcatcagca cccagtgg cattccagac ttcagatcgc cggggagtgg cctgtacagc
      601 aacctccagc agtacgatct cccgtaccc gaggccattt ttgaactccc attcttcttt
      661 cacaacccca agcccttttt cactttggcc aaggagctgt accctggaaa ctacaagccc
      721 aacgtcactc actactttct ccggctgctt catgacaagg gctgcttct gcggctctac
      781 acgcagaaca tcgatgggct tgagagagtg tgggcatcc ctgcctcaaa gctggttgaa
      841 gctcatgaac cctttgcctc tgccacctgc acagtctgcc aaagaccctt cccaggggag
      901 gacattcggg ctgacgtgat ggcagacagg gttccgcgct gccggtctg caccgcgtt
      951 gtgaagcccg acattgtgtt ctttggggag ccgctgcccc agaggttctt gtgcatgtg
     1021 gttgatttcc ccatggcaga tctgctgctc atccttggga cctccctga ggtggagcct
     1081 tttgccagct tgaccgaggc cgtgcggagc tcagttcccc gactgctcat caaccgggac
     1141 ttggtggggc ccttggcttg gcatcctcgc agcagggacg tggcccagct ggggacgtg
     1201 gttcacggcg tggaaagcct agtggagctt ctggctgga cagaagagat gcgggaccct
     1261 gtgcagcggg aaactgggaa gcttgatgga ccagacaaat aggatgatgg ctgcccccac
     1321 acaataaatg gtaacatagg agacatccac atccaattc tgacaagacc tcatgcctga
     1381 agacagcttg ggcaggtgaa accagaatat gtgaactgag tggacaccg aggctgccac
     1441 tggaatgtct tctcaggcca tgagctgcag tgactggtag ggctgtgttc acagtcaggg
     1501 ccacccgtc acatatacaa aggagctgcc tgcctgttg ctgtgttgaa ctcttcactc
     1561 tgctgaagct cctaatggaa aaagctttct tctgactgtg accctcttga actgaatcag
     1621 accaactgga atccagacc gagtctgctt tctgtgccta gttgaacggc aagctcggca
     1681 tctgttggtt acaagatcca gacttgggcc gagcggtcc cagccctctt catgttccga
     1741 agtgtagtct tgaggccctg gtgccgcact tctagcatgt tggtctcctt tagtggggct
     1801 attttaatg agagaaaatc tgttctttcc agcatgaaat acatttagtc tcctcaaaaa
     1861 aaaaaaaca
```

Figure 18

NCBI Sequence Viewer

☐ 1: AF083109 Homo sapiens sirtuin type PubMed, Protein, Related Sequences, Taxonomy, OMIM, LinkOut
4 (SIRT4) mRNA,
complete cds

```
LOCUS       AF083109    1174 bp    mRNA            PRI       26-JUN-1999
DEFINITION  Homo sapiens sirtuin type 4 (SIRT4) mRNA, complete cds.
ACCESSION   AF083109
VERSION     AF083109.1  GI:5225323
KEYWORDS
SOURCE      human.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 1174)
  AUTHORS   Frye,R.A.
  TITLE     Characterization of five human cDNAs with homology to the yeast
            SIR2 gene: Sir2-like proteins (sirtuins) metabolize NAD and may
            have protein ADP-ribosyltransferase activity
  JOURNAL   Biochem. Biophys. Res. Commun. 260 (1), 273-279 (1999)
  MEDLINE   99319604
REFERENCE   2  (bases 1 to 1174)
  AUTHORS   Frye,R.A.
  TITLE     Direct Submission
  JOURNAL   Submitted (10-AUG-1998) Pathology, VA Med. Cent. (132L), Univ. of
            Pittsburgh, University Drive C, Pittsburgh, PA 15240, USA
FEATURES             Location/Qualifiers
     source          1..1174
                     /organism="Homo sapiens"
                     /db_xref="taxon:9606"
                     /chromosome="12"
                     /map="12q"
                     /tissue_type="testis"
     gene            1..1174
                     /gene="SIRT4"
     CDS             21..965
                     /gene="SIRT4"
                     /note="yeast silent information regulator 2 (Sir2p)
                     homolog; similar to prokaryotic sirtuins"
                     /codon_start=1
                     /product="sirtuin type 4"
                     /protein_id="AAD40852.1"
                     /db_xref="GI:5225324"
                     /translation="MKMSFALTFRSAKGRWIANPSQPCSKASIGLFVPASPPLDPEKV
                     KELQRFITLSKRLLVMTGAGISTESGIPDYRSEKVGLYARTDRRPIQHGDFVRSAPIR
                     QRYWARNFVGWPQFSSHQPNPAHWALSTWEKLGKLYWLVTQNVDALHTKAGSRRLTEL
                     HGCMDRVLCLDCGEQTPRGVLQERFQVLNPTWSARAHGLAPDGDVFLSEEQVRSFQVP
                     TCVQCGGHLKPDVVFFGDTVNPDKVDFVHKRVKEADSLLVVGSSLQVYSGYRFILTAW
                     EKKLPIAILNIGPTRSDDLACLKLNSRCGELLPLIDPC"
BASE COUNT      283 a    292 c    310 g    289 t
```

Figure 19A

NCBI Sequence Viewer

```
ORIGIN
        1 gtcagtagag ctgtgagaga atgaagatga gctttgcgtt gactttcagg tcagcaaaag
       61 gccgttggat cgcaaacccc agccagccgt gctcgaaagc ctccattggg ttatttgtgc
      121 cagcaagtcc tcctctggac cctgagaagg tcaaagagtt acagcgcttc atcacccttt
      181 ccaagagact ccttgtgatg actggggcag gaatctccac cgaatcgggg ataccagact
      241 acaggtcaga aaaagtgggg ctttatgccc gcactgaccg caggcccatc cagcatggtg
      301 attttgtccg gagtgcccca atccgccagc ggtactgggc gagaaacttc gtaggctggc
      361 ctcaattctc ctcccaccag cctaaccctg cacactgggc tttgagcacc tgggagaaac
      421 tggaaagct gtactggttg gtgacccaaa atgtggatgc tttgcacacc aaggcgggga
      481 gtcggcgcct gacagagctc cacggatgca tgacagggt cctgtgcttg gattgtgggg
      541 aacagactcc ccgggggtg ctgcaagagc gtttccaagt cctgaaccc acctggagtg
      601 ctgaggccca tggcctgct cctgatggtg acgtctttct ctcagaggag caagtccgga
      661 gctttcaggt cccaacctgc gttcaatgtg gaggccatct gaaccagat gtcgttttct
      721 tcggggacac agtgaaccct gacaaggttg attttgtgca caagcgtgta aaagaagccg
      781 actccctctt ggtggtggga tcatccttgc aggtatactc tggttacagg tttatcctca
      841 ctgcctggga gaagaagctc ccgattgcaa tactgaacat tgggcccaca cggtcggatg
      901 acttggcgtg tctgaaactg aattctcgtt gtggagagtt gctgcctttg atagacccat
      961 gctgaccaca gctgatatt ccagaacctg gaacagggac tttcacttga atcttgctgc
     1021 taaatgtaaa tgccttctca aatgacagat tccagttccc attcaacaga gtagggtgca
     1081 ctgacaaagt atagaaggtt ctaggtatct taatgtgtgg atattcttaa ttaaaactca
     1141 ttttcttcaa ataaaaaatt gttcagcttt aaaa
```

Figure 19B

NCBI Sequence Viewer

☐ 1: AF083110 Homo sapiens sirtuin type PubMed, Protein, Related Sequences, Taxonomy, OMIM, LinkOut
            5 (SIRT5) mRNA,
            complete cds

```
LOCUS       AF083110              1633 bp    mRNA            PRI       26-JUN-1999
DEFINITION  Homo sapiens sirtuin type 5 (SIRT5) mRNA, complete cds.
ACCESSION   AF083110
VERSION     AF083110.1  GI:5225325
KEYWORDS    .
SOURCE      human.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 1633)
  AUTHORS   Frye,R.A.
  TITLE     Characterization of five human cDNAs with homology to the yeast
            SIR2 gene: Sir2-like proteins (sirtuins) metabolize NAD and may
            have protein ADP-ribosyltransferase activity
  JOURNAL   Biochem. Biophys. Res. Commun. 260 (1), 273-279 (1999)
  MEDLINE   99310604
REFERENCE   2  (bases 1 to 1633)
  AUTHORS   Frye,R.A.
  TITLE     Direct Submission
  JOURNAL   Submitted (10-AUG-1998) Pathology, VA Med. Cent. (132L), Univ. of
            Pittsburgh, University Drive C, Pittsburgh, PA 15240, USA
FEATURES             Location/Qualifiers
     source          1..1633
                     /organism="Homo sapiens"
                     /db_xref="taxon:9606"
                     /tissue_type="testis"
     gene            1..1633
                     /gene="SIRT5"
     CDS             274..1206
                     /gene="SIRT5"
                     /note="yeast silent information regulator 2 (Sir2p)
                     homolog; similar to prokaryotic sirtuins"
                     /codon_start=1
                     /product="sirtuin type 5"
                     /protein_id="AAD40853.1"
                     /db_xref="GI:5225326"
                     /translation="MRPLQIVPSRLISQLYCGLKPPASTRNQICLKMARPSSNADFR
                     KFPAKAKHIVIISGAGVSAESGVPTFRGASGYWRKWQAQDLATPLAFAHNPSRVWEFY
                     HYRREVMGSKEPNAGHRAIASCETRLGKQGRRVVVITQNIDELHRKAGTKNLLEIHGS
                     LFKTRCTSCGVVASNYKSPICPALSGKGAPEPGTQEASIPVEKLPRCEEAGCGGLLRP
                     HVVWFGENLDPAILEEVDRELANCDLCLVVGTSSVVYPAAMFAPQVAARGVPVAEFNT
                     ETTPATNRFRFHFQGPCGTTLPEALACHENETVS"
BASE COUNT       455 a    357 c    422 g    399 t
ORIGIN
        1 cgcctatagg agaaagcctg gaacgcgtac cggagggtac cagagctctt agcgggccgg
```

Figure 20A

NCBI Sequence Viewer

```
  61 cagcatgtgc ggggccaagt aaatggaaat gttttctaac atataaaaac ctacagaaga
 121 agaaaataat tttctggatc aaattagaag tctgtattat attgatgtct ccagattcaa
 181 atatattaga aagcagccgt ggagacaacc atcttcattt tgggagaaat aactaaagcc
 241 cgcctcaagc attagaacta cagacaaacc ctgatgcgac ctctccagat tgtcccaagt
 301 cgattgattt cccagctata ttgtggcctg aagcctccag cgtccacacg aaaccagatt
 361 tgcctgaaaa tggctggcc aagttcaagt atggcagatt ttcgaaagtt ttttgcaaaa
 421 gcaaagcaca tagtcatcat ctcaggagct ggtgttagtg cagaaagtgg tgttccgacc
 481 ttcagaggag ctggaggtta ttggagaaaa tggcaagccc aggacctggc gactccctg
 541 gcctttgccc acaaccccgtc ccgggtgtgg gagttctacc actaccggcg ggaggtcatg
 601 gggagcaagg agcccaacgc cgggcaccgc gccatagccg agtgtgagac ccggctgggc
 661 aagcagggcc gggcgagtcgt ggtcatcacc cagaacatcg atgagctgca ccgcaaggct
 721 ggcaccaaga accttctgga gatccatggt agcttattta aaactcgatg tacctcttgt
 781 ggagttgtgg ctgagaatta caagagtcca atttgtccag ctttatcagg aaaaggtgct
 841 ccagaacctg gaactcaaga tgccagcatc ccagttgaga aacttcaccg gtgtgaagag
 901 gcaggctgcg ggggcttgct gcgacctcac gtcgtgtggt ttggagaaaa cctggatcct
 961 gccattctgg aggaggttga cagagagctc gcccactgtg atttatgtct agtggtgggc
1021 acttcctctg tggtgtaccc agcagccatg tttgccccc aggtggctgc cagggcgtg
1081 ccagtggctg aatttaacac ggagaccacc ccagctacga acagattcag gtttcatttc
1141 cagggaccct gtggaacgac tcttcctgaa gcccttgcct gtcatgaaaa tgaaactgtt
1201 tcttaagtgt cctggggaag aaagaaatta cagtatatct aagaactagg ccacacgcag
1261 aggagaaatg gtcttatggg tggtgagctg agtactgaac aatccaaaaa tagcctctga
1321 ttccctcgct ggaatccaac ctgttgataa gtgatggggg tttagaagta gcaaagagca
1381 cccacattca aaagtcacag aactggaaag ttaattcata ttattggtt tgaactgaaa
1441 cgtgaggtat ctttgatgtg tatggttggt tattgggagg gaaaaatttt gtaaattaga
1501 ttgtctaaaa aaatagtta ttctgattat atttttgtta tctgggcaaa gtagaagtca
1561 aggggtaaaa accctactat tctgattttt gcacaagttt tagtggaaaa taaaatcaca
1621 ctcacagta ggt
```

Figure 20B

```
                        SEQUENCE LISTING

<160> NUMBER OF SEQ ID NOS: 24

<210> SEQ ID NO 1
<211> LENGTH: 15
<212> TYPE: PRT
<213> ORGANISM: Homo sapiens
<220> FEATURE:
<221> NAME/KEY: VARIANT
<222> LOCATION: 2, 3, 11, 12
<223> OTHER INFORMATION: acetylated lysine

<400> SEQUENCE: 1

Ser Xaa Xaa Gly Gln Ser Thr Ser Arg His Xaa Xaa Leu Met Phe
1               5                   10                  15

<210> SEQ ID NO 2
<211> LENGTH: 1546
<212> TYPE: DNA
<213> ORGANISM: Homo sapiens
<220> FEATURE:
<221> NAME/KEY: CDS
<222> LOCATION: (1)...(1179)
<221> NAME/KEY: CDS
<222> LOCATION: (1183)...(1206)
<221> NAME/KEY: CDS
<222> LOCATION: (1210)...(1278)
<221> NAME/KEY: CDS
<222> LOCATION: (1282)...(1440)
<221> NAME/KEY: CDS
<222> LOCATION: (1444)...(1488)
<221> NAME/KEY: CDS
<222> LOCATION: (1492)...(1539)
<221> NAME/KEY: CDS
<222> LOCATION: (1543)...(1545)

<400> SEQUENCE: 2 atg gag gag ccg cag tca gat cct agc gtc gag ccc cct ctg agt cag      48
Met Glu Glu Pro Gln Ser Asp Pro Ser Val Glu Pro Pro Leu Ser Gln
```

```
       1               5                  10                 15
gaa aca ttt tca gac cta tgg aaa cta ctt cct gaa aac aac gtt ctg           96
Glu Thr Phe Ser Asp Leu Trp Lys Leu Leu Pro Glu Asn Asn Val Leu
             20                  25                  30 tcc ccc ttg ccg tcc caa gca atg gat gat ttg atg ctg tcc ccg gac          144
Ser Pro Leu Pro Ser Gln Ala Met Asp Asp Leu Met Leu Ser Pro Asp
         35                  40                  45 gat att gaa caa tgg ttc act gaa gac cca ggt cca gat gaa gct ccc          192
Asp Ile Glu Gln Trp Phe Thr Glu Asp Pro Gly Pro Asp Glu Ala Pro
     50                  55                  60 aga atg cca gag gct gct ccc ccc gtg gcc cct gca cca gca gct cct          240
Arg Met Pro Glu Ala Ala Pro Pro Val Ala Pro Ala Pro Ala Ala Pro
 65                  70                  75                  80 aca ccg gcg gcc cct gca cca gcc ccc tcc tgg ccc ctg tca tct tct          288
Thr Pro Ala Ala Pro Ala Pro Ala Pro Ser Trp Pro Leu Ser Ser Ser
                 85                  90                  95 gtc cct tcc cag aaa acc tac cag ggc agc tac ggt ttc cgt ctg ggc          336
Val Pro Ser Gln Lys Thr Tyr Gln Gly Ser Tyr Gly Phe Arg Leu Gly
             100                 105                 110 ttc ttg cat tct ggg aca gcc aag tct gtg act tgc acg tac tcc cct          384
Phe Leu His Ser Gly Thr Ala Lys Ser Val Thr Cys Thr Tyr Ser Pro
         115                 120                 125 gcc ctc aac aag atg ttt tgc caa ctg gcc aag acc tgc cct gtg cag          432
Ala Leu Asn Lys Met Phe Cys Gln Leu Ala Lys Thr Cys Pro Val Gln
     130                 135                 140 ctg tgg gtt gat tcc aca ccc ccg ccc ggc acc cgt gtc cgc gcc atg          480
Leu Trp Val Asp Ser Thr Pro Pro Pro Gly Thr Arg Val Arg Ala Met
145                 150                 155                 160 gcc atc tac aag cag tca cag cac atg acg gag gtt gtg agg cgc tgc          528
Ala Ile Tyr Lys Gln Ser Gln His Met Thr Glu Val Val Arg Arg Cys
                 165                 170                 175 ccc cac cat gag cgc tgc tca gat agc gat ggt ctg gcc cct cct cag          576
Pro His His Glu Arg Cys Ser Asp Ser Asp Gly Leu Ala Pro Pro Gln
             180                 185                 190 cat ctt atc cga gtg gaa gga aat ttg cgt gtg gag tat ttg gat gac          624
His Leu Ile Arg Val Glu Gly Asn Leu Arg Val Glu Tyr Leu Asp Asp
         195                 200                 205 aga aac act ttt cga cat agt gtg gtg gtg ccc tat gag ccg cct gag          672
Arg Asn Thr Phe Arg His Ser Val Val Val Pro Tyr Glu Pro Pro Glu
     210                 215                 220 gtt ggc tct gac tgt acc acc atc cac tac aac tac atg tgt aac agt          720
Val Gly Ser Asp Cys Thr Thr Ile His Tyr Asn Tyr Met Cys Asn Ser
225                 230                 235                 240 tcc tgc atg ggc ggc atg aac cgg agg ccc atc ctc acc atc atc aca          768
Ser Cys Met Gly Gly Met Asn Arg Arg Pro Ile Leu Thr Ile Ile Thr
                 245                 250                 255 ctg gaa gac tcc agt ggt aat cta ctg gga cgg aac agc ttt gag gtg          816
Leu Glu Asp Ser Ser Gly Asn Leu Leu Gly Arg Asn Ser Phe Glu Val
             260                 265                 270 cat gtt tgt gcc tgt cct ggg aga gac cgg cgc aca gag gaa gag aat          864
His Val Cys Ala Cys Pro Gly Arg Asp Arg Arg Thr Glu Glu Glu Asn
         275                 280                 285 ctc cgc aag aaa ggg gag cct cac cac gag ctg ccc cca ggg agc act          912
Leu Arg Lys Lys Gly Glu Pro His His Glu Leu Pro Pro Gly Ser Thr
     290                 295                 300 aag cga gca ctg ccc aac aac acc agc tcc tct ccc cag cca aag aag          960
Lys Arg Ala Leu Pro Asn Asn Thr Ser Ser Ser Pro Gln Pro Lys Lys
305                 310                 315                 320 aaa cca ctg gat gga gaa tat ttc acc ctt cag atc cgt ggg cgt gag         1008
Lys Pro Leu Asp Gly Glu Tyr Phe Thr Leu Gln Ile Arg Gly Arg Glu
```

```
                        325                     330                     335
cgc ttc gag atg ttc cga gag ctg aat gag gcc ttg gaa ctc aag gat        1056
Arg Phe Glu Met Phe Arg Glu Leu Asn Glu Ala Leu Glu Leu Lys Asp
            340                     345                     350 gcc cag gct ggg aag gag cca ggg ggg agc agg gct cac tcc agc cac        1104
Ala Gln Ala Gly Lys Glu Pro Gly Gly Ser Arg Ala His Ser Ser His
        355                     360                     365 ctg aag tcc aaa aag ggt cag tct acc tcc cgc cat aaa aaa ctc atg        1152
Leu Lys Ser Lys Lys Gly Gln Ser Thr Ser Arg His Lys Lys Leu Met
370                     375                     380 ttc aag aca gaa ggg cct gac tca gac tga cat tct cca ctt ctt gtt       1200
Phe Lys Thr Glu Gly Pro Asp Ser Asp     His Ser Pro Leu Leu Val
385                     390                         395 ccc cac tga cag cct ccc acc ccc atc tct ccc tcc cct gcc att ttg       1248
Pro His     Gln Pro Pro Thr Pro Ile Ser Pro Ser Pro Ala Ile Leu
400                 405                     410 ggt ttt ggg tct ttg aac cct tgc ttg caa tag gtg tgc gtc aga agc       1296
Gly Phe Gly Ser Leu Asn Pro Cys Leu Gln     Val Cys Val Arg Ser
415                     420                         425 acc cag gac ttc cat ttg ctt tgt ccc ggg gct cca ctg aac aag ttg       1344
Thr Gln Asp Phe His Leu Leu Cys Pro Gly Ala Pro Leu Asn Lys Leu
430                     435                     440                 445 gcc tgc act ggt gtt ttg ttg tgg gga gga tgg gga gta gga cat           1392
Ala Cys Thr Gly Val Leu Leu Trp Gly Gly Gly Trp Gly Val Gly His
                450                     455                     460 acc agc tta gat ttt aag gtt ttt act gtg agg gat gtt tgg gag atg       1440
Thr Ser Leu Asp Phe Lys Val Phe Thr Val Arg Asp Val Trp Glu Met
            465                     470                     475 taa gaa atg ttc ttg cag tta agg gtt agt tta caa tca gcc aca ttc       1488
    Glu Met Phe Leu Gln Leu Arg Val Ser Leu Gln Ser Ala Thr Phe
                480                     485                     490 tag gta ggg acc cac ttc acc gta cta acc agg gaa gct gtc cct cac       1536
    Val Gly Thr His Phe Thr Val Leu Thr Arg Glu Ala Val Pro His
                495                     500                     505 tgt tga att c                                                          1546
Cys     Ile <210> SEQ ID NO 3
<211> LENGTH: 393
<212> TYPE: PRT
<213> ORGANISM: Homo sapiens

<400> SEQUENCE: 3

Met Glu Glu Pro Gln Ser Asp Pro Ser Val Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125
```

```
Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

His Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 4
<211> LENGTH: 1760
<212> TYPE: DNA
<213> ORGANISM: Homo sapiens

<400> SEQUENCE: 4
gtcgacccct tccaccctg gaagatggaa ataaacctgc gtgtgggtgg agtgttagga    60
caaaaaaaaa aaaaaaaag tctagagcca ccgtccaggg agcaggtagc tgctgggctc   120
cggggacact ttgcgttcgg gctgggagcg tgctttccac gacggtgaca cgcttccctg   180
gattggcagc cagactgcct tccgggtcac tgccatggag gagccgcagt cagatcctag   240
cgtcgagccc cctctgagtc aggaaacatt tcagaccta tggaaactac ttcctgaaaa   300
caacgttctg tcccccttgc cgtcccaagc aatggatgat tgatgctgt ccccggacga   360 tattgaacaa tggttcactg aagacccagg tccagatgaa gctcccagaa tgccagaggc   420
tgctcccccc gtggcccctg caccagcagc tcctacaccg gcggcccctg caccagcccc   480
ctcctggccc ctgtcatctt ctgtcccttc ccagaaaacc taccagggca gctacgttt    540 ccgtctgggc ttcttgcatt ctgggacagc caagtctgtg acttgcacgt actcccctgc   600
```

-continued

```
cctcaacaag atgttttgcc aactggccaa gacctgccct gtgcagctgt gggttgattc    660
cacacccccg cccggcaccc gcgtccgcgc catggccatc tacaagcagt cacagcacat    720
gacggaggtt gtgaggcgct gccccccacca tgagcgctgc tcagatagcg atggtctggc    780
ccctcctcag catcttatcc gagtggaagg aaatttgcgt gtggagtatt tggatgacag    840
aaacactttt cgacatagtg tggtggtgcc ctatgagccg cctgaggttg gctctgactg    900
taccaccatc cactacaact acatgtgtaa cagttcctgc atgggcggca tgaaccggag    960
gcccatcctc accatcatca cactggaaga ctccagtggt aatctactgg acggaacag    1020
ctttgaggtg catgtttgtg cctgtcctgg gagagaccgg cgcacagagg aagagaatct    1080
ccgcaagaaa ggggagcctc accacgagct gcccccaggg agcactaagc gagcactgcc    1140
caacaacacc agctcctctc cccagccaaa gaagaaacca ctggatggag aatatttcac    1200
ccttcagatc cgtgggcgtg agcgcttcga gatgttccga gagctgaatg aggccttgga    1260
actcaaggat gcccaggctg gaaggagcc agggggagc agggctcact ccagccacct    1320
gaagtccaaa aagggtcagt ctacctcccg ccataaaaaa ctcatgttca agacagaagg    1380
gcctgactca gactgacatt ctccacttct tgttccccac tgacagcctc cacccccat    1440
ctctccctcc cctgccattt tgggttttgg gtctttgaac ccttgcttgc aataggtgtg    1500
cgtcagaagc acccaggact tccatttgct ttgtcccggg gctccactga acaagttggc    1560
ctgcactggt gttttgttgt ggggaggagg atggggagta ggacatacca gcttagattt    1620
taaggttttt actgtgaggg atgtttggga gatgtaagaa atgttcttgc agttaagggt    1680
tagtttacaa tcagccacat tctaggtagg gacccacttc accgtactaa ccagggaagc    1740
tgtccctcac tgttgaattc                                                1760

<210> SEQ ID NO 5
<211> LENGTH: 3869
<212> TYPE: DNA
<213> ORGANISM: Mus musculus
<220> FEATURE:
<221> NAME/KEY: CDS
<222> LOCATION: (48)...(2258)

<400> SEQUENCE: 5
gcggagcaga ggaggcgagg gcggagggcc agagaggcag ttggaag atg gcg gac       56
                                                    Met Ala Asp
                                                     1 gag gtg gcg ctc gcc ctt cag gcc gcc ggc tcc cct tcc gcg gcg gcc      104
Glu Val Ala Leu Ala Leu Gln Ala Ala Gly Ser Pro Ser Ala Ala Ala
    5                   10                  15 gcc atg gag gcc gcg tcg cag ccg gcg gac gag ccg ctc cgc aag agg      152
Ala Met Glu Ala Ala Ser Gln Pro Ala Asp Glu Pro Leu Arg Lys Arg
 20                  25                  30                  35 ccc cgc cga gac ggg cct ggc ctc ggg cgc agc ccg ggc gag ccg agc      200
Pro Arg Arg Asp Gly Pro Gly Leu Gly Arg Ser Pro Gly Glu Pro Ser
                40                  45                  50 gca gca gtg gcg ccg gcg gcc gcg ggg tgt gag gcg gcg agc gcc gcg      248
Ala Ala Val Ala Pro Ala Ala Ala Gly Cys Glu Ala Ala Ser Ala Ala
             55                  60                  65 gcc ccg gcg gcg ctg tgg cgg gag gcg gca ggg gcg gcg agc gcg           296
Ala Pro Ala Ala Leu Trp Arg Glu Ala Ala Gly Ala Ala Ser Ala
     70                  75                  80 gag cgg gag gcc ccg gcg acg gcc gtg gcc ggg gac gga gac aat ggg      344
Glu Arg Glu Ala Pro Ala Thr Ala Val Ala Gly Asp Gly Asp Asn Gly
 85                  90                  95 tcc ggc ctg cgg cgg gag ccg agg gcg gct gac gac ttc gac gac gac      392
```

|  |  |  |  |  |  |  |  |  |  |  |  |  |  |  |  |
|---|---|---|---|---|---|---|---|---|---|---|---|---|---|---|---|
| Ser | Gly | Leu | Arg | Arg | Glu | Pro | Arg | Ala | Ala | Asp | Asp | Phe | Asp | Asp | Asp |
| 100 |  |  |  |  | 105 |  |  |  |  | 110 |  |  |  |  | 115 |

```
gag ggc gag gag gag gac gag gcg gcg gca gcg gcg gcg gca gcg          440
Glu Gly Glu Glu Glu Asp Glu Ala Ala Ala Ala Ala Ala Ala Ala
            120                 125                 130 atc ggc tac cga gac aac ctc ctg ttg acc gat gga ctc ctc act aat      488
Ile Gly Tyr Arg Asp Asn Leu Leu Leu Thr Asp Gly Leu Leu Thr Asn
                135                 140                 145 ggc ttt cat tcc tgt gaa agt gat gac gat gac aga acg tca cac gcc      536
Gly Phe His Ser Cys Glu Ser Asp Asp Asp Asp Arg Thr Ser His Ala
            150                 155                 160 agc tct agt gac tgg act ccg cgg ccg cgg ata ggt cca tat act ttt      584
Ser Ser Ser Asp Trp Thr Pro Arg Pro Arg Ile Gly Pro Tyr Thr Phe
        165                 170                 175 gtt cag caa cat ctc atg att ggc acc gat cct cga aca att ctt aaa      632
Val Gln Gln His Leu Met Ile Gly Thr Asp Pro Arg Thr Ile Leu Lys
180                 185                 190                 195 gat tta tta cca gaa aca att cct cca cct gag ctg gat gat atg acg      680
Asp Leu Leu Pro Glu Thr Ile Pro Pro Pro Glu Leu Asp Asp Met Thr
                200                 205                 210 ctg tgg cag att gtt att aat atc ctt tca gaa cca cca aag cgg aaa      728
Leu Trp Gln Ile Val Ile Asn Ile Leu Ser Glu Pro Pro Lys Arg Lys
            215                 220                 225 aaa aga aaa gat atc aat aca att gaa gat gct gtg aag tta ctg cag      776
Lys Arg Lys Asp Ile Asn Thr Ile Glu Asp Ala Val Lys Leu Leu Gln
        230                 235                 240 gag tgt aaa aag ata ata gtt ctg act gga gct ggg gtt tct gtc tcc      824
Glu Cys Lys Lys Ile Ile Val Leu Thr Gly Ala Gly Val Ser Val Ser
245                 250                 255 tgt ggg att cct gac ttc aga tca aga gac ggt atc tat gct cgc ctt      872
Cys Gly Ile Pro Asp Phe Arg Ser Arg Asp Gly Ile Tyr Ala Arg Leu
260                 265                 270                 275 gcg gtg gac ttc cca gac ctc cca gac cct caa gcc atg ttt gat att      920
Ala Val Asp Phe Pro Asp Leu Pro Asp Pro Gln Ala Met Phe Asp Ile
            280                 285                 290 gag tat ttt aga aaa gac cca aga cca ttc ttc aag ttt gca aag gaa      968
Glu Tyr Phe Arg Lys Asp Pro Arg Pro Phe Phe Lys Phe Ala Lys Glu
        295                 300                 305 ata tat ccc gga cag ttc cag ccg tct ctg tgt cac aaa ttc ata gct     1016
Ile Tyr Pro Gly Gln Phe Gln Pro Ser Leu Cys His Lys Phe Ile Ala
    310                 315                 320 ttg tca gat aag gaa gga aaa cta ctt cga aat tat act caa aat ata     1064
Leu Ser Asp Lys Glu Gly Lys Leu Leu Arg Asn Tyr Thr Gln Asn Ile
325                 330                 335 gat acc ttg gag cag gtt gca gga atc caa agg atc ctt cag tgt cat     1112
Asp Thr Leu Glu Gln Val Ala Gly Ile Gln Arg Ile Leu Gln Cys His
340                 345                 350                 355 ggt tcc ttt gca aca gca tct tgc ctg att tgt aaa tac aaa gtt gat     1160
Gly Ser Phe Ala Thr Ala Ser Cys Leu Ile Cys Lys Tyr Lys Val Asp
            360                 365                 370 tgt gaa gct gtt cgt gga gac att ttt aat cag gta gtt cct cgg tgc     1208
Cys Glu Ala Val Arg Gly Asp Ile Phe Asn Gln Val Val Pro Arg Cys
        375                 380                 385 cct agg tgc cca gct gat gag cca ctt gcc atc atg aag cca gag att     1256
Pro Arg Cys Pro Ala Asp Glu Pro Leu Ala Ile Met Lys Pro Glu Ile
    390                 395                 400 gtc ttc ttt ggt gaa aac tta cca gaa cag ttt cat aga gcc atg aag     1304
Val Phe Phe Gly Glu Asn Leu Pro Glu Gln Phe His Arg Ala Met Lys
405                 410                 415 tat gac aaa gat gaa gtt gac ctc ctc att gtt att gga tct tct ctg     1352
```

```
Tyr Asp Lys Asp Glu Val Asp Leu Leu Ile Val Ile Gly Ser Ser Leu
420                 425                 430                 435 aaa gtg aga cca gta gca cta att cca agt tct ata ccc cat gaa gtg   1400
Lys Val Arg Pro Val Ala Leu Ile Pro Ser Ser Ile Pro His Glu Val
                    440                 445                 450 cct caa ata tta ata aat agg gaa cct ttg cct cat cta cat ttt gat   1448
Pro Gln Ile Leu Ile Asn Arg Glu Pro Leu Pro His Leu His Phe Asp
                455                 460                 465 gta gag ctc ctt gga gac tgc gat gtt ata att aat gag ttg tgt cat   1496
Val Glu Leu Leu Gly Asp Cys Asp Val Ile Ile Asn Glu Leu Cys His
            470                 475                 480 agg cta ggt ggt gaa tat gcc aaa ctt tgt tgt aac cct gta aag ctt   1544
Arg Leu Gly Gly Glu Tyr Ala Lys Leu Cys Cys Asn Pro Val Lys Leu
        485                 490                 495 tca gaa att act gaa aaa cct cca cgc cca caa aag gaa ttg gtt cat   1592
Ser Glu Ile Thr Glu Lys Pro Pro Arg Pro Gln Lys Glu Leu Val His
500                 505                 510                 515 tta tca gag ttg cca cca aca cct ctt cat att tcg gaa gac tca agt   1640
Leu Ser Glu Leu Pro Pro Thr Pro Leu His Ile Ser Glu Asp Ser Ser
                520                 525                 530 tca cct gaa aga act gta cca caa gac tct tct gtg att gct aca ctt   1688
Ser Pro Glu Arg Thr Val Pro Gln Asp Ser Ser Val Ile Ala Thr Leu
            535                 540                 545 gta gac caa gca aca aac aac aat gtt aat gat tta gaa gta tct gaa   1736
Val Asp Gln Ala Thr Asn Asn Asn Val Asn Asp Leu Glu Val Ser Glu
        550                 555                 560 tca agt tgt gtg gaa gaa aaa cca caa gaa gta cag act agt agg aat   1784
Ser Ser Cys Val Glu Glu Lys Pro Gln Glu Val Gln Thr Ser Arg Asn
565                 570                 575 gtt gag aac att aat gtg gaa aat cca gat ttt aag gct gtt ggt tcc   1832
Val Glu Asn Ile Asn Val Glu Asn Pro Asp Phe Lys Ala Val Gly Ser
580                 585                 590                 595 agt act gca gac aaa aat gaa aga act tca gtt gca gaa aca gtg aga   1880
Ser Thr Ala Asp Lys Asn Glu Arg Thr Ser Val Ala Glu Thr Val Arg
                600                 605                 610 aaa tgc tgg cct aat aga ctt gca aag gag cag att agt aag cgg ctt   1928
Lys Cys Trp Pro Asn Arg Leu Ala Lys Glu Gln Ile Ser Lys Arg Leu
            615                 620                 625 gag ggt aat caa tac ctg ttt gta cca cca aat cgt tac ata ttc cac   1976
Glu Gly Asn Gln Tyr Leu Phe Val Pro Pro Asn Arg Tyr Ile Phe His
        630                 635                 640 ggt gct gag gta tac tca gac tct gaa gat gac gtc ttg tcc tct agt   2024
Gly Ala Glu Val Tyr Ser Asp Ser Glu Asp Asp Val Leu Ser Ser Ser
645                 650                 655 tcc tgt ggc agt aac agt gac agt ggc aca tgc cag agt cca agt tta   2072
Ser Cys Gly Ser Asn Ser Asp Ser Gly Thr Cys Gln Ser Pro Ser Leu
660                 665                 670                 675 gaa gaa ccc ttg gaa gat gaa agt gaa att gaa gaa ttc tac aat ggc   2120
Glu Glu Pro Leu Glu Asp Glu Ser Glu Ile Glu Glu Phe Tyr Asn Gly
                680                 685                 690 ttg gaa gat gat acg gag agg ccc gaa tgt gct gga gga tct gga ttt   2168
Leu Glu Asp Asp Thr Glu Arg Pro Glu Cys Ala Gly Gly Ser Gly Phe
            695                 700                 705 gga gct gat gga ggg gat caa gag gtt gtt aat gaa gct ata gct aca   2216
Gly Ala Asp Gly Gly Asp Gln Glu Val Val Asn Glu Ala Ile Ala Thr
        710                 715                 720 aga cag gaa ttg aca gat gta aac tat cca tca gac aaa tca              2258
Arg Gln Glu Leu Thr Asp Val Asn Tyr Pro Ser Asp Lys Ser
725                 730                 735 taacactatt gaagctgtcc ggattcagga attgctccac cagcattggg aactttagca   2318
```

-continued

```
tgtcaaaaaa atgaatgttt acttgtgaac ttgaacaagg aaatctgaaa gatgtattat    2378
ttatagactg gaaaatagat tgtcttcttg gataatttct aaagttccat catttctgtt    2438
tgtacttgta cattcaacac tgttggttga cttcatcttc ctttcaaggt tcatttgtat    2498
gatacattcg tatgtatgta taattttgtt ttttgcctaa tgagtttcaa cctttaaag     2558 ttttcaaaag ccattggaat gttaatgtaa agggaacagc ttatctagac caaagaatgg    2618
tatttcacac ttttttgttt gtaacattga atagtttaaa gccctcaatt tctgttctgc    2678 tgaacttta ttttaggac agttaacttt ttaaacactg cattttcca aaacttgtgg       2738 cagctaactt tttaaaatca cagatgactt gtaatgtgag gagtcagcac cgtgtctgga    2798
gcactcaaaa cttgggctca gtgtgtgaag cgtacttact gcatcgtttt tgtacttgct    2858
gcagacgtgg taatgtccaa acaggcccct gagactaatc tgataaatga tttggaaatg    2918
tgtttcagtt gttctagaaa caatagtgcc tgtctatata ggtccccta gtttgaatat     2978 ttgccattgt ttaattaaat acctatcact gtggtagagc ctgcatagat cttcaccaca    3038
aatactgcca agatgtgaat atgcaaagcc tttctgaatc taataatggt acttctactg    3098
gggagagtgt aatattttgg actgctgttt ttccattaat gaggaaagca ataggcctct    3158
taattaaagt cccaaagtca taagataaat tgtagctcaa ccagaaagta cactgttgcc    3218
tgttgaggat ttggtgtaat gtatcccaag gtgttagcct tgtattatgg agatgaatac    3278
agatccaata gtcaaatgaa actagttctt agttatttaa aagcttagct tgccttaaaa    3338
ctagggatca attttctcaa ctgcagaaac ttttagcctt tcaaacagtt cacacctcag    3398
aaagtcagta tttattttac agacttcttt ggaacattgc ccccaaattt aaatattcat    3458
gtgggtttag tatttattac aaaaaaatga tttgaaatat agctgttctt tatgcataaa    3518
atacccagtt aggaccatta ctgccagagg agaaaagtat taagtagctc atttccctac    3578
ctaaaagata actgaattta tttggctaca ctaaagaatg cagtatattt agttttccat    3638
ttgcatgatg tgtttgtgct atagacaata ttttaaattg aaaaatttgt tttaaattat    3698
ttttacagtg aagactgttt tcagctcttt ttatattgta catagacttt tatgtaatct    3758
ggcatatgtt ttgtagaccg tttaatgact ggattatctt cctccaactt tgaaataca    3818 aaaacagtgt tttatactaa aaaaaaaaaa agtcgacgcg ccgcgaattc               3869
```

<210> SEQ ID NO 6
<211> LENGTH: 737
<212> TYPE: PRT
<213> ORGANISM: Mus musculus

<400> SEQUENCE: 6

```
Met Ala Asp Glu Val Ala Leu Ala Leu Gln Ala Gly Ser Pro Ser
1               5                   10                  15

Ala Ala Ala Ala Met Glu Ala Ala Ser Gln Pro Ala Asp Glu Pro Leu
                20                  25                  30

Arg Lys Arg Pro Arg Arg Asp Gly Pro Gly Leu Gly Arg Ser Pro Gly
            35                  40                  45

Glu Pro Ser Ala Ala Val Ala Pro Ala Ala Gly Cys Glu Ala Ala
    50                  55                  60

Ser Ala Ala Ala Pro Ala Ala Leu Trp Arg Glu Ala Ala Gly Ala Ala
65                  70                  75                  80

Ala Ser Ala Glu Arg Glu Ala Pro Ala Thr Ala Val Ala Gly Asp Gly
                85                  90                  95

Asp Asn Gly Ser Gly Leu Arg Arg Glu Pro Arg Ala Ala Asp Asp Phe
```

```
                 100                 105                 110
Asp Asp Asp Glu Gly Glu Glu Asp Glu Ala Ala Ala Ala Ala
        115                 120                 125
Ala Ala Ala Ile Gly Tyr Arg Asp Asn Leu Leu Leu Thr Asp Gly Leu
        130                 135                 140
Leu Thr Asn Gly Phe His Ser Cys Glu Ser Asp Asp Asp Arg Thr
145                 150                 155                 160
Ser His Ala Ser Ser Ser Asp Trp Thr Pro Arg Pro Arg Ile Gly Pro
                165                 170                 175
Tyr Thr Phe Val Gln Gln His Leu Met Ile Gly Thr Asp Pro Arg Thr
                180                 185                 190
Ile Leu Lys Asp Leu Leu Pro Glu Thr Ile Pro Pro Glu Leu Asp
        195                 200                 205
Asp Met Thr Leu Trp Gln Ile Val Ile Asn Ile Leu Ser Glu Pro Pro
        210                 215                 220
Lys Arg Lys Lys Arg Lys Asp Ile Asn Thr Ile Glu Asp Ala Val Lys
225                 230                 235                 240
Leu Leu Gln Glu Cys Lys Lys Ile Ile Val Leu Thr Gly Ala Gly Val
                245                 250                 255
Ser Val Ser Cys Gly Ile Pro Asp Phe Arg Ser Arg Asp Gly Ile Tyr
                260                 265                 270
Ala Arg Leu Ala Val Asp Phe Pro Asp Leu Pro Asp Pro Gln Ala Met
        275                 280                 285
Phe Asp Ile Glu Tyr Phe Arg Lys Asp Pro Arg Pro Phe Phe Lys Phe
        290                 295                 300
Ala Lys Glu Ile Tyr Pro Gly Gln Phe Gln Pro Ser Leu Cys His Lys
305                 310                 315                 320
Phe Ile Ala Leu Ser Asp Lys Glu Gly Lys Leu Leu Arg Asn Tyr Thr
                325                 330                 335
Gln Asn Ile Asp Thr Leu Glu Gln Val Ala Gly Ile Gln Arg Ile Leu
                340                 345                 350
Gln Cys His Gly Ser Phe Ala Thr Ala Ser Cys Leu Ile Cys Lys Tyr
                355                 360                 365
Lys Val Asp Cys Glu Ala Val Arg Gly Asp Ile Phe Asn Gln Val Val
        370                 375                 380
Pro Arg Cys Pro Arg Cys Pro Ala Asp Glu Pro Leu Ala Ile Met Lys
385                 390                 395                 400
Pro Glu Ile Val Phe Phe Gly Glu Asn Leu Pro Glu Gln Phe His Arg
                405                 410                 415
Ala Met Lys Tyr Asp Lys Asp Glu Val Asp Leu Leu Ile Val Ile Gly
                420                 425                 430
Ser Ser Leu Lys Val Arg Pro Val Ala Leu Ile Pro Ser Ser Ile Pro
        435                 440                 445
His Glu Val Pro Gln Ile Leu Ile Asn Arg Glu Pro Leu Pro His Leu
        450                 455                 460
His Phe Asp Val Glu Leu Leu Gly Asp Cys Asp Val Ile Ile Asn Glu
465                 470                 475                 480
Leu Cys His Arg Leu Gly Gly Glu Tyr Ala Lys Leu Cys Cys Asn Pro
                485                 490                 495
Val Lys Leu Ser Glu Ile Thr Glu Lys Pro Pro Arg Pro Gln Lys Glu
        500                 505                 510
Leu Val His Leu Ser Glu Leu Pro Pro Thr Pro Leu His Ile Ser Glu
        515                 520                 525
```

-continued

```
Asp Ser Ser Pro Glu Arg Thr Val Pro Gln Asp Ser Val Ile
        530                 535                 540

Ala Thr Leu Val Asp Gln Ala Thr Asn Asn Val Asn Asp Leu Glu
545                 550                 555                 560

Val Ser Glu Ser Cys Val Glu Glu Lys Pro Gln Glu Val Gln Thr
                565                 570                 575

Ser Arg Asn Val Glu Asn Ile Asn Val Glu Asn Pro Asp Phe Lys Ala
                580                 585                 590

Val Gly Ser Ser Thr Ala Asp Lys Asn Glu Arg Thr Ser Val Ala Glu
            595                 600                 605

Thr Val Arg Lys Cys Trp Pro Asn Arg Leu Ala Lys Glu Gln Ile Ser
        610                 615                 620

Lys Arg Leu Glu Gly Asn Gln Tyr Leu Phe Val Pro Pro Asn Arg Tyr
625                 630                 635                 640

Ile Phe His Gly Ala Glu Val Tyr Ser Asp Ser Glu Asp Val Leu
                645                 650                 655

Ser Ser Ser Ser Cys Gly Ser Asn Ser Asp Ser Gly Thr Cys Gln Ser
                660                 665                 670

Pro Ser Leu Glu Glu Pro Leu Glu Asp Glu Ser Glu Ile Glu Glu Phe
            675                 680                 685

Tyr Asn Gly Leu Glu Asp Asp Thr Glu Arg Pro Glu Cys Ala Gly Gly
        690                 695                 700

Ser Gly Phe Gly Ala Asp Gly Gly Asp Gln Glu Val Val Asn Glu Ala
705                 710                 715                 720

Ile Ala Thr Arg Gln Glu Leu Thr Asp Val Asn Tyr Pro Ser Asp Lys
                725                 730                 735

Ser

<210> SEQ ID NO 7
<211> LENGTH: 3849
<212> TYPE: DNA
<213> ORGANISM: Mus musculus

<400> SEQUENCE: 7
gcggagcaga ggaggcgagg gcggagggcc agagaggcag ttggaagatg gcggacgagg     60
tggcgctcgc ccttcaggcc gccggctccc cttccgcggc ggccgccatg gaggccgcgt    120
cgcagccggc ggacgagccg ctccgcaaga ggccccgccg agacgggcct ggcctcgggc    180
gcagcccggg cgagccgagc gcagcagtgg cgccggcggc cgcggggtgt gaggcggcga    240
gcgccgcggc cccggcggcg ctgtggcggg aggcggcagg ggcggcggcg agcgcggagc    300
gggaggcccc ggcgacggcc gtggccgggg acggagacaa tgggtccggc ctgcggcggg    360
agccgagggc ggctgacgac ttcgacgacg acagggcga ggaggaggac gaggcggcgg    420
cggcagcggc ggcggcagcg atcggctacc gagacaacct cctgttgacc gatggactcc    480
tcactaatgg ctttcattcc tgtgaaagtg atgacgatga cagaacgtca cacgccagct    540
ctagtgactg gactccgcgg ccgcggatag gtccatatac ttttgttcag caacatctca    600
tgattggcac cgatcctcga acaattctta agatttatt accagaaaca attcctccac    660
ctgagctgga tgtatgacg ctgtggcaga ttgttattaa tatcctttca gaaccaccaa    720
agcggaaaaa aagaaaagat atcaatacaa ttgaagatgt gtgaagtta ctgcaggagt    780 gtaaaaagat aatagttctg actggagctg gggtttctgt ctcctgtggg attcctgact    840
tcagatcaag agacggtatc tatgctcgcc ttgcggtgga cttcccagac ctcccagacc    900
ctcaagccat gtttgatatt gagtatttta gaaaagaccc aagaccattc ttcaagtttg    960
```

```
caaaggaaat atatcccgga cagttccagc cgtctctgtg tcacaaattc atagctttgt    1020
cagataagga aggaaaacta cttcgaaatt atactcaaaa tatagatacc ttggagcagg    1080
ttgcaggaat ccaaaggatc cttcagtgtc atggttcctt tgcaacagca tcttgcctga    1140
tttgtaaata caaagttgat tgtgaagctg ttcgtggaga catttttaat caggtagttc    1200
ctcggtgccc taggtgccca gctgatgagc cacttgccat catgaagcca gagattgtct    1260
tctttggtga aaacttacca gaacagtttc atagagccat gaagtatgac aaagatgaag    1320
ttgacctcct cattgttatt ggatcttctc tgaaagtgag accagtagca ctaattccaa    1380
gttctatacc ccatgaagtg cctcaaatat aataaaatag ggaacctttg cctcatctac    1440
attttgatgt agagctcctt ggagactgcg atgttataat taatgagttg tgtcataggc    1500
taggtggtga atatgccaaa ctttgttgta accctgtaaa gctttcagaa attactgaaa    1560
aacctccacg cccacaaaag gaattggttc atttatcaga gttgccacca cacctcttc     1620 atatttcgga agactcaagt tcacctgaaa gaactgtacc acaagactct tctgtgattg    1680
ctacacttgt agaccaagca acaaacaaca atgttaatga tttagaagta tctgaatcaa    1740
gttgtgtgga agaaaaacca caagaagtac agactagtag gaatgttgag aacattaatg    1800
tggaaaatcc agattttaag gctgttggtt ccagtactgc agacaaaaat gaaagaactt    1860
cagttgcaga aacagtgaga aaatgctggc ctaatagact tgcaaaggag cagattagta    1920
agcggcttga gggtaatcaa tacctgtttg taccaccaaa tcgttacata ttccacggtg    1980
ctgaggtata ctcagactct gaagatgacg tcttgtcctc tagttcctgt ggcagtaaca    2040
gtgacagtgg cacatgccag agtccaagtt tagaagaacc cttggaagat gaaagtgaaa    2100
ttgaagaatt ctacaatggc ttggaagatg atacggagag gcccgaatgt gctgaggat     2160 ctggatttgg agctgatgga ggggatcaag aggttgttaa tgaagctata gctacaagac    2220
aggaattgac agatgtaaac tatccatcag acaaatcata acactattga agctgtccgg    2280
attcaggaat tgctccacca gcattgggaa ctttagcatg tcaaaaaaat gaatgtttac    2340
ttgtgaactt gaacaaggaa atctgaaaga tgtattattt atagactgga aaatagattg    2400
tcttcttgga taatttctaa agttccatca tttctgtttg tacttgtaca ttcaacactg    2460
ttggttgact tcatcttcct ttcaaggttc atttgtatga tacattcgta tgtatgtata    2520
attttgtttt ttgcctaatg agtttcaacc ttttaaagtt ttcaaaagcc attggaatgt    2580
taatgtaaag ggaacagctt atctagacca aagaatggta tttcacactt ttttgtttgt    2640
aacattgaat agtttaaagc cctcaatttc tgttctgctg aacttttatt tttaggacag    2700
ttaacttttt aaaacactgg cattttccaaa acttgtggca gctaacttt taaaaatcaca    2760 gatgacttgt aatgtgagga gtcagcaccg tgtctggagc actcaaaact tgggctcagt    2820
gtgtgaagcg tacttactgc atcgttttg tacttgctgc agacgtggta atgtccaaac    2880
aggcccctga gactaatctg ataaatgatt tggaaatgtg tttcagttgt tctagaaaca    2940
atagtgcctg tctatatagg tccccttagt ttgaatattt gccattgttt aattaaatac    3000
ctatcactgt ggtagagcct gcatagatct tcaccacaaa tactgccaag atgtgaatat    3060
gcaaagcctt tctgaatcta ataatggtac ttctactggg gagagtgtaa tattttggac    3120
tgctgttttt ccattaatga ggaaagcaat aggcctctta attaaagtcc caagtcata     3180 agataaattg tagctcaacc agaaagtaca ctgttgcctg ttgaggattt ggtgtaatgt    3240
atcccaaggt gttagccttg tattatggag atgaatacag atccaatagt caaatgaaac    3300
tagttcttag ttatttaaaa gcttagcttg ccttaaaact agggatcaat tttctcaact    3360
```

-continued

```
gcagaaactt ttagccttc aaacagttca cacctcagaa agtcagtatt tattttacag    3420
acttctttgg aacattgccc ccaaatttaa atattcatgt gggtttagta tttattacaa    3480
aaaaatgatt tgaaatatag ctgttcttta tgcataaaat acccagttag gaccattact    3540
gccagaggag aaaagtatta agtagctcat ttccctacct aaaagataac tgaatttatt    3600
tggctacact aaagaatgca gtatatttag ttttccattt gcatgatgtg tttgtgctat    3660
agacaatatt ttaaattgaa aaatttgttt taaattattt ttacagtgaa gactgttttc    3720
agctcttttt atattgtaca tagactttta tgtaatctgg catatgtttt gtagaccgtt    3780
taatgactgg attatcttcc tccaactttt gaaatacaaa aacagtgttt tatactaaaa    3840
aaaaaaaaa                                                            3849
```

<210> SEQ ID NO 8
<211> LENGTH: 737
<212> TYPE: PRT
<213> ORGANISM: Mus musculus

<400> SEQUENCE: 8

```
Met Ala Asp Glu Val Ala Leu Ala Leu Gln Ala Gly Ser Pro Ser
1               5                   10                  15

Ala Ala Ala Ala Met Glu Ala Ala Ser Gln Pro Ala Asp Glu Pro Leu
                20                  25                  30

Arg Lys Arg Pro Arg Arg Asp Gly Pro Gly Leu Gly Arg Ser Pro Gly
            35                  40                  45

Glu Pro Ser Ala Ala Val Ala Pro Ala Ala Gly Cys Glu Ala Ala
    50                  55                  60

Ser Ala Ala Pro Ala Ala Leu Trp Arg Glu Ala Ala Gly Ala Ala
65                  70                  75                  80

Ala Ser Ala Glu Arg Glu Ala Pro Ala Thr Ala Val Ala Gly Asp Gly
                85                  90                  95

Asp Asn Gly Ser Gly Leu Arg Arg Glu Pro Arg Ala Ala Asp Asp Phe
            100                 105                 110

Asp Asp Asp Glu Gly Glu Glu Asp Glu Ala Ala Ala Ala Ala
        115                 120                 125

Ala Ala Ala Ile Gly Tyr Arg Asp Asn Leu Leu Leu Thr Asp Gly Leu
    130                 135                 140

Leu Thr Asn Gly Phe His Ser Cys Glu Ser Asp Asp Asp Arg Thr
145                 150                 155                 160

Ser His Ala Ser Ser Ser Asp Trp Thr Pro Arg Pro Arg Ile Gly Pro
                165                 170                 175

Tyr Thr Phe Val Gln Gln His Leu Met Ile Gly Thr Asp Pro Arg Thr
            180                 185                 190

Ile Leu Lys Asp Leu Leu Pro Glu Thr Ile Pro Pro Glu Leu Asp
        195                 200                 205

Asp Met Thr Leu Trp Gln Ile Val Ile Asn Ile Leu Ser Glu Pro Pro
    210                 215                 220

Lys Arg Lys Lys Arg Lys Asp Ile Asn Thr Ile Glu Asp Ala Val Lys
225                 230                 235                 240

Leu Leu Gln Glu Cys Lys Lys Ile Ile Val Leu Thr Gly Ala Gly Val
                245                 250                 255

Ser Val Ser Cys Gly Ile Pro Asp Phe Arg Ser Arg Asp Gly Ile Tyr
            260                 265                 270

Ala Arg Leu Ala Val Asp Phe Pro Asp Leu Pro Asp Pro Gln Ala Met
        275                 280                 285
```

-continued

```
Phe Asp Ile Glu Tyr Phe Arg Lys Asp Pro Arg Pro Phe Lys Phe
    290                 295                 300
Ala Lys Glu Ile Tyr Pro Gly Gln Phe Gln Pro Ser Leu Cys His Lys
305                 310                 315                 320
Phe Ile Ala Leu Ser Asp Lys Glu Gly Lys Leu Leu Arg Asn Tyr Thr
                325                 330                 335
Gln Asn Ile Asp Thr Leu Glu Gln Val Ala Gly Ile Gln Arg Ile Leu
            340                 345                 350
Gln Cys His Gly Ser Phe Ala Thr Ala Ser Cys Leu Ile Cys Lys Tyr
        355                 360                 365
Lys Val Asp Cys Glu Ala Val Arg Gly Asp Ile Phe Asn Gln Val Val
    370                 375                 380
Pro Arg Cys Pro Arg Cys Pro Ala Asp Glu Pro Leu Ala Ile Met Lys
385                 390                 395                 400
Pro Glu Ile Val Phe Phe Gly Glu Asn Leu Pro Glu Gln Phe His Arg
                405                 410                 415
Ala Met Lys Tyr Asp Lys Asp Glu Val Asp Leu Leu Ile Val Ile Gly
            420                 425                 430
Ser Ser Leu Lys Val Arg Pro Val Ala Leu Ile Pro Ser Ser Ile Pro
        435                 440                 445
His Glu Val Pro Gln Ile Leu Ile Asn Arg Glu Pro Leu Pro His Leu
    450                 455                 460
His Phe Asp Val Glu Leu Leu Gly Asp Cys Asp Val Ile Ile Asn Glu
465                 470                 475                 480
Leu Cys His Arg Leu Gly Gly Glu Tyr Ala Lys Leu Cys Cys Asn Pro
                485                 490                 495
Val Lys Leu Ser Glu Ile Thr Glu Lys Pro Pro Arg Pro Gln Lys Glu
            500                 505                 510
Leu Val His Leu Ser Glu Leu Pro Pro Thr Pro Leu His Ile Ser Glu
        515                 520                 525
Asp Ser Ser Ser Pro Glu Arg Thr Val Pro Gln Asp Ser Ser Val Ile
    530                 535                 540
Ala Thr Leu Val Asp Gln Ala Thr Asn Asn Asn Val Asn Asp Leu Glu
545                 550                 555                 560
Val Ser Glu Ser Ser Cys Val Glu Glu Lys Pro Gln Glu Val Gln Thr
                565                 570                 575
Ser Arg Asn Val Glu Asn Ile Asn Val Glu Asn Pro Asp Phe Lys Ala
            580                 585                 590
Val Gly Ser Ser Thr Ala Asp Lys Asn Glu Arg Thr Ser Val Ala Glu
        595                 600                 605
Thr Val Arg Lys Cys Trp Pro Asn Arg Leu Ala Lys Glu Gln Ile Ser
    610                 615                 620
Lys Arg Leu Glu Gly Asn Gln Tyr Leu Phe Val Pro Pro Asn Arg Tyr
625                 630                 635                 640
Ile Phe His Gly Ala Glu Val Tyr Ser Asp Ser Glu Asp Asp Val Leu
                645                 650                 655
Ser Ser Ser Ser Cys Gly Ser Asn Ser Asp Ser Gly Thr Cys Gln Ser
            660                 665                 670
Pro Ser Leu Glu Glu Pro Leu Glu Asp Glu Ser Glu Ile Glu Glu Phe
        675                 680                 685
Tyr Asn Gly Leu Glu Asp Asp Thr Glu Arg Pro Glu Cys Ala Gly Gly
    690                 695                 700
Ser Gly Phe Gly Ala Asp Gly Gly Asp Gln Glu Val Val Asn Glu Ala
```

```
                705                 710                 715                 720
           Ile Ala Thr Arg Gln Glu Leu Thr Asp Val Asn Tyr Pro Ser Asp Lys
                           725                 730                 735
           Ser

<210> SEQ ID NO 9
<211> LENGTH: 1963
<212> TYPE: DNA
<213> ORGANISM: Homo sapiens

<400> SEQUENCE: 9
gtgttgtacg aaagcgcgtc tgcggccgca atgtctgctg agagttgtag ttctgtgccc        60
tatcacggcc actcccattt ctggtgccgt cacgggacag agcagtcggt gacaggacag       120
agcagtcggt gacgggacac agtggttggt gacgggacag agcggtcggt gacagcctca       180
agggcttcag caccgcgccc atggcagagc cagacccctc tcaccctctg gagacccagg       240
cagggaaggt gcaggaggct caggactcag attcagactc tgagggagga gccgctggtg       300
gagaagcaga catggacttc ctgcggaact tattctccca gacgctcagc ctgggcagcc       360
agaaggagcg tctgctggac gagctgacct tggaaggggt ggcccggtac atgcagagcg       420
aacgctgtcg cagagtcatc tgtttggtgg gagctggaat ctccacatcc gcaggcatcc       480
ccgactttcg ctctccatcc accggcctct atgacaacct agagaagtac catcttccct       540
acccagaggc catctttgag atcagctatt tcaagaaaca tccggaaccc ttcttcgccc       600
tcgccaagga actctatcct gggcagttca agccaaccat ctgtcactac ttcatgcgcc       660
tgctgaagga caaggggcta ctcctgcgct gctacacgca gaacatagat accctggagc       720
gaatagccgg gctggaacag gaggacttgg tggaggcgca cggcaccttc tacacatcac       780
actgcgtcag cgccagctgc cggcacgaat accgctaag ctggatgaaa gagaagatct       840
tctctgaggt gacgcccaag tgtgaagact gtcagagcct ggtgaagcct gatatcgtct       900
tttttggtga gagcctccca gcgcgtttct tctcctgtat gcagtcagac ttcctgaagg       960
tggacctcct cctggtcatg ggtacctcct tgcaggtgca gcccttttgcc tcctcatca      1020 gcaaggcacc cctctccacc cctcgcctgc tcatcaacaa ggagaaagct ggccagtcgg      1080
accctttcct ggggatgatt atgggcctcg gaggaggcat ggactttgac tccaagaagg      1140
cctacaggga cgtggcctgg ctgggtgaat gcgaccaggg ctgcctggcc cttgctgagc      1200
tccttggatg gaagaaggag ctggaggacc ttgtccggag ggagcacgcc agcatagatg      1260
cccagtcggg ggcggggtc cccaaccca gcacttcagc ttcccccaag aagtccccgc      1320
cacctgccaa ggacgaggcc aggacaacag agagggagaa accccagtga cagctgcatc      1380
tcccaggcgg gatgccgagc tcctcaggga cagctgagcc caaccgggc ctggccccct       1440 cttaaccagc agttcttgtc tggggagctc agaacatccc ccaatctctt acagctccct      1500
ccccaaaact ggggtcccag caaccctggc ccccaacccc agcaaatctc taacacctcc      1560
tagaggccaa ggcttaaaca ggcatctcta ccagccccac tgtctctaac cactcctggg      1620
ctaaggagta acctccctca tctctaactg ccccacggg gccagggcta ccccagaact      1680
tttaactctt ccaggacagg gagcttcggg ccccactct gtctcctgcc cccgggggcc      1740
tgtggctaag taaccatac ctaacctacc ccagtgtggg tgtgggcctc tgaatataac       1800
ccacacccag cgtaggggga gtctgagccg ggagggctcc cgagtctctg ccttcagctc      1860
ccaaagtggg tggtgggccc ccttcacgtg ggacccactt cccatgctgg atgggcagaa      1920
gacattgctt attggagaca aattaaaaac aaaaacaact aac                        1963
```

<210> SEQ ID NO 10
<211> LENGTH: 389
<212> TYPE: PRT
<213> ORGANISM: Homo sapiens

<400> SEQUENCE: 10

Met Ala Glu Pro Asp Pro Ser His Pro Leu Glu Thr Gln Ala Gly Lys
1               5                   10                  15

Val Gln Glu Ala Gln Asp Ser Asp Ser Asp Ser Glu Gly Gly Ala Ala
            20                  25                  30

Gly Gly Glu Ala Asp Met Asp Phe Leu Arg Asn Leu Phe Ser Gln Thr
        35                  40                  45

Leu Ser Leu Gly Ser Gln Lys Glu Arg Leu Leu Asp Glu Leu Thr Leu
    50                  55                  60

Glu Gly Val Ala Arg Tyr Met Gln Ser Glu Arg Cys Arg Arg Val Ile
65                  70                  75                  80

Cys Leu Val Gly Ala Gly Ile Ser Thr Ser Ala Gly Ile Pro Asp Phe
                85                  90                  95

Arg Ser Pro Ser Thr Gly Leu Tyr Asp Asn Leu Glu Lys Tyr His Leu
            100                 105                 110

Pro Tyr Pro Glu Ala Ile Phe Glu Ile Ser Tyr Phe Lys Lys His Pro
        115                 120                 125

Glu Pro Phe Phe Ala Leu Ala Lys Glu Leu Tyr Pro Gly Gln Phe Lys
    130                 135                 140

Pro Thr Ile Cys His Tyr Phe Met Arg Leu Leu Lys Asp Lys Gly Leu
145                 150                 155                 160

Leu Leu Arg Cys Tyr Thr Gln Asn Ile Asp Thr Leu Glu Arg Ile Ala
                165                 170                 175

Gly Leu Glu Gln Glu Asp Leu Val Glu Ala His Gly Thr Phe Tyr Thr
            180                 185                 190

Ser His Cys Val Ser Ala Ser Cys Arg His Glu Tyr Pro Leu Ser Trp
        195                 200                 205

Met Lys Glu Lys Ile Phe Ser Glu Val Thr Pro Lys Cys Glu Asp Cys
    210                 215                 220

Gln Ser Leu Val Lys Pro Asp Ile Val Phe Phe Gly Glu Ser Leu Pro
225                 230                 235                 240

Ala Arg Phe Phe Ser Cys Met Gln Ser Asp Phe Leu Lys Val Asp Leu
                245                 250                 255

Leu Leu Val Met Gly Thr Ser Leu Gln Val Gln Pro Phe Ala Ser Leu
            260                 265                 270

Ile Ser Lys Ala Pro Leu Ser Thr Pro Arg Leu Leu Ile Asn Lys Glu
        275                 280                 285

Lys Ala Gly Gln Ser Asp Pro Phe Leu Gly Met Ile Met Gly Leu Gly
    290                 295                 300

Gly Gly Met Asp Phe Asp Ser Lys Lys Ala Tyr Arg Asp Val Ala Trp
305                 310                 315                 320

Leu Gly Glu Cys Asp Gln Gly Cys Leu Ala Leu Ala Glu Leu Leu Gly
                325                 330                 335

Trp Lys Lys Glu Leu Glu Asp Leu Val Arg Arg Glu His Ala Ser Ile
            340                 345                 350

Asp Ala Gln Ser Gly Ala Gly Val Pro Asn Pro Ser Thr Ser Ala Ser
        355                 360                 365

Pro Lys Lys Ser Pro Pro Ala Lys Asp Glu Ala Arg Thr Thr Glu
    370                 375                 380

Arg Glu Lys Pro Gln
385

<210> SEQ ID NO 11
<211> LENGTH: 4086
<212> TYPE: DNA
<213> ORGANISM: Homo sapiens

<400> SEQUENCE: 11

| | | | | | |
|---|---|---|---|---|---|
| gtcgagcggg | agcagaggag | gcgagggagg | agggccagag | aggcagttgg | aagatggcgg | 60 |
| acgaggcggc | cctcgccctt | cagcccggcg | gctccccctc | ggcggcgggg | gccgacaggg | 120 |
| aggccgcgtc | gtccccgcc | ggggagccgc | tccgcaagag | gccgcggaga | gatggtcccg | 180 |
| gcctcgagcg | gagcccgggc | gagcccggtg | gggcggcccc | agagcgtgag | gtgccggcgg | 240 |
| cggccagggg | ctgcccgggt | gcggcggcgg | cggcgctgtg | gcgggaggcg | gaggcagagg | 300 |
| cggcggcggc | aggcggggag | caagaggccc | aggcgactgc | ggcggctggg | gaaggagaca | 360 |
| atgggccggg | cctgcagggc | ccatctcggg | agccaccgct | ggccgacaac | ttgtacgacg | 420 |
| aagacgacga | cgacgagggc | gaggaggagg | aagaggcggc | ggcggcggcg | attgggtacc | 480 |
| gagataacct | tctgttcggt | gatgaaatta | tcactaatgg | ttttcattcc | tgtgaaagtg | 540 |
| atgaggagga | tagagcctca | catgcaagct | ctagtgactg | gactccaagg | ccacggatag | 600 |
| gtccatatac | ttttgttcag | caacatctta | tgattggcac | agatcctcga | acaattctta | 660 |
| aagatttatt | gccggaaaca | ataccctccac | ctgagttgga | tgatatgaca | ctgtggcaga | 720 |
| ttgttattaa | tatcctttca | gaaccaccaa | aaaggaaaaa | aagaaaagat | attaatacaa | 780 |
| ttgaagatgc | tgtgaaatta | ctgcaagagt | gcaaaaaaat | tatagttcta | actggagctg | 840 |
| gggtgtctgt | ttcatgtgga | atacctgact | tcaggtcaag | ggatggtatt | tatgctcgcc | 900 |
| ttgctgtaga | cttcccagat | cttccagatc | ctcaagcgat | gtttgatatt | gaatatttca | 960 |
| gaaaagatcc | aagaccattc | ttcaagtttg | caaaggaaat | atatcctgga | caattccagc | 1020 |
| catctctctg | tcacaaattc | atagccttgt | cagataagga | aggaaaaacta | cttcgcaact | 1080 |
| ataccccagaa | catagacacg | ctggaacagg | ttgcgggaat | ccaaaggata | attcagtgtc | 1140 |
| atggttcctt | tgcaacagca | tcttgcctga | tttgtaaata | caaagttgac | tgtgaagctg | 1200 |
| tacgaggaga | tatttttaat | caggtagttc | ctcgatgtcc | taggtgccca | gctgatgaac | 1260 |
| cgcttgctat | catgaaacca | gagattgtgt | ttttggtga | aaatttacca | gaacagtttc | 1320 |
| atagagccat | gaagtatgac | aaagatgaag | ttgacctcct | cattgttatt | gggtcttccc | 1380 |
| tcaaagtaag | accagtagca | ctaattccaa | gttccatacc | ccatgaagtg | cctcagatat | 1440 |
| taattaatag | agaacctttg | cctcatctgc | attttgatgt | agagcttctt | ggagactgtg | 1500 |
| atgtcataat | taatgaattg | tgtcataggt | taggtggtga | atatgccaaa | ctttgctgta | 1560 |
| accctgtaaa | gctttcagaa | attactgaaa | aacctccacg | aacacaaaaa | gaattggctt | 1620 |
| atttgtcaga | gttgccaccc | acacctcttc | atgtttcaga | agactcaagt | tcaccagaaa | 1680 |
| gaacttcacc | accagattct | tcagtgattg | tcacactttt | agaccaagca | gctaagagta | 1740 |
| atgatgattt | agatgtgtct | gaatcaaaag | gttgtatgga | agaaaaacca | caggaagtac | 1800 |
| aaacttctag | gaatgttgaa | agtattgctg | aacagatgga | aaatccggat | ttgaagaatg | 1860 |
| ttggttctag | tactggggag | aaaaatgaaa | gaacttcagt | ggctggaaca | gtgagaaaat | 1920 |
| gctggcctaa | tagagtggca | aaggagcaga | ttagtaggcg | gcttgatggt | aatcagtatc | 1980 |
| tgttttttgcc | accaaatcgt | tacatttttcc | atggcgctga | ggtatattca | gactctgaag | 2040 |

-continued

```
atgacgtctt atcctctagt tcttgtggca gtaacagtga tagtgggaca tgccagagtc    2100
caagtttaga agaacccatg gaggatgaaa gtgaaattga agaattctac aatggcttag    2160
aagatgagcc tgatgttcca gagagagctg gaggagctgg atttgggact gatggagatg    2220
atcaagaggc aattaatgaa gctatatctg tgaaacagga agtaacagac atgaactatc    2280
catcaaacaa atcatagtgt aataattgtg caggtacagg aattgttcca ccagcattag    2340
gaactttagc atgtcaaaat gaatgtttac ttgtgaactc gatagagcaa ggaaaccaga    2400
aaggtgtaat atttataggt tggtaaaata gattgttttt catggataat ttttaacttc    2460
attatttctg tacttgtaca aactcaacac taactttttt tttttttaaaa aaaaaaggt    2520 actaagtatc ttcaatcagc tgttgggtca agactaactt tcttttaaag gttcatttgt    2580
atgataaatt catatgtgta tatataattt ttttgttttt gtctagtgag tttcaacatt    2640
tttaaagttt tcaaaaagcc atcggaatgt taaattaatg taaagggaca gctaatctag    2700
accaaagaat ggtattttca ctttctttg taacattgaa tggtttgaag tactcaaaat    2760
ctgttacgct aaacttttga ttctttaaca caattatttt taaacactgg catttttccaa   2820 aactgtggca gctaactttt taaaatctca atgacatgc agtgtgagta aaggaagtc     2880 aacaatatgt ggggagagca ctcggttgtc tttacttta aaagtaatac ttggtgctaa    2940
gaatttcagg attattgtat ttacgttcaa atgaagatgg cttttgtact tcctgtggac    3000
atgtagtaat gtctatattg gctcataaaa ctaacctgaa aaacaaataa atgctttgga    3060
aatgtttcag ttgctttaga aacattagtg cctgcctgga tccccttagt tttgaaatat    3120
ttgccattgt tgtttaaata cctatcactg tggtagagct tgcattgatc ttttccacaa    3180
gtattaaact gccaaaatgt gaatatgcaa agcctttctg aatctataat aatggtactt    3240
ctactgggga gagtgtaata ttttggactg ctgtttccca ttaatgagga gagcaacagg    3300
cccctgatta tacagttcca aagtaataag atgttaattg taattcagcc agaaagtaca    3360
tgtctcccat tgggaggatt tggtgttaaa taccaaactg ctagccctag tattatggag    3420
atgaacatga tgatgtaact tgtaatagca gaatagttaa tgaatgaaac tagttcttat    3480
aatttatctt tatttaaaag cttagcctgc cttaaaacta gagatcaact ttctcagctg    3540
caaaagcttc tagtctttca agaagttcat actttatgaa attgcacagt aagcatttat    3600
ttttcagacc atttttgaac atcactccta aattaataaa gtattcctct gttgctttag    3660
tatttattac aataaaaagg gtttgaaata tagctgttct ttatgcataa aacacccagc    3720
taggaccatt actgccagag aaaaaaatcg tattgaatgg ccatttccct acttataaga    3780
tgtctcaatc tgaatttatt tggctacact aaagaatgca gtatatttag ttttccattt    3840
gcatgatgtt tgtgtgctat agatgatatt ttaaattgaa aagtttgttt taaattattt    3900
ttacagtgaa gactgttttc agctcttttt atattgtaca tagtcttta tgtaatttac    3960 tggcatatgt tttgtagact gtttaatgac tggatatctt ccttcaactt ttgaaataca    4020 aaccagtgt ttttacttg tacactgttt taaagtctat taaaattgtc atttgacttt     4080
tttctg                                                              4086
```

<210> SEQ ID NO 12
<211> LENGTH: 747
<212> TYPE: PRT
<213> ORGANISM: Homo sapiens

<400> SEQUENCE: 12

```
Met Ala Asp Glu Ala Ala Leu Ala Leu Gln Pro Gly Gly Ser Pro Ser
1               5                   10                  15
```

```
Ala Ala Gly Ala Asp Arg Glu Ala Ala Ser Ser Pro Ala Gly Glu Pro
            20                  25                  30

Leu Arg Lys Arg Pro Arg Arg Asp Gly Pro Gly Leu Glu Arg Ser Pro
            35                  40                  45

Gly Glu Pro Gly Gly Ala Ala Pro Glu Arg Glu Val Pro Ala Ala Ala
        50                  55                  60

Arg Gly Cys Pro Gly Ala Ala Ala Ala Leu Trp Arg Glu Ala
65                  70                  75                  80

Ala Glu Ala Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
                100                 105                 110

Glu Pro Pro Leu Ala Asp Asn Leu Tyr Asp Glu Asp Asp Asp Glu
            115                 120                 125

Gly Glu Glu Glu Glu Glu Ala Ala Ala Ala Ile Gly Tyr Arg Asp
        130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
        195                 200                 205

Thr Ile Pro Pro Pro Glu Leu Asp Asp Met Thr Leu Trp Gln Ile Val
210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
                260                 265                 270

Phe Arg Ser Arg Asp Gly Ile Tyr Ala Arg Leu Ala Val Asp Phe Pro
            275                 280                 285

Asp Leu Pro Asp Pro Gln Ala Met Phe Asp Ile Glu Tyr Phe Arg Lys
        290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
                325                 330                 335

Gly Lys Leu Leu Arg Asn Tyr Thr Gln Asn Ile Asp Thr Leu Glu Gln
                340                 345                 350

Val Ala Gly Ile Gln Arg Ile Ile Gln Cys His Gly Ser Phe Ala Thr
            355                 360                 365

Ala Ser Cys Leu Ile Cys Lys Tyr Lys Val Asp Cys Glu Ala Val Arg
        370                 375                 380

Gly Asp Ile Phe Asn Gln Val Val Pro Arg Cys Pro Arg Cys Pro Ala
385                 390                 395                 400

Asp Glu Pro Leu Ala Ile Met Lys Pro Glu Ile Val Phe Phe Gly Glu
                405                 410                 415

Asn Leu Pro Glu Gln Phe His Arg Ala Met Lys Tyr Asp Lys Asp Glu
                420                 425                 430

Val Asp Leu Leu Ile Val Ile Gly Ser Ser Leu Lys Val Arg Pro Val
```

```
                435             440              445
Ala Leu Ile Pro Ser Ser Ile Pro His Glu Val Pro Gln Ile Leu Ile
450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
                485                 490                 495

Tyr Ala Lys Leu Cys Cys Asn Pro Val Lys Leu Ser Glu Ile Thr Glu
                500                 505                 510

Lys Pro Pro Arg Thr Gln Lys Glu Leu Ala Tyr Leu Ser Glu Leu Pro
            515                 520                 525

Pro Thr Pro Leu His Val Ser Glu Asp Ser Ser Ser Pro Glu Arg Thr
        530                 535                 540

Ser Pro Pro Asp Ser Ser Val Ile Val Thr Leu Leu Asp Gln Ala Ala
545                 550                 555                 560

Lys Ser Asn Asp Asp Leu Asp Val Ser Glu Ser Lys Gly Cys Met Glu
                565                 570                 575

Glu Lys Pro Gln Glu Val Gln Thr Ser Arg Asn Val Glu Ser Ile Ala
                580                 585                 590

Glu Gln Met Glu Asn Pro Asp Leu Lys Asn Val Gly Ser Ser Thr Gly
            595                 600                 605

Glu Lys Asn Glu Arg Thr Ser Val Ala Gly Thr Val Arg Lys Cys Trp
        610                 615                 620

Pro Asn Arg Val Ala Lys Glu Gln Ile Ser Arg Arg Leu Asp Gly Asn
625                 630                 635                 640

Gln Tyr Leu Phe Leu Pro Pro Asn Arg Tyr Ile Phe His Gly Ala Glu
                645                 650                 655

Val Tyr Ser Asp Ser Glu Asp Val Leu Ser Ser Ser Cys Gly
                660                 665                 670

Ser Asn Ser Asp Ser Gly Thr Cys Gln Ser Pro Ser Leu Glu Glu Pro
            675                 680                 685

Met Glu Asp Glu Ser Glu Ile Glu Glu Phe Tyr Asn Gly Leu Glu Asp
690                 695                 700

Glu Pro Asp Val Pro Glu Arg Ala Gly Gly Ala Gly Phe Gly Thr Asp
705                 710                 715                 720

Gly Asp Asp Gln Glu Ala Ile Asn Glu Ala Ile Ser Val Lys Gln Glu
                725                 730                 735

Val Thr Asp Met Asn Tyr Pro Ser Asn Lys Ser
            740                 745

<210> SEQ ID NO 13
<211> LENGTH: 1869
<212> TYPE: DNA
<213> ORGANISM: Homo sapiens

<400> SEQUENCE: 13
ggcgccgggg gcggggggtgg gaggcggagg cggggccggg gcgccgcggg cggggcgccg    60
ggggcggggc gagtccggag gactcctcgg actgcgcgga acatggcgtt ctggggttgg   120
cgcgccgcgg cagccctccg gctgtggggc cgggtagttg aacgggtcga ggccggggga   180
ggcgtggggc cgtttcaggc ctgcggctgt cggctggtgc ttggcggcag ggacgatgtg   240
agtgcggggc tgagaggcag ccatggggcc cgcggtgagc ccttggaccc ggcgcgcccc   300
ttgcagaggc ctcccagacc cgaggtgccc agggcattcc ggaggcagcc gagggcagca   360
gctcccagtt tcttcttttc gagtattaaa ggtggaagaa ggtccatatc ttttctgtg    420
```

```
ggtgcttcaa gtgttgttgg aagtggaggc agcagtgaca aggggaagct ttccctgcag    480
gatgtagctg agctgattcg ggccagagcc tgccagaggg tggtggtcat ggtgggggcc    540
ggcatcagca cacccagtgg cattccagac ttcagatcgc cggggagtgg cctgtacagc    600
aacctccagc agtacgatct cccgtacccc gaggccattt ttgaactccc attcttcttt    660
cacaacccca agccctttt cactttggcc aaggagctgt accctggaaa ctacaagccc     720
aacgtcactc actactttct ccggctgctt catgacaagg ggctgcttct gcggctctac    780
acgcagaaca tcgatgggct tgagagagtg tcgggcatcc ctgcctcaaa gctggttgaa    840
gctcatggaa cctttgcctc tgccacctgc acagtctgcc aaagacccctt cccaggggag   900 gacattcggg ctgacgtgat ggcagacagg gttccccgct gccggtctg caccggcgtt     960 gtgaagcccg acattgtgtt ctttggggag ccgctgcccc agaggttctt gctgcatgtg   1020
gttgatttcc ccatggcaga tctgctgctc atccttggga cctccctgga ggtggagcct   1080
tttgccagct tgaccgaggc cgtgcggagc tcagttcccc gactgctcat caaccgggac   1140
ttggtggggc ccttggcttg gcatcctcgc agcagggacg tggcccagct gggggacgtg   1200
gttcacggcg tggaaagcct agtggagctt ctgggctgga cagaagagat gcgggacctt   1260
gtgcagcggg aaactgggaa gcttgatgga ccagacaaat aggatgatgg ctgcccccac   1320
acaataaatg gtaacatagg agacatccac atcccaattc tgacaagacc tcatgcctga   1380
agacagcttg ggcaggtgaa accagaatat gtgaactgag tggacacccg aggctgccac   1440
tggaatgtct tctcaggcca tgagctgcag tgactggtag ggctgtgttt acagtcaggg   1500 ccacccccgtc acatatacaa aggagctgcc tgcctgtttg ctgtgttgaa ctcttcactc   1560
tgctgaagct cctaatggaa aaagctttct tctgactgtg accctcttga actgaatcag   1620
accaactgga atcccagacc gagtctgctt tctgtgccta gttgaacggc aagctcggca   1680
tctgttggtt acaagatcca gacttgggcc gagcggtccc cagccctctt catgttccga   1740
agtgtagtct tgaggccctg gtgccgcact tctagcatgt tggtctcctt tagtggggct   1800
atttttaatg agagaaaatc tgttctttcc agcatgaaat acatttagtc tcctcaaaaa   1860
aaaaaaaca                                                          1869
```

<210> SEQ ID NO 14
<211> LENGTH: 399
<212> TYPE: PRT
<213> ORGANISM: Homo sapiens

<400> SEQUENCE: 14

```
Met Ala Phe Trp Gly Trp Arg Ala Ala Ala Leu Arg Leu Trp Gly
 1               5                  10                  15

Arg Val Val Glu Arg Val Glu Ala Gly Gly Val Gly Pro Phe Gln
                20                  25                  30

Ala Cys Gly Cys Arg Leu Val Leu Gly Gly Arg Asp Asp Val Ser Ala
        35                  40                  45

Gly Leu Arg Gly Ser His Gly Ala Arg Gly Glu Pro Leu Asp Pro Ala
    50                  55                  60

Arg Pro Leu Gln Arg Pro Pro Arg Pro Glu Val Pro Arg Ala Phe Arg
65                  70                  75                  80

Arg Gln Pro Arg Ala Ala Ala Pro Ser Phe Phe Ser Ser Ile Lys
                85                  90                  95

Gly Gly Arg Arg Ser Ile Ser Phe Ser Val Gly Ala Ser Val Val
            100                 105                 110
```

Gly Ser Gly Gly Ser Ser Asp Lys Gly Lys Leu Ser Leu Gln Asp Val
            115                 120                 125

Ala Glu Leu Ile Arg Ala Arg Ala Cys Gln Arg Val Val Met Val
130                 135                 140

Gly Ala Gly Ile Ser Thr Pro Ser Gly Ile Pro Asp Phe Arg Ser Pro
145                 150                 155                 160

Gly Ser Gly Leu Tyr Ser Asn Leu Gln Gln Tyr Asp Leu Pro Tyr Pro
                165                 170                 175

Glu Ala Ile Phe Glu Leu Pro Phe Phe His Asn Pro Lys Pro Phe
            180                 185                 190

Phe Thr Leu Ala Lys Glu Leu Tyr Pro Gly Asn Tyr Lys Pro Asn Val
            195                 200                 205

Thr His Tyr Phe Leu Arg Leu Leu His Asp Lys Gly Leu Leu Leu Arg
210                 215                 220

Leu Tyr Thr Gln Asn Ile Asp Gly Leu Glu Arg Val Ser Gly Ile Pro
225                 230                 235                 240

Ala Ser Lys Leu Val Glu Ala His Gly Thr Phe Ala Ser Ala Thr Cys
                245                 250                 255

Thr Val Cys Gln Arg Pro Phe Pro Gly Glu Asp Ile Arg Ala Asp Val
            260                 265                 270

Met Ala Asp Arg Val Pro Arg Cys Pro Val Cys Thr Gly Val Val Lys
            275                 280                 285

Pro Asp Ile Val Phe Phe Gly Glu Pro Leu Pro Gln Arg Phe Leu Leu
290                 295                 300

His Val Val Asp Phe Pro Met Ala Asp Leu Leu Leu Ile Leu Gly Thr
305                 310                 315                 320

Ser Leu Glu Val Glu Pro Phe Ala Ser Leu Thr Glu Ala Val Arg Ser
                325                 330                 335

Ser Val Pro Arg Leu Leu Ile Asn Arg Asp Leu Val Gly Pro Leu Ala
            340                 345                 350

Trp His Pro Arg Ser Arg Asp Val Ala Gln Leu Gly Asp Val Val His
            355                 360                 365

Gly Val Glu Ser Leu Val Glu Leu Leu Gly Trp Thr Glu Glu Met Arg
            370                 375                 380

Asp Leu Val Gln Arg Glu Thr Gly Lys Leu Asp Gly Pro Asp Lys
385                 390                 395

<210> SEQ ID NO 15
<211> LENGTH: 1174
<212> TYPE: DNA
<213> ORGANISM: Homo sapiens

<400> SEQUENCE: 15
gtccgtagag ctgtgagaga atgaagatga gctttgcgtt gactttcagg tcagcaaaag    60
gccgttggat cgcaaacccc agccagccgt gctcgaaagc ctccattggg ttatttgtgc   120
cagcaagtcc tcctctggac cctgagaagg tcaaagagtt acagcgcttc atcacccttt   180
ccaagagact ccttgtgatg actggggcag gaatctccac cgaatcgggg ataccagact   240
acaggtcaga aaagtggggc tttatgcccg cactgaccg caggcccatc agcatggtg    300 attttgtccg gagtgcccca atccgccagc ggtactgggc gagaaacttc gtaggctggc   360
ctcaattctc ctcccaccag cctaaccctg cacactgggc tttgagcacc tgggagaaac   420
tcggaaagct gtactggttg gtgacccaaa atgtggatgc tttgcacacc aaggcgggga   480
gtcggcgcct gacagagctc cacggatgca tggacagggt cctgtgcttg gattgtgggg   540

```
aacagactcc ccgggggtg ctgcaagagc gtttccaagt cctgaacccc acctggagtg      600
ctgaggccca tggcctggct cctgatggtg acgtctttct ctcagaggag caagtccgga      660
gctttcaggt cccaacctgc gttcaatgtg gaggccatct gaaaccagat gtcgttttct      720
tcggggacac agtgaaccct gacaaggttg attttgtgca caagcgtgta aaagaagccg      780
actccctctt ggtggtggga tcatccttgc aggtatactc tggttacagg tttatcctca      840
ctgcctggga gaagaagctc ccgattgcaa tactgaacat tgggcccaca cggtcggatg      900
acttggcgtg tctgaaactg aattctcgtt gtggagagtt gctgcctttg atagacccat      960
gctgaccaca gcctgatatt ccagaacctg aacagggac tttcacttga atcttgctgc     1020
taaatgtaaa tgccttctca aatgacagat tccagttccc attcaacaga gtagggtgca     1080
ctgacaaagt atagaaggtt ctaggtatct taatgtgtgg atattcttaa ttaaaactca     1140
ttttttttaa ataaaaaatt gttcagcttt aaaa                                  1174
```

<210> SEQ ID NO 16
<211> LENGTH: 314
<212> TYPE: PRT
<213> ORGANISM: Homo sapiens

<400> SEQUENCE: 16

```
Met Lys Met Ser Phe Ala Leu Thr Phe Arg Ser Ala Lys Gly Arg Trp
1               5                   10                  15

Ile Ala Asn Pro Ser Gln Pro Cys Ser Lys Ala Ser Ile Gly Leu Phe
            20                  25                  30

Val Pro Ala Ser Pro Pro Leu Asp Pro Glu Lys Val Lys Glu Leu Gln
        35                  40                  45

Arg Phe Ile Thr Leu Ser Lys Arg Leu Leu Val Met Thr Gly Ala Gly
    50                  55                  60

Ile Ser Thr Glu Ser Gly Ile Pro Asp Tyr Arg Ser Glu Lys Val Gly
65                  70                  75                  80

Leu Tyr Ala Arg Thr Asp Arg Arg Pro Ile Gln His Gly Asp Phe Val
                85                  90                  95

Arg Ser Ala Pro Ile Arg Gln Arg Tyr Trp Ala Arg Asn Phe Val Gly
            100                 105                 110

Trp Pro Gln Phe Ser Ser His Gln Pro Asn Pro Ala His Trp Ala Leu
        115                 120                 125

Ser Thr Trp Glu Lys Leu Gly Lys Leu Tyr Trp Leu Val Thr Gln Asn
    130                 135                 140

Val Asp Ala Leu His Thr Lys Ala Gly Ser Arg Arg Leu Thr Glu Leu
145                 150                 155                 160

His Gly Cys Met Asp Arg Val Leu Cys Leu Asp Cys Gly Glu Gln Thr
                165                 170                 175

Pro Arg Gly Val Leu Gln Glu Arg Phe Gln Val Leu Asn Pro Thr Trp
            180                 185                 190

Ser Ala Glu Ala His Gly Leu Ala Pro Asp Gly Asp Val Phe Leu Ser
        195                 200                 205

Glu Glu Gln Val Arg Ser Phe Gln Val Pro Thr Cys Val Gln Cys Gly
    210                 215                 220

Gly His Leu Lys Pro Asp Val Val Phe Phe Gly Asp Thr Val Asn Pro
225                 230                 235                 240

Asp Lys Val Asp Phe Val His Lys Arg Val Lys Glu Ala Asp Ser Leu
                245                 250                 255

Leu Val Val Gly Ser Ser Leu Gln Val Tyr Ser Gly Tyr Arg Phe Ile
            260                 265                 270
```

Leu Thr Ala Trp Glu Lys Lys Leu Pro Ile Ala Ile Leu Asn Ile Gly
         275                 280                 285

Pro Thr Arg Ser Asp Asp Leu Ala Cys Leu Lys Leu Asn Ser Arg Cys
         290                 295                 300

Gly Glu Leu Leu Pro Leu Ile Asp Pro Cys
305                 310

<210> SEQ ID NO 17
<211> LENGTH: 1633
<212> TYPE: DNA
<213> ORGANISM: Homo sapiens

<400> SEQUENCE: 17

| | | | | | | |
|---|---|---|---|---|---|---|
| cgcctctagg | agaaagcctg | gaacgcgtac | cggagggtac | cagagctctt | agcgggccgg | 60 |
| cagcatgtgc | ggggccaagt | aaatggaaat | gttttctaac | atataaaaac | ctacagaaga | 120 |
| agaaaataat | tttctggatc | aaattagaag | tctgtattat | attgatgtct | ccagattcaa | 180 |
| atatattga | aagcagccgt | ggagacaacc | atcttcattt | tgggagaaat | aactaaagcc | 240 |
| cgcctcaagc | attagaacta | cagacaaacc | ctgatgcgac | ctctccagat | tgtcccaagt | 300 |
| cgattgattt | cccagctata | ttgtggcctg | aagcctccag | cgtccacacg | aaaccagatt | 360 |
| tgcctgaaaa | tggctcggcc | aagttcaagt | atggcagatt | tcgaaagtt | ttttgcaaaa | 420 |
| gcaaagcaca | tagtcatcat | ctcaggagct | ggtgttagtg | cagaaagtgg | tgttccgacc | 480 |
| ttcagaggag | ctggaggtta | ttggagaaaa | tggcaagccc | aggacctggc | gactcccctg | 540 |
| gcctttgccc | acaacccgtc | ccgggtgtgg | gagttctacc | actaccggcg | ggaggtcatg | 600 |
| gggagcaagg | agcccaacgc | cgggcaccgc | gccatagccg | agtgtgagac | ccggctgggc | 660 |
| aagcagggcc | ggcgagtcgt | ggtcatcacc | cagaacatcg | atgagctgca | ccgcaaggct | 720 |
| ggcaccaaga | accttctgga | gatccatggt | agcttattta | aaactcgatg | tacctcttgt | 780 |
| ggagttgtgg | ctgagaatta | caagagtcca | atttgtccag | ctttatcagg | aaaaggtgct | 840 |
| ccagaacctg | gaactcaaga | tgccagcatc | ccagttgaga | acttccccg | tgtgaagag | 900 |
| gcaggctgcg | ggggcttgct | gcgacctcac | gtcgtgtggt | ttggagaaaa | cctggatcct | 960 |
| gccattctgg | aggaggttga | cagagagctc | gcccactgtg | atttatgtct | agtggtgggc | 1020 |
| acttcctctg | tggtgtaccc | agcagccatg | tttgccccc | aggtggctgc | caggggcgtg | 1080 |
| ccagtggctg | aatttaacac | ggagaccacc | ccagctacga | acagattcag | gtttcatttc | 1140 |
| cagggaccct | gtggaacgac | tcttcctgaa | gcccttgcct | gtcatgaaaa | tgaaactgtt | 1200 |
| tcttaagtgt | cctggggaag | aaagaaatta | cagtatatct | aagaactagg | ccacacgcag | 1260 |
| aggagaaatg | gtcttatggg | tggtgagctg | agtactgaac | aatctaaaaa | tagcctctga | 1320 |
| ttccctcgct | ggaatccaac | ctgttgataa | gtgatggggg | tttagaagta | gcaaagagca | 1380 |
| cccacattca | aaagtcacag | aactggaaag | ttaattcata | ttatttggtt | tgaactgaaa | 1440 |
| cgtgaggtat | ctttgatgtg | tatggttggt | tattgggagg | gaaaaatttt | gtaaattaga | 1500 |
| ttgtctaaaa | aaaatagtta | ttctgattat | attttttgtta | tctgggcaaa | gtagaagtca | 1560 |
| agggtaaaa | accctactat | tctgattttt | gcacaagttt | tagtggaaaa | taaaatcaca | 1620 |
| ctctacagta | ggt | | | | | 1633 |

<210> SEQ ID NO 18
<211> LENGTH: 310
<212> TYPE: PRT
<213> ORGANISM: Homo sapiens

<400> SEQUENCE: 18

```
Met Arg Pro Leu Gln Ile Val Pro Ser Arg Leu Ile Ser Gln Leu Tyr
1               5                   10                  15

Cys Gly Leu Lys Pro Ala Ser Thr Arg Asn Gln Ile Cys Leu Lys
            20                  25                  30

Met Ala Arg Pro Ser Ser Met Ala Asp Phe Arg Lys Phe Phe Ala
        35                  40                  45

Lys Ala Lys His Ile Val Ile Ser Gly Ala Gly Val Ser Ala Glu
50                  55                  60

Ser Gly Val Pro Thr Phe Arg Gly Ala Gly Gly Tyr Trp Arg Lys Trp
65                  70                  75                  80

Gln Ala Gln Asp Leu Ala Thr Pro Leu Ala Phe Ala His Asn Pro Ser
                85                  90                  95

Arg Val Trp Glu Phe Tyr His Tyr Arg Arg Glu Val Met Gly Ser Lys
                100                 105                 110

Glu Pro Asn Ala Gly His Arg Ala Ile Ala Glu Cys Glu Thr Arg Leu
                115                 120                 125

Gly Lys Gln Gly Arg Arg Val Val Ile Thr Gln Asn Ile Asp Glu
130                 135                 140

Leu His Arg Lys Ala Gly Thr Lys Asn Leu Leu Glu Ile His Gly Ser
145                 150                 155                 160

Leu Phe Lys Thr Arg Cys Thr Ser Cys Gly Val Val Ala Glu Asn Tyr
                165                 170                 175

Lys Ser Pro Ile Cys Pro Ala Leu Ser Gly Lys Gly Ala Pro Glu Pro
                180                 185                 190

Gly Thr Gln Asp Ala Ser Ile Pro Val Glu Lys Leu Pro Arg Cys Glu
                195                 200                 205

Glu Ala Gly Cys Gly Gly Leu Leu Arg Pro His Val Val Trp Phe Gly
210                 215                 220

Glu Asn Leu Asp Pro Ala Ile Leu Glu Glu Val Asp Arg Glu Leu Ala
225                 230                 235                 240

His Cys Asp Leu Cys Leu Val Val Gly Thr Ser Ser Val Val Tyr Pro
                245                 250                 255

Ala Ala Met Phe Ala Pro Gln Val Ala Ala Arg Gly Val Pro Val Ala
                260                 265                 270

Glu Phe Asn Thr Glu Thr Thr Pro Ala Thr Asn Arg Phe Arg Phe His
                275                 280                 285

Phe Gln Gly Pro Cys Gly Thr Thr Leu Pro Glu Ala Leu Ala Cys His
                290                 295                 300

Glu Asn Glu Thr Val Ser
305                 310
```

<210> SEQ ID NO 19
<211> LENGTH: 8
<212> TYPE: PRT
<213> ORGANISM: Homo sapiens

<400> SEQUENCE: 19

```
His Ser Pro Leu Leu Val Pro His
1               5
```

<210> SEQ ID NO 20
<211> LENGTH: 23
<212> TYPE: PRT
<213> ORGANISM: Homo sapiens

<400> SEQUENCE: 20

```
Gln Pro Pro Thr Pro Ile Ser Pro Ser Pro Ala Ile Leu Gly Phe Gly
1               5                   10                  15

Ser Leu Asn Pro Cys Leu Gln
            20

<210> SEQ ID NO 21
<211> LENGTH: 53
<212> TYPE: PRT
<213> ORGANISM: Homo sapiens

<400> SEQUENCE: 21

Val Cys Val Arg Ser Thr Gln Asp Phe His Leu Leu Cys Pro Gly Ala
1               5                   10                  15

Pro Leu Asn Lys Leu Ala Cys Thr Gly Val Leu Leu Trp Gly Gly Gly
            20                  25                  30

Trp Gly Val Gly His Thr Ser Leu Asp Phe Lys Val Phe Thr Val Arg
        35                  40                  45

Asp Val Trp Glu Met
    50

<210> SEQ ID NO 22
<211> LENGTH: 15
<212> TYPE: PRT
<213> ORGANISM: Homo sapiens

<400> SEQUENCE: 22

Glu Met Phe Leu Gln Leu Arg Val Ser Leu Gln Ser Ala Thr Phe
1               5                   10                  15

<210> SEQ ID NO 23
<211> LENGTH: 16
<212> TYPE: PRT
<213> ORGANISM: Homo sapiens

<400> SEQUENCE: 23

Val Gly Thr His Phe Thr Val Leu Thr Arg Glu Ala Val Pro His Cys
1               5                   10                  15

<210> SEQ ID NO 24
<211> LENGTH: 20
<212> TYPE: PRT
<213> ORGANISM: Homo sapiens
<220> FEATURE:
<221> NAME/KEY: VARIANT
<222> LOCATION: 6, 15
<223> OTHER INFORMATION: acetylated lysine

<400> SEQUENCE: 24

His Leu Lys Ser Lys Xaa Gly Gln Ser Thr Ser Arg His Lys Xaa Leu
1               5                   10                  15

Met Phe Lys Cys
            20
```

SIR2 ACTIVITY

RELATED APPLICATIONS

This application is a continuation of U.S. application Ser. No. 12/408,575, filed Mar. 20, 2009, now abandoned which is a divisional of U.S. application Ser. No. 11/404,146, filed Apr. 13, 2006, now U.S. Pat. No. 7,572,575, which is a continuation-in-part of U.S. application Ser. No. 09/735,786, filed Dec. 13, 2000, and is a continuation-in-part of U.S. application Ser. No. 11/155,025, filed Jun. 15, 2005, now abandoned which is a continuation-in-part of U.S. application Ser. No. 10/191,121, filed Jul. 8, 2002, now abandoned which is a continuation-in-part of U.S. application Ser. No. 10/190,159, filed Jul. 5, 2002, now abandoned which claims the benefit of U.S. Provisional Application No. 60/303,456, filed on Jul. 6, 2001 and U.S. Provisional Application No. 60/303,370, filed on Jul. 6, 2001.

The entire teachings of the above application(s) are incorporated herein by reference.

GOVERNMENT SUPPORT

This invention was made with government support under Grant No. R01 AG011119 awarded by the National Institutes of Health. The government has certain rights in the invention.

BACKGROUND OF THE INVENTION

Regulation of the cell cycle is important in homeostasis of both cells and organisms (e.g., mammalian cells or mammals). Disruptions in the normal regulation of the cell cycle can occur, for example, in tumors which proliferate uncontrollably, in response to DNA damage (e.g., ionizing radiation) to the cell or organism, and under conditions of stress (e.g., oxidative stress) in the cell or organism.

The p53 tumor suppressor protein exerts anti-proliferative effects, including growth arrest, apoptosis, and cell senescence, in response to various types of stress, e.g., DNA damage (Levine, 1997; Giaccia and Kastan, 1998; Prives and Hall, 1999; Oren, 1999; Vogelstein et al., 2000). Inactivation of p53 function appears to be critical to tumorigenesis (Hollstein et al., 1999). Mutations in the p53 gene have been shown in more than half of all human tumors (Hollstein et al., 1994). Accumulating evidence further indicates that, in the cells that retain wild-type p53, other defects in the p53 pathway also play an important role in tumorigenesis (Prives and Hall, 1999; Lohrum and Vousden, 1999; Vousden, 2000). The molecular function of p53 that is required for tumor suppression involves its ability to act as a transcriptional factor in regulating endogenous gene expression. A number of genes which are critically involved in either cell growth arrest or apoptosis have been identified as p53 direct targets, including p21CIP1/WAF1, Mdm2, GADD45, Cyclin G, 14-3-3F, Noxa, p53AIP1, PUMA and others (Nakano and Vousden, 2001; Yu et al., 2001; Oda et al., 2000a, 2000b; El-Deriry et al., 1993; Wu et al., 1993; Barak et al., 1993; Kastan et al., 1992; Okamoto and Beach, 1994).

p53 is a short-lived protein whose activity is maintained at low levels in normal cells. Tight regulation of p53 is essential for its effect on tumorigenesis as well as maintaining normal cell growth. The precise mechanism by which p53 is activated by cellular stress is not completely understood. It is generally thought to involve primarily post-translational modifications of p53, including phosphorylation and acetylation (reviewed in Appella and Anderson, 2000; Giaccia and Kastan, 1998). Early studies demonstrated that CBP/p300, a histone acetyl-transferase (HAT), acts as a coactivator of p53 and potentiates its transcriptional activity as well as biological function in vivo (Gu et al., 1997; Lill et al., 1997; Avantaggiati et al., 1997). Genetic studies have also revealed that p300 mutations are present in several types of tumors, and that mutations of CBP in human Rubinstein-Taybi syndrome as well as CBP knockout mice lead to higher risk of tumorigenesis, further supporting an important role for this interaction in the tumor suppressor pathway (reviewed in Goodman and Smolik, 2000; Gile et al., 1998; Kung et al., 2000; Gayther et al., 2000). Significantly, the observation of functional synergism between p53 and CBP/p300 together with its intrinsic HAT activity led to the discovery of a novel FAT (Transcriptional factor acetyl-transferase) activity of CBP/p300 on p53 which suggests that acetylation represents a general functional modification for non-histone proteins in vivo (Gu and Roeder, 1997) which has been shown for other transcriptional factors (reviewed in Kouzarides, 2000; Sterner and Berger, 2000; Muth et al., 2001).

p53 is specifically acetylated at multiple lysine residues (Lys 370, 371, 372, 381, 382) of the C-terminal regulatory domain by CBP/p300. The acetylation of p53 can dramatically stimulate its sequence-specific DNA binding activity, perhaps as a result of an acetylation-induced conformational change (Gu and Roeder, 1997; Sakaguchi et al., 1998; Liu et al., 1999). By developing site-specific acetylated p53 antibodies, CBP/p300 mediated acetylation of p53 was confirmed in vivo by a number of studies (reviewed in Chao et al., 2000; Ito et al., 2001). In addition, p53 can be acetylated at Lys320 by another HAT cofactor, PCAF, although the in vivo functional consequence needs to be further elucidated (Sakaguchi et al., 1998; Liu et al., 1999; Liu et al., 2000). Steady-state levels of acetylated p53 are stimulated in response to various types of stress (reviewed in Ito et al., 2001).

Recently, by introducing a transcription defective p53 mutant (p53Q25S26) into mice, it was found that the mutant mouse thymocytes and ES cells failed to undergo DNA damage-induced apoptosis (Chao et al., 2000; Jimenez et al., 2000). Interestingly, this mutant protein was phosphorylated normally at the N-terminus in response to DNA damage but could not be acetylated at the C-terminus (Chao et al., 2000), supporting a critical role of p53 acetylation in transactivation as well as p53-dependent apoptotic response (Chao et al., 2000; Luo et al., 2000). Furthermore, it has been found that oncogenic Ras and PML upregulate acetylated p53 in normal primary fibroblasts, and induce premature senescence in a p53-dependent manner (Pearson et al., 2000; Ferbeyre et al., 2000). Additionally acetylation, not phosphorylation of the p53 C-terminus, may be required to induce metaphase chromosome fragility in the cell (Yu et al., 2000). Thus, CBP/p300-dependent acetylation of p53 may be a critical event in p53-mediated transcriptional activation, apoptosis, senescence, and chromosome fragility.

In contrast, much less is known about the role of deacetylation in modulating p53 function. Under normal conditions, the proportion of acetylated p53 in cells remains low. This may reflect the action of strong deacetylase activities in vivo. The acetylation level of p53 is enhanced when the cells are treated with histone deacetylase (HDAC) inhibitors such as Trichostatin A (TSA). These observations led to identification of a HDAC1 complex which is directly involved in p53 deacetylation and functional regulation (Luo et al., 2000; Juan et al., 2000). PID/MTA2, a component of the HDAC 1 complex, acts as an adaptor protein to enhance HDAC 1-mediated deacetylation of p53 which is repressed by TSA (Luo et al., 2000). In addition, Mdm2, a negative regulator of p53, actively suppresses CBP/p300-mediated p53 acetylation, and this inhibitory effect can be abrogated by tumor suppressor p19ARF. Acetylation may have a critical role in the p53-MDM2-p19ARF feed back loop (Ito et al., 2001; Kobet et al., 2000).

The Silent Information Regulator (SIR) family of genes represents a highly conserved group of genes present in the genomes of organisms ranging from archaebacteria to a variety of eukaryotes (Frye, 2000). The encoded SIR proteins are involved in diverse processes from regulation of gene silencing to DNA repair. The proteins encoded by members of the SIR2 gene family show high sequence conservation in a 250 amino acid core domain. A well-characterized gene in this family is *S. cerevisiae* SIR2, which is involved in silencing HM loci that contain information specifying yeast mating type, telomere position effects and cell aging (Guarente, 1999; Kaeberlein et al., 1999; Shore, 2000). The yeast Sir2 protein belongs to a family of histone deacetylases (reviewed in Guarente, 2000; Shore, 2000). The Sir2 homolog, CobB, in *Salmonella typhimurium*, functions as an NAD (nicotinamide adenine dinucleotide)-dependent ADP-ribosyl transferase (Tsang and Escalante-Semerena, 1998).

The Sir2 protein is a deacetylase which uses NAD as a cofactor (Imai et al., 2000; Moazed, 2001; Smith et al., 2000; Tanner et al., 2000; Tanny and Moazed, 2001). Unlike other deacetylases, many of which are involved in gene silencing, Sir2 is insensitive to histone deacetylase inhibitors like trichostatin A (TSA) (Imai et al., 2000; Landry et al., 2000a; Smith et al., 2000).

Deacetylation of acetyl-lysine by Sir2 is tightly coupled to NAD hydrolysis, producing nicotinamide and a novel acetyl-ADP ribose compound (1-O-acetyl-ADP-ribose) (Tanner et al., 2000; Landry et al., 2000b; Tanny and Moazed, 2001). The NAD-dependent deacetylase activity of Sir2 is essential for its functions which can connect its biological role with cellular metabolism in yeast (Guarente, 2000; Imai et al., 2000; Lin et al., 2000; Smith et al., 2000). Mammalian Sir2 homologs have NAD-dependent histone deacetylase activity (Imai et al., 2000; Smith et al., 2000). Most information about Sir2 mediated functions comes from the studies in yeast (Gartenberg, 2000; Gottschling, 2000).

Among Sir2 and its homolog proteins (HSTs) in yeast, Sir2 is the only protein localized in nuclei, which is critical for both gene silencing and extension of yeast life-span (reviewed in Guarente, 2000). Based on protein sequence homology analysis, mouse Sir2α and its human ortholog SIRT1 (or human Sir2α or hSir2) are the closest homologs to yeast Sir2 (Imai et al., 2000; Frye, 1999, 2000) and both exhibit nuclear localization (FIG. 7C). Homologues of Sir2 have been identified in almost all organisms examined including bacteria, which has no histone proteins (reviewed in Gray and Ekstrom, 2001; Frye, 1999; 2000; Brachmann et al., 1995). For this reason it is likely that Sir2 also targets non-histone proteins for functional regulation (Muth et al., 2001).

The *S. cerevisiae* Sir2 is involved in DNA damage responses (Martin et al., 1999; McAinsh et al., 1999; Mills et al., 1999). In mammalian cells, one of the primary mediators of the DNA damage response is the p53 protein (Levine, 1997; Oren, 1999; Vogelstein et al., 2000). Following DNA damage, the p53 protein is protected from rapid degradation and acquires transcription-activating functions, these changes being achieved largely through post-translational modifications (Abraham et al., 2000; Canman et al., 1998; Chehab et al., 1999; Sakaguchi et al., 1998; Shieh et al., 2000; Siliciano et al., 1997). Transcriptional activation of p53 protein in turn upregulates promoters of a number of genes including p21WAF1 (el-Deiry et al., 1993) that promotes cell cycle exit or death-inducing proteins like PIDD (Lin et al., 2000).

The p53 protein is phosphorylated in response to DNA damage (Siliciano et al., 1997). There are at least 13 different residues both at the N and C terminal portions of p53 protein that are phosphorylated by various kinases (Appella and Anderson, 2000). For example, the ATM and ATR proteins phosphorylate p53 at residue Ser15 (Khanna et al., 1998; Siliciano et al., 1997; Tibbetts et al., 1999) and Chk1/2 kinases at residue Ser20 (Chehab et al., 1999; Shieh et al., 2000).

Modification of Ser15 is important for the functional activation of the p53 protein. Phosphorylation of Ser15 may increase the affinity of the p300 acetylase for p53 (Dumaz and Meek, 1999; Lambert et al., 1998).

p53 is acetylated in vitro by p300 at Lys 370-372, 381 and 382 (Gu and Roeder, 1997). In response to DNA damage, p53 is also acetylated in vivo at Lys 373 and Lys 382 (Abraham et al., 2000; Sakaguchi et al., 1998). Other factors that can affect acetylation of p53 include MDM2 protein, which is involved in the negative regulation of p53 (Oren, 1999) and can suppress acetylation of p53 protein by p300 (Ito et al., 2001; Kobet et al., 2000). While acetylation by p300 and deacetylation by the TSA-sensitive HDAC1 complex (Luo et al., 2000) have been shown to be important in regulation of p53 protein activity, the remaining factors responsible for its regulation as a transcription factor remain elusive.

Analogs of NAD that inhibit endogenous ADP-ribosylases reduce induction of p21WAF1 in response to DNA damage and overcome p53-dependent senescence (Vaziri et al., 1997). In addition, p53 protein can bind to the NAD-dependent poly-ADP-ribose polymerase.

The SIR complex in *Saccharomyces cerevisiae* was originally identified through its involvement in the maintenance of chromatin silencing at telomeres and at mating type loci. It is composed of four components, Sir1p, Sir2p, Sir3p, and Sir4p, that normally reside at yeast telomeres. In response to DNA damage, the SIR complexes relocate to the site of double-stranded breaks where they participate in the repair of the lesions by non-homologous end joining This DNA damage response is dependent on the function of the MEC1/RAD9 DNA checkpoint pathway. MEC 1 is a homolog of the ATM protein that coordinates the DNA damage response in mammalian cells, in part by triggering the cascade of events that lead to the stabilization of the p53 protein (Canman et al., 1998). Another major function of Sir2, gene silencing, is closely tied to the regulation of lifespan in *S. cerevisiae* (Guarente, 1999).

Double-strand breaks in the genome of mammals invoke a cascade of signaling events that ultimately cause phosphorylation and subsequent stabilization of p53 protein. In addition, these strand breaks lead to activation of p53 protein as a transcription factor. This activation may be due largely to its acetylation (Gu and Roeder, 1997; Sakaguchi et al., 1998). The resulting stabilized, activated p53 protein contributes to the upregulation of cyclin-dependent kinase inhibitors such as p21 WAF1 and hence to the cytostatic effects of p53. Alternatively, depending on the cellular background or degree of damage, the apoptotic effects of p53 may predominate through its ability to induce expression of pro-apoptotic proteins such as PIDD (Lin et al., 2000). These various phenomena indicate that specific components of the machinery that monitors the integrity of the genome are clearly able to alert p53 to the presence of genetic damage, leading to its functional activation. Conversely, in the event that damage has been successfully repaired, signals must be conveyed to p53 in order to deactivate it. Thus, a cell cycle advance that has been halted by p53 to enable repair to proceed should be relieved following completion of repair, enabling the cell to return to its active growth state. For this reason, the inactivation of p53 becomes as important physiologically as its activation.

In light of this information, modulators of Sir2 and/or p53 activity would be useful in modulating various cellular processes including, e.g., repair of DNA damage, apoptosis, oncogenesis, gene silencing and senescence, inter alia.

SUMMARY OF THE INVENTION

In one aspect, the present invention relates to methods and compositions employing p53 and Sir2 proteins. Cellular and organismal processes are regulated by modulating the activity of Sir2 and/or p53. In some cases the regulated processes control a program of regulated aging and/or metabolism of a cell or an organism. Compounds that regulate the activity of Sir2 and/or p53 can be identified, for example, by a method described herein.

As used herein, the term "Sir2" refers to a protein that is at least 25% identical to the 250 amino acid conserved Sir2 core catalytic domain, amino acids 258-451 of SEQ ID NO: 12. A Sir2 protein can be for example, at least 30, 40, 50, 60, 70, 80, 85, 90, 95, 99% identical to amino acids 258-451 of SEQ ID NO: 12. For example, the Sir2 protein is human SIRT1, GenBank Accession No: AF083106. There are at least seven different Sir2 homologs present in mammalian cells (Frye, 1999, 2000; Imai et al., 2000; Gray and Ekstrom, 2001). The mouse Sir2α and human SIRT1, are preferred Sir2 proteins.

Sir2 can be a protein (e.g., SEQ ID NOS. 8, 10, 12, 14, 16 or 18) or a fragment of the protein capable of deacetylating a substrate in the presence or NAD and/or an NAD analog and/or a fragment capable of binding to a target protein, e.g., a transcription factor. Such functions can be evaluated by a method described herein. A Sir2 fragment can include a "domain" which is a structurally stable folded unit of the full-length protein. The Sir2 protein can be encoded by the nucleic acid sequence of SEQ ID NOS. 7, 9, 11, 13, 15 or 17. In a preferred embodiment, the Sir2 is a human Sir2. A model of the three-dimensional structure of a Sir2 protein has been determined (see, e.g., Bedalov et al. (2001), Min et al. (2001), Finnin et al., (2001)) and provides guidance for identifying domains of Sir2.

A "full length" Sir2 protein refers to a protein that has at least the length of a naturally-occurring Sir2 protein. A "full length" Sir2 protein or a fragment thereof can also include other sequences, e.g., a purification tag., or other attached compounds, e.g., an attached fluorophore, or cofactor.

The invention includes sequences and variants that include one or more substitutions, e.g., between one and six substitutions, e.g., with respect to a naturally-occurring protein. Whether or not a particular substitution will be tolerated can be determined by a method described herein. One or more or all substitutions may be conservative. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "identical" or percent "identity," in the context of two or more nucleic acids or polypeptide sequences, refer to two or more sequences or subsequences that are the same or have a specified percentage of amino acid residues or nucleotides that are the same (i.e., about 50% identity, preferably 55%, 60%, 65%, 70%, 75%, 80%, 85%, 90%, 91%, 92%, 93%, 94%, 95%, 96%, 97%, 98%, 99%, or higher identity over a specified region (e.g., the C. elegans proteins provided herein), when compared and aligned for maximum correspondence over a comparison window or designated region) as measured using a sequence comparison methodology such as BLAST or BLAST 2.0 with default parameters described below, or by manual alignment and visual inspection. Such sequences are then said to be "substantially identical." This definition also refers to, or may be applied to, the complement of a test nucleic acid sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is at least 50 or 100 amino acids or nucleotides in length.

The p53 polypeptide can have greater than or equal to 25%, 50%, 75%, 80%, 90% overall identity or greater than or equal to 30%, 50%, 75%, 80%, 90% overall similarity to SEQ ID NO: 3. Preferably, the Sir2 or p53 polypeptide is a human protein (e.g., as described herein), although it may also be desirable to analyze Sir2 or p53 polypeptides isolated from other organisms such as yeast, worms, flies, fish, reptiles, birds, mammals (especially rodents), and primates using the methods of the invention.

In one aspect, the invention features a method of screening a compound. The method includes providing a reaction mixture including Sir2, a transcription factor, and the compound, and determining if the compound modulates Sir2 interaction with, e.g., binding, of the transcription factor. Determining if the compound modulates Sir2binding may be accomplished by methods known in the art, including comparing the binding of Sir2 to the transcription factor at a first concentration of the compound and at a second concentration of the compound. In a further embodiment, either of the first or second concentration of the compound may be zero, e.g., as a reference or control.

In a further embodiment, the reaction mixture also includes a Sir2 cofactor, such as NAD or an NAD analog.

In a further embodiment, the transcription factor is p53 or a Sir-2 binding fragment thereof. The transcription factor, e.g., p53, or fragment thereof may be acetylated or labeled. In a preferred embodiment, the transcription factor is an acetylated p53 fragment, and the fragment includes lysine 382.

In a further embodiment, the Sir2 included in the reaction mixture is a Sir2 variant, e.g., a variant that has reduced deacetylase activity, such as the H363Y mutation. The Sir2 may be human, e.g., human SIRT1. Alternatively, the Sir2 may be murine, e.g., Sir2α. In one embodiment of the inventions, the Sir2 is exogenous and expressed from a heterologous nucleic acid. Additionally, in a further embodiment, the transcription factor may be exogenous and expressed from a heterologous nucleic acid.

The method of screening can be used to identify compounds that modulate, e.g., increase or decrease, cell growth, modulate, e.g., slow or speed, aging, modulate, e.g., increase or decrease, lifespan, modulate cellular metabolism, e.g., by increasing or decreasing a metabolic function or rate.

In another aspect, the invention features a method of screening a compound by providing a reaction mixture comprising Sir2, a transcription factor, and the compound, and determining if the compound modulates Sir2-mediated deacetylation of the transcription factor. The step of determining if the compound modulates Sir2-mediated deacetylation of the transcription factor may be performed by methods known in the art, including comparing the binding of Sir2 to the transcription factor at a first concentration of the compound and at a second concentration of the compound. In a further embodiment, either of the first or second concentration of the compound may be zero, e.g., as a reference or control. In a further embodiment, the reaction mixture also includes a Sir2 cofactor, such as NAD or an NAD analog.

In a further embodiment, the transcription factor is p53 or a Sir-2 binding fragment thereof. The p53 or fragment thereof may be acetylated or labeled. In a preferred embodiment, the transcription factor is an acetylated p53 fragment, and the fragment includes lysine 382.

In a further embodiment, the Sir2 included in the reaction mixture is a Sir2 variant that has reduced deacetylase activity, such as the H363Y mutation. The Sir2 may be human, e.g., human SIRT1. Alternatively, the Sir2 may be murine, e.g., Sir2α.

In one embodiment of the inventions, the Sir2 is exogenous and expressed from a heterologous nucleic acid. Additionally, in a further embodiment, the transcription factor may be exogenous and expressed from a heterologous nucleic acid.

The method of screening can be used to identify compounds that modulate, e.g., increase or decrease, cell growth, modulate, e.g., slow or speed, aging, modulate, e.g., increase or decrease, lifespan, modulate cellular metabolism, e.g., by increasing or decreasing a metabolic function or rate.

The present invention also relates to a method of screening a compound by providing a compound that interacts with Sir2, e.g., a compound that binds Sir2; contacting the compound with a cell or a system; and determining if the compound modulates transcription of a p53-regulated gene. Determining if the compound modulates transcription of a p53-regulated gene may be by any of the methods known in the art, including comparing the modulation of transcription of a p53-regulated gene at a first concentration of the compound and at a second concentration of the compound. In a further embodiment, either of the first or second concentration of the compound may be zero, e.g., as a reference or control.

In a related aspect, the invention features a method of evaluating a compound, the method comprising: contacting Sir2 or a transcription factor, e.g., p53, with a test compound; evaluating an interaction between the test compound and the Sir2 or the transcription factor, e.g., p53; contacting a cell or organism that produces the Sir2 or transcription factor polypeptide with the test compound; and evaluating the effect of the test compound on the rate of aging on the cell or organism. The interaction can, for example, be a physical interaction, e.g., a direct binding interaction, a covalent change in one or both of the test compound or the Sir2 or transcription factor, a change in location of the test compound (e.g., a change in subcellular localization), or a functional interaction (e.g., an alteration in activity, stability, structure, or activity of the polypeptide).

In some embodiments, the method is repeated one or more times such that, e.g., a library of test compounds can be evaluated. In an related embodiment, the evaluating of the interaction with the test compound and the Sir2 or the transcription factor, e.g., p53, is repeated, and the evaluating of the rate of aging is selectively used for compounds for which an interaction is detected. Possible test compounds include, e.g., small organic molecules, peptides, antibodies, and nucleic acid molecules.

In some embodiments, the interaction between the test compound and the Sir2 or transcription factor, e.g., p53, is evaluated in vitro, e.g., using an isolated polypeptide. The Sir2 or transcription factor, e.g., p53, polypeptide can be in solution (e.g., in a micelle) or bound to a solid support, e.g., a column, agarose beads, a plastic well or dish, or a chip (e.g., a microarray). Similarly, the test compound can be in solution or bound to a solid support.

In other embodiments, the interaction between the test compound and the Sir2 or transcription factor, e.g., p53, is evaluated using a cell-based assay. For example, the cell can be a yeast cell, an invertebrate cell (e.g., a fly cell), or a vertebrate cell (e.g., a *Xenopus oocyte* or a mammalian cell, e.g., a mouse or human cell). In preferred embodiments, the cell-based assay measures the activity of the Sir2 or transcription factor, e.g., p53, polypeptide.

In preferred embodiments, the effect of the test compound on the rate of aging of a cell or animal is evaluated only if an interaction between the test compound and the Sir2 or transcription factor, e.g., p53, is observed.

In some embodiments, the cell is a transgenic cell, e.g., a cell having a transgene. In some embodiments, the transgene encodes a protein that is normally exogenous to the transgenic cell. In some embodiments, the transgene encodes a human protein, e.g., a human Sir2 or transcription factor, e.g., p53, polypeptide. In some embodiments, the transgene is linked to a heterologous promoter. In other embodiments, the transgene is linked to its native promoter. In some embodiments, the cell is isolated from an organism that has been contacted with the test compound. In other embodiments, the cell is contacted directly with the test compound.

In other embodiments, the rate of aging of an organism, e.g., an invertebrate (e.g., a worm or a fly) or a vertebrate (e.g., a rodent, e.g., a mouse) is determined. The rate of aging of an organism can be determined by a variety of methods, e.g., by one or more of: a) assessing the life span of the cell or the organism; (b) assessing the presence or abundance of a gene transcript or gene product in the cell or organism that has a biological age-dependent expression pattern; (c) evaluating resistance of the cell or organism to stress, e.g., genotoxic stress (e.g., etopicide, UV irradiation, exposure to a mutagen, and so forth) or oxidative stress; (d) evaluating one or more metabolic parameters of the cell or organism; (e) evaluating the proliferative capacity of the cell or a set of cells present in the organism; (f) evaluating physical appearance or behavior of the cell or organism, and (g) assessing the presence or absence of a gene transcript or gene product in the cell or organism that has a p53-regulation-dependent expression pattern. In one example, evaluating the rate of aging includes directly measuring the average life span of a group of animals (e.g., a group of genetically matched animals) and comparing the resulting average to the average life span of a control group of animals (e.g., a group of animals that did not receive the test compound but are genetically matched to the group of animals that did receive the test compound). Alternatively, the rate of aging of an organism can be determined by measuring an age-related parameter. Examples of age-related parameters include: appearance, e.g., visible signs of age; the expression of one or more genes or proteins (e.g., genes or proteins that have an age-related expression pattern); resistance to oxidative stress; metabolic parameters (e.g., protein synthesis or degradation, ubiquinone biosynthesis, cholesterol biosynthesis, ATP levels, glucose metabolism, nucleic acid metabolism, ribosomal translation rates, etc.); and cellular proliferation (e.g., of retinal cells, bone cells, white blood cells, etc.). In some embodiments, the organism is a transgenic animal. The transgenic animal can include a transgene that encodes, e.g., a copy of a Sir2 or transcription factor protein, e.g., a p53 protein, e.g., the Sir2 or transcription factor, e.g., a p53 polypeptide that was evaluated for an interaction with the test compound. In some embodiments, the transgene encodes a protein that is normally exogenous to the transgenic animal. For example, the transgene can encode a human protein, e.g., a human Sir2 or transcription factor, e.g., p53, polypeptide. In some embodiments, the transgene is linked to a heterologous promoter. In other embodiments, the transgene is linked to its native promoter. In some embodiments, the transgenic animal further comprises a genetic alteration, e.g., a point mutation, insertion, or deficiency, in a gene encoding an endogenous Sir2 or transcription factor, e.g., p53, protein, such that the expression or activity of the endogenous Sir2 or transcription factor protein is reduced or eliminated.

In some embodiments, the organism is on a calorically rich diet, while in other embodiments the organism is on a calorically restricted diet.

In some embodiments, a portion of the organism's life, e.g., at least 20%, 30%, 40%, 50%, 60%, 70%, 80%, 90%, or more, of the expected life span of the organism, has elapsed prior to the organism being contacted with the test compound.

In another aspect, the invention features a method of evaluating a protein, comprising: identifying or selecting a candidate protein, wherein the candidate protein is a Sir2 or transcription factor, e.g. p53, polypeptide; altering the sequence, expression or activity of the candidate protein in a cell or in one or more cells of an organism; and determining whether the alteration has an effect on the interaction, e.g., binding, of Sir2 with a transcription factor, e.g. p53, or on the deacetylation of transcription factor, e.g. p53.

In some embodiments, the candidate protein is identified by amplification of the gene or a portion thereof encoding the candidate protein, e.g., using a method described herein, e.g., PCR amplification or the screening of a nucleic acid library. In preferred embodiments, the candidate protein is identified by searching a database, e.g., searching a sequence database for protein sequences homologous to Sir2 or a transcription factor, e.g., p53.

In preferred embodiments, the candidate protein is a human protein. In other embodiments, the candidate protein is a mammalian protein, e.g., a mouse protein. In other embodiments, the protein is a vertebrate protein, e.g., a fish, bird or reptile protein, or an invertebrate protein, e.g., a worm or insect protein. In still other embodiments, the protein is a eukaryotic protein, e.g., yeast protein.

In another aspect, the invention features method of evaluating a protein, the method comprising a) identifying or selecting a candidate protein, wherein the candidate protein is Sir2 or a transcription factor, e.g., p53; b) identifying one or more polymorphisms in a gene, e.g., one or more SNPs that encodes the candidate protein; and c) assessing correspondence between the presence of one or more of the polymorphisms and an interaction, e.g., binding, of Sir2 with the transcription factor, e.g., p53, or with the deacetylation of the transcription factor, e.g., p53. The polymorphisms can be naturally occurring or laboratory induced. In one embodiment, the organism is an invertebrate, e.g., a fly or nematode; in another embodiment the organism is a mammal, e.g., a rodent or human. A variety of statistical and genetic methods can be used to assess correspondence between a polymorphism and longevity. Such correlative methods include determination of linkage disequilibrium, LOD scores, and the like.

In another aspect, the invention features a method of modulating cell growth in an animal, e.g., a mammal, by modulating the Sir2-mediated deacetylation of a transcription factor in the animal.

In one embodiment, the method includes modulating cell growth by increasing acetylation of p53. In a further embodiment, the method includes inactivating Sir2, e.g., by the use of antisense, RNAi, antibodies, intrabodies, NAD depletion, a dominant negative mutant of Sir2, or by the addition of Sir2 cofactor-analogs, e.g., NAD analogs such as those described in Vaziri et al. (1997) or nicotinamide. In a further embodiment, the method includes introducing a deacetylation-resistant form of p53. In still another embodiment, the invention is a method for treating a mammal, e.g., a mammal having a disease characterized by unwanted cell proliferation, e.g., cancer, accelerated senescence-related disorders, inflammatory and autoimmune disorders, Alzheimer's disease, and aging-related disorders.

In another embodiment, the method includes modulating cell growth by decreasing acetylation of p53. In a further embodiment, the method includes increasing NAD concentrations. In a further embodiment, the method includes increasing Sir2 concentrations, e.g. by addition of purified Sir2, by expression of Sir2 from heterologous genes, or by increasing the expression of endogenous Sir2, or by the addition of Sir2 cofactor-analogs, e.g., NAD analogs such as those described in Vaziri et al. (1997).

The present invention also relates to a method of modulating the growth of a cell in vivo or in vitro by modulating the Sir2-mediated deacetylation of a transcription factor in the cell.

In one embodiment, the method includes modulating the growth of a cell by increasing acetylation of p53, thereby decreasing cell growth. In a further embodiment, the method includes inactivating Sir2, e.g., by the use of antisense, RNAi, antibodies, intrabodies, NAD depletion, a dominant negative mutant of Sir2, or nicotinamide, or decreasing Sir2 activity by the addition of Sir2 cofactor-analogs, e.g., NAD analogs such as those described in Vaziri et al. (1997). In a further embodiment, the method includes introducing a deacetylation-resistant form of p53.

In one embodiment, the method includes modulating the growth of a cell by decreasing acetylation of p53, thereby increasing cell growth. In a further embodiment, the method includes increasing NAD concentrations. In a further embodiment, the method includes increasing Sir2 concentrations, e.g. by addition of purified Sir2, by expression of Sir2 from heterologous genes, or by increasing the expression of endogenous Sir2, or by the addition of Sir2 cofactor-analogs, e.g., NAD analogs such as those described in Vaziri et al. (1997).

In one aspect the invention features a method of directing Sir2 to a transcription factor binding site, e.g., a p53 binding site, and thereby modifying the acetylation status of the binding site on histone or DNA. The method includes providing a Sir2-transcription factor complex under conditions such that the transcription factor targets Sir2 to the transcription factor binding site, allowing the Sir 2 to modify the acetylation status of histones and DNA at the transcription factor binding site.

In a preferred embodiment, the method is performed in vivo or in vitro, e.g., in an animal or in a cell.

In a preferred embodiment, the Sir2-transcription factor complex is provided at a different stage of development of the cell or animal or at a greater concentration than occurs naturally.

In a preferred embodiment, the Sir2 or transcription factor or both is increased, e.g., by supplying exogenous Sir2 and/or transcription factor, e.g., p53, by supplying an exogenous nucleic acid encoding Sir2 or transcription factor, e.g., p53, or by inducing endogenous production of Sir2 or a transcription factor, e.g., p53.

In one embodiment, the present invention relates to a method of evaluating a compound, e.g., a potential modulator of Sir2 or transcription factor, e.g., p53 activity, comprising the steps of contacting the transcription factor, e.g., p53, Sir2, and NAD or an NAD analog with the compound; evaluating an interaction between the compound and one or more of the transcription factor, e.g., p53, Sir2, and a cofactor such as NAD or an NAD analog; contacting the compound with a cell or organism having transcription factor, e.g., p53 or Sir2 activity; and evaluating the rate of aging of the cell or organism. In a preferred embodiment, evaluating the rate of aging comprises one or more of:

a) assessing the life span of the cell or organism;
  b) assessing the presence or absence of a gene transcript or gene product in the cell or organism that has a biological age-dependent expression pattern;
  c) evaluating resistance of the cell or organism to stress;
  d) evaluating one or more metabolic parameters of the cell or organism;
  e) evaluating the proliferative capacity of the cell or a set of cells present in the organism;
  f) evaluating physical appearance, behavior, or other characteristic of the cell or organism; and
  g) assessing the presence or absence of a gene transcript or gene product in the cell or organism that has a p53-regulation-dependent expression pattern.

In another aspect, the invention relates to a method of identifying an agent which alters the activity of a Sir2 protein or a Sir2-like protein by assessing the NAD-dependent acetylation status of at least one amino acid in an acetylated protein (e.g., a nuclear protein such as a histone protein or p53), comprising combining the acetylated protein, the Sir2 protein or the Sir2-like protein, NAD or a NAD-like compound and the agent to be tested, thereby producing a combination; detecting the NAD-dependent acetylation status of an amino acid in the acetylated protein; and comparing the NAD-dependent acetylation status in the presence of the agent to be tested with the NAD-dependent acetylation status of the amino acid in the acetylated protein in the absence of the agent to be tested, wherein a difference in the NAD-dependent acetylation status of the amino acid of the acetylated protein between the presence of the agent and the absence of the agent indicates that the agent alters the NAD-dependent acetylation status of at least one amino acid of the acetylated protein.

The invention also provides a method of identifying an agent which alters aging of a cell or organism (e.g., C. elegans) by altering the activity of Sir2 or a Sir2-like protein by assessing the NAD-dependent acetylation status of at least one amino acid (e.g., lysine) in a protein such as a nuclear protein. The nuclear protein can be, for example, p53 or a histone protein (e.g., H2B, H3 or H4). The histone protein, a Sir2 protein or Sir2-like protein, NAD or a NAD-like compound and the agent to be tested are combined to produce a combination, the NAD-dependent acetylation status of an amino acid in the histone protein is detected (e.g., electron-spray mass spectroscopy); and compared the NAD-dependent acetylation status in the presence of the agent to be tested with the acetylation status of the amino acid in the histone protein in the absence of the agent to be tested. A difference in the acetylation status of the amino acid of the histone protein in the presence of the agent alters aging of the cell or organism (e.g., C. elegans). The agent tested can increase the aging of a cell or an organism (e.g., C. elegans) by NAD-dependent acetylation of the histone protein. Alternatively, the agent can decrease aging of the cell or the organism by NAD-dependent deacetylation of histone proteins. The agent can be an agonist of Sir2 or an antagonist of Sir2.

Agents to be tested for activity in the assays described herein can include proteins (including post-translationally modified proteins), peptides (including chemically or enzymatically modified peptides), or small molecules (including carbohydrates, steroids, lipids, anions or cations, drugs, small organic molecules, oligonucleotides, antibodies, and genes encoding proteins of the agents or antisense molecules), including libraries of compounds. The agents can be naturally occurring (e.g., found in nature or isolated from nature) or can be non-naturally occurring (e.g., synthetic, chemically synthesized or man-made). Agents which alter the level of NAD-dependent acetylation status of histone proteins or the mono-ADP-ribosylation of nuclear proteins of the invention can be agonists (e.g., stimulators/enhancers) or antagonists (e g., inhibitors) of NAD-dependent acetylation or mono-ADP-ribosylase activity. In a particular embodiment, the agents are agonists or antagonists of Sir2 (e.g., mSir2α, ySir2) dependent NAD-dependent acetylation and mono-ADP-ribosylation of proteins. The proteins can be nuclear proteins such as p53 or histone proteins (e.g., H2A, H2B, H3, H4). A "nuclear protein" refers to any protein, polypeptide or peptide that is located in or performs a function in the nucleus of a eukaryotic cell (e.g., a yeast cell, a zebrafish cell, a C. elegans cell, Drosophila melanogaster cell, or a mammalian cell, such as a murine cell or a human cell). In a preferred embodiment, the nuclear proteins are histone proteins. Histone proteins are highly conserved DNA-binding nuclear proteins that form the nucleosome, the basic subunit of the chromatin. Histone proteins can be one or more core histone proteins (e.g., H2A, H2B, H3, H4) or an outer histone protein (e.g., H1), or combinations thereof. In a more preferred embodiment, the substrate for mono-ADP-ribosylation is histone H2B or H3. In a preferred embodiment, the substrate for NAD-dependent deacetylation is a protein such as an acetylated p53 protein or an acetylated histone protein.

The details of one or more embodiments of the invention are set forth in the accompanying drawings and the description below. Other features, objects, and advantages of the invention will be apparent from the description and drawings, and from the claims.

Figure 1:
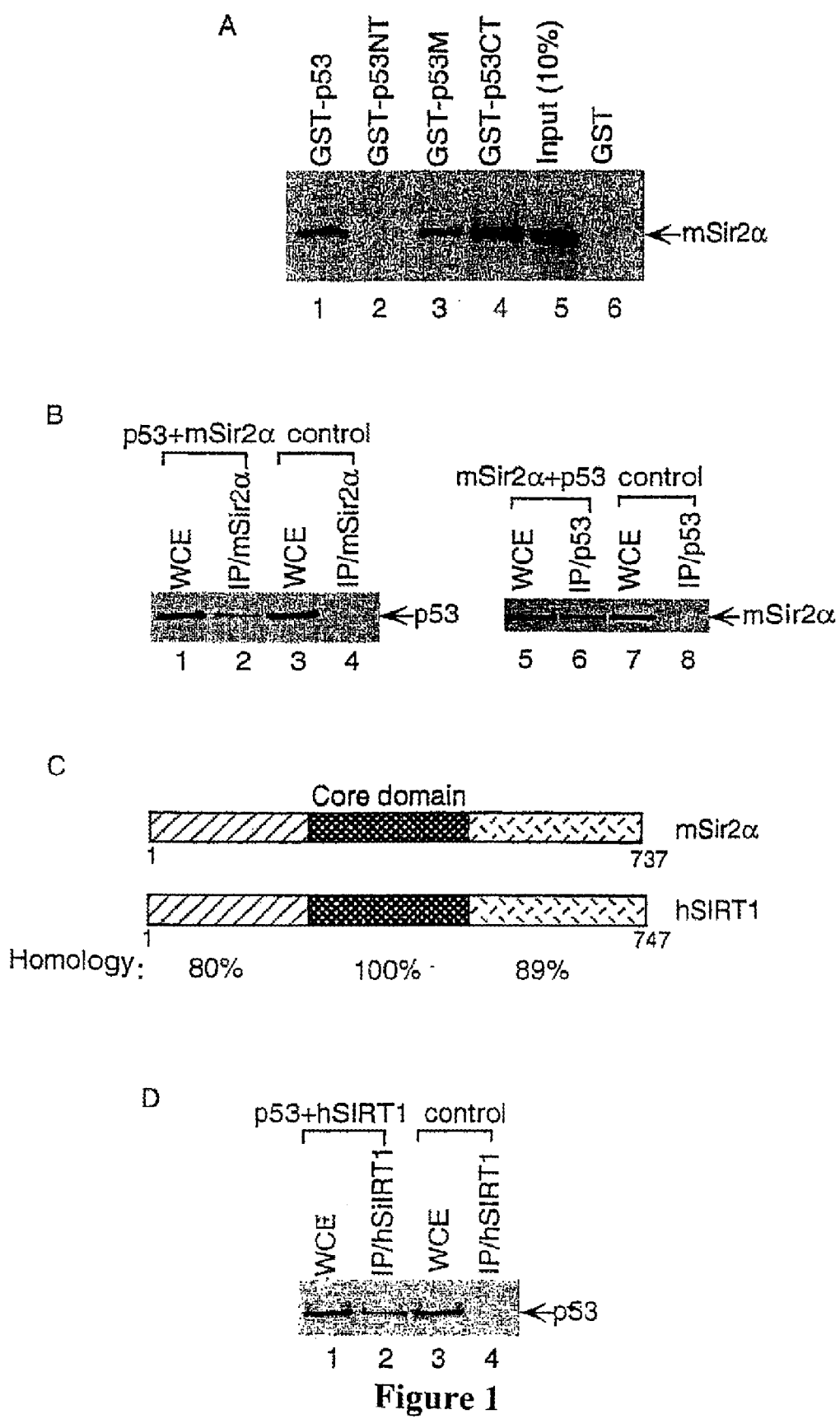
FIG. 1. Interactions between p53 and mammalian Sir2α both in vitro and in vivo.

(A) is an autoradiograph demonstrating direct interactions of Sir2α with GST-p53. The GST-p53 full length protein (GST-p53) (lane 1), the N-terminus of p53 protein (1-73) (lane 2), the middle part of p53 (100-290) (lane 3), the C-terminus of p53 (290-393) (lane 4), and GST alone (lane 6) were used in GST pull-down assay with in vitro translated $^{35}$S-labeled full length mouse Sir2α. (B) is two western blots demonstrating p53 interactions with Sir2α in H1299 cells. Western blot analyses of the indicated whole cell extract (WCE) (lanes 1, 3, 5, 7), or the p53 immunoprecipitates with M2 antibody (IP/Flag-p53) prepared from the transfected H1299 cells (lane 6, 8), or the Sir2α immunoprecipitates (IP/Flag-Sir2α) with M2 antibody prepared from the transfected H1299 cells (lanes 2, 4) with either anti-p53 monoclonal antibody (DO-1) (lanes 1-4), or anti-Sir2α polyclonal antibody (lanes 5-8). The cells were either transfected with p53 (lanes 3, 4) or Sir2α (lanes 7, 8) alone, or cotransfected with p53 and Sir2α (lanes 1, 2, 5, 6). (C) is a schematic representation of the high homology regions between mouse Sir2α and human SIRT1 (hSIRT1). The core domain represents the very conserved enzymatic domain among all Sir2 family proteins (Frye, 1999, 2000). (D) is a western blot demonstrating p53 interactions with human SIRT1 in H1299 cells. Western blot analyses of the indicated whole cell extract (WCE) (lanes 1, 3) or the Flag-hSIRT1 immunoprecipitates with M2 antibody (IP/hSIRT1) (lanes 2, 4) prepared from either the hSIRT1 and p53 cotransfected H1299 cells (lanes 1, 2) or the p53 alone transfected cells (lanes 3, 4) with anti-p53 monoclonal antibody (DO-1).

Figure 2:
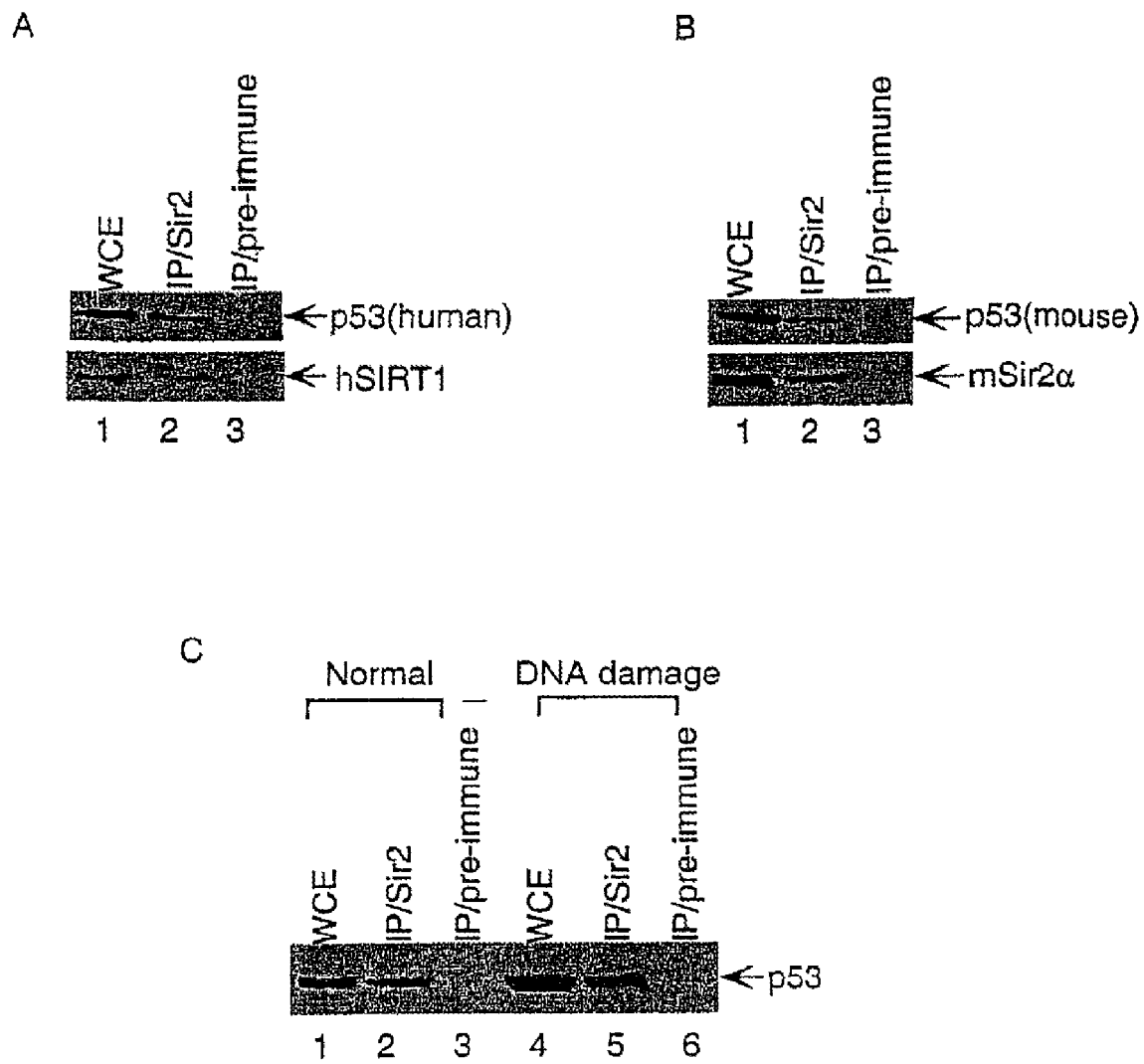

FIG. 2. P53 interacts with mammalian Sir2α (mouse Sir2α and hSIRT1) in normal cells.

(A) is two western blots demonstrating the interaction between p53 and hSIRT1 in H460 cells. (B) is two western blots demonstrating the interaction between p53 and Sir2α in F9 cells. (C) The interaction between p53 and hSIRT1 un HCT116 cells either at the normal condition (lanes, 1-3) or after DNA damage treatment by etoposide (lanes, 4-6). Western blot analyses of the indicated whole cell extract (WCE) (lanes 1, 4), or immunoprecipitates with anti-Sir2α antibody (IP/anti-Sir2α) (lanes 2, 5) prepared from different cell extracts, or control immunoprecipitates with pre-immunoserum from the same extracts (lanes 3, 6), with anti-p53 monoclonal antibodies (DO-1 for human p53, 421 for mouse p53), or anti-Sir2α antibody.

Figure 3:
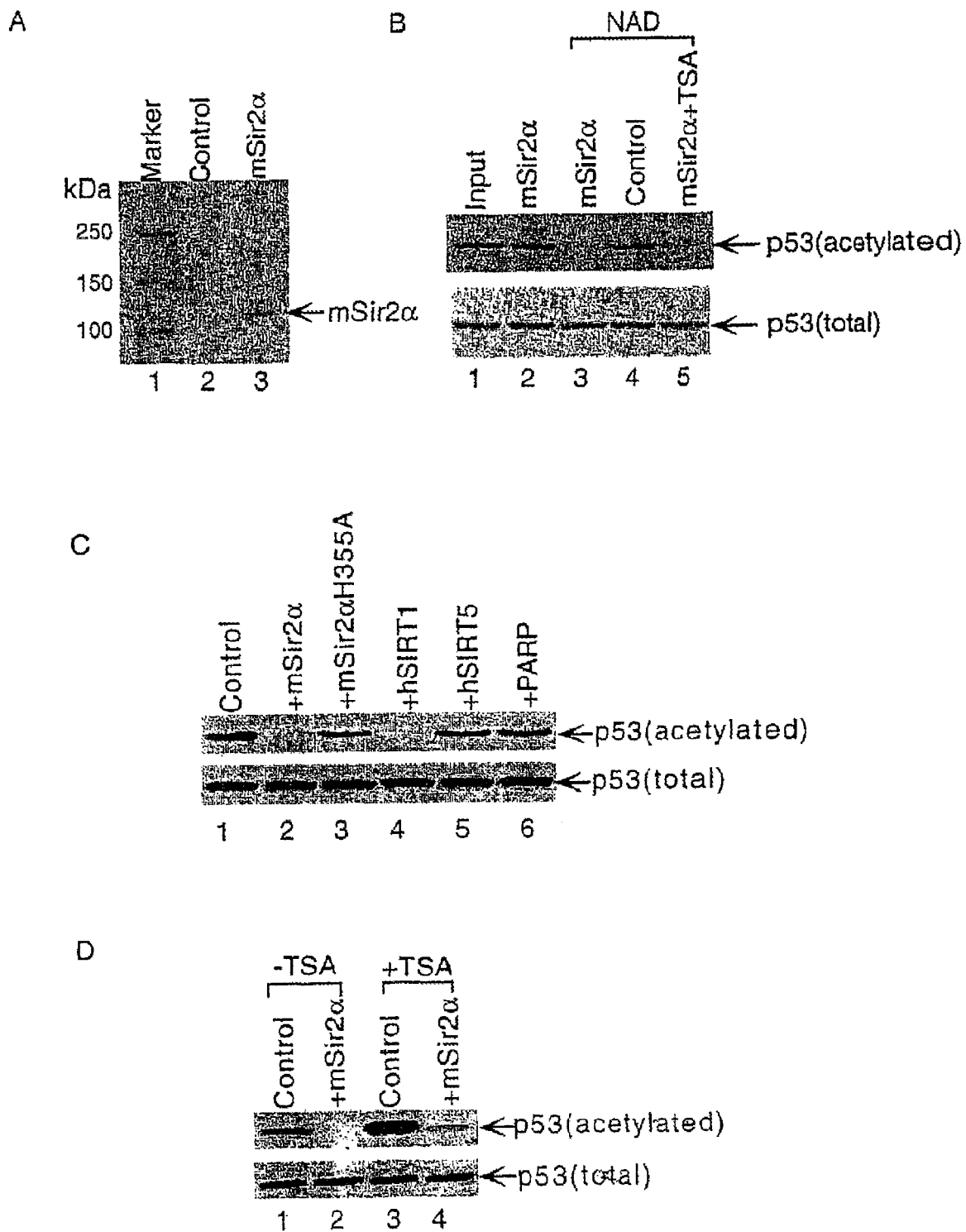

FIG. 3. TSA-insensitive deacetylation of p53 by mammalian Sir2α

(A) Colloidal blue staining of a SDS-PAGE gel containing protein Marker (lane 1), a control eluate from M2 loaded with untransfected cell extract (lane 2), and 100 ng of the highly purified Flag-tagged Sir2α recombinant protein (lane 3). (B) Deacetylation of p53 by Sir2α, 2.5 Tg of 14C-labeled acetylated p53 (lane 1) was incubated with either the control eludate (lane 4), the purified 10 ng of Sir2α (lanes 2 and 3), or the same amount of Sir2α in the presence of 500 nM TSA (lane 5) for 60 min at 30 EC. NAD (50 Tm) was also added in each reaction except lane 2. The proteins were analyzed by resolution on SDS-PAGE and autoradiography (upper) or Coomassie blue staining (lower). (C). Reduction of the steady-state levels of acetylated p53 by both mouse Sir2α and human SIRT1 expression. Western blot analysis of H1299 cell extracts from the cells cotransfected with p53 and p300 (lane 1), or in combination with Sir2α (lane 2), or in combination with hSIRT1 (lane 4), or in combination with Sir2α H355A (lane 3), in combination with hSIRT5 (lane 5), or in combination with PARP (lane 6) by acetylated p53-specific antibody (upper) or DO-1 for total p53 (lower). (D) Deacetylation of p53 by Sir2α in the presence of TSA. Western blot analysis of acetylated p53 levels in H1299 cells cotransfected with p53 and p300 (lanes 1, 3), or cotransfected with p53, p300 and Sir2α (lanes 2, 4) by acetylated p53-specific antibody (upper) or OF-1 for total p53 (lower). Cells were either not treated (lanes 1, 2) or treated with 500 nM TSA (lanes 3, 4).

Figure 4:
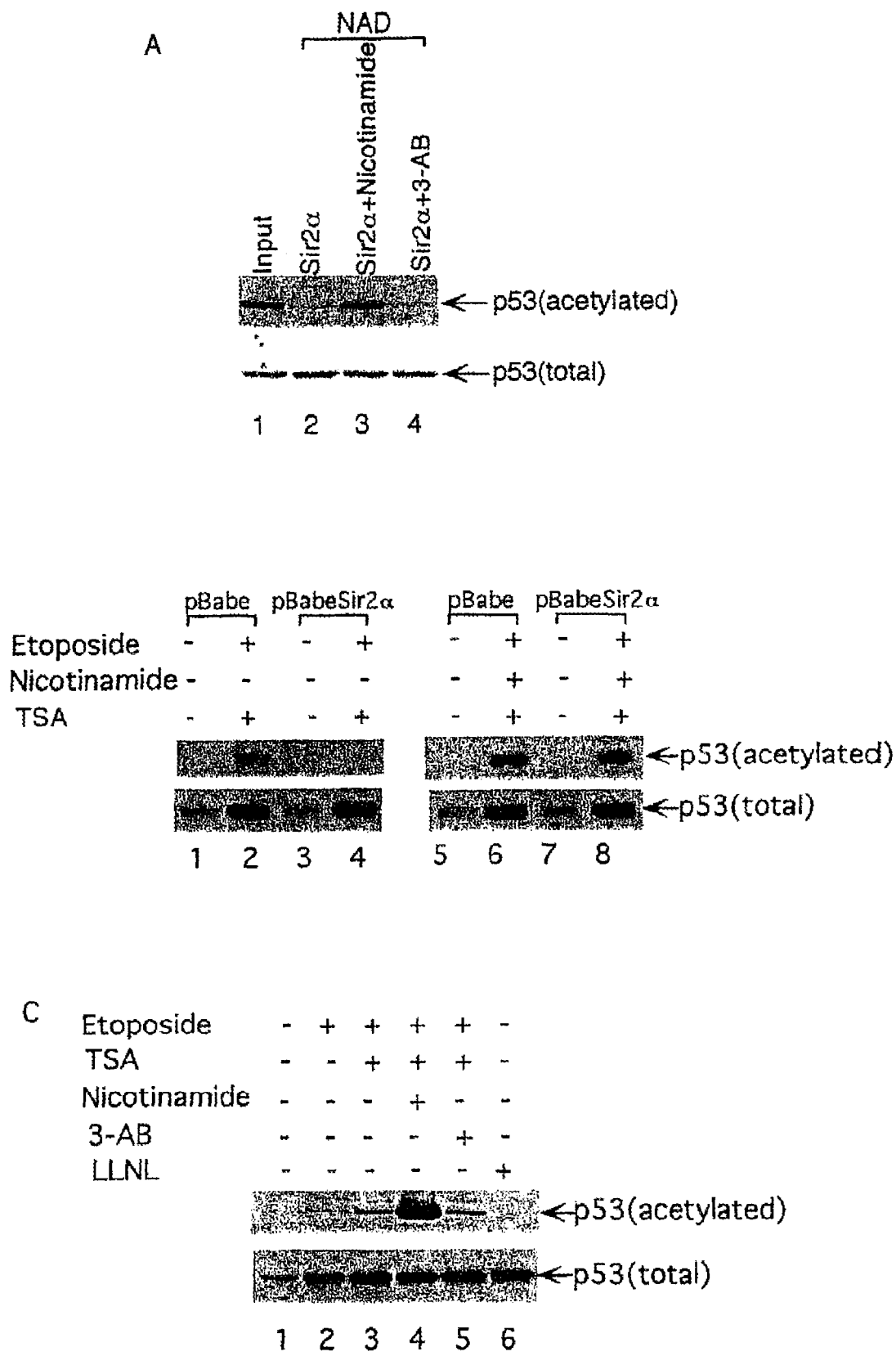

FIG. 4. Abrogation of mammalian Sir2α mediated deacetylation of p53 by nicotinamide.

(A) Sir2α-mediated deacetylation of p53 is inhibited by nicotinamide. 2.5:g of 14C-labeled acetylated p53 (lane 1) was incubated with 10 ng of purified Sir2α and 50 μM NAD alone (lane 2), or in the presence of either 5 mM of nicotinamide (lane 3) or 3 mM of 3-AB (3-aminobenzamide) (lane 4) for 60 min at 30 EC. The proteins were analyzed by resolution on SDS-PAGE and autoradiography (upper) or Coomassie blue staining (lower). (B) The Sir2α-mediated deacetylation of endogenous p53 was abrogated in the presence of nicotinamide. Cell extracts from the mock-infected MEF p53 (+/+) cell (lanes 1-2, 5-6), or the p/Babe-Sir2α-infected cells (lanes 3-4, 7-8), either untreated (lanes 1, 3, 5, 7), or treated with etoposide and TSA (lane 2, 4), or in combination with nicotinamide (lanes 6, 8) for 6 hr were analyzed by Western blot with acetylated p53-specific antibody (upper) or DO-1 for total p53 (lower). (C) Synergistic induction of p53 acetylation levels by TSA and nicotinamide during DNA damage response. Western blot analysis of cell extracts from the H460 cells treated with etoposide alone (lane 2), or in combination with TSA (lane 3), or TSA and nicotinamide (lane 4), or TSA and 3-AB (lane 5) for 6 hr by acetylated p53-specific antibody (upper) or DO-1 for total p53 (lower). The cell extracts from untreated cells (lane 1), or treated with a proteasome inhibitor LLNL (50:M) were also included (lane 6).

Figure 5:
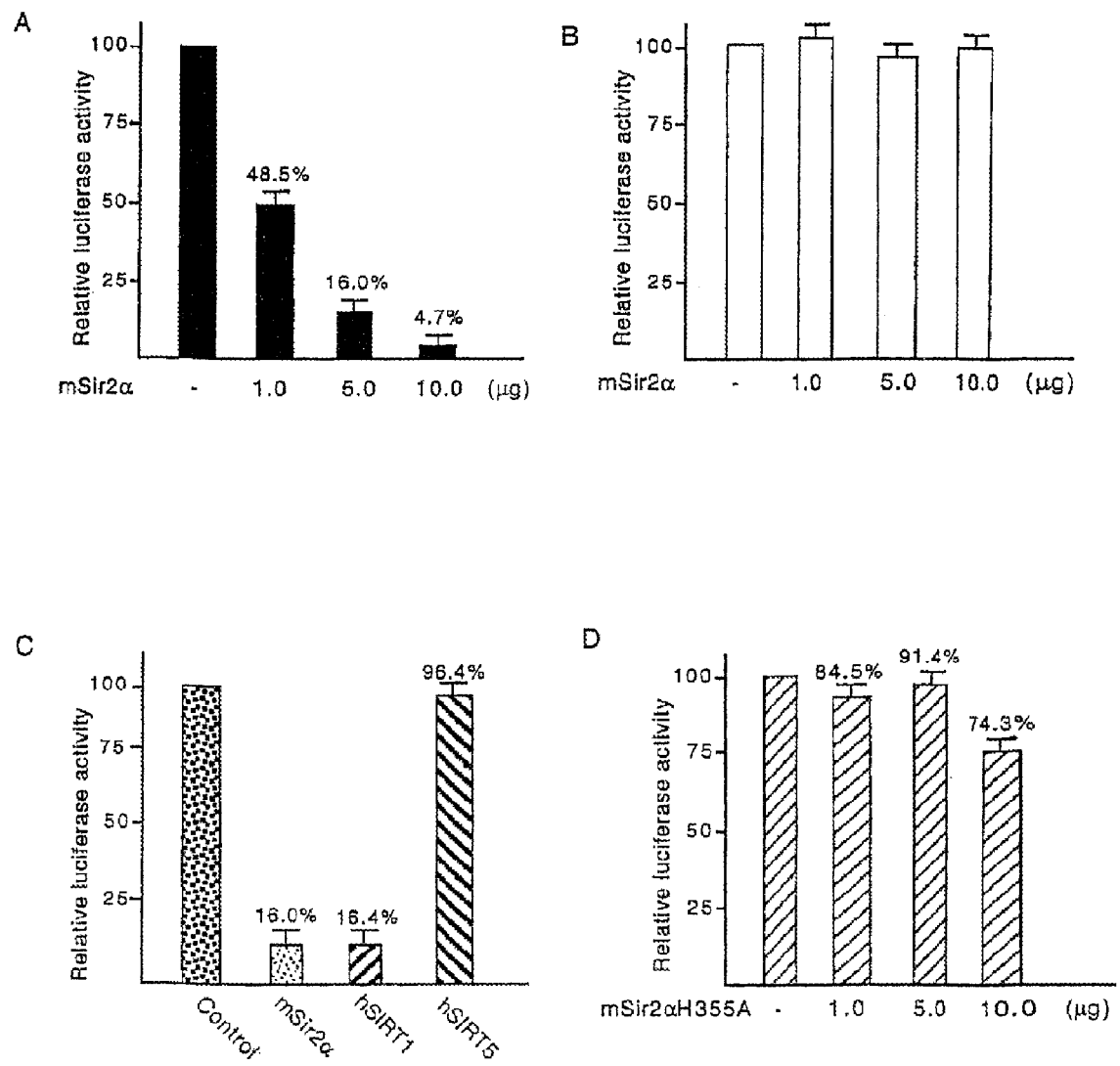

FIG. 5. Bar graphs illustrating repression of p53-mediated transcriptional activation by mammalian Sir2α.

(A), (B) MEF (p53–/–) cells were transiently transfected with 10 ng of CMV-p53 alone, or in combination with indicated Sir2α constructs together with either the PG13-Luc reporter construct (A), or a control reporter construct (TK-Luc) (B) by calcium phosphate precipitation essentially as previously described (Luo et al., 2000). (C), (D) MEF (p53–/–) cells were transiently transfected with 10 ng of CMV-p53 alone, or in combination with 5:g of either CMV-Sir2α, or CMV-hSIRT1, or CMV-hSIRT5 (C), or CMV-Sir2α H355A as indicated (D) together with the PG13-Luc reporter construct. All transfections were done in duplicate and representative experiments depict the average of three experiments with standard deviations indicated.

Figure 6A:
Figure 6B:
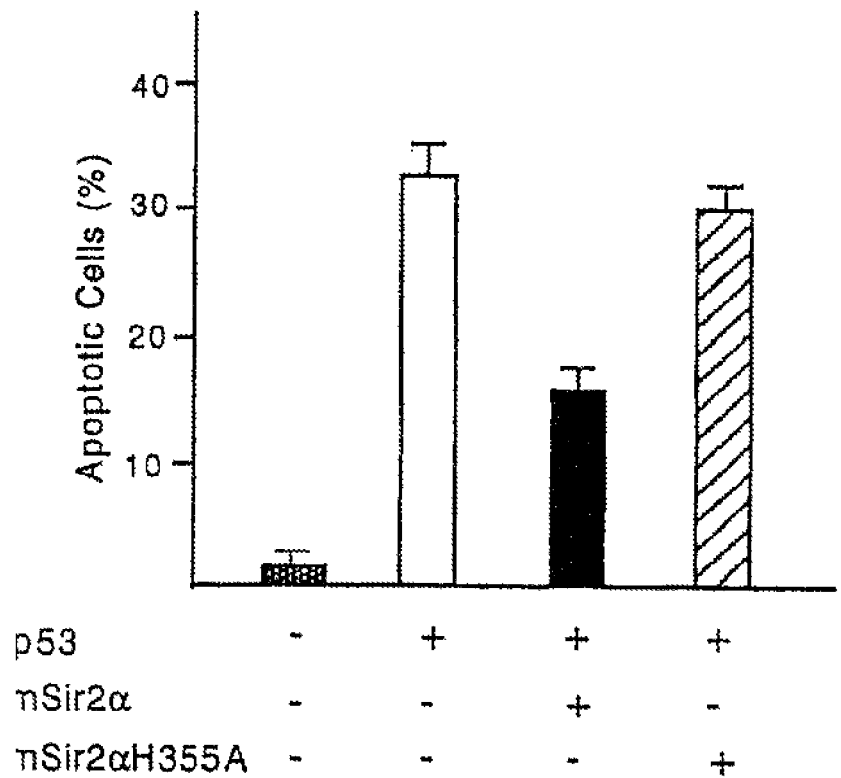

FIG. 6. Inhibition of p53-dependent apoptosis by Sir2α.

(A) H1299 cells were transfected with p53 alone, or cotransfected with p53 and Sir2α, or cotransfected with p53 and Sir2α H355A. After transfection, the cells were fixed, stained for p53 by FITC-conjugated α-p53 antibody, and analyzed by flow cymtometry for apoptotic cells (subG1) according to DNA content (PI staining) (B) The experiments were repeated at least three times; this bar graph depicts the average of three experiments with standard deviations indicated.

Figure 7A:
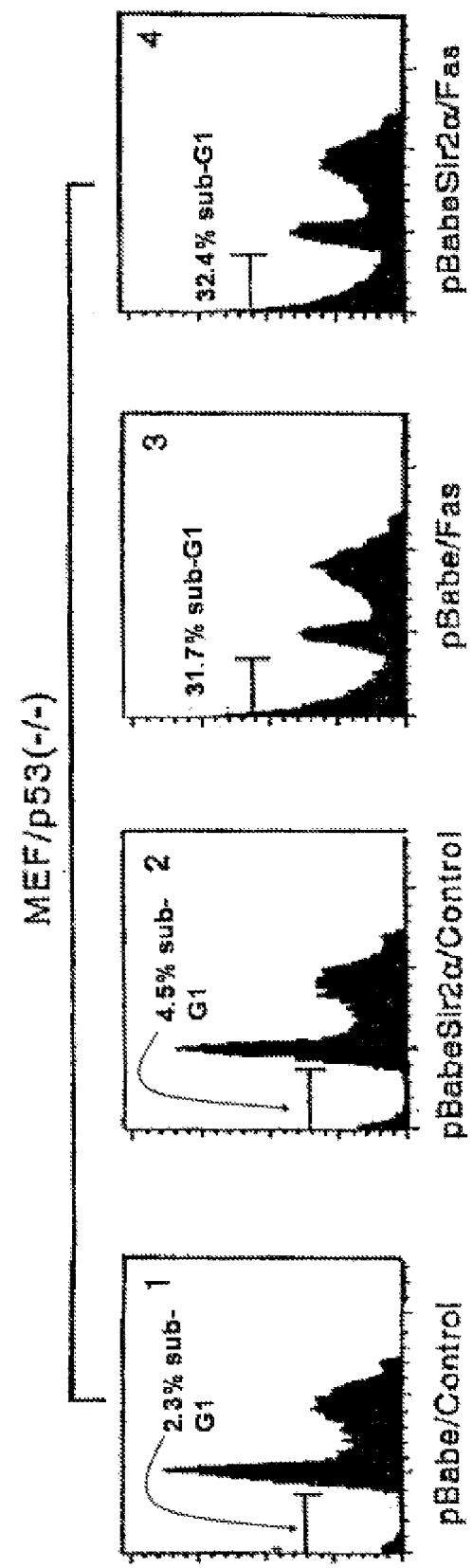
Figure 7B:
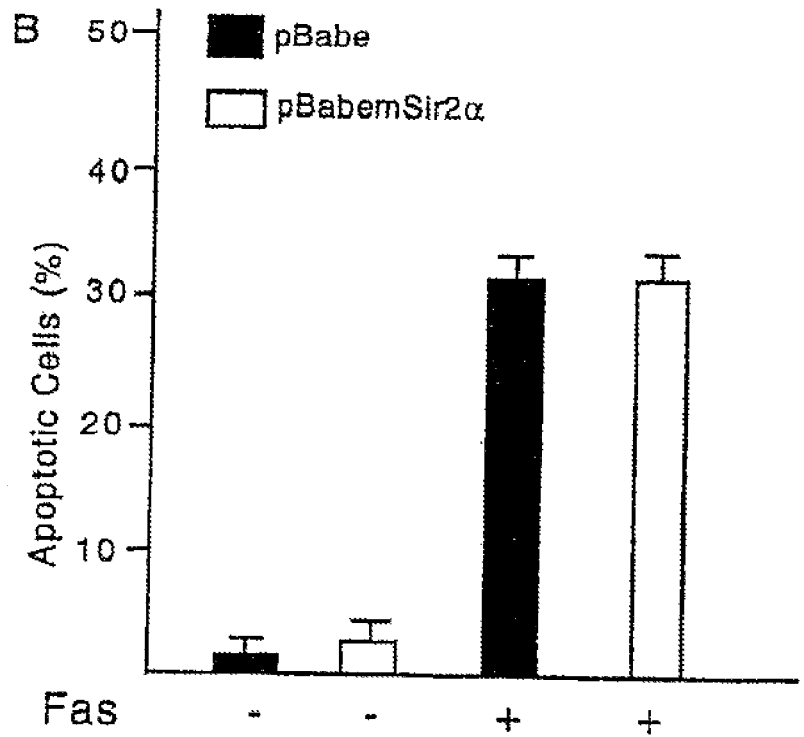

FIG. 7 Inhibition of p53-dependent apoptotic response to stress by mammalian Sir2α.

(A) Repression of the apoptotic response to DNA damage by Sir2α. Both mock infected cells and p/babe-Sir2α infected MEF p53(+/+) cells were either not treated (1 and 2) or treated with either 20 μM etoposide. The cells were analyzed by flow cytometry for apoptotic cells (subG1) according to DNA content (PI staining) (B) Similar results were obtained for three times, and this bar graph of representative data depicts the average of three experiments with standard deviations indicated (B).

Figure 8:
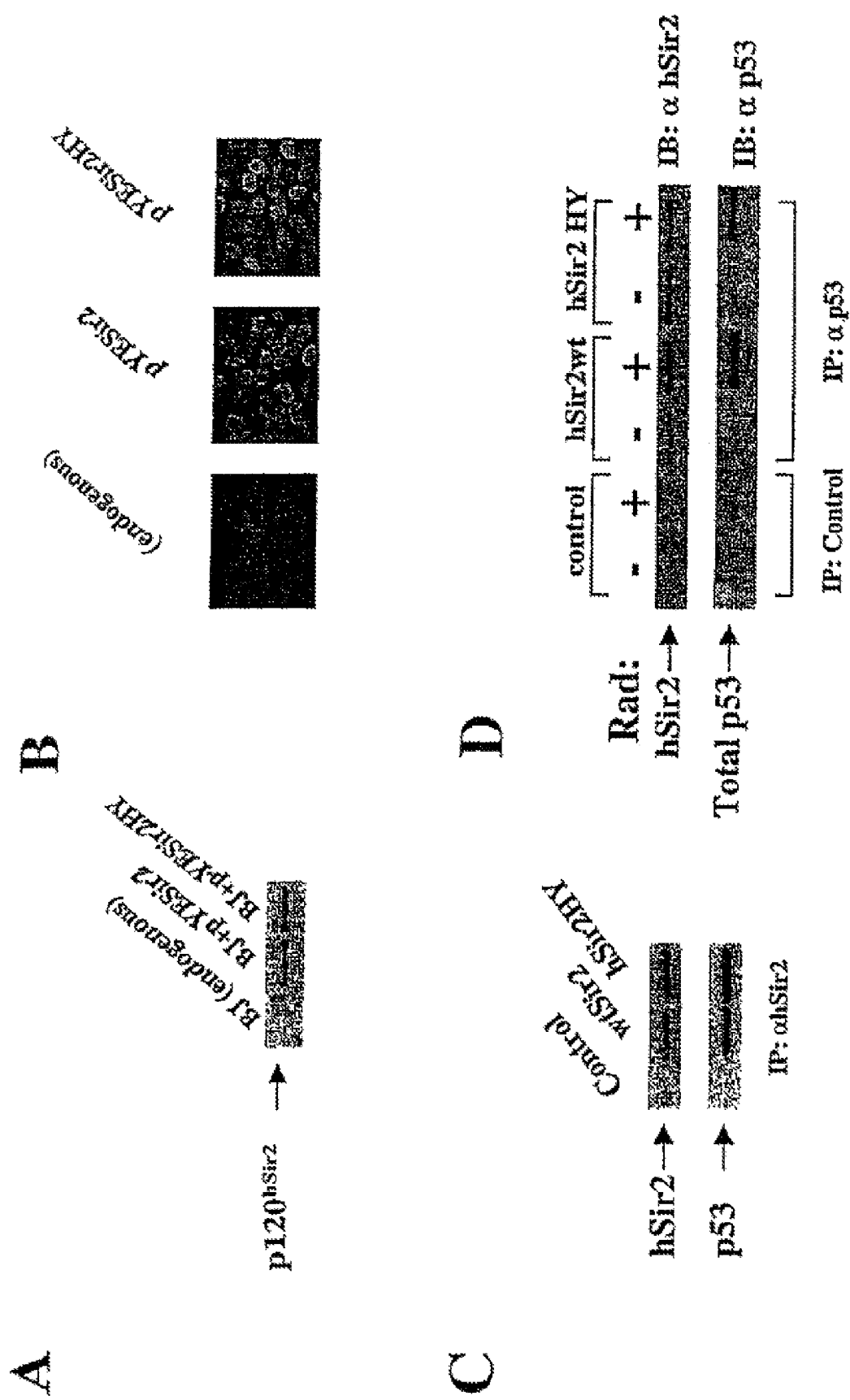

FIG. 8. Co-precipitation of hSir2 and p53 protein.

(A) Immunoprecipitation of hSir2 with a C-terminal polyclonal rabbit antibody followed by immunoblotting with the same antibody revealed the existence of a 120 Kd protein in normal BJ fibroblasts (left panel), and increased levels in these cells expressing the wild type (middle panel) and HY mutant (right panel) of hSir2. (B) Immunofluorescence analysis of hSir2 indicated the existence of a nuclear protein with a punctuate staining pattern. (C) Nuclear lysates from H1299 cells ectopically expressing p53 and hSir2 were precipitated with the anti-hSir2 antibody. The blot was probed the anti-hSir2 antibody and a polyclonal sheep anti-p53 antibody (bottom panel). (D) p53 protein was immunoprecipitated with the Do-1 anti-p53 antibody from lysates of non-irradiated and irradiated (6Gy) BJT cells (expressing telomerase) that had been stably infected with pYESir2wt and pYESir2HY mutant vectors. The blot was probed with anti-hSir2 antibody and rabbit anti-p53 polyclonal antibodies (CM1+SC6243).

Figure 9:
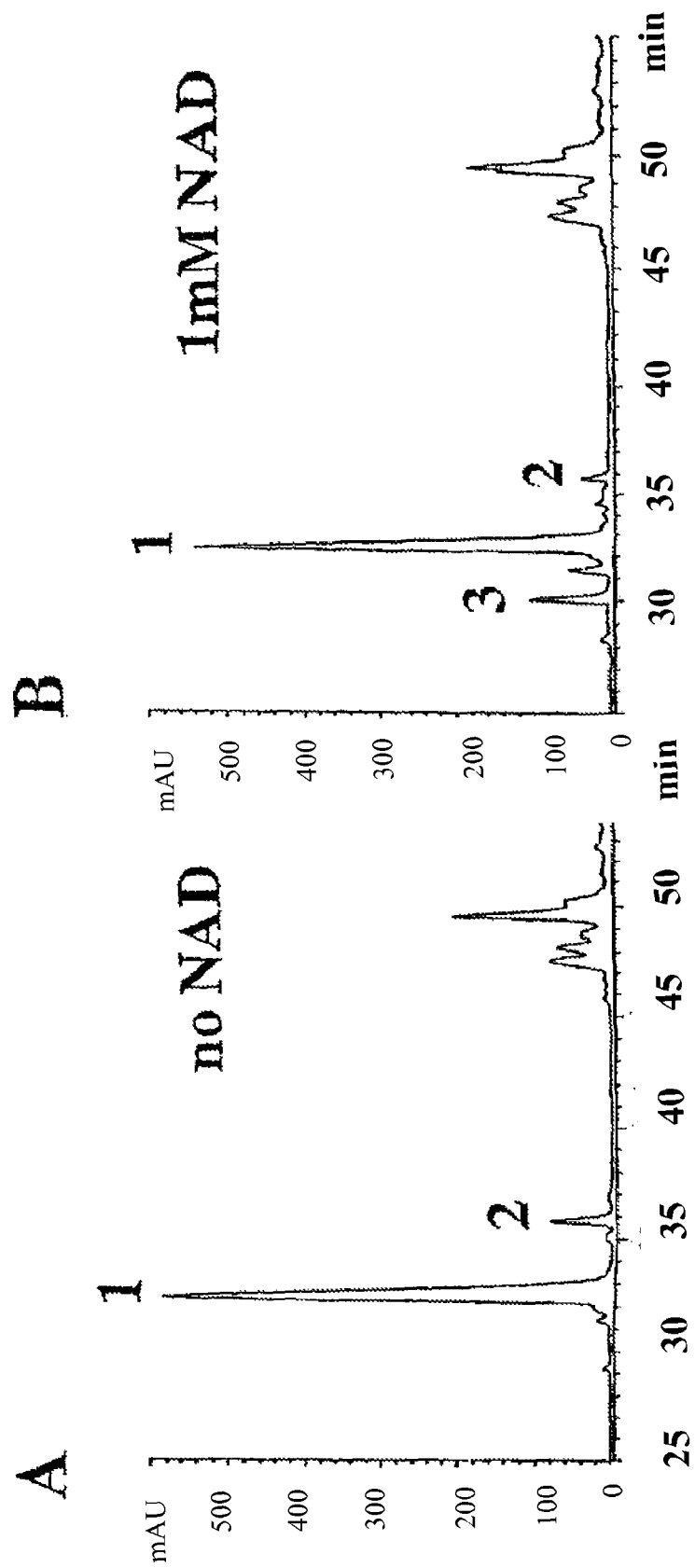
Figure 9:
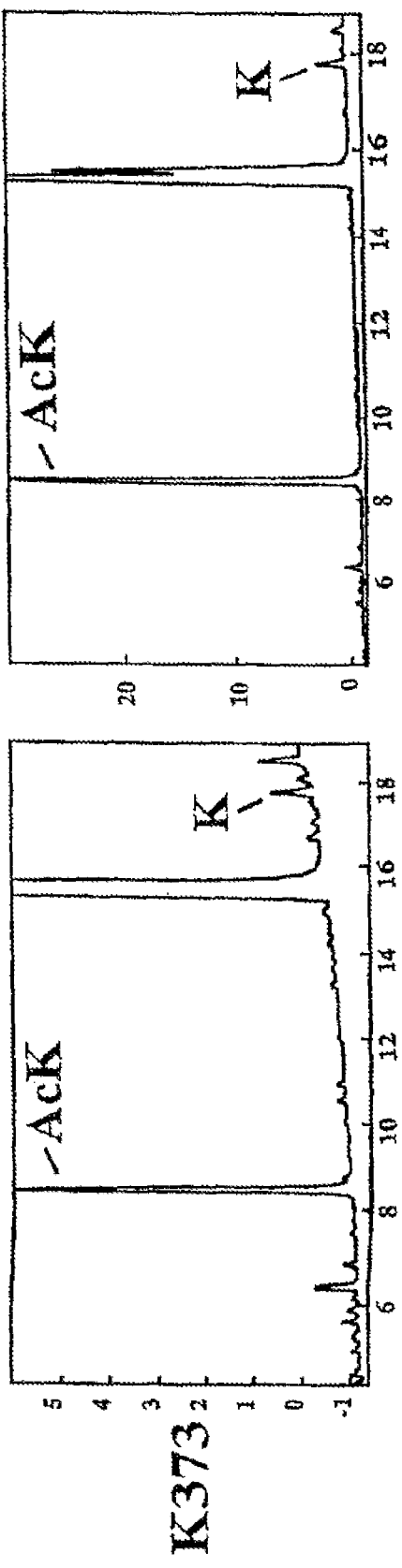
Figure 9:
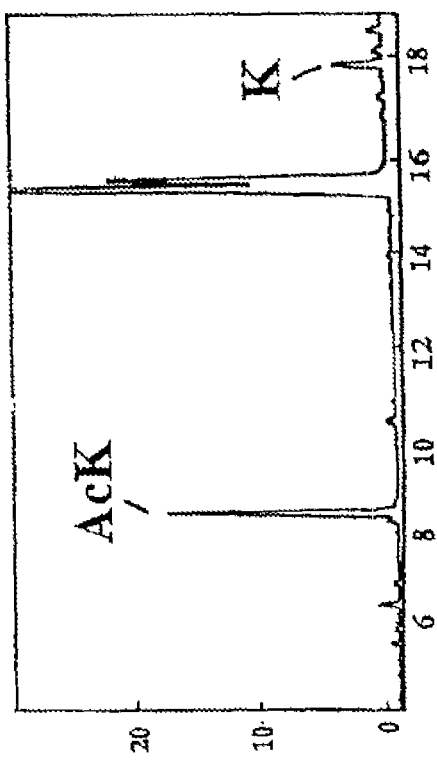
Figure 9:
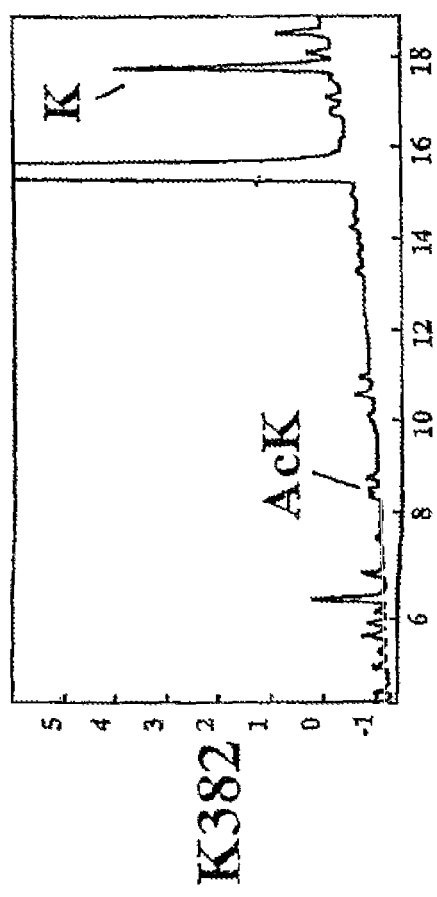

FIG. 9. Effect of hSir2 expression on p53 acetylation in vitro.

The deacetylation activity of mSir2 on the human p53 C-terminal peptide (residues 368-386) di-acetylated at positions 373 and 382. (A, B) HPLC chromatograms of products of deacetylation assays with mSir2 and the indicated concentrations of NAD. Peaks 1 and 2 correspond to the monomeric and dimeric forms of the p53 peptide, respectively. Peak 3 corresponds to the singly deacetylated monomer identified by mass spectroscopy. (C-F) Amino-terminal Edman sequencing of peaks 1 and 3. Chromatograms of positions 373 and 382 are shown. Peaks of acetyl-lysine (AcK) and simple lysine (K) are indicated in each panel. Small peaks of lysine in panels C, D and F are due to residual fractions of previous lysines at positions 372 and 381.

Figure 10:
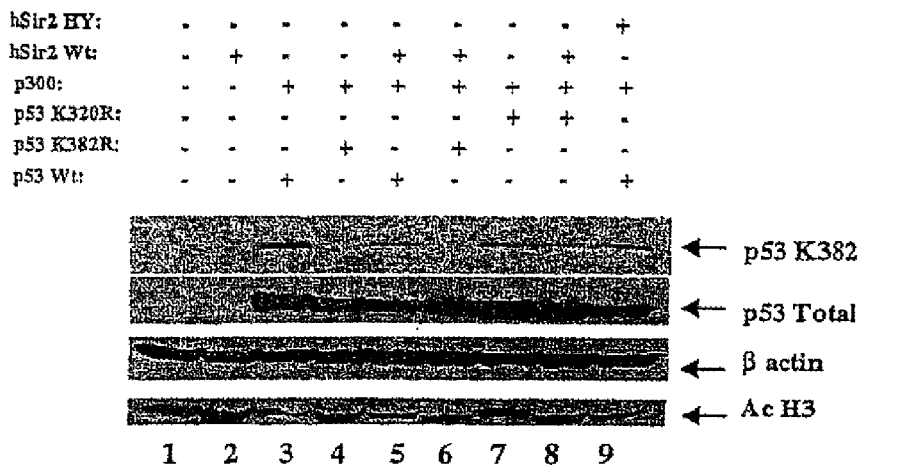
Figure 10:
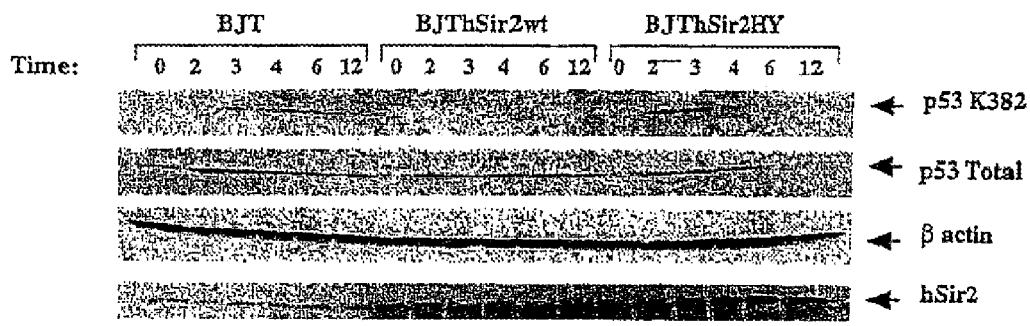
Figure 10:
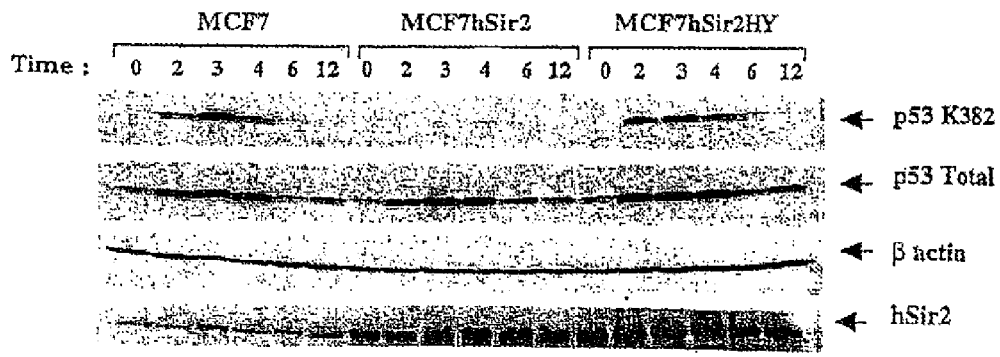

FIG. 10. hSir2 effects on p53 acetylation in vivo.

(A) Reconstitution of the acetylation and deacetylation cascade in immortal human epithelial H1299 cells by transient co-transfection of the indicated genes. After co-transfection of the mentioned constructs, the cellular lysates were analyzed by Western blot analysis, using Ab-1 to detect K382 p53, DO-1 for total p53 or θ actin for loading control. Lane 3, co-transfection of CMVwtp53 and p300 generates acetylated p53 at K382, lane 4, co-transfection of the acetylation mutant K382R of p53 with p300. Lane 5, Same as 4 but with co-transfected wild type hSir2. Lanes 7-8, co-transfection of the acetylation mutant K320R with or without wild type hSir2. Lane 9, Co-transfection of CMVwtp53, CMVp300 and wild type hSir2.

(B) BJ cells expressing telomerase (BJT), were stably infected with either a wild type hSir2 or a mutant hSir2HY virus. The hSir2-expressing mass cultures were subjected to 6Gy of ionizing radiation in presence of low concentrations of TSA (0.1 mg/ml) and the p53 acetylation was measured at indicated time points by immunoblotting with Ab-1 that recognizes specifically the deacetylated K382 p53 protein. The blots were subsequently probed with anti-p53, anti-p21, anti-σ~actin and anti-hSir2 antibodies. Time (hrs) post 6 Gy of irradiation is shown inside the brackets.

(C) Deacetylation of p53 in vivo in MCF7 cells. Four-fold ectopic expression of wild type hSir2 or hSir2HY mutant in MCF7 cells radiated with 6Gy of ionizing radiation and its effect on p53 acetylation at K382. The blot was probed for acetylation with Ab-1 and reprobed with other antibodies as in (B). Times shown are post irradiation in hours.

Figure 11:
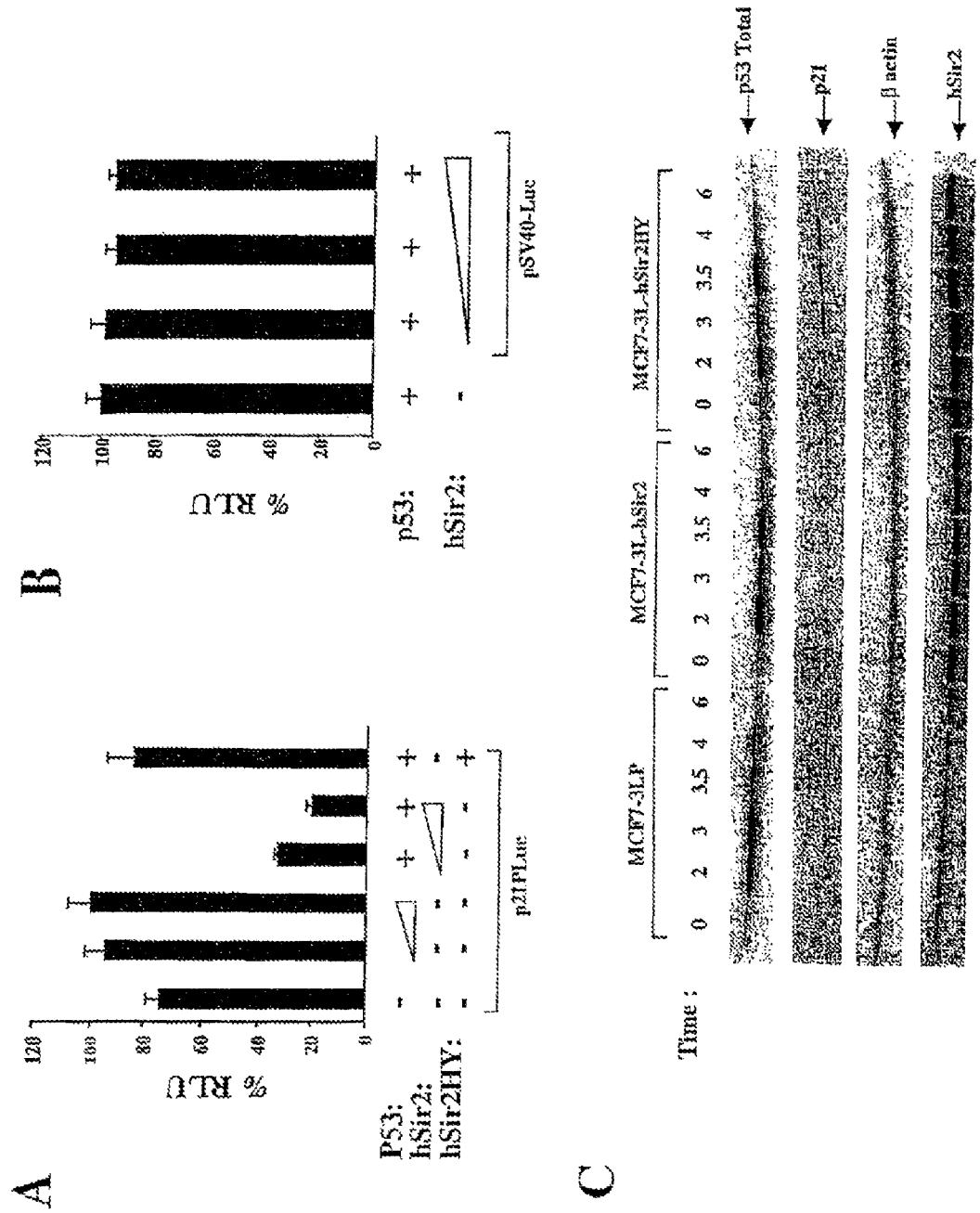

FIG. 11. hSir2 expression and its influence on p53 activity.

(A) is a bar graph depicting transcriptional activity of p53 protein, as measured in H1299 cells by co-transfection p53 with a p21WAF1 promoter-luciferase construct (p21Pluc). Transcriptional activity of p53 protein was measured upon ectopic expression of wild type hSir2, hSir2HY. (B) is a bar graph illustrating results from control SV40-Luciferase transfections with CMVp53 and increasing amounts of wild type hSir2 in to H1299 cells and luciferase activity was measured and expressed as Relative Light Unit (% RLU). (C) Is an immunoblot demonstrating levels of p21WAF1 in MCF73L cells expressing wt hSir2 or hSir2HY protein in response to 6Gy of ionizing radiation. The blot was probed with DO1 for detection of p53 and σ actin for loading control.

FIGS. 12A, 12B and 12C. The coding nucleic acid (SEQ ID NO: 2) and deduced amino acid (SEQ ID NO: 3) of human p53.

FIG. 13. The nucleic acid (SEQ ID NO: 4) sequence of human p53 (GenBank Accession No: K03199).

FIGS. 14A, B, C and D. The nucleic acid (SEQ ID NO: 5) and deduced amino acid sequence (SEQ ID NO: 6) of mouse Sir2.

FIGS. 15A, B and C. The nucleic acid (SEQ ID NO: 7) and deduced amino acid sequence (SEQ ID NO: 8) of mouse Sir2 GenBank Accession No: AF214646.

FIGS. 16A and B. The nucleic acid (SEQ ID NO: 9) and deduced amino acid sequence (SEQ ID NO: 10) of human Sir2 SIRT2 GenBank Accession No: AF083107.

FIGS. 17A, B and C. The nucleic acid (SEQ ID NO: 11) and deduced amino acid sequence (SEQ ID NO: 12) of human Sir2 SIRT1 GenBank Accession No: AF083106.

FIG. 18. The nucleic acid (SEQ ID NO: 13) and deduced amino acid sequence (SEQ ID NO: 14) of human Sir2 SIRT3 GenBank Accession No: AF083108.

FIGS. 19A and B. The nucleic acid (SEQ ID NO: 15) and deduced amino acid sequence (SEQ ID NO: 16) of human Sir2 SIRT4 GenBank Accession No: AF083109.

FIGS. 20A and B. The nucleic acid (SEQ ID NO: 17) and deduced amino acid sequence (SEQ ID NO: 18) of human Sir2 SIRT5 GenBank Accession No: AF083110.

DETAILED DESCRIPTION OF THE INVENTION

As described below, hSir2 directly binds the human p53 protein both in vitro and in vivo and can deacetylate p53, e.g., at the K382 residue of p53. A functional consequence of this deacetylation is an attenuation of the p53 protein's activity, e.g., as a transcription factor operating at a cellular promoter, e.g., the p21WAF1 promoter. In another cellular context, in which the DNA damage response leads to apoptosis, hSir2 activity attenuates the p53-dependent apoptotic response. Hence, hSir2 can negatively regulate a program of cellular death.

Sir2 proteins can also deacetylate histones. For example, Sir2 can deacetylate lysines 9 or 14 of histone H3. Histone deacetylation alters local chromatin structure and consequently can regulate the transcription of a gene in that vicinity. Sir2 proteins can bind to a number of other proteins, termed "Sir2-binding partners." For example, hSIRT1 binds to p53. In many instances the Sir-2 binding partners are transcription factors, e.g., proteins that recognize specific DNA sites. Interaction between Sir2 and Sir2-binding partners delivers Sir2 to specific regions of a genome and can result in local modification of substrates, e.g., histones and transcription factors localized to the specific region. Accordingly, cellular processes can be regulated by compounds that alter (e.g., enhance or diminish) the ability of a Sir2 protein to interact with a Sir2-binding partner or that alter that ability of a Sir2 protein to modify a substrate. While not wishing to be bound by theory, a Sir2-transcription factor complex may be directed to a region of DNA with a transcription factor binding site; once there, Sir2 may alter the acetylation status of the region, e.g., by deacetylating histones, non-histone proteins, and/or DNA. This would locally raise the concentration of Sir2 and may potentially result in the Sir2-mediated silencing of genes located at or near transcription-factor binding sites. Certain organismal programs such as aging or metabolism and disorders such as cancer can be controlled using such compounds.

While not wishing to be bound by theory, in mammalian cells, signals indicating the successful completion of DNA repair may be relayed via hSir2 to acetylated proteins like p53 that have been charged with the task of imposing a growth arrest following DNA damage. These signals enable hSir2 to reverse part or all of the damage-induced activation of p53 as a transcription factor by deacetylating the K382 residue of p53. By doing so, hSir2 reduces the likelihood of subsequent apoptosis and, at the same time, makes it possible for cells to re-enter the active cell cycle, enabling them to return to the physiological state that they enjoyed prior to sustaining damage to their genomes.

Inactivation of the p53 signaling pathway is involved in the pathogenesis of most if not all human tumors (Hollstein et al., 1994; Lohrum and Vousden, 1999). In about half of these tumors, mutation of the p53 gene itself suffices to derail function. In some of the remaining tumors, loss of $p14^{ARF}$, which acts to down-regulate p53 protein levels, has been implicated (Lohrum and Vousden, 1999; Prives and Hall, 1999). The present invention is related to the discovery of a novel mode by which an incipient cancer cell attenuate at least some p53 functions via modulation of the activity of hSir2, which, like the other two genetic strategies, may result in the inactivation of both the cytostatic and pro-apoptotic functions of p53.

The invention is thus based in part on the discovery of the existence of a p53 regulatory pathway that is regulated by mammalian Sir2α. Sir2α is involved in gene silencing and extension of life span in yeast and C. elegans (reviewed in Guarente, 2000; Shore, 2000; Kaeberlein et al., 1999; Tissenbaun and Guarente, 2001). p53 binds to mouse Sir2α as well as its human ortholog hSIRT1 both in vitro and in vivo. p53 is a substrate for the NAD-dependent deacetylase activity of mammalian Sir2α. Sir2α-mediated deacetylation antagonizes p53-dependent transcriptional activation and apoptosis. Sir2α-mediated deacetylation of p53 is inhibited by nicotinamide both in vitro and in vivo. Sir2α specifically inhibits p53-dependent apoptosis in response to DNA damage and/or oxidative stress, but not p53-independent, Fas-mediated cell death. Accordingly, compounds that alter (e.g., decrease or enhance) the interaction between Sir2 and p53 can be used to regulate processes downstream of p53, e.g., apoptosis. Such compounds may alter the catalytic activity of Sir2 for a substrate such as p53 or may alter the interaction between Sir2 and p53.

The present invention relates to the discovery that p53 is a binding partner of mammalian Sir2α, which physically binds to p53 both in vitro and in vivo. In some cases, p53 is also a substrate of Sir2. Sir2α specifically represses p53-mediated functions including p53-dependent apoptotic response to stress.

p53 can be, for example, the mature protein (e.g., SEQ ID NO: 3) or a fragment thereof. The p53 protein can be encoded by the nucleic acid sequence of SEQ ID NOS. 2 and/or 4). In a preferred embodiment, p53 is the human p53. Deacetylation of p53 can be mediated by Sir2, e.g., in combination with a cofactor, such as NAD and/or an NAD analog.

The phrase "deacetylating p53" refers to the removal of one or more acetyl groups (e.g., $CH_3CO^{2-}$) from p53 that is acetylated on at least one amino acid residue. In a preferred embodiment, p53 is deacetylated at a lysine of p53 selected from the group consisting of lysine 370, lysine 371, lysine 372, lysine 381 and lysine 382 of SEQ ID NO: 3. p53 can be deacetylated in the presence or absence of DNA damage or oxidative cellular stress. The DNA damage can be caused by, for example, ionizing radiation (e.g., 6 Gy of ionizing radiation), or a tumor or some other uncontrolled cell proliferation. p53 is deacetylated in the presence of DNA damage or oxidative stress by combining p53, Sir2, NAD and/or an NAD analog.

Sir2 can be the mature protein (e.g., SEQ ID NOS. 8, 10, 12, 14, 16 or 18) or a fragment of the mature protein capable of deacetylating p53 in the presence or NAD and/or an NAD analog. The Sir2 protein can be encoded by the nucleic acid sequence of SEQ ID NOS. 7, 9, 11, 13, 15 or 17). In a preferred embodiment, the Sir2 is human Sir2.

In one embodiment, the invention is a method of deacetylating p53 comprising the step of combining Sir2 and NAD and/or an NAD analog with p53. The combination can be performed in the presence or the absence of cells. Such combinations can be in tissue culture (e.g., BJT cells, MCF-7 cells) or in an organism (e.g., a mammal, e.g., as a human). Combination of p53, Sir2 and NAD and/or an NAD analog can be any placement of p53, Sir 2 and NAD or a NAD analog in sufficient proximity to cause Sir2 to deacetylate p53 that is acetylated on at least one amino acid residue, which deacetylation by Sir2 requires the presence of NAD and/or an NAD analog.

"NAD" refers to nicotinamide adenine dinucleotide. An "NAD analog" as used herein refers to a compound (e.g., a synthetic or naturally occurring chemical, drug, protein, peptide, small organic molecule) which possesses structural similarity to component groups of NAD (e.g., adenine, ribose and phosphate groups) or functional similarity (e.g., deacetylates p53 in the presence of Sir2). For example, an NAD analog can be 3-aminobenzamide or 1,3-dihydroisoquinoline (H. Vaziri et al., EMBO J. 16:6018-6033 (1997), the entire teachings of which are hereby incorporated by reference).

"p53 activity" refers to one or more activity of p53, e.g., p-53 mediated apoptosis, cell cycle arrest, and/or senescence.

"Modulating p53 activity" refers to increasing or decreasing p53 activity, e.g., p-53 mediated apoptosis, cell cycle arrest, and/or senescence, e.g. by altering the acetylation or phosphorylation status of p53.

"Acetylation status" refers to the presence or absence of one or more acetyl groups (e.g., $CH_3CO^{2-}$) at one or more lysine (K) residues, e.g., K370, K371, K372, K381, and/or K382 of SEQ ID NO: 3. "Altering the acetylation status" refers to adding or removing one or more acetyl groups (e.g., $CH_3CO^{2-}$) at one or more lysine (K) residues, e.g., K370, K371, K372, K381, and/or K382 of SEQ ID NO: 3, e.g., by modulating Sir2 activity.

Similarly, "phosphorylation status" refers to the presence or absence of one or more phosphate groups ($PO_3^-$) at one or more residues, e.g., serine 15 and/or serine 20 of SEQ ID NO: 3. "Altering the phosphorylation status" refers to adding or removing one or more phosphate groups ($PO_3^-$) at one or more residues, e.g., serine 15 and/or serine 20 of SEQ ID NO: 3.

"Sir2 activity" refers to one or more activity of Sir2, e.g., deacetylation of p53 or histone proteins.

"Modulating Sir2 activity" refers to increasing or decreasing one or more activity of Sir2, e.g., deacetylation of p53 or histone proteins, e.g., by altering the binding affinity of Sir2 and p52, introducing exogenous Sir2 (e.g., by expressing or adding purified recombinant Sir2), increasing or decreasing levels of NAD and/or an NAD analog (e.g., 3-aminobenzamide, 1,3-dihydroxyisoquinoline), and/or increasing or decreasing levels of a Sir2 inhibitor, e.g., nicotinamide and/or a nicotinamide analog. Additionally or alternatively, modulating Sir2 activity can be accomplished by expressing, e.g. by transfection, a dominant negative gene of Sir2 (e.g., SirHY). The dominant negative gene can, for example, reduce the activity of endogenous Sir2 on p53 deacetylation thereby modulating the activity of Sir2.

A "nicotinamide analog" as used herein refers to a compound (e.g., a synthetic or naturally occurring chemical, drug, protein, peptide, small organic molecule) which possesses structural similarity to component groups of nicotinamide or functional similarity (e.g., reduces Sir2 deacetylation activity of p53).

The Sir2α-Mediated Pathway is Critical for Cells Under Stress

It is believed that there are multiple pathways in cells for regulation of p53 function (Prives and Hall, 1999; Giaccia and Kastan, 1998; Ashcroft et al., 2000). In normal cells, Mdm2 is the major negative regulator for p53, and Mdm2-mediated repression appears sufficient to downregulate p53 activity. Sir2 regulation of p53 may be an Mdm2-independent, negative regulatory pathway for p53. Interestingly, while no obvious effect by Sir2α expression was observed in cells at normal conditions, Sir2α became critical in protecting cells from apoptosis when cells were either treated by DNA damage or under oxidative stress (FIG. 7). Thus, Sir2α-mediated pathway can be critical for cell survival when the p53 negative-control mediated by Mdm2 is severely attenuated in response to DNA damage or other types of stress.

p53 is often found in latent or inactive forms and the levels of p53 protein are very low in unstressed cells, mainly due to the tight regulation by Mdm2 through functional inhibition and protein degradation mechanisms (reviewed in Freedman et al., 1999). However, in response to DNA damage, p53 is phosphorylated at multiple sites at the N-terminus; these phosphorylation events contribute to p53 stabilization and activation by preventing Mdm2 binding to p53 (reviewed in Appella and Anderson, 2000; Giaccia and Kastan, 1998; Shieh et al., 1997, 2000; Unger et al., 1999; Hirao et al., 2000). Mdm2 itself is also phosphorylated by ATM during DNA damage response, and this modification attenuates its inhibitory potential on p53 (Maya et al., 2001). Furthermore, while p53 is strongly stabilized and highly acetylated in stressed cells, acetylation of the C-terminal multiple lysine sites may occur at the same sites responsible for Mdm2-mediated ubiquitination (Rodriguez et al., 2000; Nakamura et al., 2000), and the highly acetylated p53 may not be effectively degraded by Mdm2 without deacetylation (Ito et al., 2001). Thus, in contrast to unstressed cells, the main p53 negative regulatory pathway mediated by Mdm2 is blocked at several levels in response to DNA damage (Maya et al., 2001). Under these circumstances, Sir2α-mediated regulation may become a major factor in controlling p53 activity, making it possible for cells to adjust p53 activity to allow time for DNA repair before committing to apoptosis.

In oncogene-induced premature senescence of cells, the p53 negative regulatory pathway controlled by Mdm2 may be blocked (reviewed in Sherr and Weber, 2000; Sharpless and Depinho, 1999; Serrano et al., 1997). However, in contrast to DNA damage response, the Mdm2-mediated pathway is abrogated by induction of p14$^{ARF}$ (or mouse p19$^{ARF}$) in these cells (Honda and Yasuda, 1999; Weber et al., 1999; Tao et al., 1999a, 1999b; Zhang et al., 1998; Pomerantz et al., 1998). Furthermore, when primary fibroblasts undergo senescence, a progressive increase of the p53 acetylation levels was observed in serially passaged cells (Pearson et al., 2000). Oncogenic Ras and PML induced p53-dependent premature senescence, and upregulated the p53 acetylation levels in both mouse and human normal fibroblasts (Pearson et al., 2000; Ferbeyre et al., 2000). Thus, mammalian Sir2α-mediated regulation may also play an important role in oncogene-induced premature senescence.

Attenuation of p53-Mediated Transactivation by Sir2α

Earlier studies indicated that p53-mediated transcriptional activation is sufficient and also absolutely required for its effect on cell growth arrest, while both transactivation-dependent and -independent pathways are involved in p53-mediated apoptosis (reviewed in Prives and Hall, 1999; Vousden, 2000). p53 may be effective to induce apoptosis by activating pro-apoptotic genes in vivo (reviewed in Nakano and Vousden, 2001; Yu et al., 2001). Thus, tight regulation of p53-mediated transactivation is critical for its effect on both cell growth and apoptosis (Chao et al., 2000; Jimenez et al., 2000).

Recent studies indicate that the intrinsic histone deacetylase activity of Sir2α is essential for its mediated functions (reviewed in Gurante, 2000). Reversible acetylation was originally identified in histones (reviewed in Cheung et al., 2000; Wolffe et al., 2000); however, accumulating evidence indicates that transcriptional factors are also functional targets of acetylation (reviewed in Serner and Berger, 2000; Kouzarides, 2000). Thus, the transcriptional attenuation mediated by histone deacetylases may act through the effects on both histone and non-histone transcriptional factors (Sterner and Berger, 2000; Kuo and Allis, 1998). Microarray surveys for transcriptional effects of Sir2 in yeast revealed that Sir2 appears to repress amino acid biosynthesis genes, which are not located at traditional "silenced" loci (Bernstein et al., 2000). Thus, in addition to silencing (repression) at telomeres, mating type loci and ribosomal DNA (reviewed in Guarente, 2000; Shore, 2000), Sir2 may also be targeted to specific endogenous genes for transcriptional regulation in yeast.

In contrast to the yeast counterpart Sir2, the mouse Sir2α protein does not colocalize with nucleoli, telomeres or centromeres by co-immunofluorescence assay, indicating that this protein is not associated with the most highly tandemly repeated DNA in the mouse genome. The immunostaining pattern of human SIRT1 as well as mouse Sir2α indicates that mammalian Sir2α is, similar to HDAC1, broadly localized in the nucleus, further supporting the notion that mammalian Sir2α may be recruited to specific target genes for transcriptional regulation in vivo.

Mammalian Sir2α may inhibit p53-mediated functions by attenuation of the transcriptional activation potential of p53. Since deacetylation of p53 is critical, but may not be the only function mediated by this Sir2α-p53 interaction, additional functions mediated by Sir2α, such as histone deacetylation, may also contribute to this regulation. As one theory, not meant to be limiting, p53 and Sir2α may strongly interact to deacetylate p53 and possibly recruit the p53-Sir2α complex to the target promoter. The subsequent transcription repression may act both through decreasing p53 transactivation capability and through Sir2α-mediated histone deacetylation at the target promoter region. In contrast to HDAC 1-mediated effect, this transcriptional regulation is not affected by TSA treatment. Other cellular factors may use a similar mechanism to recruit Sir2α for TSA-insensitive transcriptional regulation in mammalian cells.

Novel Implications for Cancer Therapy

Inactivation of p53 functions has been well documented as a common mechanism for tumorigenesis (Hollstein et al., 1999; Vogelstein et al., 2000). Many cancer therapy drugs have been designed based on either reactivating p53 functions or inactivating p53 negative regulators. Since p53 is strongly activated in response to DNA damage, mainly through attenuation of the Mdm2-mediated negative regulatory pathway (Maya et al., 2001), many DNA damage-inducing drugs such as etoposide are very effective antitumor drugs in cancer therapy (reviewed in Chresta and Hickman, 1996; Lutzker and Levine, 1996). Maximum induction of p53 acetylation in normal cells, however, requires both types of deacetylase inhibitors in addition to DNA damage, and there may be at least three different p53 negative regulatory pathways in mammalian cells Inhibitors for HDAC-mediated deacetylases, including sodium butyrate, TSA, SAHA and others, have been also proposed as antitumor drugs (Butler et al., 2000; Finnin et al., 1999; Taunton et al., 1996; Yoshida et al., 1995; Buckley et al., 1996). Combining DNA damage drugs, HDAC-mediated deacetylase inhibitors, and Sir2α-mediated deacetylase inhibitors, may have synergistic effects in cancer therapy for maximally activating p53.

In contrast to PID/HDAC1-mediated p53 regulation (Luo et al., 2000), the invention shows that mammalian Sir2α-mediated effect on p53 is NAD-dependent, indicating that this type of regulation is closely linked to cellular metabolism (reviewed Guarente 2000; Alfred, 2000; Campisi, 2000; Min et al., 2001). In fact, null mutants of NPT1, a gene that functions in NAD synthesis, show phenotypes similar to that of Sir2 mutants in gene silencing (Smith et al., 2000) and in life extension in response to caloric restriction in yeast (Lin et al., 2000). Thus, metabolic rate may play a role in Sir2α-mediated regulation of p53 function and, perhaps, modulate the sensitivity of cells in p53-dependent apoptotic response.

In yet another embodiment, the invention is a method of modulating p53-mediated apoptosis by modulating Sir2 activity. Sir2 activity can be modulated as described herein (e.g., overexpressing Sir2, transfecting a cell with a dominant negative regulating gene). An increase in Sir2 activity (e.g., by overexpressing Sir2) can result in a decrease in p53-mediated apoptosis. A decrease in Sir2 activity (e.g., transfecting a cell with a dominant negative gene) can result in an increase in p53-mediated apoptosis.

In still another embodiment, the invention is a method of screening for a compound (e.g., a small organic or inorganic molecule) which modulates (e.g., increases or decreases) Sir2-mediated deacetylation of p53. In the method, Sir2, p53, NAD and/or an NAD analog, and the compound to be tested are combined, the Sir2-mediated deacetylation of p53 is measured and compared to the Sir2-mediated deacetylation of p53 measured in the absence of the compound. An increase in the Sir2-mediated deacetylation of p53 in the presence of the compound being tested compared to the Sir2-mediated deacetylation of p53 in the absence of the compound indicates that the compound increases Sir2 deacetylation of p53. Likewise, a decrease in the Sir2-mediated deacetylation of p53 in the presence of the compound being tested compared to the Sir2-mediated deacetylation of p53 in the absence of the compound indicates that the compound decreases deacetylation of p53 by Sir2. As used herein, "Sir2-mediated deacetylation" refers to the NAD-dependent removal of acetyl groups which requires Sir2.

In another embodiment, the present invention relates to a method of screening a compound by providing an in vitro test mixture comprising a transcription factor or a fragment thereof, Sir2, and a Sir2 cofactor with the compound, evaluating an activity of a component of the test mixture in the presence of the compound, and comparing the activity in the presence of the compound to a reference obtained in the absence of the compound.

In another embodiment, the present invention relates to a method of screening a compound that is a potential NAD analog by providing an in vitro test mixture comprising a transcription factor or a fragment thereof, Sir2, and the compound, evaluating an activity of a component of the test mixture in the presence of the compound, and comparing the activity in the presence of the compound to a reference obtained in the absence of the compound, In one embodiment the Sir2 is human, e.g., human SIRT1. In another embodiment, the Sir2 is murine, e.g., murine Sir2α.

In one embodiment the Sir2 cofactor is NAD or an NAD analog.

In another embodiment the transcription factor is p53 or a fragment thereof, and it may be acetylated and/or labeled.

In a further embodiment, the evaluated activity is Sir2 activity, e.g., deacetylation of a protein, e.g., deacetylation of a histone protein, and/or deacetylation of the transcription factor, e.g., deacetylation of p53. The Sir2 activity may also be binding of a protein, e.g., binding of a histone protein and/or binding of the transcription factor, e.g., binding of p53. The Sir2 activity may be evaluated by detecting production of nicotinamide.

In a further embodiment, the evaluated activity is p53 activity. The p53 activity may be evaluated by detecting cell cycle arrest, apoptosis, senescence, and/or a change in the levels of transcription or translation products of a gene regulated by p53. Methods for detecting such changes and genes regulated by p53 are known in the art and include those methods and genes disclosed in U.S. Pat. No. 6,171,789, which is incorporated herein by reference in its entirety.

In one embodiment, the test mixture is provided in a cell-free system.

In another embodiment, the test mixture is provided in a cell-based system, wherein one of the components is exogenous. The term "exogenous" refers to a component that is either added directly, or expressed from a heterologous DNA source, such as transfected DNA. Many methods are known in the art for expression of heterologous or exogenous gene products.

In a further embodiment, the evaluated activity is an effect on the rate of aging of a cell or organism. Such an effect may be evaluated by contacting the compound with a cell or organism having p53 or Sir2 activity, e.g., endogenous or exogenous p53 or Sir2 activity; and evaluating the rate of aging of the cell or organism. The rate of aging may be evaluated by several methods, including:

a) assessing the life span of the cell or organism;
b) assessing the presence or absence of a gene transcript or gene product in the cell or organism that has a biological age-dependent expression pattern;
c) evaluating resistance of the cell or organism to stress;
d) evaluating one or more metabolic parameters of the cell or organism;
e) evaluating the proliferative capacity of the cell or a set of cells present in the organism;
f) evaluating physical appearance, behavior, or other characteristic of the cell or organism; and
(g) assessing the presence or absence of a gene transcript or gene product in the cell or organism that has a p53-regulation-dependent expression pattern.

The compounds identified by the methods of the invention can be used, for example, to treat cancer (e.g., a compound which decreases Sir2-mediated deacetylation of p53) or prevent p53-mediated apoptosis (e.g., a compound which increases Sir2-mediated deacetylation of p53). The compounds can be used in methods of treating a cell or an organism, e.g., a cell or organism that has been exposed to DNA-damaging ionizing radiation, by modulating Sir2 activity in the cell. In the method of treating cancer in a mammal, Sir2 activity can be reduced. In a preferred embodiment, Sir2 activity is reduced by nicotinamide or a nicotinamide analog.

In yet another embodiment, the invention is a method of screening for analogs of NAD. In the method, Sir2, p53 and a compound to be tested as an analog of NAD (e.g., a small organic or inorganic molecule) are combined. Deacetylation of the p53 by the Sir2 is measured and compared to the measured deacetylation of p53 by Sir2 in the presence of NAD. A compound which, for example, promotes Sir2-mediated deacetylation of p53 when combined with Sir2 and p53, is an NAD analog and can be used in place of NAD, for example, as a cofactor with Sir2 to prevent or decrease p53-mediated apoptosis.

In a further embodiment, the invention is a method of treating cancer in a mammal comprising the step of modulating Sir2 activity in tumor cells to cause an increase in p53 activity. The Sir2 activity can be modulated as described herein (e.g., overexpression of Sir2, transfection of a cell with a dominant negative regulatory gene, or nicotinamide or a nicotinamide analog).

In another embodiment, the invention includes a method of treating a cell that has been exposed to ionizing radiation, the method comprising modulating Sir2 activity in the cell. In a particular embodiment, in a cell which has undergone DNA damage or oxidative stress, Sir2 activity can be modulated to reduce Sir2 activity (e.g., by transfecting a cell with a dominant negative regulatory gene, or by addition or expression of nicotinamide or a nicotinamide analog) which can result in the arrest of the growth cycle of the cell, allowing the cell to repair at least a portion of the DNA damage caused by the ionizing radiation. Once the cell has repaired a portion of the DNA damage, the reduction in Sir2 activity can be removed and the cell cycle of the cell resumed.

In still another embodiment, the invention includes an isolated protein complex of Sir2 and acetylated p53. p53 can also be phosphorylated (e.g., on one or both of serine 15 or serine 20 of SEQ ID NO: 3).

The compounds or NAD analogs identified by the methods of the invention can be used in the treatment of diseases or conditions such as cancer, or following DNA damage or oxidative stress. The compounds or NAD analogs can be administered alone or as mixtures with conventional excipients, such as pharmaceutically, or physiologically, acceptable organic, or inorganic carrier substances such as water, salt solutions (e.g., Ringer's solution), alcohols, oils and gelatins. Such preparations can be sterilized and, if desired, mixed with lubricants, preservatives, stabilizers, wetting agents, emulsifiers, salts for influencing osmotic pressure, buffers, coloring, and/or aromatic substances and the like which do not deleteriously react with the NAD analogs or compounds identified by the methods of the invention.

The dosage and frequency (single or multiple doses) of the compound or NAD analog administered to a mammal can vary depending upon a variety of factors, including the duration of DNA damage, oxidative stress or cancer condition.

In some embodiments of the present invention, the rate of aging of a cell, e.g., a yeast cell, invertebrate cell (e.g., fly cell), or vertebrate cell (e.g., mammalian cell, e.g., human or mouse cell) is determined. For example, the rate of aging of the cell can be evaluated by measuring the expression of one or more genes or proteins (e.g., genes or proteins that have an age-related expression pattern), by measuring the cell's resistance to stress, e.g., genotoxic stress or oxidative stress, by measuring one or more metabolic parameters (e.g., protein synthesis or degradation, ubiquinone biosynthesis, cholesterol biosynthesis, ATP levels within the cell, glucose metabolism, nucleic acid metabolism, ribosomal translation rates, etc.), by measuring cellular proliferation, or any combination of measurements thereof.

In other embodiments, the rate of aging of an organism, e.g., an invertebrate (e.g., a worm or a fly) or a vertebrate (e.g., a rodent, e.g., a mouse) is determined. The rate of aging of an organism can be determined by directly measuring the average life span of a group of animals (e.g., a group of genetically matched animals) and comparing the resulting average to the average life span of a control group of animals (e.g., a group of animals that did not receive the test compound but are genetically matched to the group of animals that did receive the test compound). Alternatively, the rate of aging of an organism can be determined visually, e.g., by looking for visible signs of age (e.g., physical appearance or behavior), by measuring the expression of one or more genes or proteins (e.g., genes or proteins that have an age-related expression pattern), by measuring the cell's resistance to genotoxic (e.g., caused by exposure to etoposide, UV irradiation, mutagens, etc.) or oxidative stress, by measuring one or more metabolic parameters (e.g., protein synthesis or degradation, ubiquinone biosynthesis, cholesterol biosynthesis, ATP levels, glucose metabolism, nucleic acid metabolism, ribosomal translation rates, etc.), by measuring cellular proliferation (e.g., of retinal cells, bone cells, white blood cells, etc.), or any combination of measurements thereof. In one embodiment, the visual assessment is for evidence of apoptosis, e.g., nuclear fragmentation.

All animals typically go through a period of growth and maturation followed by a period of progressive and irreversible physiological decline ending in death. The length of time from birth to death is known as the life span of an organism, and each organism has a characteristic average life span. Aging is a physical manifestation of the changes underlying the passage of time as measured by percent of average life span.

In some cases, characteristics of aging can be quite obvious. For example, characteristics of older humans include skin wrinkling, graying of the hair, baldness, and cataracts, as well as hypermelanosis, osteoporosis, cerebral cortical atrophy, lymphoid depletion, thymic atrophy, increased incidence of diabetes type II, atherosclerosis, cancer, and heart disease. Nehlin et al. (2000), Annals NY Acad Sci 980:176-79. Other aspects of mammalian aging include weight loss, lordokyphosis (hunchback spine), absence of vigor, lymphoid atrophy, decreased bone density, dermal thickening and subcutaneous adipose tissue, decreased ability to tolerate stress (including heat or cold, wounding, anesthesia, and hematopoietic precursor cell ablation), liver pathology, atrophy of intestinal villi, skin ulceration, amyloid deposits, and joint diseases. Tyner et al. (2002), Nature 415:45-53.

Careful observation reveals characteristics of aging in other eukaryotes, including invertebrates. For example, characteristics of aging in the model organism *C. elegans* include slow movement, flaccidity, yolk accumulation, intestinal autofluorescence (lipofuscin), loss of ability to eat food or dispel waste, necrotic cavities in tissues, and germ cell appearance.

Those skilled in the art will recognize that the aging process is also manifested at the cellular level, as well as in mitochondria. Cellular aging is manifested in loss of doubling capacity, increased levels of apoptosis, changes in differentiated phenotype, and changes in metabolism, e.g., decreased levels of protein synthesis and turnover.

Given the programmed nature of cellular and organismal aging, it is possible to evaluate the "biological age" of a cell or organism by means of phenotypic characteristics that are correlated with aging. For example, biological age can be deduced from patterns of gene expression, resistance to stress (e.g., oxidative or genotoxic stress), rate of cellular proliferation, and the metabolic characteristics of cells (e.g., rates of protein synthesis and turnover, mitochondrial function, ubiquinone biosynthesis, cholesterol biosynthesis, ATP levels within the cell, levels of a Krebs cycle intermediate in the cell, glucose metabolism, nucleic acid metabolism, ribosomal translation rates, etc.). As used herein, "biological age" is a measure of the age of a cell or organism based upon the molecular characteristics of the cell or organism. Biological age is distinct from "temporal age," which refers to the age of a cell or organism as measured by days, months, and years.

Described below are exemplary methods for identifying compounds that can reduce the rate of aging of an organism and thereby slow or ameliorate the pathologies associated with increased temporal age. Activation of p53 may lead to cell cycle arrest or to apoptosis; Sir2 can suppress this effect by deacetylating p53. Accordingly, the expression or activity of p53 and/or Sir2 gene products in an organism can be a determinant of the rate of aging and life span of the organism. Reduction in the level and/or activity of such gene products would reduce the rate of aging and may ameliorate (at least temporarily) the symptoms of aging. A variety of techniques may be utilized to inhibit the expression, synthesis, or activity of such target genes and/or proteins. Such molecules may include, but are not limited to small organic molecules, peptides, antibodies, antisense, ribozyme molecules, triple helix molecules, and the like.

The following assays provide methods (also referred to herein as "evaluating a compound" or "screening a compound") for identifying modulators, i.e., candidate or test compounds (e.g., peptides, peptidomimetics, small molecules or other drugs) which modulate Sir2 or p53 activity, e.g., have a stimulatory or inhibitory effect on, for example, Sir2 or p53 expression or activity, or have a stimulatory or inhibitory effect on, for example, the expression or activity of a Sir2 or p53 substrate. Such compounds can be agonists or antagonists of Sir2 or p53 function. These assays may be performed in animals, e.g., mammals, in organs, in cells, in cell extracts, e.g., purified or unpurified nuclear extracts, intracellular extracts, in purified preparations, in cell-free systems, in cell fractions enriched for certain components, e.g., organelles or compounds, or in other systems known in the art. Given the teachings herein and the state of the art, a person of ordinary skill in the art would be able to choose an appropriate system and assay for practicing the methods of the present invention.

Some exemplary screening assays for assessing activity or function include one or more of the following features:
- use of a transgenic cell, e.g., with a transgene encoding Sir2 or p53 or a mutant thereof;
- use of a mammalian cell that expresses Sir2 or p53;
- detection of binding of a labeled compound to Sir2 or a transcription factor where the compound is, for example, a peptide, protein, antibody or small organic molecule; e.g., the compound interferes with or disrupts an interaction between Sir2 and a transcription factor
- use of proximity assays that detect interaction between Sir2 and a transcription factor (e.g., p53), or fragments thereof, for example, fluorescence proximity assays.
- use of a two hybrid assay to detect interaction between Sir2 and a transcription factor (e.g., p53) or fragments thereof. In some instances, the two hybrid assay can be evaluated in the presence of a test compound, e.g., to determine if the test compound disrupts or interferes with an interaction. Two hybrid assays can, for example, be conducted using yeast or bacterial systems.
- use of radio-labelled substrates, e.g. $^{35}$S, $^3$H, $^{14}$C, e.g., to determine acetylation status, metabolic status, rate of protein synthesis, inter alia.
- use of antibodies specific for certain acetylated or de-acetylated forms of the substrate. One embodiment herein accordingly comprises methods for the identification of small molecule drug candidates from large libraries of compounds that appear to have therapeutic activity to affect metabolic maintenance and/or to reverse or prevent cell death and thus exhibits potential therapeutic utility, such as the ability to enhance longevity. Small organic molecules and peptides having effective inhibitory activity may be designed de novo, identified through assays or screens, or obtained by a combination of the two techniques. Non-protein drug design may be carried out using computer graphic modeling to design non-peptide, organic molecules able to bind to p53 or Sir2. The use of nuclear magnetic resonance (NMR) data for modeling is also known in the art, as described by Lam et al., *Science* 263: 380, 1994, using information from x-ray crystal structure studies of p53 or Sir2, such as that described in Min, J. et al., *Cell* 105:269-279, 2001.

Small molecules may also be developed by generating a library of molecules, selecting for those molecules which act as ligands for a specified target, (using protein functional assays, for example), and identifying the selected ligands. See, e.g., Kohl et al., *Science* 260: 1934, 1993. Techniques for constructing and screening combinatorial libraries of small molecules or oligomeric biomolecules to identify those that specifically bind to a given receptor protein are known. Suitable oligomers include peptides, oligonucleotides, carbohydrates, nonoligonucleotides (e.g., phosphorothioate oligonucleotides; see *Chem. and Engineering News*, page 20, 7 Feb. 1994) and nonpeptide polymers (see, e.g., "peptoids" of Simon et al., *Proc. Natl. Acad. Sci. USA* 89 9367, 1992). See also U.S. Pat. No. 5,270,170 to Schatz; Scott and Smith, *Science* 249: 386-390, 1990; Devlin et al., *Science* 249: 404-406, 1990; Edgington, BIO/Technology, 11: 285, 1993. Libraries may be synthesized in solution on solid supports, or expressed on the surface of bacteriophage viruses (phage display libraries).

Known screening methods may be used by those skilled in the art to screen combinatorial libraries to identify active molecules. For example, an increase (or decrease) in p53 or Sir2 activity due to contact with an agonist or antagonist can be monitored.

In one embodiment, assays for screening candidate or test compounds that are substrates of a Sir2 or p53 protein or polypeptide or biologically active portion thereof are provided. In another embodiment, assays for screening candidate or test compounds which bind to or modulate the activity of a Sir2 or p53 protein or polypeptide or biologically active portion thereof, e.g., modulate the ability of Sir2 or p53 to interact with a ligand, are provided. In still another embodiment, assays for screening candidate or test compounds for the ability to bind to or modulate the activity of a Sir2 or p53 protein or polypeptide and to also alter the rate of aging of a cell or an organism are provided.

Examples of methods for the synthesis of molecular libraries can be found in the art, for example in: DeWitt et al., *Proc. Natl. Acad. Sci. U.S.A.* 90: 6909, 1993; Erb. et al., *Proc. Natl. Acad. Sci. USA* 91: 11422, 1994; Zuckermann et al., *J. Med. Chem.* 37: 2678, 1994; Cho et al., *Science* 261: 1303, 1993; Carrell et al., *Angew. Chem. Int. Ed. Engl.* 33: 2059, 1994; Carell et al., Angew. Chem. Int. Ed. Engl. 33: 2061, 1994; and in Gallop et al., *J. Med. Chem.* 37:1233, 1994.

Libraries of compounds may be presented in solution (e.g., Houghten, *Biotechniques* 13: 412-421, 1992), or on beads (Lam, *Nature* 354: 82-84, 1991), chips (Fodor, *Nature* 364: 555-556, 1993), bacteria (Ladner U.S. Pat. No. 5,223,409), spores (Ladner U.S. Pat. No. '409), plasmids (Cull et al., *Proc Natl Acad Sci USA* 89: 1865-1869, 1992) or on phage (Scott and Smith, *Science* 249: 386-390, 1990); (Devlin, *Science*

249: 404-406, 1990); (Cwirla et al., *Proc. Natl. Acad. Sci U.S.A.* 87: 6378-6382, 1990); (Felici, *J. Mol. Biol.* 222: 301-310, 1991); (Ladner supra.).

The compounds tested as modulators of Sir2 or p53 can be any small chemical compound, or a biological entity, such as a protein, e.g., an antibody, a sugar, a nucleic acid, e.g., an antisense oligonucleotide or a ribozyme, or a lipid. Alternatively, modulators can be genetically altered versions of Sir2 or p53. Typically, test compounds will be small chemical molecules and peptides, or antibodies, antisense molecules, or ribozymes. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods known to one of ordinary skill in the art involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks. Moreover, a combinatorial library can be designed to sample a family of compounds based on a parental compound, e.g., based on the chemical structure of NAD or nicotinamide.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, e.g., where each assay includes a cell or tissue expressing Sir2 and/or p53. In a high throughput assays, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100-about 1500 different compounds. It is possible to assay many plates per day; assay screens for up to about 6,000, 20,000, 50,000, or 100,000 or more different compounds are possible using the integrated systems of the invention.

Candidate Sir2- or p53-interacting molecules encompass many chemical classes. They can be organic molecules, preferably small organic compounds having molecular weights of 50 to 2,500 Daltons. The candidate molecules comprise functional groups necessary for structural interaction with proteins, particularly hydrogen bonding, for example, carbonyl, hydroxyl, and carboxyl groups. The candidate molecules can comprise cyclic carbon or heterocyclic structures and aromatic or polyaromatic structures substituted with the above groups. In one embodiment, the candidate molecules are structurally and/or chemically related to NAD or to nicotinamide.

Other techniques are known in the art for screening synthesized molecules to select those with the desired activity, and for labeling the members of the library so that selected active molecules may be identified, as in U.S. Pat. No. 5,283,173 to Fields et al., (use of genetically altered *Saccharomyces cerevisiae* to screen peptides for interactions). As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized fragments that are potential ligands. The shape of a molecule refers to those features of a molecule that govern its interactions with other molecules, including Van der Waals, hydrophobic, electrostatic and dynamic.

Nucleic acid molecules may also act as ligands for receptor proteins. See, e.g., Edgington, *BIO/Technology* 11: 285, 1993. U.S. Pat. No. 5,270,163 to Gold and Tuerk describes a method for identifying nucleic acid ligands for a given target molecule by selecting from a library of RNA molecules with randomized sequences those molecules that bind specifically to the target molecule. A method for the in vitro selection of RNA molecules immunologically cross-reactive with a specific peptide is disclosed in Tsai et al., *Proc. Natl. Acad. Sci. USA* 89: 8864, (1992); and Tsai et al. *Immunology* 150:1137, (1993). In the method, an antiserum raised against a peptide is used to select RNA molecules from a library of RNA molecules; selected RNA molecules and the peptide compete for antibody binding, indicating that the RNA epitope functions as a specific inhibitor of the antibody-antigen interaction.

Antibodies that are both specific for a target gene protein and that interfere with its activity may be used to inhibit target gene function. Such antibodies may be generated using standard techniques, against the proteins themselves or against peptides corresponding to portions of the proteins. Such antibodies include but are not limited to polyclonal, monoclonal, Fab fragments, single chain antibodies, chimeric antibodies, and the like. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (e.g., see Sambrook et al., Eds., Molecular Cloning: A Laboratory Manual, 2nd ed., Cold Spring Harbor Laboratory Press, (1989), or Ausubel, F. M. et al., eds. Current Protocols in Molecular Biology (1994).

Alternatively, single chain neutralizing antibodies that bind to intracellular target gene epitopes may also be administered. Such single chain antibodies may be administered, for example, by expressing nucleotide sequences encoding single-chain antibodies within the target cell population by utilizing, for example, techniques such as those described in Marasco et al., *Proc. Natl. Acad. Sci. USA* 90: 7889-7893 (1993).

Also encompassed are assays for cellular proteins that interact with Sir2 or p53. Any method suitable for detecting protein-protein interactions may be used. The traditional methods that may be used include, for example, co-immunoprecipitation, crosslinking, and co-purification through gradients or chromatographic columns. For these assays, Sir2 or p53 can be a full-length protein or an active fragment. Additional methods include those methods that allow for the simultaneous identification of genes that encode proteins that interact with Sir2 or p53. These methods include, for example, probing expression libraries using a labeled Sir2 or p53 protein, Sir2 or p53 fragment, or Sir2 or p53 fusion protein.

One method to detect protein-protein interaction in vivo is the two-hybrid system, see, for example, Chien et al., *Proc. Natl. Acad. Sci, USA* 88: 9578-9582 (1991). In brief, the two-hybrid system utilizes plasmids constructed to encode two hybrid proteins: one plasmid comprises the nucleotides encoding the DNA binding domain of a transcriptional activator protein fused to the Sir2 or p53 nucleotide sequence encoding the Sir2 or p53 polypeptide, and the other plasmid comprises the nucleotides encoding the transcriptional activator protein's activation domain fused to a cDNA encoding an unknown protein that has been recombined into the plasmid from a cDNA library. The DNA binding domain fusion plasmid and the cDNA fusion protein library plasmids are transformed into a strain of yeast that contains a reporter gene, for example lacZ, whose regulatory region contains the activator's binding site. Either hybrid protein alone cannot activate translation of the reporter gene because it is lacking either the DNA binding domain or the activator domain. Interaction of the two hybrid proteins, however, reconstitutes a functional activator protein and results in activation of the reporter gene that is detected by an assay for the reporter gene product. The colonies that reconstitute activator activity are purified and the library plasmids responsible for reporter gene activity are isolated and sequenced. The DNA sequence is then used to identify the protein encoded by the library plasmid.

Macromolecules that interact with Sir2 or p53 are referred to as Sir2 or p53 binding partners. Sir2 or p53 binding partners are likely to be involved in the regulation of Sir2 or p53 function. Therefore, it is possible to identify compounds that interfere with the interaction between Sir2 or p53 and its binding partners. The basic principle of assay systems used to identify compounds that interfere with the interaction of Sir2 or p53 and a binding partner is to prepare a reaction mixture containing Sir2 or p53 or a Sir2 or p53 fragment and the binding partner under conditions that allow complex formation. The reaction mixture is prepared in the presence or absence of the test compound to test for inhibitory activity. The test compound may be added prior to or subsequent to Sir2/ or p53/binding partner complex formation. The formation of a complex in a control but not with the test compound confirms that the test compound interferes with complex formation. The assay can be conducted either in the solid phase or in the liquid phase.

In another embodiment, an assay is a cell-based assay comprising contacting a cell expressing Sir2 or p53 with a test compound and determining the ability of the test compound to modulate (e.g. stimulate or inhibit) the activity of Sir2 or p53. A preferred activity is the deacetylation function of Sir2 on p53; a further preferred activity is the ability of p53 to cause ERU cycle arrest or apoptosis. Determining the ability of the test compound to modulate the activity of Sir2 or p53 can be accomplished, for example, by determining the ability of Sir2 or p53 to bind to or interact with the test molecule, or by determining the ability of the test molecule to stimulate or inhibit the activity of Sir2 or p53. Cell-based systems can be used to identify compounds that inhibit Sir2 or p53. Such cells can be recombinant or non-recombinant, such as cell lines that express the Sir2 or p53 gene. Preferred systems are mammalian or yeast cells that express Sir2 or p53. In utilizing such systems, cells are exposed to compounds suspected of ameliorating body weight disorders or increasing lifespan. After exposure, the cells are assayed, for example, for expression of the Sir2 or p53 gene or activity of the Sir2 or p53 protein. Alternatively, the cells are assayed for phenotypes such as those resembling body weight disorders or lifespan extension. The cells may also be assayed for the inhibition of the deacetylation function of Sir2 on p53, or the apoptotic or cytostatic function of p53.

Another preferred cell for a cell-based assay comprises a yeast cell transformed with a vector comprising the Sir2 or p53 gene. One use for a yeast cell expressing Sir2 or p53 is to mutagenize the yeast and screen for yeast that will survive only when the Sir2 or p53 polypeptide is functioning normally. Synthetic lethal screens are described in Holtzman et al. (1993), *J. Cell Bio.* 122: 635-644. The yeast that require Sir2 or p53 function for survival can then be used to screen test compounds for those that inhibit Sir2 or p53 activity. Test compounds that results in a decrease in yeast survival are likely inhibitors of Sir2 or p53 in this system.

In yet another embodiment, an assay is a cell-free assay in which Sir2 or p53 protein or biologically active portion thereof is contacted with a test compound and the ability of the test compound to bind to the Sir2 or p53 protein or biologically active portion thereof is determined. Binding of the test compound to the Sir2 or p53 protein can be determined either directly or indirectly as described above. In a preferred embodiment, the assay includes contacting the Sir2 or p53 protein or biologically active portion thereof with a known compound which binds Sir2 or p53 to form an assay mixture, contacting the assay mixture with a test compound, and determining the ability of the test compound to interact with an Sir2 or p53 protein, wherein determining the ability of the test compound to interact with an Sir2 or p53 protein comprises determining the ability of the test compound to preferentially bind to Sir2 or p53 or a biologically active portion thereof as compared to the known compound.

In yet another embodiment, an assay is a cell-free system in which Sir2 protein or biologically active portion thereof is contacted with p53 protein or biologically active portion thereof, to form a mixture comprising a detectable amount bound p53:Sir complex. And a test compound is contacted with the mixture, and the ability of the compound to effect the stability or formation of the p53:Sir2 complex is determined. Interaction of the test compound with the p53:Sir2 complex may be determined directly or by methods known in the art. In a preferred embodiment, the method comprises contacting p53 with Sir2 to form a mixture comprising the p53:Sir2 complex, further contacting the mixture with a compound to be tested, and evaluating the binding kinetics of p53:Sir2 complex both in the presence and the absence of the test compound to directly bind the p53:Sir2 complex is evaluated. The cell-free assays are amenable to use of both soluble and/or membrane-bound forms of proteins. In the case of cell-free assays in which a membrane-bound form of a protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylammonio]-1-propane sulfonate (CHAPS), 3-[(3-cholamidopropyl)dimethylammonio]-2-hydroxy-1-propane sulfonate (CHAPSO), or N-dodecyl,N,N-dimethyl-3-amino-1-propane sulfonate.

In more than one embodiment of the above assay methods, it may be desirable to immobilize either Sir2 or p53 or its target molecule to facilitate separation of complexed from uncomplexed forms of one or both of the proteins, as well as to accommodate automation of the assay. Binding of a test compound to an Sir2 or p53 protein, or interaction of an Sir2 or p53 protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/Sir2 or /p53 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or Sir2 or p53 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of Sir2 or p53 binding or activity determined using standard techniques.

Other techniques for immobilizing proteins on matrices can also be used in the screening assays of the invention. For example, either a Sir2 or p53 protein or a Sir2 or p53 target molecule can be immobilized utilizing conjugation of biotin and streptavidin. Biotinylated Sir2 or p53 protein or target molecules can be prepared from biotin-NHS (N-hydroxysuccinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with Sir2 or p53 protein or target molecules but which do not interfere with binding of the Sir2 or p53 protein to its target molecule can be derivatized to the wells of the plate, and unbound target Sir2 or p53 protein trapped in the wells by antibody conjugation. Methods for detecting such complexes, in addition to those described above for the GST-immobilized complexes, include immunodetection of complexes using antibodies reactive with the Sir2 or p53 protein or target molecule, as well as enzyme-linked assays which rely on detecting an enzymatic activity associated with the Sir2 or p53 protein or target molecule.

In addition to cell-based and in vitro assay systems, non-human organisms, e.g., transgenic non-human organisms, can also be used. A transgenic organism is one in which a heterologous DNA sequence is chromosomally integrated into the germ cells of the animal. A transgenic organism will also have the transgene integrated into the chromosomes of its somatic cells. Organisms of any species, including, but not limited to: yeast, worms, flies, fish, reptiles, birds, mammals (e.g., mice, rats, rabbits, guinea pigs, pigs, micro-pigs, and goats), and non-human primates (e.g., baboons, monkeys, chimpanzees) may be used in the methods of the invention.

Accordingly, in another embodiment, the invention features a method of identifying a compound that alters the rate of aging of a cell or an organism, comprising: contacting a Sir2 or p53 polypeptide with a test compound; evaluating an interaction between the test compound and the Sir2 or p53 polypeptide; and further evaluating the effect of the test compound on the rate of aging of a cell or organism.

The interaction between a test compound and the Sir2 or p53 polypeptide can be performed by any of the methods described herein, e.g., using cell-based assays or cell-free in vitro assays. Weather the interaction between the test compound and the Sir2 or p53 polypeptide is evaluated prior to the evaluation of the effect of the text compound on the rate of aging of a cell or organism is not critical to the method. However, it is preferable to evaluate the interaction between the test compound and Sir2 or p53 polypeptide first, so that test compounds that do not interact with the Sir2 or p53 polypeptide do not have to be tested for their effect upon the rate of aging. It can also be preferable to use an assay for evaluating the interaction between the test compound and the Sir2 or p53 polypeptide that can be adapted for high throughput screening, thus making it possible to screen one or more libraries of test compounds. Possible test compounds include, e.g., small organic molecules, peptides, antibodies, and nucleic acid molecules, as described above.

The rate of aging of an organism can be determined using methods known in the art. For example, the rate of aging of an organism can be determined by directly measuring the life span of the organism. Preferably, a statistical measure, e.g., an average or median value, of the life span of a group of animals, e.g., a group of genetically matched animals, will be determined and the resulting statistical value compared to an equivalent statistical value, e.g, an average of median value, of the life span of a control group of animals, e.g., a group of animals that did not receive the test compound but are genetically matched to the group of animals that did receive the test compound. Such methods are suitable for organisms that have a short life span, such as worms or flies. See, for example, Rogina et al. (2000), Science 290:2137-40. Direct measurement of life span can also be preformed with other organisms such as rodents, as discussed, for example, in Weindruch et al. (1986), Journal of Nutrition 116(4):641-54. Those skilled in the art will recognize that there are many ways of measuring the statistical difference (e.g., using the Student's T test) between two sets of data, any of which may be suitable for the methods of the invention.

To reduce the time that it takes to measure a change in the rate of aging using data on the life span of the organisms treated with the test compound, various modifications or treatments of the organisms can be implemented. For example, animals fed on a calorically rich diet tend to live shorter lives, thus reducing the time that needs to elapse to determine when the average life span of the test group of animals has exceeded the average life span of the control group of animals. Alternatively, the test compound can be administered to test animals that have already lived for 50%, 60%, 70%, 80%, 90%, or more of their expected life span. Thus, the test compound can be administered to an adult organism, or even an old adult organism. Other possibilities include the use of genetically modified organisms. For example, the organisms could harbor mutations (e.g., a Hyperkinetic[1] or Shaker[5] mutation in Drosophila, or a mutation in a silent information regulator gene (e.g., Sir2), or a catalase or superoxide dismutase gene) or transgenes (e.g., encoding a transporter protein (e.g., a carboxylate transport protein such as INDY) or a protein involved in insulin signaling and metabolic regulation (e.g., IGF-1)) that reduce their average life span. See Rogina et al. (1997), Proc. Natl. Acad. Sci., USA 94:6303-6; Rogina and Helfand (2000), Biogerontology 1:163-9; and Guarente and Kenyon (2000), Nature 408:255-62. Those skilled in the art will understand that it may also be desirable to practice the methods of the invention using organisms that are long-lived, such as calorically restricted animals, or animals carrying mutations or transgenes that increase their life span.

A proxy for rate of aging of a cell or an organism can be determined using biomarkers that are indicative of the biological age of the organism (i.e., age-related parameters). Using biomarkers for determining biological age can greatly facilitate screens for compounds that alter the rate of aging, as they bypass the requirement of waiting for the animal to die in order to determine the rate of aging. Biomarkers suitable for use in the present invention include, but are not limited to, levels of protein modification, e.g., accumulation of glycosylated proteins, rates or levels of protein turnover, levels or composition of T-cell populations, protein activity, physical characteristics, macular degeneration, and/or increased copper and zinc concentrations in neuronal tissues. The expression of genes whose regulation is biological age-dependent is a particularly preferred biomarker for use in the methods of the invention. Numerous genes are known to be expressed in a biological age-dependent manner. In Drosophila, for example, such genes include wingless and engrailed. See Rogina and Helfand (1997), Mechanisms of Development 63:89-97. In mice, the expression of the ras oncogene is elevated in older animals. See Hass et al. (1993), Mutat. Res. 295(4-6):281-9. Similarly, in rodents and worms, genes that are differentially expressed in young and old organisms have been identified by transcriptional profiling using microarrays. See, e.g., Lee et al. (1999), Science 285:1390-93; WO 01/12851; and Hill et al. (2000), Science 290:809-812. For example, Hill et al. (2000) Science 90:809 discloses genes whose transcripts are up-regulated in nematodes that are at 2 weeks in development. Examples of such genes include the genes described in cluster (4,1):69 of Hill, supra. Any gene whose regulation is biological age-dependent is suitable for the methods of the invention. Preferably, more than one gene is analyzed so as to improve the accuracy of the determination. Analysis of gene expression can be performed by any technique known in the art, including Northern, in-situ hybridization, quantitative PCR, and transcriptional profiling using microarrays. Methods of determining biological age based on gene expression patterns are described in WO 01/12851.

Metabolic parameters can also be used to evaluate the rate of aging of a cell or organism. For example, the rate of protein synthesis and degradation decreases in biologically aged cells, and the levels proteins having advanced glycosylation end product modifications increases. See, Lambert and Merry (2000), Exp. Gerontol 35(5):583-94; and WO 01/79842. In addition, animals that harbor mutations conferring longer life span (and thus a reduced rate of aging) can show defects in ubiquinone biosynthesis, mitochondrial biogenesis, glucose metabolism, nucleic acid metabolism, ribosomal translation rates, and cholesterol biosynthesis. See, for example, WO 98/17823 and WO 99/10482. Thus, by measuring any of these parameters or some combination thereof, it is possible to indirectly evaluate the rate of aging of a cell or an organism. Methods of analyzing protein synthesis, degradation, and modification with advanced glycosylation end products are known in the art, as described in Lambert and Merry (2000), Exp. Gerontol 35(5):583-94 and WO 01/79842. Similarly, methods of analyzing ubiquinone biosynthesis, mitochondrial biogenesis, and glucose metabolism are known in the art (see, e.g., Marbois et al. J. Biol. Chem. 271:2995; Proft et al. EMBO J. 14:6116; and WO 98/17823), as are methods of analyzing nucleic acid metabolism, ribosomal translation rates, and cholesterol biosynthesis (see, e.g., WO 99/10482).

Cellular proliferation is another parameter that can be used to evaluate the biological age of a cell or organism. Cells from biologically aged organisms demonstrate reduced proliferative capacity as compared to the cells of a corresponding younger organism. See Li et al. (1997), Invest. Ophthalmol. 38(1):100-7; and Wolf and Pendergrass (1999), J Gerontol. A Biol. Sci. Med. Sci. 54(11):B502-17. It will be understood by one skilled in the art that there are many methods for evaluating the proliferative capacity of cells that are suitable for use in the methods of the invention. For example, cells can be labeled in vitro (or in vivo) with BrdU to determine the percent of dividing cells or evaluated using a colony forming assay, as described in Li et al. (1997), supra. Cells suitable for the analysis of proliferative capacity include cells grown in tissue culture, cells isolated from an animal that has been treated with a test compound, cells that are part of a live animal, or cells that are part of a tissue section obtained from an animal. With respect to cells present in an animal or tissue section thereof, preferable cells include lens epithelial cells, osteoblasts, osteoclasts, and lymphoid cells.

Basically, any biomarker that is altered in a biological age-dependent manner has the potential to be used to evaluate the effect of a test compound upon the rate of aging of a cell or an organism. Thus, additional biomarkers include visual appearance, resistance to oxidative stress, cellular transformation (the ability to adopt a transformed (i.e., cancerous or malignant) phenotype), or DNA methylation (e.g., of a ras oncogene). See, for example, Finkel and Holbrook (2000), *Nature* 408:239-47; Kari et al. (1999), *J Nutr. Health Aging* 3(2):92-101; and Hass et al. (1993), *Mutat. Res.* 295(4-6): 281-9.

A cell used in the methods of the invention can be from a stable cell line or a primary culture obtained from an organism, e.g., a organism treated with the test compound.

A transgenic cell or animal used in the methods of the invention can include a transgene that encodes, e.g., a copy of a Sir2 or p53 protein, e.g., the Sir2 or p53 polypeptide that was evaluated for an interaction with the test compound. The transgene can encode a protein that is normally exogenous to the transgenic cell or animal, including a human protein, e.g., a human Sir2 or p53 polypeptide. The transgene can be linked to a heterologous or a native promoter.

Transgenic Organisms

This disclosure further relates to a method of producing transgenic animals, e.g., mice or flies. In one embodiment, the transgenic animal is engineered to express, overexpress or ectopically express Sir2 or p53, which method comprises the introduction of several copies of a segment comprising at least the polynucleotide sequence encoding SEQ ID NO: 2 with a suitable promoter into the cells of an embryo at an early stage. Techniques known in the art may be used to introduce the Sir2 or p53 transgene into animals to produce the founder line of animals. Such techniques include, but are not limited to: pronuclear microinjection (U.S. Pat. No. 4,873,191); retrovirus mediated gene transfer into germ lines (Van der Putten et al., *Proc. Natl. Acad. Sci. USA* 82: 6148-6152, 1985; gene targeting in embryonic stem cells (Thompson et al., *Cell* 56: 313-321, 1989; electroporation of embryos (Lo, *Mol. Cell Biol.* 3: 1803-1814, 1983; and sperm-mediated gene transfer (Lavitrano, et al., *Cell* 57: 717-723, 1989; etc. For a review of such techniques, see Gordon, Intl. Rev. Cytol. 115: 171-229, 1989.

Gene targeting by homologous recombination in embryonic stem cells to produce a transgenic animal with a mutation in the Sir2 or p53 gene ("knock-out" mutation) can also be performed. In such so-called "knock-out" animals, there is inactivation of the Sir2 or p53 gene or altered gene expression, such that the animals can be useful to study the function of the Sir2 or p53 gene, thus providing animals models of human disease, which are otherwise not readily available through spontaneous, chemical or irradiation mutagenesis.

A particularly useful transgenic animal in one in which the Sir2 or p53 homolog has been disrupted or knocked out.

Transgenic animals such as mice, for example, may be used as test substrates for the identification of drugs, pharmaceuticals, therapies and interventions that can be used for the ameliorating or slowing the effects of aging.

Accordingly, the invention features a transgenic organism that contains a transgene encoding a Sir2 or p53 polypeptide. In preferred embodiments, the Sir2 or p53 r polypeptide is a human Sir2 or p53 polypeptide. The Sir2 or p53 polypeptide can be exogenous to (i.e., not naturally present in) the transgenic organism.

The transgenic organism can be a yeast cell, an insect, e.g., a worm or a fly, a fish, a reptile, a bird, or a mammal, e.g., a rodent.

The transgenic organism can further comprise a genetic alteration, e.g., a point mutation, insertion, or deficiency, in an endogenous gene. The endogenous gene harboring the genetic alteration can be a gene involved in the regulation of life span, e.g., a gene in the insulin signaling pathway, a gene encoding a Sir2 or transcription factor protein, or both. In cases where the genetically altered gene is a Sir2 or transcription factor, e.g., p53, polypeptide, it is preferable that the expression or activity of the endogenous Sir2 or transcription factor, e.g., p53, protein is reduced or eliminated.

Therapeutic

In another embodiment, the invention features a method of altering the expression or activity of a Sir2 or p53 polypeptide, comprising administering to a cell or an organism a compound that increases or decreases the expression or activity of the Sir2 or p53 polypeptide in an amount effective to increase or decrease the activity of the Sir2 or p53 polypeptide.

The Sir2 or p53 polypeptide can also be a yeast, invertebrate (e.g., worm or fly), or vertebrate (e.g., fish, reptile, bird, or mammal (e.g., mouse)) protein.

The cell to which the compound is administered can be an invertebrate cell, e.g., a worm cell or a fly cell, or a vertebrate cell, e.g., a fish cell (e.g., zebrafish cell), a bird cell (e.g., chicken cell), a reptile cell (e.g., amphibian cell, e.g., *Xenopus* cell), or a mammalian cell (e.g., mouse or human cell). Similarly, the organism to which the compound is administered can be an invertebrate, e.g., a worm or a fly, or a vertebrate, e.g., a fish (e.g., zebrafish), a bird (e.g., chicken), a reptile (e.g., amphibian, e.g., *Xenopus*), or a mammal (e.g., rodent or a human). When the organism is a human, it is preferred that the human is not obese or diabetic.

The compound that is administered to the cell or organism can be an agonist that increases the expression or activity of the Sir2 or p53 polypeptide or an antagonist that decreases the expression or activity of the Sir2 or p53 polypeptide. Whether agonist or antagonist, the compound can be a small organic compound, an antibody, a polypeptide, or a nucleic acid molecule.

The agonist or antagonist can alter the concentration of metabolites, e.g., Krebs Cycle intermediates, e.g., succinate, citrate, or a-keto-glutarate, within the cell or within one or more cells of the organism. Such action is expected to alter the cell's or the organism's resistance to oxidative stress. For example, an antagonist could increase the cell's or the organism's resistance to oxidative stress. In addition, the agonist or antagonist can alter one or more aging-related parameters, e.g., the expression of one or more genes or proteins (e.g., genes or proteins that have an age-related expression pattern), or the value of one or more metabolic parameters (e.g., one or more metabolic parameters that reflect the rate of aging of the cell or organism), the agonist or antagonist alters the rate of aging of the cell or organism.

Ideally, the compound reduces, e.g., partially reduces, the expression of the Sir2 or p53 polypeptide. For example, antisense RNA, or ribozymes can be used to reduce the expression of the Sir2 or p53 polypeptide. Double-stranded inhibitory RNA is particularly useful as it can be used to selectively reduce the expression of one allele of a gene and not the other, thereby achieving an approximate 50% reduction in the expression of the Sir2 or p53 polypeptide. See Garrus et al. (2001), *Cell* 107(1):55-65.

In one embodiment, treatment of aging comprises modulating the expression of a Sir2 or p53 polypeptide. A cell or subject can be treated with a compound that modulates the expression of a Sir2 or p53 gene. These compounds can be nucleic acid molecules substantially complementary to a Sir2 or p53 gene. Such approaches include oligonucleotide-based therapies such as antisense, ribozymes, and triple helices. Oligonucleotides may be designed to reduce or inhibit mutant target gene activity. Techniques for the production and use of such molecules are well known to those of ordinary skill in the art. Antisense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the target gene nucleotide sequence of interest, are preferred. Antisense oligonucleotides are preferably 10 to 50 nucleotides in length, and more preferably 15 to 30 nucleotides in length. An antisense compound is an antisense molecule corresponding to the entire Sir2 or p53 mRNA or a fragment thereof.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules includes one or more sequences complementary to the target gene mRNA, and includes the well known catalytic sequence responsible for mRNA cleavage disclosed, for example, in U.S. Pat. No. 5,093,246. Within the scope of this disclosure are engineered hammerhead motif ribozyme molecules that specifically and efficiently catalyze endonucleolytic cleavage of RNA sequences encoding target gene proteins. Specific ribozyme cleavage sites within any potential RNA target are initially identified by scanning the molecule of interest for ribozyme cleavage sites that include the sequences GUA, GUU, and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules used in triple helix formation for the inhibition of transcription should be single stranded and composed of deoxyribonucleotides. The base composition of these oligonucleotides are designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences targeted for triple helix formation may be increased by creating a "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The antisense, ribozyme, and/or triple helix molecules described herein may reduce or inhibit the transcription (triple helix) and/or translation (antisense, ribozyme) of mRNA produced by both normal and mutant target gene alleles. If it is desired to retain substantially normal levels of target gene activity, nucleic acid molecules that encode and express target gene polypeptides exhibiting normal activity may be introduced into cells via gene therapy methods that do not contain sequences susceptible to whatever antisense, ribozyme, or triple helix treatments are being utilized. Alternatively, it may be preferable to coadminister normal target gene protein into the cell or tissue in order to maintain the requisite level of cellular or tissue target gene activity.

Antisense RNA and DNA, ribozyme, and triple helix molecules may be prepared by any method known in the art for the synthesis of DNA and RNA molecules. These include techniques for chemically synthesizing oligodeoxyribonucleotides and oligoribonucleotides, for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. Various well-known modifications to the DNA molecules may be introduced as a means of increasing intracellular stability and half-life. Possible modifications include but are not limited to the addition of flanking sequences of ribonucleotides or deoxyribonucleotides of the 5' and/or 3' ends of the molecule or the use of phosphorothioate or 2' O-methyl rather than phosphodiesterase linkages within the oligodeoxyribonucleotide backbone.

Modulators of Sir2 or p53 expression can be identified by a method wherein a cell is contacted with a candidate compound and the expression of Sir2 or p53 mRNA or protein in the cell is determined. The level of expression of Sir2 or p53 mRNA or protein in the presence of the candidate compound is compared to the level of expression of mRNA or protein in the absence of the candidate compound. The candidate compound can then be identified as a modulator of Sir2 or p53 expression based on this comparison. For example, when expression of Sir2 or p53 mRNA or protein is greater in the presence of the candidate compound than in its absence, the candidate compound is identified as a stimulator of Sir2 or p53 mRNA or protein expression. Alternatively, when expression of Sir2 or p53 mRNA or protein is less in the presence of the candidate compound than in its absence, the candidate compound is identified as an inhibitor of Sir2 or p53 mRNA or protein expression. The level of Sir2 or p53 mRNA or protein expression in the cells can be determined by methods described herein for detecting Sir2 or p53 mRNA or protein.

Delivery of antisense, triplex agents, ribozymes, and the like can be achieved using a recombinant expression vector such as a chimeric virus or a colloidal dispersion system or by injection. Useful virus vectors include adenovirus, herpes virus, vaccinia, and/or RNA virus such as a retrovirus. The retrovirus can be a derivative of a murine or avian retrovirus such as Moloney murine leukemia virus or Rous sarcoma virus. All of these vectors can transfer or incorporate a gene for a selectable marker so that transduced cells can be identified and generated. The specific nucleotide sequences that can be inserted into the retroviral genome to allow target specific delivery of the retroviral vector containing an antisense oligonucleotide can be determined by one of skill in the art.

Another delivery system for polynucleotides is a colloidal dispersion system. Colloidal dispersion systems include macromolecular complexes, nanocapsules, microspheres, beads, and lipid-based systems including oil-in-water emulsions, micelles, mixed micelles and liposomes. A preferred colloidal delivery system is a liposome, an artificial membrane vesicle useful as in vivo or in vitro delivery vehicles. The composition of a liposome is usually a combination of phospholipids, usually in combination with steroids, particularly cholesterol.

The Sir2 or p53 gene may also be underexpressed.

Methods whereby the level of Sir2 or p53 gene activity may be increased to levels wherein disease symptoms are ameliorated also include increasing the level of gene activity, for example by either increasing the level of Sir2 or p53 gene present or by increasing the level of gene product which is present.

For example, a target gene protein, at a level sufficient to ameliorate metabolic imbalance symptoms, may be administered to a patient exhibiting such symptoms. One of skill in the art will readily know how to determine the concentration of effective, non-toxic doses of the normal target gene protein. Additionally, RNA sequences encoding target gene protein may be directly administered to a patient exhibiting disease symptoms, at a concentration sufficient to produce a level of target gene protein such that the disease symptoms are ameliorated. Administration may be by a method effective to achieve intracellular administration of compounds, such as, for example, liposome administration. The RNA molecules may be produced, for example, by recombinant techniques such as those described above.

Further, patients may be treated by gene replacement therapy. One or more copies of a normal target gene, or a portion of the gene that directs the production of a normal target gene protein with target gene function, may be inserted into cells using vectors that include, but are not limited to adenovirus, adenoma-associated virus, and retrovirus vectors, in addition to other particles that introduce DNA into cells, such as liposomes. Additionally, techniques such as those described above may be utilized for the introduction of normal target gene sequences into human cells.

Cells, preferably autologous cells, containing and expressing normal target gene sequences may then be introduced or reintroduced into the patient at positions which allow for the amelioration of metabolic disease symptoms. Such cell replacement techniques may be preferred, for example, when the target gene product is a secreted, extracellular gene product.

In instances where the target gene protein is extracellular, or is a transmembrane protein, any of the administration techniques described, below which are appropriate for peptide administration may be utilized to effectively administer inhibitory target gene antibodies to their site of action.

The identified compounds that inhibit target gene expression, synthesis and/or activity can be administered to a patient at therapeutically effective doses to treat or ameliorate or delay the symptoms of aging. A therapeutically effective dose refers to that amount of the compound sufficient to result in amelioration or delay of symptoms of aging.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

All references cited herein are incorporated by reference in their entirety. The invention is illustrated by the following non-limiting examples.

Materials and Methods
Plasmids and Antibodies

To construct mSir2α expression constructs, the full-length cDNA was subcloned from pET28a-Sir2α (Imai et al., 2000) into pcDNA3 or pBabepuro vector. Site-directed mutation was generated in the plasmid pRS305-Sir2α using the Gene Edit system (Promega). To construct the human SIRT1 expression construct, DNA sequences corresponding to the full-length hSIRT1 (Frye, 1999) were amplified by PCR from Marathon-Ready Hela cDNA (Clontech), and initially subcloned into pcDNA3.1/V5-His-Topo vector (Invitrogen), and then subcloned with a Flag-tag into a pCIN4 vector for expression (Gu et al., 1999). To prepare the Sir2α antibody that can recognize both human and mouse Sir2α, a polyclonal antibody against the highly conserved C-terminus of Sir2α was generated. DNA sequences corresponding to this region (480-737) were amplified by PCR and subcloned into pGEX-2T (Pharmacia). Anti-Sir2α antisera were raised in rabbits against the purified GST-Sir2α (480-737) fusion protein (Covance), and further affinity-purified on both protein-A and antigen columns. By Western blot analysis and immunofluorescent staining, this antibody can detect both mouse Sir2α and human SIRT1 proteins.

To construct hSir2 expression constructs, BamHI/SnaBI fragment of hSIR2SIRT1 cDNA was inserted into pBabe-Y-Puro. The resulting plasmid was designated pYESir2-puro. Similarly a BamHI/SnaBI fragment of hSir2 that was mutated at residue 363 from Histidine (H) to Tyrosine (Y) by site-directed mutagenesis (Stratagene) was used to create the retroviral vector pYESir2HY. pBabe-hTERT-hygro contained an EcoRI/SalI fragment of hTERT cloned into EcoRI/SalI site of pBabe-Hygro. pCMVwtp53, pCMVK382R and pCMVK320R were a gift from Dr. E. Appella (NIH).

Cell Culture and Derivation of Cell Lines

All cells were grown in presence of 20% $O_2$ and 5% $CO_2$ at 37 EC in humidified chambers. Human diploid fibroblast BJ cells, human epithelial breast carcinoma cell line MCF7 and H1299 human epithelial carcinoma cell lines were grown in DME+10% FCS. PBS(−/−) (phosphate buffered saline) without magnesium or calcium was used for washing cells and other applications described herein.

Amphotrophic viruses were produced by transient co-transfection of pCL-pCL-Ampho with the LTR containing pBabe vectors (Morgenstern and Land, 1990), pYESir2 or pYESir2HY in to 293T cell line using Fugene6 (Roche). Three days post transfection supernatants were collected and filtered with 0.4 micron filters. Primary BJ cells or MCF7 cells were infected with retrovirus containing media in presence of 8 mg/ml of polybrene overnight and 48 hours later cells were selected in puromycin at 1 mg/ml.

Following selection and during the experimentation all the mass cultures were maintained in presence of puromycin. These selected BJ cells were subsequently infected and selected with a pBabe-hTERT virus carrying the hygromycin resistance gene (200 mg/ml). The resulting cells were: BJT (carrying pYE-Puro backbone and pBabe-hTERT-hygro), BJThSir2wt (carrying pYESir2 wild type hSir2 and pBabe-hTERT hygro) and BJThSir2HY (pYESir2HY mutant hSir2 and pBabe-hTERT-hygro). MCF7 cells were transfected with the vector p21P-luc (Vaziri et al., 1997) and pCMVneo, clones were selected in 500 mg/ml of G418 and the clone designated MCF73L was selected that was able to upregulate the p21WAF1 promoter-luciferase in response to treatment with 6 Gy of ionizing radiation. MCF7 cells or MCF73L were infected with the same viruses as described before to yield the following cell lines: MCF73LP (carrying pBabeY-puro backbone), MCF73L-hSir2wt and MCF73L-hSir2HY. Cells were kept under appropriate selection throughout experiments.

In Vitro p53 Deacetylation Assay

The Flag-tagged Sir2α-expressing cells were established and expanded in

DMEM medium, and cell extracts were prepared essentially as previously described (Luo et al., 2000; Gu et al., 1999; Ito et al., 1999). The proteins were purified under a very high stringency condition (300 mM NaCl and 0.5% NP-40). The eluted proteins were resolved by a SDS-PAGE gel and analyzed by colloidal blue staining (Novex). Acetylated GST-p53 was prepared by p53 acetylation assay as previously described (Gu and Roeder, 1997) and further purified on glutathione-Sepharose (Luo et al., 2000). The $^{14}$C-labeled acetylated p53 (2.5:g) was incubated with purified Sir2α (10 ng) at 30 EC for 1 hr either in the presence of 50 (DM NAD or as indicated. The reactions were performed in a buffer containing 50 mM Tris-HCl (pH 9.0), 50 mM NaCl, 4 mM $MgCl_2$, 0.5 mM DTT, 0.2 mM PMSF, 0.02% NP-40 and 5% glycerol. The reactions were resolved on SDS-PAGE and analyzed by Coomassie blue staining and autoradiography.

Immunoprecipitation and Immunofluorescence

H1299 cells transiently expressing p53 and hSir2 were lysed using the NP40 buffer and lysates described above and immunoprecipitated with 1 ul of anti-hSir2 antibody overnight. Protein G-sepharose beads (50 ml) were added to the lysates and rotated at 4 EC for 3 hrs. The immune complexes were collected, washed 3 times, and resolved using the Nupage gradient 4-12% Bis-Tris MOPS (3-N-morpholino propane sulfonic acid) protein gel (Novex) in the presence of provided anti-oxidant (Novex).

The gels used were transferred to nitrocellulose and probed with anti-p53 antibody (pAb7 sheep anti human polyclonal antibody, Oncogene Science), signal detected using a goat anti-sheep HRP secondary antibody. The membranes were subsequently washed and reprobed with anti-hSir2 antibody.

For immunoprecipitation in BJ cells, 1 mg of protein per reaction were incubated with 1 ul of Ab-6(anit-p53 monoclonal, Oncogene Science) and immunoprecipitation was performed as described above except that the time of incubation in primary antibody was 2 hrs and 4 times higher concentrations of protease inhibitors were used, due to the observed high instability of p53 protein in BJ cells. Immune complexes were resolved as previously described using the Novex system (Invitrogen) and membranes were exposed to a mix of polyclonal antibodies at 1:1000 dilution (SC6432, polyclonal rabbit and CM1, polyclonal rabbit). A secondary goat anti-rabbit HRP was used at 1:30,000 concentration for detection. Membranes were subsequently blocked again and re-probed with anti-hSir2 antibody.

Immunofluorescence of U20S and BJ cells was undertaken by fixing the cells in microchamber slides (LabTek) in 70% Ethanol and subsequent staining with anti-hSir2 antibody at 1:500 dilution. A secondary goat anti-rabbit FITC antibody at 0.5 µg/ml was used for detection of signal.

GST Pull-Down Assay and Co-Immunoprecipitation Assay

GST fusion proteins were expressed in *E. coli*, extracted with buffer BC500 (20 mM Tris-HCl, pH 8.0, 0.5 mM EDTA, 20% glycerol, 1 mM DTT and 0.5 mM PMSF) containing 50 mM KCl and 1% NP-40, and purified on glutathione-sepharose (Pharmacia). $^{35}$S-labeled Sir2α was in vitro translated by a TNT kit (Promega) using pcDNA3-Sir2α as a template. 5:1 of $^{35}$S-labeled Sir2α were incubated at 4 EC for 60 min with each of the different immobilized GST fusion proteins in BC200 buffer containing 200 mM KCl and 0.2% NP-40. Beads were then washed five times in 0.5 ml of the same buffer. Bound proteins were eluted with an equal volume of SDS sample buffer, resolved by SDS-PAGE, and analyzed by Coomassie blue staining and autoradiography.

The co-immunoprecipitation assay was performed essentially as described previously (Luo et al., 2000). Cells were extracted with lysis buffer (25 mM HEPES-KOH, pH 8.0, 150 mM KCl, 2 mM EDTA, 1 mM DTT, 1 mM PMSF, 10 µg/ml aprotinin, 10 µg/ml leupeptin, 1 µg/ml pepstatin A, 20 mM NaF, 0.1% NP-40). After centrifugation, the supernatants were incubated with M2 beads (Sigma) for 4 hr at 4 EC. The M2 beads were washed five times with 0.5 ml lysis buffer, after which the associated proteins were eluted with Flag peptides to avoid the cross-reaction from the mouse IgG in western blot analysis. In the case of the co-immunoprecipitation in normal cells, 50 million cells were extracted in the same lysis buffer. The supernatants were incubated with 20 µg anti-Sir2α antibody or pre-immune antiserum from the same rabbit and 40:1 protein A/G plus-agarose (Santa Cruz) for overnight. The agarose beads were washed five times with 0.5 ml of lysis buffer, after which the associated proteins were eluted with BC1000 (20 mM Tris-HCl, pH 8.0, 0.5 mM EDTA, 20% glycerol, 1 mM DTT and 0.5 mM PMSF) containing 1 M NaCl, 1% NP-40, 0.5% Deoxycholic Acid. The eluted proteins were resolved on 8% SDS PAGE and Western blot with anti-Sir2a antibody and anti-p53 antibody (DO-1) for human cells and anti-p53 antibody (421) for mouse cell.

Immunoblot Analysis

For detection of acetylated forms of p53 in BJ cells and MCF7 cells, equal numbers of cells were plated 24 hrs before the experiment. $1.5 \times 10^6$ BJ cells or $10^7$ MCF7 cells exponentially growing phase in 150 cm$^2$ dishes were exposed to 6 Gy of ionizing radiation (137Cesium gamma source at dose rate of 1 Gy/min). At the appropriate time point, cells were washed and harvested by trypsinization and subsequent neutralization with 10% serum. After washing the cells once in PBS(−/−), cell pellets were frozen on dry ice instantly at the appropriate time point. Once all time points were collected, cell pellets were all lysed on ice at once by adding 0.5% NP40, 150 mM NaCl (in the presence of complete protease inhibitor mix, Roche), for 30 minutes and vortexing. Cell lysates were prepared by centrifugation for 20 minutes at 4 EC. Protein content of lysates were measured using Lowry based assay (BioRad DC protein assay). Protein (300 mg) was resolved on gradient 4-20% criterion Tris-HC gels (Biorad), transferred to nitrocellulose and blocked in 10% skim milk.

The resulting membrane was incubated overnight in 1:400 dilution of Ab-1 (Oncogene Science, peptide based rabbit polyclonal anti K382 p53). This membrane was then washed twice in PBS(−/−) containing 0.05% Tween 20 for 15 minutes. Secondary Goat anti-rabbit antibody conjugated to HRP (Pierce) was used at a concentration of 1:30,000 for 1 hr in 1% Milk. Membrane was subsequently washed twice for 30 minutes total time.

The membrane was incubated with Supersignal west femto maximum substrate (Pierce) for 2 minutes and exposed to X-OMAT sensitive film (Kodak) for up to 30 minutes. The membrane was subsequently blotted with a monoclonal p21WAF1 antibody (F5, Santa Cruz Biotech), p53 antibody (SC6243, polyclonal rabbit, Santa Cruz) (Ab-6, Oncogene Science), anti-hSir2 (polyclonal rabbit). ∃-actin was used (Abcam) for loading control. 9671S is an anti-acetyl H3 Lys9 was a monoclonal antibody (Cell Signaling).

Virus Infection and Stress Response

All MEF cells were maintained in DMEM medium supplemented with 10% fetal bovine serum, and the IMR-90 cells were maintained in Eagle's minimal essential medium supplemented with 10% fetal bovine serum and non-essential amino acids. The virus infection and selection were essentially as described previously (Ferbeyre et al., 2000). After one-week selection, the cells were either frozen for stock or immediately used for further analysis. About 500,000 MEF cells were plated on a 10-cm dish 24 hr before treatment. The cells were then exposed to etoposide (20:m) for 12 hr. After treatment, the cells were washed with PBS and fed with normal medium. Another 36 hrs later, the cells were stained with PI and analyzed by flow cytometric analysis for apoptotic cells (SubG1) according to DNA content. In case of the Fas-mediated apoptosis assay, the cells were treated with actinomycin D (0.25:g/ml) and Fas antibody (100 ng/ml) as previously described (Di Cristofano et al., 1999). In the case of oxidative stress response, the IMR-90 cells were treated with $H_2O_2$ (200:M) for 24 hrs.

Luciferase and Apoptosis Assays

H1299 cells were transfected using the Fugene6 protocols (Roche) with pCMVwtp53 in presence or absence of pCMVp300 and 5 µg of p21P-Luc (containing a 2.4 kb fragment of p21 linked to luciferase gene) as previously described (Vaziri et al., 1997). All experiments were performed in triplicates.

Apoptosis was measured at approximately 48 hrs post transfection using the annexin V antigen and propidium iodide exclusion (Clontech laboratories).

Radiation survival curves of BJ cells were performed as described previously (Dhar et al., 2000; Vaziri et al., 1999).

FACS Analysis for Apoptosis Assay

Both adherent and floating cells were combined and washed in cold PBS. For SubG1/FACs analysis, cells were fixed in methanol for 2 hr at −20 EC, rehydrated in PBS for 1 hr at 4 EC, and then reacted with the primary antibody (DO-1) for 30 min at room temperature. Cells were washed twice in PBS and incubated with a goat anti-mouse FITC-conjugated secondary antibody for 30 min at room temperature. Following incubation, cells were washed in PBS and treated with RNase A (50 Φg/ml) for 30 min at room temperature. Propidum iodide (PI: 2.5 Φg/ml) was added to the cells, and samples were then analyzed in a FACSCalibur (BD). A region defining high FITC fluorescence was determined, and the cells falling into this region were collected separately. The PI staining was recorded simultaneously in the red channel.

Immunofluorescence Assay

Immunofluorescence was performed essentially as the standard protocol (Guo et al., 2000). After fixation, cells were exposed to two primary antibodies: p53 monoclonal antibody DO-1 (Santa Cruz) and anti-Sir2α antibody for 1 hr at room temperature. The cells were washed three times with 1% BSA plus 0.2% Tween-20 in PBS and then treated with two secondary antibodies [a goat anti-rabbit IgG conjugated to Alexa 568 (Molecular Probes), and anti-mouse IgG-FITC (Santa-Cruz)]. DAPI was used for counter-staining to identify nuclei. The cells were further washed four times. Images were acquired from a Nikon Eclipse E600 fluorescent microscope (Hamamatsu Photonics).

Detecting Acetylation Levels of p53 in Cells

The cells (human lung carcinoma cell lines H460 (wild-type p53) and H1299 (p53-null), human colon carcinoma HCT116 (wild-type p53), mouse embryonal carcinoma cell line F9 (wild-type p53), mouse embryonic fibroblast MEFs or others) were maintained in DMEM medium supplemented with 10% fetal bovine serum. For DNA damage response, about 1 million cells were plated on a 10-cm dish 24 hr before treatment. The cells were then exposed to etoposide (20:M) and or other drugs (0.5 μM of TSA, 5 mM of nicotinamide, and 50:M of LLNL) as indicated for 6 hr.

After treatment, the cells were harvested for Western blot analysis. The rabbit polyclonal antibody specific for p300-mediated acetylated p53 [.A-inverted.-p53(Ac)-C] was raised and purified against the acetylated human p53 C-terminal peptide [p53 (Ac)-C:H-S55GQSTSRH55LMF-OH SEQ. ID No:1 (5=acetylated Lysine)] as described before (Luo et al., 2000).

This antibody recognizes the p300-mediated acetylated forms of both human and mouse p53. In the case of cotransfection assays testing for p53 acetylation levels, H1299 cells were transfected with 5:g of CMV-p53 plasmid DNA, 5 μg of CMV-p300 plasmid DNA, and 10:g of pcDNA2-Sir2α plasmid DNA as indicated. 24 hr after the transfection, the cells were lysed in a Flag-lysis buffer (50 mM Tris, 137 mM NaCl, 10 mM NaF, 1 mM EDTA, 1% Triton X-100 and 0.2% Sarkosyl, 1 mM DTT, 10% glycerol, pH 7.8) with fresh proteinase inhibitors, 10:M TSA and 5 mM nicotinamide (Sigma). The cell extracts were resolved by either 8% or 4-20% SDS-PAGE gels (Novex) and analyzed by Western blot with -∀-p53 (Ac)-C and .∀-p53 (DO-1).

Deacetylation Assay of the p53 C-Terminal Peptide

The human p53 C-terminal peptide (residues 368-386+Cys; HLKSK(AcK)GQSTSRHK(AcK)LMFKC); (SEQ ID NO: 24) di-acetylated at positions 373 and 382 was synthesized and purified with HPLC. Deacetylation assays of this peptide by Sir2 and analyses of the reaction products were performed as described previously (Imai et al., 2000).

EXAMPLES

Example 1

Mammalian Sir2α Interacts with p53 both In Vitro and In Vivo

Mouse Sir2α interacts with p53. The p53 protein can be divided into three distinct functional domains (Gu and Roeder, 1997): an amino-terminus that contains the transcriptional activation domain (NT: residues 1-73), a central core that contains the sequence-specific DNA-binding domain (M: residues 100-300), and the multifunctional carboxyl-terminus (CT: residues 300-393). The GST-p53 fusion proteins containing each domain as well as the full-length protein were expressed in bacteria and purified to near homogeneity on gluthathione-agrose beads. As shown in FIG. 1A, $^{35}$S-labeled in vitro translated Sir2α strongly bound to immobilized GST-p53 but not to immobilized GST alone (lane 1 vs. 6). Sir2α was tightly bound to the C-terminal domain of p53 (GST-p53CT) (lane 4, FIG. 1A), also bound to the central DNA-binding domain (GST-p53M), but showed no binding to the N-terminal domain of p53 (GST-p53NT) (lane 3 vs. 2, FIG. 1A).

To test for the interactions between p53 and Sir2α in cells, extracts from transiently-transfected p53-null cells (H1299) were immunoprecipitated with anti-Flag monoclonal antibody (M2). As shown in FIG. 1B, p53 was detected in the immunoprecipitate obtained from H1299 cells cotransfected with constructs encoding Flag-Sir2α and p53 (lane 2), but not from cells transfected with the p53 construct alone (lane 4). Conversely, Sir2α was detected in the immunoprecipitates obtained from H1299 cells cotransfected with constructs encoding Sir2α and Flag-p53 (lane 6, FIG. 1B), but not from cells transfected with the Sir2α construct alone (lane 8, FIG. 1B). p53 interacts similarly with human SIRT1 (hSIRT1) (FIG. 1C, D), the human ortholog of mouse Sir2α (Frye, 1999; 2000), showing that p53 and mammalian Sir2α interact.

Since mouse Sir2α shares a highly conserved region at the C-terminus with human SIRT1 (FIG. 1C), but not with any other mammalian Sir2 homologs (Frye, 1999; 2000), a polyclonal antibody against the C-terminus (amino acid 480-737) of mouse Sir2α was developed. Anti-Sir2α antisera (anti-Sir2α) was raised in rabbits against the purified GST-Sir2α (480-737) fusion protein. As shown in Western blots, this antibody can detect both mouse Sir2α and human SIRT1 proteins, but not other human Sir2 homologs (FIGS. 2A, B).

p53 interaction with Sir2α or hSIRT1 in normal cells without overexpression was studied employing this antibody. Cell extracts from human (H460) and mouse cells (F9), which express wild-type p53 proteins, were immunoprecipitated with anti-Sir2α or with the pre-immune serum. Western blot analysis revealed that this antibody immunoprecipitated both Sir2α and hSIRT1 (lower panels, FIG. 2A, 2B). Human and mouse p53 were detected in the respective anti-Sir2α immunoprecipitations from cell extracts, but not in the control immunoprecipitations with the preimmune serum, showing that p53 interacts with mammalian Sir2α in normal cells. In contrast to abrogation of the Mdm2-p53 interaction by DNA damage as previously reported (Shieh et al., 1997), this interaction was stronger in cells after DNA damage treatment (FIG. 2C), which shows mammalian Sir2α is involved in regulating p53 during the DNA-damage response. Thus, p53 interacts with mammalian Sir2α both in vitro and in vivo.

Example 2

Deacetylation of p53 by Mammalian Sir2α p53 was deacetylated by mammalian Sir2α in vitro. Mouse Sir2α protein was expressed with the N-terminal Flag epitope in cells and purified to near homogeneity on the M2-agrose affinity column (lane 3, FIG. 3A to determine). The GST-p53 fusion protein was acetylated by p300 in the presence of [$^{14}$C]-acetyl-CoA, and the acetylated p53 protein was purified on the GST affinity column. These highly purified recombinant proteins were used in this assay in order to avoid possible contamination by either inhibitory factors or other types of deacetylases.

As shown in FIG. 3B, $^{14}$C-labeled acetylated p53 was efficiently deacetylated by purified Sir2α (lane 3), but not by a control eluate (lane 4). NAD is required for Sir2α-mediated deacetylation of p53 (lane 2 vs. 3, FIG. 3B). Further, the deacetylase inhibitor TSA, which significantly abrogates HDAC1-mediated deacetylase activity on p53 (Luo et al., 2000), had no apparent effect on Sir2α-mediated p53 deacetylation (lane 5, FIG. 3B). These results show that Sir2α can strongly deacetylate p53 in vitro, and that this activity depends on NAD.

A role for mammalian Sir2α in deacetylating p53 in cells was established using acetylated p53-specific antibody to monitor the steady-state levels of acetylated p53 in vivo (Luo et al., 2000). As shown in FIG. 3C, a high level of acetylated p53 was detected in the cells cotransfected with p300 and p53 (lane 1). However, p53 acetylation levels were significantly abolished by expression of either Sir2α or hSIRT1 (lanes 2, 4). In contrast, a Sir2α mutant (Sir2αH355A) containing a point mutation at the highly conserved core domain causing defective histone deacetylase activity in vitro had almost no effect (lane 3 vs. 2, FIG. 3C). Furthermore, neither SIRT5, another human Sir2 homolog, nor poly (ADP-ribose) polymerase (PARP), whose activity is also NAD-dependent (reviewed in Vaziri et al., 1997), had any significant effect on p53 acetylation (lanes 5, 6, FIG. 3C). In addition, in contrast to HDAC-mediated deacetylation of p53 (Luo et al., 2000) Sir2α still strongly deacetylated p53 in the presence of TSA (lane 4 vs. 3, FIG. 3D) even though the steady state level of acetylated p53 was elevated when the cells were treated with TSA (lane 3 vs. 1, FIG. 3D). Thus, mammalian Sir2α has robust TSA-independent p53 deacetylation activity.

Example 3

Inhibition of Sir2α-Mediated p53 Deacetylation by Nicotinamide

Sir2α-mediated deacetylase activity of p53 can be inhibited. Deacetylation of acetyl-lysine by Sir2α is tightly coupled to NAD hydrolysis, producing nicotinamide and a novel acetyl-ADP-ribose compound (1-O-acetyl-ADPribose) (Landry et al., 2000b; Tanner et al., 2000; Tanny and Moazed, 2001). The formation of an enzyme-ADP-ribose intermediate through NAD hydrolysis may be critical for this chemical reaction (Landry et al., 2000b). Since nicotinamide is the first product from hydrolysis of the pyridinium-N-glycosidic bond of NAD, it may function as an inhibitor for its deacetylase activity (Landry et al., 2000b). Nicotinamide is able to inhibit the deacetylase activity of Sir2α on acetylated p53 in vitro.

Similar reactions as described above (FIG. 3B), were set up by incubating labeled p53 substrate, recombinant Sir2α and NAD (50:M) alone, or in combination with nicotinamide (5 mM). As shown in FIG. 4A, $^{14}$C-labeled acetylated p53 was efficiently deacetylated by Sir2α (lane 2) however, the deacetylation activity was completely inhibited in the presence of nicotinamide (lane 3 vs. lane 2 FIG. 4A). As a negative control, 3-AB (3-aminobenzamide), a strong inhibitor of PARP which is involved in another type of NAD-dependent protein modification (Vaziri et al., 1997), showed no significant effect on Sir2α-mediated deacetylation (lane 4 vs. 3, FIG. 4A).

To further investigate the role of mammalian Sir2α-mediated regulation in vivo, the effect of Sir2α expression on p53 acetylation levels during the DNA damage response was determined. Mouse embryonic fibroblast (MEF) cells, which express the wild type of p53, were infected with either a pBabe-puro retrovirus empty vector or a pBabe-puro retrovirus containing Sir2α, and cultured for a week under pharmacological selection. The protein levels of p53 activation in response to DNA damage in these cells was determined by Western blot analysis. Similar protein levels of p53 activation were induced in the pBabe vector infected cells and pBabe-Sir2α infected cells after etoposide treatment for 6 hrs (lanes 3, 4 vs. lanes 1, 2, lower panel, FIG. 4B).

In the mock-infected cells, the acetylation level of p53 was significantly enhanced by DNA damage (lane 2 vs. lane 1, Upper panel, FIG. 4B). However, DNA damage treatment failed to stimulate the p53 acetylation in the pBabe-Sir2α infected cells even in the presence of TSA (lane 4 vs. lane 2, Upper panel, FIG. 4B), showing that Sir2α expression results in deacetylation of endogenous p53. This Sir2α-mediated effect was completely abrogated by nicotinamide treatment (lane 8 vs. lane 6, FIG. 4B). Thus, Sir2α mediated deacetylation of p53 can be inhibited by nicotinamide both in vitro and in vivo.

Example 4

Maximum Induction of p53 Acetylation Levels in Normal Cells Requires Inhibition of Endogenous Sir2α Activity Endogenous Sir2α in the regulation of p53 acetylation levels in normal cells during the DNA damage response was determined.

As shown in FIG. 4C, after the wild-type p53 containing human lung carcinoma cells (H460) were treated by etoposide, acetylation of p53 was induced (lane 2 vs. lane 1). No significant p53 acetylation was detected in the cells treated with a proteasome inhibitor LLNL (lane 6, FIG. 4C), indicating that the observed stimulation of p53 acetylation is induced by DNA damage, not through p53 stabilization.

p53 can be deacetylated by a PID/MTA2/HDAC1 complex, whose activity is completely abrogated in the presence of TSA (Luo et al., 2000). The mild enhancement of the acetylation level of p53 by TSA during DNA damage response may be due mainly to its inhibitory effect on endogenous HDAC 1-mediated deacetylase activity (lane 3 vs. lane 2, FIG. 4C). A super induction of p53 acetylation was showed when the cells were treated with both TSA and nicotinamide (lane 4 vs. lane 3, FIG. 4C). In contrast, 3-AB treatment had no effect on the level of p53 acetylation (lane 5 vs. lane 3, FIG. 4C), indicating that PARD-mediated poly-ADP ribosylation has no effect on p53 acetylation. Similar results were also observed in other cell types including either mouse cells (MEFs, F9) or human cells (BL2, HCT116). Thus, maximum induction of p53 acetylation requires inhibitors for both types of deacetylases (HDAC1 and Sir2α), and endogenous Sir2α plays a major role in the regulation of the p53 acetylation levels induced by DNA damage.

Example 5

Repression of p53-Mediated Functions by Mammalian Sir2α Requires its Deacetylase Activity The functional consequence of mammalian Sir2α-mediated deacetylation of p53 was determined by testing its effect on p53-mediated transcriptional activation. A mammalian p53 expression vector (CMV-p53), alone or in combination with different amounts of mouse Sir2α expressing vector (CMV-Sir2α), was cotransfected into MEF (p53$^{-/-}$) cells along with a reporter construct containing synthetic p53 binding sites placed upstream of the luciferase gene (PG13-Luc).

As shown in FIG. 5A, Sir2α strongly repressed p53-mediated transactivation in a dose-dependent manner (up to 21 fold), but had no significant effect on the transcriptional activity of the control reporter construct (TK-Luc) (FIG. 5B), which has no p53 binding site at the promoter region. Also, expression of human SIRT1 showed a similar effect on the p53 target promoter (FIG. 5C). Neither the Sir2α H355A mutant or SIRTS, both of which are defective in p53 deacetylation (FIG. 3C), had any effect on the p53-mediated transactivation (FIGS. 5C, D). Thus, mammalian Sir2α specifically represses p53-dependent transactivation, and that this repression requires its deacetylase activity.

The modulation of Sir2 on p53-dependent apoptosis was determined. p53 null cells (H1299) were transfected with p53 alone or cotransfected with p53 and Sir2α. The transfected cells were fixed, stained for p53, and analyzed for apoptotic cells (SubG1) (Luo et al., 2000). As indicated in FIG. 6A, overexpression of p53 alone induced significant apoptosis (32.3% SubG1). However, co-transfection of p53 with Sir2α significantly reduced the level of apoptosis (16.4% SubG1), while the mutant Sir2αH355A was impaired in this effect (29.5% SubG1) (FIG. 6A, B). Thus, mammalian Sir2α is involved in the regulation of both p53 mediated transcriptional activation and p53-dependent apoptosis, and deacetylase activity is required for these Sir2α-mediated effects on p53.

Example 6

The Role of Mammalian Sir2α in Stress Induced Apoptotic Response

Mammalian Sir2α can deacetylate p53 both in vitro and in vivo (FIG. 3). Sir2α can block the induction of endogenous p53 acetylation levels by DNA damage (FIGS. 4B, 4C). To elucidate the physiological significance for this Sir2α mediated regulation, the effect on DNA damage-induced apoptotic response was determined. MEF ($p53^{+/+}$) cells as described above (FIG. 4B), were infected with either a pBabe-puro retrovirus empty vector or a pBabe-puro retrovirus containing Sir2α. After the DNA damage treatment by etoposide, the cells were stained with PI and analyzed by flow cytometric analysis for apoptotic cells (SubG1) according to DNA content. As shown in FIG. 7A, the cells mock infected with the pBabe-vector, were susceptible to etoposide-induced cell death, with about 48% of the cells apoptotic after exposure to 20:M of etoposide (3 vs. 1, FIG. 7A). In contrast, the pBabe-Sir2α infected MEF ($p53^{+/+}$) cells were more resistant to apoptosis induced by the same dose of etoposide, with only 16.4% apoptotic cells (4 vs. 3, FIG. 7A). Since no significant apoptosis was detected in MEF ($p53^{-/-}$) cells by the same treatment, the induced apoptosis observed in MEF ($p53^{+/+}$) cells is totally p53-dependent. Thus, Sir2α significantly inhibits p53-dependent apoptosis in response to DNA damage.

The role of mammalian Sir2α in the oxidative stress response was determined. Recent studies have indicated that oxidative stress-induced cell death is p53-dependent (Yin et al., 1998; Migliaccio et al., 1999). Early-passage normal human fibroblast (NHF) IMR-90 cells were employed for this study since p53-dependent apoptosis can be induced by hydrogen peroxide treatment in these cells (Chen et al., 2000).

IMR-90 cells were infected with either a pBabe-puro retrovirus empty vector or a pBabe-puro retrovirus containing Sir2α, and cultured for a week under pharmacological selection. By immunofluorescence staining, p53, in these infected cells, was induced significantly after hydrogen peroxide treatment, along with Sir2α localized in the nuclei detected by immunostaining with specific antibodies (FIG. 7C). Sir2α expression significantly promotes cell survival under oxidative stress. As indicated in FIG. 7D, the cells mock infected with the pBabe-vector, were susceptible to $H_2O_2$-induced cell death, with more than 80% of the cells being killed after 24 hr exposure to 200:M $H_2O_2$ (II vs. I). In contrast, the pBabe-Sir2α infected cells were much more resistant to death by the same dose of $H_2O_2$, with about 70% of the cells surviving after 24 hr of $H_2O_2$ treatment (IV vs. III, FIG. 7D). Mammalian Sir2α promotes cell survival under stress by inhibiting p53-dependent apoptosis.

Example 7

Mammalian Sir2α has No Effect on p53-Independent Cell Death Induced by Anti-Fas

The specificity of mammalian Sir2α-mediated protection of cells from apoptosis was examined by determining whether Sir2α has any effect of p53-independent, Fas-mediated apoptosis. The MEF ($p53^{-/-}$) cells were first infected with either a pBabe-puro retrovirus empty vector or a pBabe-puro retrovirus containing Sir2α, then cultured for a week under pharmacological selection. After the treatment by anti-Fas (100 ng/ml) for 24 hrs, the cells were harvested and further analyzed for apoptotic cells (SubG1).

Cells mock infected with the pBabe vector, were susceptible to anti-Fas induced cell death, with about 31.7% of the cells becoming apoptotic. However, in contrast to the strong protection of p53-dependent apoptosis by Sir2α during DNA damage response in the MEF ($p53^{+/+}$) cells (FIG. 7A, B), Sir2α expression had no significant effect on Fas-mediated apoptosis in the MEF ($p53^{-/-}$) cells. Thus, mammalian Sir2α regulates p53-mediated apoptosis.

Mammalian Sir2α has no effect on the Fas mediated apoptosis. (A) Both mock infected cells and pBabe-Sir2α infected MEF p53(−/−) cells were either not treated (1 and 2) or treated with 100 ng/ml Fas antibody in presence of actinomycin D (0.25:g/ml) (3 and 4). The cells were analyzed for apoptotic cells (subG1) according to DNA content (PI staining) The representative results depict the average of three experiments with standard deviations indicated.

Example 8

Physical Interaction of hSir2 with p53 p53 protein is acetylated in response to DNA damage and the acetylation contributed to the functional activation of p53 as a transcription factor (Abraham et al., 2000; Sakaguchi et al., 1998). Sir2 is a deacetylase of p53, thereby modulating functioning of p53 as a transcription factor.

In order to study the functional interaction between p53 and hSir2, a full length human hSir2SIRT1 cDNA clone (obtained from the IMAGE consortium (Frye, 1999)) was introduced into a pBabe-based retroviral expression vector which also carries puromycin resistance gene as a selectable marker. The resulting construct was termed pYESirwt. A retroviral construct bearing a derived, mutant allele of Sir2 and termed pYESirHY was constructed and used in parallel as control. This mutant allele encodes an amino acid substitution at residue 363, at which site the normally present histidine is replaced by tyrosine. This H to Y substitution results in an alteration of the highly conserved catalytic site of the hSir2 protein and subsequent neutralization of its deacetylase activity. These vector constructs were used to transduce the hSIR2SIRT1 gene both by transfection and retroviral infection.

A polyclonal rabbit antibody that specifically recognizes the C-terminal portion of hSir2 was developed and its specificity validated by immunoprecipitation and Western blotting (FIG. 8A). Both the endogenous and the ectopically expressed hSir2 proteins were detected as protein species of 120 Kilodalton (Kd) rather than as 80 Kd polypeptide predicted from the known primary sequence of hSIR2SIRT1 (FIG. 8A). Localization of hSir2 protein by immunofluorescence using the hSir2 antibody showed a punctate nuclear staining pattern (FIG. 8B).

The physical interactions between hSir2 and p53 were evaluated by co-transfecting the pYESir2wt plasmid and a vector expressing wt p53 under the control of the cytomegalovirus promoter (pCMV-wtp53) transiently into H1299 human non-small cell lung carcinoma cells (Brower et al., 1986) which have a homozygous deletion of the p53 gene and produce no p53 mRNA or protein (Mitsudomi et al., 1992). Cell lysates were subsequently mixed with the rabbit anti-hSir2 antibody and resulting immune complexes were collected by protein G and analyzed by SDS-PAGE electrophoresis and immunoblotting. The immunoblot was probed with a sheep anti-p53 antibody (FIG. 8C) and reprobed it subsequently with an anti-hSir2 antibody (top panel) to verify presence of hSir2 in the complex. As indicated in FIG. 8C, immunoprecipitation of hSir2 resulted in co-precipitation of p53.

In the reciprocal experiment, lysates of BJT cells, human fibroblasts into which the telomerase gene has been introduced, were examined. In addition, these cells express either the wild type hSir2 vector or the hSir2HY mutant. Two cell populations were created by infection of mass cultures of BJT cells with the respective vectors and subsequent selection in puromycin. The anti-p53 antibody was employed to immunoprecipitate complexes and subsequently probe the resulting immunoblot with either polyclonal anti-p53 antibodies or an anti-hSir2 antibody. These immunoblots demonstrated a physical interaction between hSir2 and p53 proteins (FIG. 8D). Formation of these complexes was unaffected by the H to Y mutation introduced into the hSir2 catalytic site (FIG. 8D). Furthermore, radiation used to increase the levels of p53 protein in BJ cells had no effect on the levels of p53:hSir2 complexes. Comparison of the immunoprecipitated p53 to total input p53 resulted in an estimate of approximately 1% of the cells complement of p53 protein was present in physical complexes with hSir2.

Example 9

Deacetylation of p53 by hSir2 In Vitro

Since hSir2 forms physical complexes with p53, the ability of Sir2 to deacetylate human p53 in vitro was evaluated. Since adequate quantities of bacterially produced hSir2 were not available, bacterially expressed mouse SIR2 (mSir2α) enzyme was used in in vitro assays (Imai et al., 2000). A 20 residue-long oligopeptide that contains the sequence corresponding to residues 368-386+Cys of the human p53 protein was used as a substrate in these reactions. Lysine residues corresponding to residues 373 and 382 of the p53 protein were synthesized in acetylated form in this oligopeptide substrate. These two residues of p53 are known to be acetylated by p300 (Gu and Roeder, 1997) following (or UV irradiation (Liu et al., 1999; Sakaguchi et al., 1998) with acetylation of lysine residue 382 being favored in response to ionizing radiation in vivo (Abraham et al., 2000). This p53 oligopeptide serves as an excellent surrogate p53 substrate in vitro for acetylation studies (Gu and Roeder, 1997).

The deacetylase activity of hSir2 utilizes NAD as a cofactor (Imai et al., 2000; Moazed, 2001; Smith et al., 2000; Tanner et al., 2000; Tanny et al., 1999). In the absence of added NAD, incubation of mSir2 with p53 oligopeptide gave rise to a single prominent peak (peak 1) and a small, minor peak (peak 2) upon high pressure liquid chromatography (HPLC), corresponding to the monomeric and dimeric forms of the peptide, respectively (FIG. 9A). However, incubation in the presence of 1 mM NAD produced a singly deacetylated species as the major product (peak 3, FIG. 9B). Edman sequencing of this singly deacetylated species revealed that mSir2 preferentially deacetylated the residue corresponding to Lys 382 of p53 (FIG. 9, C-F), having relatively weak effect on Lys 373. Thus, the acetylated p53 peptide acted as a substrate for hSir2 and indicated that the de-acetylation of p53 at Lys 382 by mammalian Sir2 is specific and not the result of an indiscriminate deacetylase function.

Example 10

Deacetylation of p53 by hSir2 In Vivo

The ability of hSir2 to deacetylate intact p53 protein in vivo was evaluated. To produce acetylated p53 in vivo, the p53 expression plasmid was co-transfected with one expressing p300. This protocol leads to acetylation of p53 in the absence of exposure to DNA-damaging agents (Luo et al., 2000). The ability of hSir2 to deacetylate the p53 protein at its K382 residue in H1299 cells that lack endogenous p53 gene was determined. The levels of acetylation of p53 at Lys382 were monitored by using a rabbit polyclonal antibody, termed Ab-1, which had been raised against the acetylated K382 of p53 protein. The specificity of the Ab-1 antibody has been demonstrated (Sakaguchi et cd., 1998).

Co-transfection of plasmids expressing wild-type p53 and p300 into H1299 cells showed that p53 protein is readily acetylated at K382, as detected by probing the immunoblot with the Ab-1 antibody (FIG. 10A, lane 3). Recognition of this acetylated form of p53 by the Ab-1 antibody was specific, since a mutant p53 protein that was expressed in a parallel culture of H1299 cells and carries an arginine rather than a lysine at residue 382 was not recognized by the Ab-1 antibody, despite ectopic expression of the p300 acetylase. (FIG. 10A, lane 6).

Co-transfection of the hSir2-expression plasmid with the p53- and p300-expressing plasmids substantially decreased the acetylated p53 that could be detected by the Ab-1 antibody. (FIG. 10A, lane 5). The residual level of acetylated p53 could be further reduced by increasing the amount of co-transfected hSir2 expression plasmid. Thus, hSir2 can deacetylate p53 protein at the Lys382 residue in vivo.

The hSir2HY vector, which expresses the mutant-catalytically inactive hSir2, was introduced into these H1299 cells. The mouse equivalent of this hSir2HY mutant lacks 95% of its deacetylase activity (Imai et al., 2000). The hSir2HY mutant failed to deacetylate wt p53 efficiently, indicating that the catalytic activity of the introduced wild type hSir2 gene product was required for specific deacetylation of p53 Lys 382 (FIG. 10A, lane 9).

The lysine 320 residue of p53 is also acetylated by PCAF in response to DNA damage (Sakaguchi et al., 1998). Whether the state of acetylation of residue 320 affected the ability of hSir2 to deacetylate residue 382 was determined. A mutant p53 allele that specifies a lysine-to-arginine substitution at residue 320 was expressed. This amino acid substitution did not affect the ability of hSir2 to deacetylate the K382 residue in H1299 cells, indicating that the action of hSir2 on the acetylated K382 residue is independent of the state of acetylation of the K320 residue (FIG. 10A, lanes 7, 8).

As a measure of the substrate specificity of hSir2, the effects of hSir2 on histone acetylation, specifically the acetylated residue lysine 9 of histone H3, were determined using cell nuclei from the above experiments. H3 Lys9 acetylation was monitored through the use of the 9671 S monoclonal antibody. The 9671 S antibody specifically recognizes histone H3 that is acetylated at this position.

Neither wildtype hSir2 nor the catalytically inactive hSir2HY altered the acetylation of histone H3 at this position (FIG. 10A, bottom). Thus, de-acetylation of p53 Lys382 in vivo reflects a defined substrate specificity of hSir2 and not a non-specific consequence of its over-expression.

Example 11 hSir2 and p53 Acetylation in Primary and Tumor Cell Lines

Acetylation of lysine residue 382 of p53 accompanies and mediates the functional activation of p53 as a transcription factor following exposure of a cell to ionizing radiation (Sakaguchi et al., 1998). To determine whether hSir2 could antagonize and reverse this activation of p53, by its deacetylase function, either wildtype hSir2 or the mutant form specified by the hSir2HY vector was expressed in BJT human fibroblast cells. Ectopic expression of the telomerase enzyme in these BJT cells, undertaken to extend their lifespan, had no effect on either their activation of p53 protein or their responses to DNA damage (Vaziri et al., 1999).

In order to facilitate detection of in vivo acetylated p53 protein, BJT cells were expressed to 6Gy of ionizing radiation in the presence of low trichostatin A (TSA) concentrations. While not directly inhibiting hSir2 catalytic activity (Imai et al., 2000), TSA appears to increase the stability of acetylated p53 protein (Sakaguchi et al., 1998), perhaps by inhibiting non-hSir2 deacetylases that also recognize the acetylated p53 K382 residue. The resulting immunoblot was probed with the polyclonal rabbit antiserum (Ab-1) which specifically recognizes the acetylated K382 form of p53.

Following 6 Gy of ionizing radiation, a 1.5-2 fold increase in the level of acetylated p53 protein was observed, as indicated by the levels of p53 protein recognized by the Ab-1 antiserum (FIG. 10B). A four-fold increase in hSir2 levels, achieved through ectopic expression of hSir2, resulted in the reversal of the radiation-induced increase in acetylated K382 p53 protein (FIG. 10B). In contrast, expression of the catalytically inactive hSirHY protein at comparable levels increased the radiation-induced levels of p53 acetylated at residue K382 (FIG. 10B) suggesting that the hSir2HY mutant may act in a dominant negative fashion in BJT cells. A re-probing of this immunoblot with a polyclonal anti-p53 antibody showed normal stabilization of p53 in control cells in response to DNA damage and at most, slightly reduced levels of stabilization in the presence of ectopically expressed wild type hSir2 (FIG. 10B). Hence, while hSir2 is able to reverse the radiation-induced acetylation of p53 in these cells, it has only minimal effects on the metabolic stabilization of p53 induced by exposure to radiation.

A similar phenomenon was observed in MCF-7 human breast carcinoma line cells, which have retained an apparently intact p53-dependent checkpoint in response to ionizing radiation. Irradiation of these cells led to a three-fold increase in acetylated p53 levels, while a four-fold ectopic expression of wild type hSir2 in irradiated MCF-7 cells led to deacetylation of p53 protein (FIG. 10C). In contrast to BJT cells, no significant change in the stability of total p53 protein was observed. However, MCF-7 cells expressing the hSirHY mutant showed a level of radiation-induced acetylation that was comparable to control irradiated cells (FIG. 10C). Thus, hSir2 is able to reverse the radiation-induced acetylation in both BJT and MCF-7 cells, suggesting that hSir2 acts as an antagonist of p53 function in vivo.

The differences observed in deacetylation activities of hSir2HY in MCF7 and BJT cells may reflect the ability of hSir2HY to act as a dominant-negative allele in BJT cells. BJT cells do express significantly lower levels of endogenous hSir2 when compared with MCF7 cells. These lower levels of hSir2 in BJT cells may enable hSir2HY to form inhibitory complexes with endogenous wild type hSir2 or with other proteins required for its function. In this context, evidence in yeast suggests that H363Y mutant does indeed act as a potent dominant-negative (Tanny et al., 1999).

Example 12

Effects of hSir2 on the Transcriptional Activity of p53 Protein

The effects of hSir2 on the transcriptional activity of p53 were determined by co-transfecting H1299 cells transiently with a p53 expression plasmid and a reporter construct in which the promoter of the p21WAF1 gene (el-Deiry et al., 1993), a known target of transcriptional activity by p53, is able to drive expression of a luciferase reporter gene (Vaziri et al., 1997). As indicated in FIG. 11A, luciferase activity increased in response to increasing amount of co-transfected wtp53 expression vector. Conversely, the transcriptional activity of p53 protein was suppressed by co-expression of wild type hSir2 in a dose-dependent fashion. The catalytically inactive hSir2HY mutant had no effect on p53 transcriptional activity (FIG. 11A). The specificity of hSir2 in affecting promoter activity was determined using a constitutively active SV40 promoter linked to the luciferase gene. Expression of this control construct was not affected by increasing amounts of hSir2 expression vector at any level (FIG. 11B).

The above observations were confirmed in a more physiologic context using a subline of MCF-7L cells. The subline of MCF-7 cells was stably transfected with a p21 WAF 1 promoter-reporter construct. In addition, these cells were infected stably with retroviral vector constructs expressing either the wild type hSir2 or the mutant hSir2HY. These cells were expressed to 6 Gy of ionizing radiation and subsequently measured total p53 and p21WAF1 protein levels (FIG. 11C).

p53 protein levels increased normally in all cell populations in response to irradiation of these cells. However, the levels of p21WAF1 protein were reduced in cells expressing wild type hSir2 (FIG. 11C). Moreover, MCF-7L cells expressing the mutant hSir2HY protein had a higher level of p21WAF1 when compared with the irradiated controls and with the wild type hSir2-overexpressing cells (FIG. 11C) showing that the hSir2HY mutant may act in a dominant-negative fashion in these cells. Thus, hSir2 can antagonize the transcriptional activities of p53 that enable it to exert cytostatic effects via transcriptional activation of the p21WAF1 gene.

REFERENCES

Appella E. and Anderson C. W. (2000) Signaling to p53: breaking the posttranslational modification code. *Pathol. Biol.*, 48:227-245.

Avantaggiati M. L., Ogryzko V., Gardner K., Giordano A., Levine A. S. and Kelly K. (1997) Recruitment of p300/CBP in p53-dependent signal pathways. *Cell*, 89:1175-1184.

Bernstein B. E., Tong J. K. and Schreiber S. L. (2000) Genomewide studies of histone deacetylase function in yeast. *Proc. Natl. Acad. Sci. USA*, 97:13708-13713.

Butler L. M., Agus D. B., Scher H. I., Higgins B., Rose A., Cordon-Cardo C., Thaler H. T., Rifkind R. A., Marks P. A. and Richon V. M. (2000) Suberoylanilide hydroxamic acid, an inhibitor of histone deacetylase suppresses the growth of prostate cancer cells in vitro and in vivo. *Cancer Res.*, 60:5165-5170.

Campisi J. (2000) Aging, chromatin, and food restriction—connecting the dots. *Science*, 289:2062-2063.

Chao C., Saito S., Kang J., Anderson C. W., Appella E. and Xu Y. (2000) p53 transcriptional activity is essential for p53-dependent apoptosis following DNA damage. *EMBO J.*, 19:4967-4975.

Chen Q. M., Liu J. and Merrett J. B. (2000) Apoptosis or senescence-like growth arrest: influence of cell-cycle position, p53, p21 and bax in H2O2 response of normal human fibroblasts. *Biochem. J.*, 347:543-551.

Chresta C. M. and Hickman J. A. (1996) Oddball p53 in testicular tumors. *Nat. Med.*, 2:745-746.

Di Cristofano A., Kotsi P., Peng Y. F., Cordon-Cardo C., Elkon K. B. and Pandolfi P. P. (1999) Impaired Fas response and autoimmunity in Pten.+-. mice. *Science*, 285:2122-2125.

Ferbeyre G., de Stanchina E., Querido E., Baptiste N., Prives C. and Lowe S. W. (2000) PML is induced by oncogenic ras and promotes premature senescence. *Genes Dev.*, 14:2015-2027.

Frye R. A. (1999) Characterization of five human cDNAs with homology to the yeast SIR2 gene: Sir2-like proteins (sirtuins) metabolize NAD and may have protein ADP-ribosyltransferase activity. *Biochem. Biophys. Res. Commun.*, 260:273-279.

Frye R. A. (2000) Phylogenetic classification of prokaryotic and eukaryotic Sir2-like proteins. *Biochem. Biophys. Res. Commun.*, 273:793-798.

Gu W. and Roeder R. G. (1997) Activation of p53 sequence-specific DNA binding by acetylation of the p53 C-terminal domain. *Cell*, 90:595-606.

Gu W., Shi X. L. and Roeder R. G. (1997) Synergistic activation of transcription by CBP and p53. *Nature*, 387:819-823.

Gu W., Malik S., Ito M., Yuan C. X., Fondell J. D., Zhang X., Martinez E., Qin J. and Roeder R. G. (1999) A novel human SRB/MED-containing cofactor complex, SMCC, involved in transcription regulation. *Mol. Cell*, 3:97-108.

Guarente L. (2000) Sir2 links chromatin silencing, metabolism, and aging. *Genes Dev.*, 14:1021-1026.

Guo A., Salomoni P., Luo J., Shih A., Zhong S., Gu W. and Pandolfi P. P. (2000) The function of PML in p53-dependent apoptosis. *Nat. Cell Biol.*, 2:730-736.

Imai S., Armstrong C. M., Kaeberlein M. and Guarente L. (2000) Transcriptional silencing and longevity protein Sir2 is an NAD-dependent histone deacetylase. *Nature*, 403:795-800.

Ito A., Lai C., Zhao X., Saito S., Hamilton M., Appella E. and Yao T. (2001) p300/CBP-mediated p53 acetylation is commonly induced by p53-activating agents and inhibited by MDM2. *EMBO J.*, 20:1331-1340.

Jimenez G. S., Nister M., Stommel J. M., Beeche M., Barcarse E. A., Zhang X. Q., O'Gorman S. and Wahl G. M. (2000) A transactivation-deficient mouse model provides insights into Trp53 regulation and function. *Nat. Genet.*, 26:37-43.

Kouzarides T. (2000) Acetylation: a regulatory modification to rival phosphorylation? *EMBO J.*, 19:1176-1179.

Landry J., Slama J. T. and Sternglanz R. (2000) Role of NAD(+) in the deacetylase activity of the SIR2-like proteins. *Biochem. Biophys. Res. Commun.*, 278:685-690.

Landry J., Sutton A., Tafrov S. T., Heller R. C., Stebbins J., Pillus L. and Sternglanz R. (2000) The silencing protein SIR2 and its homologs are NAD-dependent protein deacetylases. *Proc. Natl. Acad. Sci. USA*, 97:5807-5811.

Levine A. J. (1997) p53, the cellular gatekeeper for growth and division. *Cell*, 88:323-331.

Lill N. L., Grossman S. R., Ginsberg D., DeCaprio J. and Livingston D. M. (1997) Binding and modulation of p53 by p300/CBP coactivators. *Nature*, 387:823-827.

Lin S. J., Defossez P. A. and Guarente L. (2000) Requirement of NAD and SIR2 for life-span extension by calorie restriction in *Saccharomyces cerevisiae*. *Science*, 289:2126-2128.

Luo J., Su F., Chen D., Shiloh A. and Gu W. (2000) Deacetylation of p53 modulates its effect on cell growth and apoptosis. *Nature*, 408:377-381.

Lutzker S. G. and Levine A. J. (1996) A functionally inactive p53 protein in teratocarcinoma cells is activated by either DNA damage or cellular differentiation. *Nat. Med.*, 2:804-810.

Marks P. A., Rifkind R. A., Richon V. M. and Breslow R. (2001) Inhibitors of histone deacetylase are potentially effective anticancer agents. *Clin. Cancer Res.*, 7:759-760.

Maya R., Balass M., Kim S. T., Shkedy D., Leal J. F., Shifman O., Moas M., Buschmann T., Ronai Z. and Shiloh Y. et al. (2001) ATM-dependent phosphorylation of Mdm2 on serine 395: role in p53 activation by DNA damage. *Genes Dev.*, 15:1067-1077.

Migliaccio E., Giorgio M., Mele S., Pelicci G., Reboldi P., Pandolfi P. P., Lanfrancone L. and Pelicci P. G. (1999) The p66shc adaptor protein controls oxidative stress response and life span in mammals. *Nature*, 402:309-313.

Nakamura S., Roth J. A. and Mukhopadhyay T. (2000) Multiple lysine mutations in the C-terminal domain of p53 interfere with MDM2-dependent protein degradation and ubiquitination. *Mol. Cell. Biol.*, 20:9391-9398.

Nakano K. and Vousden K. (2001) PUMA, a novel proapoptotic gene, is induced by p53. *Mol. Cell*, 7:683-694.

Pearson M., Carbone R., Sebastiani C., Cioce M., Fagioli M., Saito S., Higashimoto Y., Appella E., Minucci S., Pandolfi P. P. and Pelicci P. G. (2000) PML regulates p53 acetylation and premature senescence induced by oncogenic Ras. *Nature*, 406:207-210.

Prives C. and Hall P. A. (1999) The p53 pathway. *Pathol. J.*, 187:112-126.

Rodriguez M. S., Desterro J. M., Lain S., Lane D. P. and Hay R. T. (2000) Multiple C-terminal lysine residues target p53 for ubiquitin-proteasome-mediated degradation. *Mol. Cell. Biol.*, 20:8458-8467.

Shieh S. Y., Ikeda M., Taya Y. and Prives C. (1997) DNA damage-induced phosphorylation of p53 alleviates inhibition MDM2. *Cell*, 91:325-334.

Shore D. (2000) The Sir2 protein family: A novel deacetylase for gene silencing and more. *Proc. Natl. Acad. Sci. USA*, 97:14030-14032.

Smith J. S., Brachmann C. B., Celic I., Kenna M. A., Muhammad S., Starai V. J., Avalos J. L., Escalante-Semerena J. C., Grubmeyer C., Wolberger C. and Boeke J. D. (2000) A phylogenetically conserved NAD-dependent protein deacetylase activity in the Sir2 protein family. *Proc. Natl. Acad. Sci. USA,* 97:6658-6663.

Sterner D. E. and Berger S. L. (2000) Acetylation of histones and transcription-related factors. *Microbiol. Mol. Biol.,* 64:435-459.

Tanner K. G., Landry J., Sternglanz R. and Denu J. M. (2000) Silent information regulator 2 family of NAD-dependent histone/protein deacetylases generates a unique product, 1-O-acetyl-ADP-ribose. *Proc. Natl. Acad. Sci. USA,* 97:14178-14182.

Tanny J. C. and Moazed D. (2001) Coupling of histone deacetylation to NAD breakdown by the yeast silencing protein Sir2: Evidence for acetyl transfer from substrate to an NAD breakdown product. *Proc. Natl. Acad. Sci. USA,* 98:415-420.

Tissenbaum H. A. and Guarente L. (2001) Increased dosage of a sir-2 gene extends lifespan in *Caenorhabditis elegans. Nature,* 410:227-230.

Vaziri H., West M. D., Allsopp R. C., Davison T. S., Wu Y. S., Arrowsmith C. H., Poirier G. G. and Benchimol S. (1997) ATM-dependent telomere loss in aging human diploid fibroblasts and DNA damage lead to the post-translational activation of p53 protein involving poly(ADP-ribose) polymerase. *EMBO J.,* 16:6018-6033.

Vaziri H., Dessain S. K., Ng-Eaton E., Imai S. I., Frye R. A., Pandita T. K., Guarente L. and Weinberg R. A. (2001) hSIR2SIRT1 functions as an NAD-dependent p53 deacetylase. *Cell,* 107:149-159.

Vogelstein B., Lane D. and Levine A. J. (2000) Surfing the p53 network. *Nature,* 408:307-310.

Yin Y., Terauchi Y., Solomon G. G., Aizawa S., Rangarajan P. N., Yazaki Y., Kadowaki T. and Barrett J. C. (1998) Involvement of p85 in p53-dependent apoptotic response to oxidative stress. *Nature,* 391:707-710.

Yoshida M., Horinouchi S. and Beppu T. (1995) Trichostatin A and trapoxin: novel chemical probes for the role of histone acetylation in chromatin structure and function. *Bioessays,* 5:423-430.

Yu A., Fan H., Lao D., Bailey A. D. and Weiner A. M. (2000) Activation of p53 or loss of the Cockayne syndrome group B repair protein causes metaphase fragility of human U1, U2, and 5S genes. *Mol. Cell,* 5:801-810.

Yu J., Zhang L., Hwang P., Kinzler K. and Vogelstein B. (2001) PUMA induces the rapid apoptosis of colorectal cancer cells. *Mol. Cell,* 7:673-682.

All patents, patent applications, and published references cited herein are hereby incorporated by reference.

A number of embodiments of the invention have been described. Nevertheless, it will be understood that various modifications may be made without departing from the spirit and scope of the invention. Accordingly, other embodiments are within the scope of the following claims.

What is claimed is:

1. A method of screening a compound, comprising the steps of:
   (a) contacting a compound that modulates Sir2-mediated deacetylation of a transcription factor, with a cell or a system that includes a Sir2 protein or an active portion thereof and the transcription factor or an active portion thereof; and
   (b) measuring modulation of transcription of a gene whose expression is regulated by the transcription factor in the cell or the system, thereby screening for the compound.

2. The method of claim 1, wherein the transcription factor is a p53 protein or an active portion thereof.

3. The method of claim 1, wherein the transcription factor binds a specific DNA site.

4. The method of claim 1, wherein measuring modulation of transcription of the gene includes comparing the transcription of the gene at a first concentration of the compound and at a second concentration of the compound.

5. The method of claim 4, wherein the first or second concentration of the compound is zero.

6. The method of claim 1, wherein the cell or system further includes a Sir2 cofactor.

7. The method of claim 6, wherein the Sir2 cofactor is NAD or an NAD analog.

8. The method of claim 1, wherein the Sir2 protein is a Sir2 variant that has reduced deacetylase activity.

9. The method of claim 1, wherein the Sir2 protein is a human Sir2 protein.

10. The method of claim 9, wherein the human Sir2 protein is human SIRT1.

11. The method of claim 1, wherein the Sir2 protein is a murine Sir2 protein.

12. The method of claim 11, wherein the murine Sir2 protein is murine Sir2α.

13. The method of claim 1, wherein the Sir2 protein is exogenous and expressed from a heterologous nucleic acid.

14. The method of claim 1, wherein the transcription factor is exogenous and expressed from a heterologous nucleic acid.

15. The method of claim 1, further including the steps of:
(c) administering the compound to a cell or an animal, wherein modulation of transcription of the gene is measured by evaluating the effect of the compound on the cell or animal.

16. The method of claim 1, wherein the active portion includes a core domain of the Sir2 protein.

17. The method of claim 16, wherein the core domain includes amino acid residues 258-451 of SEQ ID No: 12.

18. The method of claim 10, wherein the human SIRT1 comprises the amino acid sequence of SEQ ID NO: 12.

19. The method of claim 9, wherein the human Sir2 protein is selected from the group consisting of SIRT3, SIRT4, and SIRT5.

20. The method of claim 19, wherein the human Sir2 protein comprises an amino acid sequence selected from the group consisting of SEQ ID NO: 14, SEQ ID NO: 16, and SEQ ID NO: 18.

21. The method of claim 2, wherein the p53 protein or active portion thereof comprises K382 of p53.

* * * * *